(12) United States Patent
Erickson et al.

(10) Patent No.: US 9,382,304 B2
(45) Date of Patent: Jul. 5, 2016

(54) ENGINEERED POLYPEPTIDES HAVING ENHANCED DURATION OF ACTION WITH REDUCED IMMUNOGENICITY

(75) Inventors: Mary Erickson, San Diego, CA (US); David C. Litzinger, San Diego, CA (US); Soumitra S. Ghosh, San Diego, CA (US); Zijian Guo, San Diego, CA (US); Manoj P. Samant, San Diego, CA (US); Abhinandini Sharma, San Diego, CA (US); Lala Mamedova, San Diego, CA (US); Esther Odile Levy, San Diego, CA (US); Caroline Ekblad, San Diego, CA (US)

(73) Assignees: Amylin Pharmaceuticals, LLC, Wilmington, DE (US); AstraZeneca Pharmaceuticals LP, Wilmington, DE (US)

( * ) Notice: Subject to any disclaimer, the term of this patent is extended or adjusted under 35 U.S.C. 154(b) by 0 days.

(21) Appl. No.: 14/129,815

(22) PCT Filed: Jul. 3, 2012

(86) PCT No.: PCT/US2012/045451
§ 371 (c)(1),
(2), (4) Date: Apr. 3, 2014

(87) PCT Pub. No.: WO2013/009545
PCT Pub. Date: Jan. 17, 2013

(65) Prior Publication Data
US 2014/0235535 A1  Aug. 21, 2014

Related U.S. Application Data

(60) Provisional application No. 61/585,577, filed on Jan. 11, 2012, provisional application No. 61/505,982, filed on Jul. 8, 2011.

(51) Int. Cl.
| C07K 14/605 | (2006.01) |
| A61K 47/48 | (2006.01) |
| C12N 15/62 | (2006.01) |

(52) U.S. Cl.
CPC ......... *C07K 14/605* (2013.01); *A61K 47/48338* (2013.01); *C12N 15/62* (2013.01); *C07K 2319/31* (2013.01); *C07K 2319/70* (2013.01)

(58) Field of Classification Search
CPC .................................................... C07K 14/605
See application file for complete search history.

(56) References Cited

U.S. PATENT DOCUMENTS

| 7,638,299 B2 * | 12/2009 | Cho et al. ...................... 435/69.1 |
| 8,642,743 B2 * | 2/2014 | Herne .......................... 530/402 |
| 8,969,289 B2 * | 3/2015 | Gosselin et al. ............. 514/13.6 |
| 2007/0244047 A1 | 10/2007 | Rosen et al. |
| 2009/0214534 A1 | 8/2009 | Holmes et al. |
| 2010/0330108 A1 | 12/2010 | Song et al. |
| 2011/0092417 A1 | 4/2011 | Artymiuk et al. |

FOREIGN PATENT DOCUMENTS

| WO | WO 00/66629 | * | 11/2000 | ........... C07K 14/575 |
| WO | WO 2005/027978 | * | 3/2005 | ............ A61K 47/48 |
| WO | 2005087797 A1 | | 9/2005 | |
| WO | 2008043821 A1 | | 4/2008 | |
| WO | WO 2009/016043 | * | 2/2009 | ........... C07K 14/195 |
| WO | WO 2009/016043 A2 | | 2/2009 | |
| WO | WO 2010/054699 | | 5/2010 | |
| WO | WO 2011/039096 A1 | | 4/2011 | |
| WO | 2012004384 A2 | | 1/2012 | |
| WO | WO 2013/009539 | | 2/2014 | |

OTHER PUBLICATIONS

International Search Report for PCT/US2012/045398 mailed Sep. 28, 2012.
International Search Report for PCT/US2012/045451 mailed Nov. 16, 2012.
European Search Report for PCT/US2012/045451 mailed Jan. 5, 2015.
Goetsch, L. et al., "Identification of B- and T-Cell Epitopes of BB, a Carrier Protein Derived from the G Protein of *Streptococcus*Strain G148," Clinical and Diagnostic Laboratory Immunology; vol. 10, No. 1; pp. 125-132 (Jan. 2003).
Jonsson, A. et al., "Engineering of a femtomolar affinity binding protein to human serum albumin," Protein Engineering, Design & Selection; vol. 21 No. 8 pp. 515-527 (2008; Published online May 22, 2008.
Sletten, E. et al., "Bioorthogonal Chemistry: Fishing for Selectivity in a Sea of Functionality," Angew Chem Int Ed Engl.; 48(38): 6974-6998 (2009).
Tanaka, T. et al., "N-terminal glycine-specific protein conjugation catalyzed by microbial transglutaminase," FEBS Letters 579:2092-2096 (2005).

* cited by examiner

*Primary Examiner* — Amber D Steele
(74) *Attorney, Agent, or Firm* — Mintz Levin Cohn Ferris Glovsky and Popeo, P.C.

(57) ABSTRACT

Compounds are provided having inter alia good duration of action, high potency and/or convenient dosing regimens including oral administration, and reduced immunogenicity. The compounds are engineered polypeptides which incorporate an albumin binding domain in combination with one or more biologically active polypeptides. Also provided are pharmaceutical compositions and methods of treatment for diseases and disorders including obesity and overweight, diabetes, dyslipidemia, hyperlipidemia, Alzheimer's disease, fatty liver disease, Short Bowel Syndrome, Parkinson's disease, and cardiovascular disease.

11 Claims, 28 Drawing Sheets

Figure 1A

| ABD | Amino acid sequence | INFORMAL SEQ ID NO: |
|---|---|---|
|  | LA X3 AK X6 X7 AN X10 ELD X14 YGVSDF YKRLIDKAKT VEGVEALKDA ILAALP | 678 |
| Formula i) | LA X3 AK X6 X7 AN X10 ELD X14 YGVSDF YKRLI X26 KAKTVEGVEALK X39 X40 IL X43 X44 LP | 300 |
| PP001 | LASAKEAANAELDAYGVSDFYKRLIDKAKTVEGVEALKDAILAALP | 301 |
| PP002 | LASAKEAANSELDAYGVSDFYKRLIDKAKTVEGVEALKDAILAALP | 302 |
| PP003 | LASAKESANSELDAYGVSDFYKRLIDKAKTVEGVEALKDAILAALP | 303 |
| PP004 | LASAKESANAELDAYGVSDFYKRLIDKAKTVEGVEALKDAILAALP | 304 |
| PP005 | LASAKSAANAELDAYGVSDFYKRLIDKAKTVEGVEALKDAILAALP | 305 |
| PP006 | LASAKSAANSELDAYGVSDFYKRLIDKAKTVEGVEALKDAILAALP | 306 |
| PP007 | LASAKEAANAELDSYGVSDFYKRLIDKAKTVEGVEALKDAILAALP | 307 |
| PP008 | LASAKEAANSELDSYGVSDFYKRLIDKAKTVEGVEALKDAILAALP | 308 |
| PP009 | LASAKESANSELDSYGVSDFYKRLIDKAKTVEGVEALKDAILAALP | 309 |
| PP010 | LASAKESANAELDSYGVSDFYKRLIDKAKTVEGVEALKDAILAALP | 310 |
| PP011 | LASAKSAANAELDSYGVSDFYKRLIDKAKTVEGVEALKDAILAALP | 311 |
| PP012 | LASAKSAANSELDSYGVSDFYKRLIDKAKTVEGVEALKDAILAALP | 312 |
| PP013 | LAEAKEAANAELDSYGVSDFYKRLIDKAKTVEGVEALKDAILAALP | 313 |
| PP014 | LAEAKEAANSELDSYGVSDFYKRLIDKAKTVEGVEALKDAILAALP | 314 |
| PP015 | LAEAKESANSELDSYGVSDFYKRLIDKAKTVEGVEALKDAILAALP | 315 |
| PP016 | LAEAKESANAELDSYGVSDFYKRLIDKAKTVEGVEALKDAILAALP | 316 |
| PP017 | LAEAKSAANAELDSYGVSDFYKRLIDKAKTVEGVEALKDAILAALP | 317 |
| PP018 | LAEAKSAANSELDSYGVSDFYKRLIDKAKTVEGVEALKDAILAALP | 318 |
| PP019 | LAEAKEAANAELDAYGVSDFYKRLIDKAKTVEGVEALKDAILAALP | 319 |
| PP020 | LAEAKEAANSELDAYGVSDFYKRLIDKAKTVEGVEALKDAILAALP | 320 |
| PP021 | LAEAKESANSELDAYGVSDFYKRLIDKAKTVEGVEALKDAILAALP | 321 |
| PP022 | LAEAKESANELDAYGVSDFYKRLIDKAKTVEGVEALKDAILAALP | 322 |
| PP023 | LAEAKSAANSELDAYGVSDFYKRLIDKAKTVEGVEALKDAILAALP | 323 |
| PP024 | LAEAKSAANELDAYGVSDFYKRLIDKAKTVEGVEALKDAILAALP | 324 |
| PP025 | LAQAKEAANAELDAYGVSDFYKRLIDKAKTVEGVEALKDAILAALP | 325 |
| PP026 | LAQAKEAANSELDAYGVSDFYKRLIDKAKTVEGVEALKDAILAALP | 326 |
| PP027 | LAQAKESANSELDAYGVSDFYKRLIDKAKTVEGVEALKDAILAALP | 327 |
| PP028 | LAQAKESANAELDAYGVSDFYKRLIDKAKTVEGVEALKDAILAALP | 328 |
| PP029 | LAQAKSAANAELDAYGVSDFYKRLIDKAKTVEGVEALKDAILAALP | 329 |
| PP030 | LAQAKSAANSELDAYGVSDFYKRLIDKAKTVEGVEALKDAILAALP | 330 |
| PP031 | LAQAKEAANAELDSYGVSDFYKRLIDKAKTVEGVEALKDAILAALP | 331 |
| PP032 | LAQAKEAANSELDSYGVSDFYKRLIDKAKTVEGVEALKDAILAALP | 332 |
| PP033 | LAQAKESANSELDSYGVSDFYKRLIDKAKTVEGVEALKDAILAALP | 333 |
| PP034 | LAQAKESANAELDSYGVSDFYKRLIDKAKTVEGVEALKDAILAALP | 334 |
| PP035 | LAQAKSAANAELDSYGVSDFYKRLIDKAKTVEGVEALKDAILAALP | 335 |

Figure 1B

| PP036 | LAQAKSAANSELDSYGVSDFYKRLIDKAKTVEGVEALKDAILAALP | 336 |
|---|---|---|
| PP037 | LASAKEAANAELDCYGVSDFYKRLIDKAKTVEGVEALKDAILAALP | 337 |
| PP038 | LASAKEAANSELDCYGVSDFYKRLIDKAKTVEGVEALKDAILAALP | 338 |
| PP039 | LASAKESANSELDCYGVSDFYKRLIDKAKTVEGVEALKDAILAALP | 339 |
| PP040 | LASAKESANAELDCYGVSDFYKRLIDKAKTVEGVEALKDAILAALP | 340 |
| PP041 | LASAKSAANAELDCYGVSDFYKRLIDKAKTVEGVEALKDAILAALP | 341 |
| PP042 | LASAKSAANSELDCYGVSDFYKRLIDKAKTVEGVEALKDAILAALP | 342 |
| PP043 | LASAKEAANAELDKYGVSDFYKRLIDKAKTVEGVEALKDAILAALP | 343 |
| PP044 | LASAKEAANSELDKYGVSDFYKRLIDKAKTVEGVEALKDAILAALP | 344 |
| PP045 | LASAKESANSELDKYGVSDFYKRLIDKAKTVEGVEALKDAILAALP | 345 |
| PP046 | LASAKESANAELDKYGVSDFYKRLIDKAKTVEGVEALKDAILAALP | 346 |
| PP047 | LASAKSAANAELDKYGVSDFYKRLIDKAKTVEGVEALKDAILAALP | 347 |
| PP048 | LASAKSAANSELDKYGVSDFYKRLIDKAKTVEGVEALKDAILAALP | 348 |
| PP049 | LAEAKEAANAELDCYGVSDFYKRLIDKAKTVEGVEALKDAILAALP | 349 |
| PP050 | LAEAKEAANSELDCYGVSDFYKRLIDKAKTVEGVEALKDAILAALP | 350 |
| PP051 | LAEAKESANSELDCYGVSDFYKRLIDKAKTVEGVEALKDAILAALP | 351 |
| PP052 | LAEAKESANAELDCYGVSDFYKRLIDKAKTVEGVEALKDAILAALP | 352 |
| PP053 | LAEAKSAANAELDCYGVSDFYKRLIDKAKTVEGVEALKDAILAALP | 353 |
| PP054 | LAEAKSAANSELDCYGVSDFYKRLIDKAKTVEGVEALKDAILAALP | 354 |
| PP055 | LAEAKEAANAELDKYGVSDFYKRLIDKAKTVEGVEALKDAILAALP | 355 |
| PP056 | LAEAKEAANSELDKYGVSDFYKRLIDKAKTVEGVEALKDAILAALP | 356 |
| PP057 | LAEAKESANSELDKYGVSDFYKRLIDKAKTVEGVEALKDAILAALP | 357 |
| PP058 | LAEAKESANAELDKYGVSDFYKRLIDKAKTVEGVEALKDAILAALP | 358 |
| PP059 | LAEAKSAANAELDKYGVSDFYKRLIDKAKTVEGVEALKDAILAALP | 359 |
| PP060 | LAEAKSAANSELDKYGVSDFYKRLIDKAKTVEGVEALKDAILAALP | 360 |
| PP061 | LAQAKEAANAELDCYGVSDFYKRLIDKAKTVEGVEALKDAILAALP | 361 |
| PP062 | LAQAKEAANSELDCYGVSDFYKRLIDKAKTVEGVEALKDAILAALP | 362 |
| PP063 | LAQAKESANSELDCYGVSDFYKRLIDKAKTVEGVEALKDAILAALP | 363 |
| PP064 | LAQAKESANAELDCYGVSDFYKRLIDKAKTVEGVEALKDAILAALP | 364 |
| PP065 | LAQAKSAANAELDCYGVSDFYKRLIDKAKTVEGVEALKDAILAALP | 365 |
| PP066 | LAQAKSAANSELDCYGVSDFYKRLIDKAKTVEGVEALKDAILAALP | 366 |
| PP067 | LAQAKEAANAELDKYGVSDFYKRLIDKAKTVEGVEALKDAILAALP | 367 |
| PP068 | LAQAKEAANSELDKYGVSDFYKRLIDKAKTVEGVEALKDAILAALP | 368 |
| PP069 | LAQAKESANSELDKYGVSDFYKRLIDKAKTVEGVEALKDAILAALP | 369 |
| PP070 | LAQAKESANAELDKYGVSDFYKRLIDKAKTVEGVEALKDAILAALP | 370 |
| PP071 | LAQAKSAANAELDKYGVSDFYKRLIDKAKTVEGVEALKDAILAALP | 371 |
| PP072 | LAQAKSAANSELDKYGVSDFYKRLIDKAKTVEGVEALKDAILAALP | 372 |
| PP073 | LACAKEAANAELDCYGVSDFYKRLIDKAKTVEGVEALKDAILAALP | 373 |
| PP074 | LACAKEAANSELDCYGVSDFYKRLIDKAKTVEGVEALKDAILAALP | 374 |
| PP075 | LACAKESANSELDCYGVSDFYKRLIDKAKTVEGVEALKDAILAALP | 375 |
| PP076 | LACAKESANAELDCYGVSDFYKRLIDKAKTVEGVEALKDAILAALP | 376 |

Figure 1C

| PP077 | LACAKSAANAELDCYGVSDFYKRLIDKAKTVEGVEALKDAILAALP | 377 |
|---|---|---|
| PP078 | LACAKSAANSELDCYGVSDFYKRLIDKAKTVEGVEALKDAILAALP | 378 |
| PP079 | LACAKEAANAELDKYGVSDFYKRLIDKAKTVEGVEALKDAILAALP | 379 |
| PP080 | LACAKEAANSELDKYGVSDFYKRLIDKAKTVEGVEALKDAILAALP | 380 |
| PP081 | LACAKESANAELDKYGVSDFYKRLIDKAKTVEGVEALKDAILAALP | 381 |
| PP082 | LACAKESANSELDKYGVSDFYKRLIDKAKTVEGVEALKDAILAALP | 382 |
| PP083 | LACAKSAANAELDKYGVSDFYKRLIDKAKTVEGVEALKDAILAALP | 383 |
| PP084 | LACAKSAANSELDKYGVSDFYKRLIDKAKTVEGVEALKDAILAALP | 384 |
| PP085 | LACAKEAANAELDSYGVSDFYKRLIDKAKTVEGVEALKDAILAALP | 385 |
| PP086 | LACAKEAANSELDSYGVSDFYKRLIDKAKTVEGVEALKDAILAALP | 386 |
| PP087 | LACAKESANAELDSYGVSDFYKRLIDKAKTVEGVEALKDAILAALP | 387 |
| PP088 | LACAKESANSELDSYGVSDFYKRLIDKAKTVEGVEALKDAILAALP | 388 |
| PP089 | LACAKSAANAELDSYGVSDFYKRLIDKAKTVEGVEALKDAILAALP | 389 |
| PP090 | LACAKSAANSELDSYGVSDFYKRLIDKAKTVEGVEALKDAILAALP | 390 |
| PP091 | LACAKEAANAELDAYGVSDFYKRLIDKAKTVEGVEALKDAILAALP | 391 |
| PP092 | LACAKEAANSELDAYGVSDFYKRLIDKAKTVEGVEALKDAILAALP | 392 |
| PP093 | LACAKESANAELDAYGVSDFYKRLIDKAKTVEGVEALKDAILAALP | 393 |
| PP094 | LACAKESANSELDAYGVSDFYKRLIDKAKTVEGVEALKDAILAALP | 394 |
| PP095 | LACAKSAANAELDAYGVSDFYKRLIDKAKTVEGVEALKDAILAALP | 395 |
| PP096 | LACAKSAANSELDAYGVSDFYKRLIDKAKTVEGVEALKDAILAALP | 396 |
| PP097 | LAQAKCAANAELDAYGVSDFYKRLIDKAKTVEGVEALKDAILAALP | 397 |
| PP098 | LAQAKCAANSELDAYGVSDFYKRLIDKAKTVEGVEALKDAILAALP | 398 |
| PP099 | LAQAKCSANSELDAYGVSDFYKRLIDKAKTVEGVEALKDAILAALP | 399 |
| PP100 | LAQAKCSANAELDAYGVSDFYKRLIDKAKTVEGVEALKDAILAALP | 400 |
| PP101 | LAQAKCAANAELDCYGVSDFYKRLIDKAKTVEGVEALKDAILAALP | 401 |
| PP102 | LAQAKCAANSELDCYGVSDFYKRLIDKAKTVEGVEALKDAILAALP | 402 |
| PP103 | LAQAKCAANAELDSYGVSDFYKRLIDKAKTVEGVEALKDAILAALP | 403 |
| PP104 | LAQAKCAANSELDSYGVSDFYKRLIDKAKTVEGVEALKDAILAALP | 404 |
| PP105 | LAQAKCSANSELDSYGVSDFYKRLIDKAKTVEGVEALKDAILAALP | 405 |
| PP106 | LAQAKCSANAELDSYGVSDFYKRLIDKAKTVEGVEALKDAILAALP | 406 |
| PP107 | LAQAKCAANAELDKYGVSDFYKRLIDKAKTVEGVEALKDAILAALP | 407 |
| PP108 | LAQAKCAANSELDKYGVSDFYKRLIDKAKTVEGVEALKDAILAALP | 408 |
| PP109 | LASAKCAANAELDAYGVSDFYKRLIDKAKTVEGVEALKDAILAALP | 409 |
| PP110 | LASAKCAANSELDAYGVSDFYKRLIDKAKTVEGVEALKDAILAALP | 410 |
| PP111 | LASAKCSANSELDAYGVSDFYKRLIDKAKTVEGVEALKDAILAALP | 411 |
| PP112 | LASAKCSANAELDAYGVSDFYKRLIDKAKTVEGVEALKDAILAALP | 412 |
| PP113 | LASAKCAANAELDCYGVSDFYKRLIDKAKTVEGVEALKDAILAALP | 413 |
| PP114 | LASAKCAANSELDCYGVSDFYKRLIDKAKTVEGVEALKDAILAALP | 414 |
| PP115 | LASAKCAANAELDSYGVSDFYKRLIDKAKTVEGVEALKDAILAALP | 415 |
| PP116 | LASAKCAANSELDSYGVSDFYKRLIDKAKTVEGVEALKDAILAALP | 416 |
| PP117 | LASAKCSANSELDSYGVSDFYKRLIDKAKTVEGVEALKDAILAALP | 417 |

Figure 1D

| | | |
|---|---|---|
| PP118 | LASAKCSANAELDSYGVSDFYKRLIDKAKTVEGVEALKDAILAALP | 418 |
| PP119 | LASAKCAANAELDKYGVSDFYKRLIDKAKTVEGVEALKDAILAALP | 419 |
| PP120 | LASAKCAANSELDKYGVSDFYKRLIDKAKTVEGVEALKDAILAALP | 420 |
| PP121 | LAEAKCAANAELDAYGVSDFYKRLIDKAKTVEGVEALKDAILAALP | 421 |
| PP122 | LAEAKCAANSELDAYGVSDFYKRLIDKAKTVEGVEALKDAILAALP | 422 |
| PP123 | LAEAKCSANSELDAYGVSDFYKRLIDKAKTVEGVEALKDAILAALP | 423 |
| PP124 | LAEAKCSANAELDAYGVSDFYKRLIDKAKTVEGVEALKDAILAALP | 424 |
| PP125 | LAEAKCAANAELDCYGVSDFYKRLIDKAKTVEGVEALKDAILAALP | 425 |
| PP126 | LAEAKCAANSELDCYGVSDFYKRLIDKAKTVEGVEALKDAILAALP | 426 |
| PP127 | LAEAKCAANAELDSYGVSDFYKRLIDKAKTVEGVEALKDAILAALP | 427 |
| PP128 | LAEAKCAANSELDSYGVSDFYKRLIDKAKTVEGVEALKDAILAALP | 428 |
| PP129 | LAEAKCSANSELDSYGVSDFYKRLIDKAKTVEGVEALKDAILAALP | 429 |
| PP130 | LAEAKCSANAELDSYGVSDFYKRLIDKAKTVEGVEALKDAILAALP | 430 |
| PP131 | LAEAKCAANAELDKYGVSDFYKRLIDKAKTVEGVEALKDAILAALP | 431 |
| PP132 | LAEAKCAANSELDKYGVSDFYKRLIDKAKTVEGVEALKDAILAALP | 432 |
| PP133 | LACAKCAANAELDAYGVSDFYKRLIDKAKTVEGVEALKDAILAALP | 433 |
| PP134 | LACAKCAANSELDAYGVSDFYKRLIDKAKTVEGVEALKDAILAALP | 434 |
| PP135 | LACAKCSANSELDAYGVSDFYKRLIDKAKTVEGVEALKDAILAALP | 435 |
| PP136 | LACAKCSANAELDAYGVSDFYKRLIDKAKTVEGVEALKDAILAALP | 436 |
| PP137 | LACAKCAANAELDCYGVSDFYKRLIDKAKTVEGVEALKDAILAALP | 437 |
| PP138 | LACAKCAANSELDCYGVSDFYKRLIDKAKTVEGVEALKDAILAALP | 438 |
| PP139 | LACAKCAANAELDSYGVSDFYKRLIDKAKTVEGVEALKDAILAALP | 439 |
| PP140 | LACAKCAANSELDSYGVSDFYKRLIDKAKTVEGVEALKDAILAALP | 440 |
| PP141 | LACAKCSANSELDSYGVSDFYKRLIDKAKTVEGVEALKDAILAALP | 441 |
| PP142 | LACAKCSANAELDSYGVSDFYKRLIDKAKTVEGVEALKDAILAALP | 442 |
| PP143 | LACAKCAANAELDKYGVSDFYKRLIDKAKTVEGVEALKDAILAALP | 443 |
| PP144 | LACAKCAANSELDKYGVSDFYKRLIDKAKTVEGVEALKDAILAALP | 444 |
| PP145 | GSLASAKEAANAELDSYGVSDFYKRLIDKAKTVEGVEALKDAILAALPG | 445 |
| PP146 | GSLAEAKEAANAELDSYGVSDFYKRLIDKAKTVEGVEALKDAILAALPG | 446 |
| PP147 | GSLASAKEAANAELDCYGVSDFYKRLIDKAKTVEGVEALKDAILAALPG | 447 |
| PEP08185 | GSLAEAKEAANAELDCYGVSDFYKRLIDKAKTVEGVEALKDAILAALPG | 448 |
| PP149 | GSLASAKEAANAELDSYGVSDFYKRLIDKAKTVEGVEALKDAILAALPCG | 449 |
| PP150 | GSLAEAKEAANAELDSYGVSDFYKRLIDKAKTVEGVEALKDAILAALPCG | 450 |
| PP151 | GCSLASAKEAANAELDKYGVSDFYKRLIDKAKTVEGVEALKDAILAALPG | 451 |
| PP152 | GCSLAEAKEAANAELDKYGVSDFYKRLIDKAKTVEGVEALKDAILAALPG | 452 |
| PEP07913 | GLAEAKVLANRELDKYGVSDYYKNLINNAKTVEGVKALIDEILAALP | 453 |
| PEP06923 | GSSLAEAKVLANRELDKYGVSDFYKRLINKAKTVEGVEALKLHILAALP | 454 |
| PEP07271 | GSSLASAKEAANAELDAYGVSDFYKRLIDKAKTVEGVEALKDAILAALP | 455 |
| PEP07554 | GSSLASAKEAANAELDSYGVSDFYKRLIDKAKTVEGVEALKDAILAALP | 456 |
| PEP07912 | GLASAKEAANAELDSYGVSDFYKRLIDKAKTVEGVEALKDAILAALP | 457 |
| PEP07914 | GLAEAKEAANAELDSYGVSDFYKRLIDKAKTVEGVEALKDAILAALP | 458 |

Figure 1E

| | | |
|---|---|---|
| PEP07911 | GLASAKEAANAELDCYGVSDFYKRLIDKAKTVEGVEALKDAILAALP | 459 |
| PEP07834 | ALASAKEAANAELDCYGVSDFYKRLIDKAKTVEGVEALKDAILAALP | 460 |
| PEP07844 | GSSLASAKEAANAELDKYGVSDFYKRLIDKAKTVEGVEALKDAILAALP | 461 |
| PEP07983 | GSLASAKEAANAELDSYGVSDFYKRLIDKAKTVEGVEALKDAILAALP | 462 |
| PEP07986 | GSLAEAKEAANAELDSYGVSDFYKRLIDKAKTVEGVEALKDAILAALP | 463 |
| PP013+NtermS | SLAEAKEAANAELDSYGVSDFYKRLIDKAKTVEGVEALKDAILAALP | 500 |
| 501 | LAEAKEAANAELDCYGVSDFYKRLIDKAKTVEGVEALKDAILAALPG | 501 |
| 501+NtermS | SLAEAKEAANAELDCYGVSDFYKRLIDKAKTVEGVEALKDAILAALPG | 502 |
| | GSLAQAKEAANAELDSYGVSDFYKRLIDKAKTVEGVEALKDAILAALP | 862 |
| | GSLAEAKEAANRELDSYGVSDFYKRLIDKAKTVEGVEALKDAILAALP | 863 |
| | GSLAQAKEAANRELDSYGVSDFYKRLIDKAKTVEGVEALKDAILAALP | 864 |
| | GSLAEAKEAANRELDAYGVSDFYKRLIDKAKTVEGVEALKDAILAALP | 865 |
| | GSLAEAKVLANRELDKYGVSDFYKRLIDKAKTVEGVEALKDAILAALP | 866 |
| | SLAQAKEAANAELDSYGVSDFYKRLIDKAKTVEGVEALKDAILAALP | 867 |
| | SLAEAKEAANRELDSYGVSDFYKRLIDKAKTVEGVEALKDAILAALP | 868 |
| | SLAQAKEAANRELDSYGVSDFYKRLIDKAKTVEGVEALKDAILAALP | 869 |
| | SLAEAKEAANRELDAYGVSDFYKRLIDKAKTVEGVEALKDAILAALP | 870 |
| | SLAEAKVLANRELDKYGVSDFYKRLIDKAKTVEGVEALKDAILAALP | 871 |
| | LAQAKEAANAELDSYGVSDFYKRLIDKAKTVEGVEALKDAILAALP | 331 |
| | LAEAKEAANRELDSYGVSDFYKRLIDKAKTVEGVEALKDAILAALP | 872 |
| | LAQAKEAANRELDSYGVSDFYKRLIDKAKTVEGVEALKDAILAALP | 873 |
| | LAEAKEAANRELDAYGVSDFYKRLIDKAKTVEGVEALKDAILAALP | 874 |
| | LAEAKVLANRELDKYGVSDFYKRLIDKAKTVEGVEALKDAILAALP | 875 |
| | GSLAQAKEAANAELDSYGVSDFYKRLIEKAKTVEGVEALKDAILAALP | 876 |
| | GSLAEAKEAANRELDSYGVSDFYKRLIEKAKTVEGVEALKDAILAALP | 877 |
| | GSLAQAKEAANRELDSYGVSDFYKRLIEKAKTVEGVEALKDAILAALP | 878 |
| | GSLAEAKEAANRELDAYGVSDFYKRLIEKAKTVEGVEALKDAILAALP | 879 |
| | GSLAEAKVLANRELDKYGVSDFYKRLIEKAKTVEGVEALKDAILAALP | 880 |
| | SLAQAKEAANAELDSYGVSDFYKRLIEKAKTVEGVEALKDAILAALP | 881 |
| | SLAEAKEAANRELDSYGVSDFYKRLIEKAKTVEGVEALKDAILAALP | 882 |
| | SLAQAKEAANRELDSYGVSDFYKRLIEKAKTVEGVEALKDAILAALP | 883 |
| | SLAEAKEAANRELDAYGVSDFYKRLIEKAKTVEGVEALKDAILAALP | 884 |
| | SLAEAKVLANRELDKYGVSDFYKRLIEKAKTVEGVEALKDAILAALP | 885 |
| | LAQAKEAANAELDSYGVSDFYKRLIEKAKTVEGVEALKDAILAALP | 886 |
| | LAEAKEAANRELDSYGVSDFYKRLIEKAKTVEGVEALKDAILAALP | 887 |
| | LAQAKEAANRELDSYGVSDFYKRLIEKAKTVEGVEALKDAILAALP | 888 |
| | LAEAKEAANRELDAYGVSDFYKRLIEKAKTVEGVEALKDAILAALP | 889 |
| | LAEAKVLANRELDKYGVSDFYKRLIEKAKTVEGVEALKDAILAALP | 890 |
| | GSLAQAKEAANAELDSYGVSDFYKRLIEKAKTVEGVEALKEAILAALP | 891 |
| | GSLAEAKEAANRELDSYGVSDFYKRLIEKAKTVEGVEALKEAILAALP | 892 |
| | GSLAQAKEAANRELDSYGVSDFYKRLIEKAKTVEGVEALKEAILAALP | 893 |
| | GSLAEAKEAANRELDAYGVSDFYKRLIEKAKTVEGVEALKEAILAALP | 894 |
| | GSLAEAKVLANRELDKYGVSDFYKRLIEKAKTVEGVEALKEAILAALP | 895 |
| | SLAQAKEAANAELDSYGVSDFYKRLIEKAKTVEGVEALKEAILAALP | 896 |
| | SLAEAKEAANRELDSYGVSDFYKRLIEKAKTVEGVEALKEAILAALP | 897 |
| | SLAQAKEAANRELDSYGVSDFYKRLIEKAKTVEGVEALKEAILAALP | 898 |
| | SLAEAKEAANRELDAYGVSDFYKRLIEKAKTVEGVEALKEAILAALP | 899 |
| | SLAEAKVLANRELDKYGVSDFYKRLIEKAKTVEGVEALKEAILAALP | 900 |
| | LAQAKEAANAELDSYGVSDFYKRLIEKAKTVEGVEALKEAILAALP | 901 |
| | LAEAKEAANRELDSYGVSDFYKRLIEKAKTVEGVEALKEAILAALP | 902 |
| | LAQAKEAANRELDSYGVSDFYKRLIEKAKTVEGVEALKEAILAALP | 903 |

Figure 1F

| | Sequence | # |
|---|---|---|
| | LAEAKEAANRELDAYGVSDFYKRLIEKAKTVEGVEALKEAILAALP | 904 |
| | LAEAKVLANRELDKYGVSDFYKRLIEKAKTVEGVEALKEAILAALP | 905 |
| | GSLAQAKEAANAELDSYGVSDFYKRLIDKAKTVEGVEALKDAILASLP | 906 |
| | GSLAEAKEAANRELDSYGVSDFYKRLIDKAKTVEGVEALKDAILASLP | 907 |
| | GSLAQAKEAANRELDSYGVSDFYKRLIDKAKTVEGVEALKDAILASLP | 908 |
| | GSLAEAKEAANRELDAYGVSDFYKRLIDKAKTVEGVEALKDAILASLP | 909 |
| | GSLAEAKVLANRELDKYGVSDFYKRLIDKAKTVEGVEALKDAILASLP | 910 |
| | SLAQAKEAANAELDSYGVSDFYKRLIDKAKTVEGVEALKDAILASLP | 911 |
| | SLAEAKEAANRELDSYGVSDFYKRLIDKAKTVEGVEALKDAILASLP | 912 |
| | SLAQAKEAANRELDSYGVSDFYKRLIDKAKTVEGVEALKDAILASLP | 913 |
| | SLAEAKEAANRELDAYGVSDFYKRLIDKAKTVEGVEALKDAILASLP | 914 |
| | SLAEAKVLANRELDKYGVSDFYKRLIDKAKTVEGVEALKDAILASLP | 915 |
| | LAQAKEAANAELDSYGVSDFYKRLIDKAKTVEGVEALKDAILASLP | 916 |
| | LAEAKEAANRELDSYGVSDFYKRLIDKAKTVEGVEALKDAILASLP | 917 |
| | LAQAKEAANRELDSYGVSDFYKRLIDKAKTVEGVEALKDAILASLP | 918 |
| | LAEAKEAANRELDAYGVSDFYKRLIDKAKTVEGVEALKDAILASLP | 919 |
| | LAEAKVLANRELDKYGVSDFYKRLIDKAKTVEGVEALKDAILASLP | 920 |
| | GSLAQAKEAANAELDSYGVSDFYKRLIDKAKTVEGVEALKDAILAELP | 921 |
| | GSLAEAKEAANRELDSYGVSDFYKRLIDKAKTVEGVEALKDAILAELP | 922 |
| | GSLAQAKEAANRELDSYGVSDFYKRLIDKAKTVEGVEALKDAILAELP | 923 |
| | GSLAEAKEAANRELDAYGVSDFYKRLIDKAKTVEGVEALKDAILAELP | 924 |
| | GSLAEAKVLANRELDKYGVSDFYKRLIDKAKTVEGVEALKDAILAELP | 925 |
| | SLAQAKEAANAELDSYGVSDFYKRLIDKAKTVEGVEALKDAILAELP | 926 |
| | SLAEAKEAANRELDSYGVSDFYKRLIDKAKTVEGVEALKDAILAELP | 927 |
| | SLAQAKEAANRELDSYGVSDFYKRLIDKAKTVEGVEALKDAILAELP | 928 |
| | SLAEAKEAANRELDAYGVSDFYKRLIDKAKTVEGVEALKDAILAELP | 929 |
| | SLAEAKVLANRELDKYGVSDFYKRLIDKAKTVEGVEALKDAILAELP | 930 |
| | LAQAKEAANAELDSYGVSDFYKRLIDKAKTVEGVEALKDAILAELP | 931 |
| | LAEAKEAANRELDSYGVSDFYKRLIDKAKTVEGVEALKDAILAELP | 932 |
| | LAQAKEAANRELDSYGVSDFYKRLIDKAKTVEGVEALKDAILAELP | 933 |
| | LAEAKEAANRELDAYGVSDFYKRLIDKAKTVEGVEALKDAILAELP | 934 |
| | LAEAKVLANRELDKYGVSDFYKRLIDKAKTVEGVEALKDAILAELP | 935 |
| | GSLAQAKEAANAELDSYGVSDFYKRLIDKAKTVEGVEALKDAILKALP | 936 |
| | GSLAEAKEAANRELDSYGVSDFYKRLIDKAKTVEGVEALKDAILKALP | 937 |
| | GSLAQAKEAANRELDSYGVSDFYKRLIDKAKTVEGVEALKDAILKALP | 938 |
| | GSLAEAKEAANRELDAYGVSDFYKRLIDKAKTVEGVEALKDAILKALP | 939 |
| | GSLAEAKVLANRELDKYGVSDFYKRLIDKAKTVEGVEALKDAILKALP | 940 |
| | SLAQAKEAANAELDSYGVSDFYKRLIDKAKTVEGVEALKDAILKALP | 941 |
| | SLAEAKEAANRELDSYGVSDFYKRLIDKAKTVEGVEALKDAILKALP | 942 |
| | SLAQAKEAANRELDSYGVSDFYKRLIDKAKTVEGVEALKDAILKALP | 943 |
| | SLAEAKEAANRELDAYGVSDFYKRLIDKAKTVEGVEALKDAILKALP | 944 |
| | SLAEAKVLANRELDKYGVSDFYKRLIDKAKTVEGVEALKDAILKALP | 945 |
| | LAQAKEAANAELDSYGVSDFYKRLIDKAKTVEGVEALKDAILKALP | 946 |
| | LAEAKEAANRELDSYGVSDFYKRLIDKAKTVEGVEALKDAILKALP | 947 |
| | LAQAKEAANRELDSYGVSDFYKRLIDKAKTVEGVEALKDAILKALP | 948 |
| | LAEAKEAANRELDAYGVSDFYKRLIDKAKTVEGVEALKDAILKALP | 949 |
| | LAEAKVLANRELDKYGVSDFYKRLIDKAKTVEGVEALKDAILKALP | 950 |

SEQUENCE LISTING

```
<160> NUMBER OF SEQ ID NOS: 988

<210> SEQ ID NO 1
<211> LENGTH: 39
<212> TYPE: PRT
<213> ORGANISM: Heloderma horridum
<220> FEATURE:
<223> OTHER INFORMATION: May be C-term NH2

<400> SEQUENCE: 1

His Ser Asp Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35
```

```
<210> SEQ ID NO 2
<211> LENGTH: 39
<212> TYPE: PRT
<213> ORGANISM: Heloderma suspectum
<220> FEATURE:
<223> OTHER INFORMATION: May be C-term NH2

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Heloderma suspectum
<220> FEATURE:
<223> OTHER INFORMATION: May be C-term NH2

<400> SEQUENCE: 3

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 5
<211> LENGTH: 31
<212> TYPE: PRT
<213> ORGANISM: Unknown
<220> FEATURE:
<223> OTHER INFORMATION: Description of Unknown: Glucagon-like peptide

<400> SEQUENCE: 5

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 6
<211> LENGTH: 37
<212> TYPE: PRT
<213> ORGANISM: Rattus sp.
```

-continued

<400> SEQUENCE: 6

Lys Cys Asn Thr Ala Thr Cys Ala Thr Gln Arg Leu Ala Asn Phe Leu
1               5                   10                  15

Val Arg Ser Ser Asn Asn Leu Gly Pro Val Leu Pro Pro Thr Asn Val
            20                  25                  30

Gly Ser Asn Thr Tyr
        35

<210> SEQ ID NO 7
<211> LENGTH: 37
<212> TYPE: PRT
<213> ORGANISM: Homo sapiens

<400> SEQUENCE: 7

Lys Cys Asn Thr Ala Thr Cys Ala Thr Gln Arg Leu Ala Asn Phe Leu
1               5                   10                  15

Val His Ser Ser Asn Asn Phe Gly Ala Ile Leu Ser Ser Thr Asn Val
            20                  25                  30

Gly Ser Asn Thr Tyr
        35

<210> SEQ ID NO 8
<211> LENGTH: 37
<212> TYPE: PRT
<213> ORGANISM: Homo sapiens

<400> SEQUENCE: 8

Lys Cys Asn Thr Ala Thr Cys Ala Thr Gln Arg Leu Ala Asn Phe Leu
1               5                   10                  15

Val His Ser Ser Asn Asn Phe Gly Pro Ile Leu Pro Pro Thr Asn Val
            20                  25                  30

Gly Ser Asn Thr Tyr
        35

<210> SEQ ID NO 9
<211> LENGTH: 32
<212> TYPE: PRT
<213> ORGANISM: Homo sapiens

<400> SEQUENCE: 9

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

<210> SEQ ID NO 10
<211> LENGTH: 32
<212> TYPE: PRT
<213> ORGANISM: Oncorhynchus sp.

<400> SEQUENCE: 10

Cys Ser Asn Leu Ser Thr Cys Val Leu Gly Lys Leu Ser Gln Glu Leu
1               5                   10                  15

His Lys Leu Gln Thr Tyr Pro Arg Thr Asn Thr Gly Ser Gly Thr Pro
            20                  25                  30

<210> SEQ ID NO 11
<211> LENGTH: 32
<212> TYPE: PRT
<213> ORGANISM: Oncorhynchus sp.

```
<400> SEQUENCE: 11

Lys Cys Asn Thr Ala Thr Cys Val Leu Gly Arg Leu Ser Gln Glu Leu
1               5                   10                  15

His Arg Leu Gln Thr Tyr Pro Arg Thr Asn Thr Gly Ser Asn Thr Tyr
            20                  25                  30

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 13

<400> SEQUENCE: 13

000

<210> SEQ ID NO 14

<400> SEQUENCE: 14

000

<210> SEQ ID NO 15

<400> SEQUENCE: 15

000

<210> SEQ ID NO 16

<400> SEQUENCE: 16

000

<210> SEQ ID NO 17

<400> SEQUENCE: 17

000

<210> SEQ ID NO 18

<400> SEQUENCE: 18

000

<210> SEQ ID NO 19

<400> SEQUENCE: 19

000
```

<210> SEQ ID NO 20

<400> SEQUENCE: 20

000

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25

<400> SEQUENCE: 25

000

<210> SEQ ID NO 26

<400> SEQUENCE: 26

000

<210> SEQ ID NO 27

<400> SEQUENCE: 27

000

<210> SEQ ID NO 28

<400> SEQUENCE: 28

000

<210> SEQ ID NO 29

<400> SEQUENCE: 29

000

<210> SEQ ID NO 30

<400> SEQUENCE: 30

000

-continued

<210> SEQ ID NO 31
<400> SEQUENCE: 31
000

<210> SEQ ID NO 32
<400> SEQUENCE: 32
000

<210> SEQ ID NO 33
<400> SEQUENCE: 33
000

<210> SEQ ID NO 34
<400> SEQUENCE: 34
000

<210> SEQ ID NO 35
<400> SEQUENCE: 35
000

<210> SEQ ID NO 36
<400> SEQUENCE: 36
000

<210> SEQ ID NO 37
<400> SEQUENCE: 37
000

<210> SEQ ID NO 38
<400> SEQUENCE: 38
000

<210> SEQ ID NO 39
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42

```
<400> SEQUENCE: 42

000

<210> SEQ ID NO 43

<400> SEQUENCE: 43

000

<210> SEQ ID NO 44

<400> SEQUENCE: 44

000

<210> SEQ ID NO 45

<400> SEQUENCE: 45

000

<210> SEQ ID NO 46

<400> SEQUENCE: 46

000

<210> SEQ ID NO 47

<400> SEQUENCE: 47

000

<210> SEQ ID NO 48

<400> SEQUENCE: 48

000

<210> SEQ ID NO 49
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 49

His His His His His His
1               5

<210> SEQ ID NO 50

<400> SEQUENCE: 50

000

<210> SEQ ID NO 51

<400> SEQUENCE: 51

000

<210> SEQ ID NO 52

<400> SEQUENCE: 52
```

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59

<400> SEQUENCE: 59

000

<210> SEQ ID NO 60

<400> SEQUENCE: 60

000

<210> SEQ ID NO 61

<400> SEQUENCE: 61

000

<210> SEQ ID NO 62

<400> SEQUENCE: 62

000

<210> SEQ ID NO 63

<400> SEQUENCE: 63

000

```
<210> SEQ ID NO 64
<400> SEQUENCE: 64
000

<210> SEQ ID NO 65
<400> SEQUENCE: 65
000

<210> SEQ ID NO 66
<400> SEQUENCE: 66
000

<210> SEQ ID NO 67
<400> SEQUENCE: 67
000

<210> SEQ ID NO 68
<400> SEQUENCE: 68
000

<210> SEQ ID NO 69
<400> SEQUENCE: 69
000

<210> SEQ ID NO 70
<400> SEQUENCE: 70
000

<210> SEQ ID NO 71
<400> SEQUENCE: 71
000

<210> SEQ ID NO 72
<400> SEQUENCE: 72
000

<210> SEQ ID NO 73
<400> SEQUENCE: 73
000

<210> SEQ ID NO 74
<400> SEQUENCE: 74
000

<210> SEQ ID NO 75
```

```
<400> SEQUENCE: 75
000

<210> SEQ ID NO 76
<400> SEQUENCE: 76
000

<210> SEQ ID NO 77
<400> SEQUENCE: 77
000

<210> SEQ ID NO 78
<400> SEQUENCE: 78
000

<210> SEQ ID NO 79
<400> SEQUENCE: 79
000

<210> SEQ ID NO 80
<400> SEQUENCE: 80
000

<210> SEQ ID NO 81
<400> SEQUENCE: 81
000

<210> SEQ ID NO 82
<400> SEQUENCE: 82
000

<210> SEQ ID NO 83
<400> SEQUENCE: 83
000

<210> SEQ ID NO 84
<400> SEQUENCE: 84
000

<210> SEQ ID NO 85
<400> SEQUENCE: 85
000

<210> SEQ ID NO 86
<400> SEQUENCE: 86
```

000

<210> SEQ ID NO 87

<400> SEQUENCE: 87

000

<210> SEQ ID NO 88

<400> SEQUENCE: 88

000

<210> SEQ ID NO 89

<400> SEQUENCE: 89

000

<210> SEQ ID NO 90

<400> SEQUENCE: 90

000

<210> SEQ ID NO 91

<400> SEQUENCE: 91

000

<210> SEQ ID NO 92

<400> SEQUENCE: 92

000

<210> SEQ ID NO 93

<400> SEQUENCE: 93

000

<210> SEQ ID NO 94

<400> SEQUENCE: 94

000

<210> SEQ ID NO 95

<400> SEQUENCE: 95

000

<210> SEQ ID NO 96

<400> SEQUENCE: 96

000

<210> SEQ ID NO 97

<400> SEQUENCE: 97

000

<210> SEQ ID NO 98

<400> SEQUENCE: 98

000

<210> SEQ ID NO 99

<400> SEQUENCE: 99

000

<210> SEQ ID NO 100

<400> SEQUENCE: 100

000

<210> SEQ ID NO 101

<400> SEQUENCE: 101

000

<210> SEQ ID NO 102

<400> SEQUENCE: 102

000

<210> SEQ ID NO 103

<400> SEQUENCE: 103

000

<210> SEQ ID NO 104

<400> SEQUENCE: 104

000

<210> SEQ ID NO 105

<400> SEQUENCE: 105

000

<210> SEQ ID NO 106

<400> SEQUENCE: 106

000

<210> SEQ ID NO 107

<400> SEQUENCE: 107

000

<210> SEQ ID NO 108

<400> SEQUENCE: 108

000

<210> SEQ ID NO 109

<400> SEQUENCE: 109

000

<210> SEQ ID NO 110

<400> SEQUENCE: 110

000

<210> SEQ ID NO 111
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
        35

<210> SEQ ID NO 112
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 113
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 113

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 114
<211> LENGTH: 43
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 114

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Lys Lys Lys Lys Lys Lys
        35                  40

<210> SEQ ID NO 115
<211> LENGTH: 45
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 115

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Lys Lys Lys Lys Lys Lys
        35                  40                  45

<210> SEQ ID NO 116
<211> LENGTH: 43
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 116

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Lys Lys Lys Lys Lys Lys
        35                  40

<210> SEQ ID NO 117
<211> LENGTH: 44
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 117

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 118
<211> LENGTH: 44
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 118

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Lys
        35                  40

<210> SEQ ID NO 119

<400> SEQUENCE: 119

000

<210> SEQ ID NO 120

<400> SEQUENCE: 120

000

<210> SEQ ID NO 121

<400> SEQUENCE: 121

000

<210> SEQ ID NO 122

<400> SEQUENCE: 122

000

<210> SEQ ID NO 123

<400> SEQUENCE: 123

000

<210> SEQ ID NO 124

<400> SEQUENCE: 124

000

<210> SEQ ID NO 125
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Gly Gly Gly
1

<210> SEQ ID NO 126
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 126

Gly Gly Gly Gly Gly
1               5

<210> SEQ ID NO 127
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This region may encompass 1 to 6 residues

<400> SEQUENCE: 127

Gly Gly Gly Gly Gly Gly Glu
1               5

<210> SEQ ID NO 128
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This region may encompass 1 to 6 residues

<400> SEQUENCE: 128

Gly Gly Gly Gly Gly Gly Lys
1               5

<210> SEQ ID NO 129
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This region may encompass 1 to 6 residues

<400> SEQUENCE: 129

Gly Gly Gly Gly Gly Gly Asp
1               5

<210> SEQ ID NO 130
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(6)
<223> OTHER INFORMATION: This region may encompass 1 to 6 residues

<400> SEQUENCE: 130

Gly Gly Gly Gly Gly Gly Arg
1               5

```
<210> SEQ ID NO 131
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Gly Gly Gly Lys Gly Gly Gly Gly
1               5

<210> SEQ ID NO 132
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Gly Gly Gly Asn Gly Ser Gly Gly
1               5

<210> SEQ ID NO 133
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Gly Gly Cys Gly Gly Gly Gly
1               5

<210> SEQ ID NO 134
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gly Pro Asn Gly Gly
1               5

<210> SEQ ID NO 135
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(12)
<223> OTHER INFORMATION: This sequence may encompass 1 to 6 "Gly Ser"
      repeats

<400> SEQUENCE: 135

Gly Ser Gly Ser Gly Ser Gly Ser Gly Ser Gly Ser
1               5                   10

<210> SEQ ID NO 136
<211> LENGTH: 18
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: misc_feature
<222> LOCATION: (1)..(18)
<223> OTHER INFORMATION: This sequence may encompass 1 to 6 "Gly Gly
      Ser" repeats

<400> SEQUENCE: 136

Gly Gly Ser Gly Gly Ser Gly Gly Ser Gly Gly Ser Gly Gly Ser Gly
1               5                   10                  15

Gly Ser

<210> SEQ ID NO 137
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(24)
<223> OTHER INFORMATION: This sequence may encompass 1 to 6 "Gly Gly Gly
      Ser" repeats

<400> SEQUENCE: 137

Gly Gly Gly Ser Gly Gly Gly Ser Gly Gly Gly Ser Gly Gly Gly Ser
1               5                   10                  15

Gly Gly Gly Ser Gly Gly Gly Ser
            20

<210> SEQ ID NO 138
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1 to 6 "Gly Gly Gly
      Gly Ser" repeats

<400> SEQUENCE: 138

Gly Gly Gly Gly Ser Gly Gly Gly Gly Ser Gly Gly Gly Gly Ser Gly
1               5                   10                  15

Gly Gly Gly Ser Gly Gly Gly Gly Ser Gly Gly Gly Gly Ser
            20                  25                  30

<210> SEQ ID NO 139
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 1 to 10 "Gly Glu"
      repeats

<400> SEQUENCE: 139

Gly Glu Gly Glu Gly Glu Gly Glu Gly Glu Gly Glu Gly Glu Gly Glu
1               5                   10                  15
```

Gly Glu Gly Glu
        20

<210> SEQ ID NO 140
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1 to 10 "Gly Gly
      Glu" repeats

<400> SEQUENCE: 140

Gly Gly Glu Gly Gly Glu Gly Gly Glu Gly Gly Glu Gly Gly Glu Gly
1               5                   10                  15

Gly Glu Gly Gly Glu Gly Gly Glu Gly Gly Glu Gly Gly Glu
            20                  25                  30

<210> SEQ ID NO 141
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This sequence may encompass 1 to 10 "Gly Gly
      Gly Glu" repeats

<400> SEQUENCE: 141

Gly Gly Gly Glu Gly Gly Gly Glu Gly Gly Gly Glu Gly Gly Gly Glu
1               5                   10                  15

Gly Gly Gly Glu Gly Gly Gly Glu Gly Gly Gly Glu Gly Gly Gly Glu
            20                  25                  30

Gly Gly Gly Glu Gly Gly Gly Glu
        35                  40

<210> SEQ ID NO 142
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 1 to 10 "Gly Gly
      Gly Gly Glu" repeats

<400> SEQUENCE: 142

Gly Gly Gly Gly Glu Gly Gly Gly Gly Glu Gly Gly Gly Gly Glu Gly
1               5                   10                  15

Gly Gly Gly Glu Gly Gly Gly Gly Glu Gly Gly Gly Gly Glu Gly Gly
            20                  25                  30

Gly Gly Glu Gly Gly Gly Gly Glu Gly Gly Gly Gly Glu Gly Gly Gly
        35                  40                  45

Gly Glu
    50

```
<210> SEQ ID NO 143
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 1 to 10 "Gly Asp"
      repeats

<400> SEQUENCE: 143

Gly Asp Gly Asp Gly Asp Gly Asp Gly Asp Gly Asp Gly Asp Gly Asp
1               5                   10                  15

Gly Asp Gly Asp
            20

<210> SEQ ID NO 144
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1 to 10 "Gly Gly
      Asp" repeats

<400> SEQUENCE: 144

Gly Gly Asp Gly Gly Asp Gly Gly Asp Gly Gly Asp Gly Gly Asp Gly
1               5                   10                  15

Gly Asp Gly Gly Asp Gly Gly Asp Gly Gly Asp
            20                  25                  30

<210> SEQ ID NO 145
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This sequence may encompass 1 to 10 "Gly Gly
      Gly Asp" repeats

<400> SEQUENCE: 145

Gly Gly Gly Asp Gly Gly Gly Asp Gly Gly Gly Asp Gly Gly Gly Asp
1               5                   10                  15

Gly Gly Gly Asp Gly Gly Gly Asp Gly Gly Gly Asp Gly Gly Gly Asp
            20                  25                  30

Gly Gly Gly Asp Gly Gly Gly Asp
            35                  40

<210> SEQ ID NO 146
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
```

```
<223> OTHER INFORMATION: This sequence may encompass 1 to 10 "Gly Gly
      Gly Gly Asp" repeats

<400> SEQUENCE: 146

Gly Gly Gly Gly Asp Gly Gly Gly Asp Gly Gly Gly Asp Gly
1               5                   10                  15

Gly Gly Gly Asp Gly Gly Gly Gly Asp Gly Gly Gly Gly Asp Gly Gly
            20                  25                  30

Gly Gly Asp Gly Gly Gly Gly Asp Gly Gly Gly Gly Asp Gly Gly Gly
        35                  40                  45

Gly Asp
    50

<210> SEQ ID NO 147
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 1 to 10 "Gly Lys"
      repeats

<400> SEQUENCE: 147

Gly Lys Gly Lys Gly Lys Gly Lys Gly Lys Gly Lys Gly Lys Gly Lys
1               5                   10                  15

Gly Lys Gly Lys
            20

<210> SEQ ID NO 148
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1 to 10 "Gly Gly Lys"
      repeats

<400> SEQUENCE: 148

Gly Gly Lys Gly Gly Lys Gly Gly Lys Gly Gly Lys Gly Gly Lys Gly
1               5                   10                  15

Gly Lys Gly Gly Lys Gly Gly Lys Gly Gly Lys Gly Gly Lys
            20                  25                  30

<210> SEQ ID NO 149
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This sequence may encompass 1 to 10 "Gly Gly
      Gly Lys" repeats

<400> SEQUENCE: 149

Gly Gly Gly Lys Gly Gly Gly Lys Gly Gly Gly Lys Gly Gly Gly Lys
1               5                   10                  15
```

```
Gly Gly Gly Lys Gly Gly Gly Lys Gly Gly Gly Lys
            20                  25                  30

Gly Gly Gly Lys Gly Gly Gly Lys
            35                  40
```

<210> SEQ ID NO 150
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 1 to 10 "Gly Gly
      Gly Gly Lys" repeats

<400> SEQUENCE: 150

```
Gly Gly Gly Gly Lys Gly Gly Gly Gly Lys Gly Gly Gly Gly Lys Gly
1               5                   10                  15

Gly Gly Gly Lys Gly Gly Gly Gly Lys Gly Gly Gly Gly Lys Gly Gly
            20                  25                  30

Gly Gly Lys Gly Gly Gly Gly Lys Gly Gly Gly Gly Lys Gly Gly Gly
            35                  40                  45

Gly Lys
    50
```

<210> SEQ ID NO 151
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 1 to 10 "Gly Arg"
      repeats

<400> SEQUENCE: 151

```
Gly Arg Gly Arg Gly Arg Gly Arg Gly Arg Gly Arg Gly Arg Gly Arg
1               5                   10                  15

Gly Arg Gly Arg
            20
```

<210> SEQ ID NO 152
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(30)
<223> OTHER INFORMATION: This sequence may encompass 1 to 10 "Gly Gly
      Arg" repeats

<400> SEQUENCE: 152

```
Gly Gly Arg Gly Gly Arg Gly Gly Arg Gly Gly Arg Gly Gly Arg Gly
1               5                   10                  15

Gly Arg Gly Gly Arg Gly Gly Arg Gly Gly Arg Gly Gly Arg
            20                  25                  30
```

```
<210> SEQ ID NO 153
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(40)
<223> OTHER INFORMATION: This sequence may encompass 1 to 10 "Gly Gly
      Gly Arg" repeats

<400> SEQUENCE: 153

Gly Gly Gly Arg Gly Gly Gly Arg Gly Gly Gly Arg Gly Gly Gly Arg
1               5                   10                  15

Gly Gly Gly Arg Gly Gly Gly Arg Gly Gly Gly Arg Gly Gly Gly Arg
            20                  25                  30

Gly Gly Gly Arg Gly Gly Gly Arg
        35                  40

<210> SEQ ID NO 154
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 1 to 10 "Gly Gly
      Gly Gly Arg" repeats

<400> SEQUENCE: 154

Gly Gly Gly Gly Arg Gly Gly Gly Gly Arg Gly Gly Gly Gly Arg Gly
1               5                   10                  15

Gly Gly Gly Arg Gly Gly Gly Gly Arg Gly Gly Gly Gly Arg Gly Gly
            20                  25                  30

Gly Gly Arg Gly Gly Gly Gly Arg Gly Gly Gly Gly Arg Gly Gly Gly
        35                  40                  45

Gly Arg
    50

<210> SEQ ID NO 155
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(50)
<223> OTHER INFORMATION: This sequence may encompass 1 to 10 "Glu Ala
      Ala Ala Lys" repeats

<400> SEQUENCE: 155

Glu Ala Ala Ala Lys Glu Ala Ala Ala Lys Glu Ala Ala Ala Lys Glu
1               5                   10                  15

Ala Ala Ala Lys Glu Ala Ala Ala Lys Glu Ala Ala Ala Lys Glu Ala
            20                  25                  30

Ala Ala Lys Glu Ala Ala Ala Lys Glu Ala Ala Ala Lys Glu Ala Ala
        35                  40                  45

Ala Lys
```

<210> SEQ ID NO 156

<400> SEQUENCE: 156

000

<210> SEQ ID NO 157

<400> SEQUENCE: 157

000

<210> SEQ ID NO 158

<400> SEQUENCE: 158

000

<210> SEQ ID NO 159
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Gly Leu Ala Ser Ala Lys Glu Ala Ala Asn Ala Glu Leu Asp Cys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 160
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: C-term NH2

<400> SEQUENCE: 160

Ala Leu Ala Ser Ala Lys Glu Ala Ala Asn Ala Glu Leu Asp Cys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 161

<400> SEQUENCE: 161

000

<210> SEQ ID NO 162

<400> SEQUENCE: 162

000

```
<210> SEQ ID NO 163
<400> SEQUENCE: 163
000

<210> SEQ ID NO 164
<400> SEQUENCE: 164
000

<210> SEQ ID NO 165
<400> SEQUENCE: 165
000

<210> SEQ ID NO 166
<400> SEQUENCE: 166
000

<210> SEQ ID NO 167
<400> SEQUENCE: 167
000

<210> SEQ ID NO 168
<400> SEQUENCE: 168
000

<210> SEQ ID NO 169
<400> SEQUENCE: 169
000

<210> SEQ ID NO 170
<400> SEQUENCE: 170
000

<210> SEQ ID NO 171
<400> SEQUENCE: 171
000

<210> SEQ ID NO 172
<400> SEQUENCE: 172
000

<210> SEQ ID NO 173
<400> SEQUENCE: 173
000

<210> SEQ ID NO 174
```

```
<400> SEQUENCE: 174
000

<210> SEQ ID NO 175
<400> SEQUENCE: 175
000

<210> SEQ ID NO 176
<400> SEQUENCE: 176
000

<210> SEQ ID NO 177
<400> SEQUENCE: 177
000

<210> SEQ ID NO 178
<400> SEQUENCE: 178
000

<210> SEQ ID NO 179
<400> SEQUENCE: 179
000

<210> SEQ ID NO 180
<400> SEQUENCE: 180
000

<210> SEQ ID NO 181
<400> SEQUENCE: 181
000

<210> SEQ ID NO 182
<400> SEQUENCE: 182
000

<210> SEQ ID NO 183
<400> SEQUENCE: 183
000

<210> SEQ ID NO 184
<400> SEQUENCE: 184
000

<210> SEQ ID NO 185
<400> SEQUENCE: 185
```

-continued

000

<210> SEQ ID NO 186

<400> SEQUENCE: 186

000

<210> SEQ ID NO 187

<400> SEQUENCE: 187

000

<210> SEQ ID NO 188

<400> SEQUENCE: 188

000

<210> SEQ ID NO 189

<400> SEQUENCE: 189

000

<210> SEQ ID NO 190

<400> SEQUENCE: 190

000

<210> SEQ ID NO 191

<400> SEQUENCE: 191

000

<210> SEQ ID NO 192
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Gly Gly Gly Ser
1

<210> SEQ ID NO 193
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Thr Gly Gly Gly Gly Ala Ser
1               5

<210> SEQ ID NO 194
<211> LENGTH: 8
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 194

Thr Gly Gly Gly Gly Gly Ala Ser
1               5

<210> SEQ ID NO 195
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Thr Gly Gly Gly Gly Ser Ala Ser
1               5

<210> SEQ ID NO 196

<400> SEQUENCE: 196

000

<210> SEQ ID NO 197

<400> SEQUENCE: 197

000

<210> SEQ ID NO 198

<400> SEQUENCE: 198

000

<210> SEQ ID NO 199

<400> SEQUENCE: 199

000

<210> SEQ ID NO 200

<400> SEQUENCE: 200

000

<210> SEQ ID NO 201

<400> SEQUENCE: 201

000

<210> SEQ ID NO 202

<400> SEQUENCE: 202

000

<210> SEQ ID NO 203

<400> SEQUENCE: 203

000
```

```
<210> SEQ ID NO 204
<400> SEQUENCE: 204
000

<210> SEQ ID NO 205
<400> SEQUENCE: 205
000

<210> SEQ ID NO 206
<400> SEQUENCE: 206
000

<210> SEQ ID NO 207
<400> SEQUENCE: 207
000

<210> SEQ ID NO 208
<400> SEQUENCE: 208
000

<210> SEQ ID NO 209
<400> SEQUENCE: 209
000

<210> SEQ ID NO 210
<400> SEQUENCE: 210
000

<210> SEQ ID NO 211
<400> SEQUENCE: 211
000

<210> SEQ ID NO 212
<400> SEQUENCE: 212
000

<210> SEQ ID NO 213
<400> SEQUENCE: 213
000

<210> SEQ ID NO 214
<400> SEQUENCE: 214
000

<210> SEQ ID NO 215
```

```
<400> SEQUENCE: 215

000

<210> SEQ ID NO 216

<400> SEQUENCE: 216

000

<210> SEQ ID NO 217

<400> SEQUENCE: 217

000

<210> SEQ ID NO 218

<400> SEQUENCE: 218

000

<210> SEQ ID NO 219

<400> SEQUENCE: 219

000

<210> SEQ ID NO 220

<400> SEQUENCE: 220

000

<210> SEQ ID NO 221

<400> SEQUENCE: 221

000

<210> SEQ ID NO 222

<400> SEQUENCE: 222

000

<210> SEQ ID NO 223

<400> SEQUENCE: 223

000

<210> SEQ ID NO 224

<400> SEQUENCE: 224

000

<210> SEQ ID NO 225

<400> SEQUENCE: 225

000

<210> SEQ ID NO 226

<400> SEQUENCE: 226
```

000

<210> SEQ ID NO 227

<400> SEQUENCE: 227

000

<210> SEQ ID NO 228

<400> SEQUENCE: 228

000

<210> SEQ ID NO 229

<400> SEQUENCE: 229

000

<210> SEQ ID NO 230

<400> SEQUENCE: 230

000

<210> SEQ ID NO 231

<400> SEQUENCE: 231

000

<210> SEQ ID NO 232

<400> SEQUENCE: 232

000

<210> SEQ ID NO 233

<400> SEQUENCE: 233

000

<210> SEQ ID NO 234

<400> SEQUENCE: 234

000

<210> SEQ ID NO 235

<400> SEQUENCE: 235

000

<210> SEQ ID NO 236

<400> SEQUENCE: 236

000

<210> SEQ ID NO 237

<400> SEQUENCE: 237

000

<210> SEQ ID NO 238

<400> SEQUENCE: 238

000

<210> SEQ ID NO 239

<400> SEQUENCE: 239

000

<210> SEQ ID NO 240

<400> SEQUENCE: 240

000

<210> SEQ ID NO 241

<400> SEQUENCE: 241

000

<210> SEQ ID NO 242

<400> SEQUENCE: 242

000

<210> SEQ ID NO 243

<400> SEQUENCE: 243

000

<210> SEQ ID NO 244

<400> SEQUENCE: 244

000

<210> SEQ ID NO 245

<400> SEQUENCE: 245

000

<210> SEQ ID NO 246

<400> SEQUENCE: 246

000

<210> SEQ ID NO 247

<400> SEQUENCE: 247

000

<210> SEQ ID NO 248

<400> SEQUENCE: 248

000

<210> SEQ ID NO 249

<400> SEQUENCE: 249

000

<210> SEQ ID NO 250

<400> SEQUENCE: 250

000

<210> SEQ ID NO 251

<400> SEQUENCE: 251

000

<210> SEQ ID NO 252

<400> SEQUENCE: 252

000

<210> SEQ ID NO 253

<400> SEQUENCE: 253

000

<210> SEQ ID NO 254

<400> SEQUENCE: 254

000

<210> SEQ ID NO 255

<400> SEQUENCE: 255

000

<210> SEQ ID NO 256

<400> SEQUENCE: 256

000

<210> SEQ ID NO 257

<400> SEQUENCE: 257

000

<210> SEQ ID NO 258

<400> SEQUENCE: 258

000

<210> SEQ ID NO 259

<400> SEQUENCE: 259

000

<210> SEQ ID NO 260

<400> SEQUENCE: 260

000

<210> SEQ ID NO 261

<400> SEQUENCE: 261

000

<210> SEQ ID NO 262

<400> SEQUENCE: 262

000

<210> SEQ ID NO 263

<400> SEQUENCE: 263

000

<210> SEQ ID NO 264

<400> SEQUENCE: 264

000

<210> SEQ ID NO 265

<400> SEQUENCE: 265

000

<210> SEQ ID NO 266

<400> SEQUENCE: 266

000

<210> SEQ ID NO 267

<400> SEQUENCE: 267

000

<210> SEQ ID NO 268

<400> SEQUENCE: 268

000

<210> SEQ ID NO 269

<400> SEQUENCE: 269

000

<210> SEQ ID NO 270

<400> SEQUENCE: 270

000

<210> SEQ ID NO 271

<400> SEQUENCE: 271

000

<210> SEQ ID NO 272

<400> SEQUENCE: 272

000

<210> SEQ ID NO 273

<400> SEQUENCE: 273

000

<210> SEQ ID NO 274

<400> SEQUENCE: 274

000

<210> SEQ ID NO 275

<400> SEQUENCE: 275

000

<210> SEQ ID NO 276

<400> SEQUENCE: 276

000

<210> SEQ ID NO 277

<400> SEQUENCE: 277

000

<210> SEQ ID NO 278

<400> SEQUENCE: 278

000

<210> SEQ ID NO 279

<400> SEQUENCE: 279

000

<210> SEQ ID NO 280

<400> SEQUENCE: 280

000

<210> SEQ ID NO 281

<400> SEQUENCE: 281

000

<210> SEQ ID NO 282

<400> SEQUENCE: 282

000

<210> SEQ ID NO 283

<400> SEQUENCE: 283

000

<210> SEQ ID NO 284

<400> SEQUENCE: 284

000

<210> SEQ ID NO 285

<400> SEQUENCE: 285

000

<210> SEQ ID NO 286

<400> SEQUENCE: 286

000

<210> SEQ ID NO 287

<400> SEQUENCE: 287

000

<210> SEQ ID NO 288

<400> SEQUENCE: 288

000

<210> SEQ ID NO 289

<400> SEQUENCE: 289

000

<210> SEQ ID NO 290

<400> SEQUENCE: 290

000

<210> SEQ ID NO 291

<400> SEQUENCE: 291

000

<210> SEQ ID NO 292

<400> SEQUENCE: 292

000

<210> SEQ ID NO 293

<400> SEQUENCE: 293

000

<210> SEQ ID NO 294

```
<400> SEQUENCE: 294

000

<210> SEQ ID NO 295

<400> SEQUENCE: 295

000

<210> SEQ ID NO 296

<400> SEQUENCE: 296

000

<210> SEQ ID NO 297

<400> SEQUENCE: 297

000

<210> SEQ ID NO 298

<400> SEQUENCE: 298

000

<210> SEQ ID NO 299

<400> SEQUENCE: 299

000

<210> SEQ ID NO 300
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
```

```
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 300

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 301
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 301

Leu Ala Ser Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 302
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 302

Leu Ala Ser Ala Lys Glu Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 303
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 303

Leu Ala Ser Ala Lys Glu Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
```

```
                 20                  25                  30

Gly Val Glu Ala Leu Lys Asp Ala Ile Leu Ala Ala Leu Pro
            35                  40                  45

<210> SEQ ID NO 304
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 304

Leu Ala Ser Ala Lys Glu Ser Ala Asn Ala Glu Leu Asp Ala Tyr Gly
1               5                  10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 305
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 305

Leu Ala Ser Ala Lys Ser Ala Ala Asn Ala Glu Leu Asp Ala Tyr Gly
1               5                  10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 306
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 306

Leu Ala Ser Ala Lys Ser Ala Ala Asn Ser Glu Leu Asp Ala Tyr Gly
1               5                  10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 307
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 307

Leu Ala Ser Ala Lys Glu Ala Ala Asn Ala Glu Leu Asp Ser Tyr Gly
1               5                  10                  15
```

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 308
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 308

Leu Ala Ser Ala Lys Glu Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 309
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 309

Leu Ala Ser Ala Lys Glu Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 310
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 310

Leu Ala Ser Ala Lys Glu Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 311
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 311

Leu Ala Ser Ala Lys Ser Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 312
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 312

Leu Ala Ser Ala Lys Ser Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 313
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 313

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 314
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 314

Leu Ala Glu Ala Lys Glu Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 315
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 315

Leu Ala Glu Ala Lys Glu Ser Ala Asn Ser Glu Leu Asp Ser Tyr Gly

```
                1               5                   10                  15
Val Ser Asp Phe Tyr Lys Arg Leu Ile Asp Lys Ala Lys Thr Val Glu
                    20                  25                  30

Gly Val Glu Ala Leu Lys Asp Ala Ile Leu Ala Ala Leu Pro
                    35                  40                  45

<210> SEQ ID NO 316
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 316

Leu Ala Glu Ala Lys Glu Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
                    20                  25                  30

Gly Val Glu Ala Leu Lys Asp Ala Ile Leu Ala Ala Leu Pro
                    35                  40                  45

<210> SEQ ID NO 317
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 317

Leu Ala Glu Ala Lys Ser Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
                    20                  25                  30

Gly Val Glu Ala Leu Lys Asp Ala Ile Leu Ala Ala Leu Pro
                    35                  40                  45

<210> SEQ ID NO 318
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 318

Leu Ala Glu Ala Lys Ser Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
                    20                  25                  30

Gly Val Glu Ala Leu Lys Asp Ala Ile Leu Ala Ala Leu Pro
                    35                  40                  45

<210> SEQ ID NO 319
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 319
```

Leu Ala Glu Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 320
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 320

Leu Ala Glu Ala Lys Glu Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 321
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 321

Leu Ala Glu Ala Lys Glu Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 322
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 322

Leu Ala Glu Ala Lys Glu Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 323
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 323

```
Leu Ala Glu Ala Lys Ser Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 324
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 324

```
Leu Ala Glu Ala Lys Ser Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 325
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 325

```
Leu Ala Gln Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 326
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 326

```
Leu Ala Gln Ala Lys Glu Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 327
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 327

Leu Ala Gln Ala Lys Glu Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 328
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 328

Leu Ala Gln Ala Lys Glu Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 329
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 329

Leu Ala Gln Ala Lys Ser Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 330
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 330

Leu Ala Gln Ala Lys Ser Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 331
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 331

Leu Ala Gln Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 332
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 332

Leu Ala Gln Ala Lys Glu Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 333
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 333

Leu Ala Gln Ala Lys Glu Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 334
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 334

Leu Ala Gln Ala Lys Glu Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 335
<211> LENGTH: 46
<212> TYPE: PRT
<213> ORGANISM: Artificial Sequence
<220> FEATURE:
<223> OTHER INFORMATION: Description of Artificial Sequence: Synthetic

```
                          polypeptide

<400> SEQUENCE: 335

Leu Ala Gln Ala Lys Ser Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 336
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 336

Leu Ala Gln Ala Lys Ser Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 337
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 337

Leu Ala Ser Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 338
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 338

Leu Ala Ser Ala Lys Glu Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 339
<211> LENGTH: 46
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 339

Leu Ala Ser Ala Lys Glu Ser Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 340
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 340

Leu Ala Ser Ala Lys Glu Ser Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 341
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 341

Leu Ala Ser Ala Lys Ser Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 342
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 342

Leu Ala Ser Ala Lys Ser Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 343
<211> LENGTH: 46
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 343

Leu Ala Ser Ala Lys Glu Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 344
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 344

Leu Ala Ser Ala Lys Glu Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 345
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 345

Leu Ala Ser Ala Lys Glu Ser Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
35                  40                  45

<210> SEQ ID NO 346
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 346

Leu Ala Ser Ala Lys Glu Ser Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 347
<211> LENGTH: 46
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 347

Leu Ala Ser Ala Lys Ser Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 348
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 348

Leu Ala Ser Ala Lys Ser Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 349
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 349

Leu Ala Glu Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 350
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 350

Leu Ala Glu Ala Lys Glu Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 351
<211> LENGTH: 46

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 351

Leu Ala Glu Ala Lys Glu Ser Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 352
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 352

Leu Ala Glu Ala Lys Glu Ser Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 353
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 353

Leu Ala Glu Ala Lys Ser Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 354
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 354

Leu Ala Glu Ala Lys Ser Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 355
```

```
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 355

Leu Ala Glu Ala Lys Glu Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 356
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 356

Leu Ala Glu Ala Lys Glu Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 357
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 357

Leu Ala Glu Ala Lys Glu Ser Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
35                  40                  45

<210> SEQ ID NO 358
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 358

Leu Ala Glu Ala Lys Glu Ser Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

```
<210> SEQ ID NO 359
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 359

Leu Ala Glu Ala Lys Ser Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 360
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 360

Leu Ala Glu Ala Lys Ser Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 361
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 361

Leu Ala Gln Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 362
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 362

Leu Ala Gln Ala Lys Glu Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

```
<210> SEQ ID NO 363
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 363

Leu Ala Gln Ala Lys Glu Ser Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 364
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 364

Leu Ala Gln Ala Lys Glu Ser Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 365
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 365

Leu Ala Gln Ala Lys Ser Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 366
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 366

Leu Ala Gln Ala Lys Ser Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 367
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 367

Leu Ala Gln Ala Lys Glu Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 368
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 368

Leu Ala Gln Ala Lys Glu Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 369
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 369

Leu Ala Gln Ala Lys Glu Ser Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 370
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 370

Leu Ala Gln Ala Lys Glu Ser Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro 35                  40                  45

<210> SEQ ID NO 371
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 371

Leu Ala Gln Ala Lys Ser Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 372
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 372

Leu Ala Gln Ala Lys Ser Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 373
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 373

Leu Ala Cys Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 374
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 374

Leu Ala Cys Ala Lys Glu Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 375
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 375

Leu Ala Cys Ala Lys Glu Ser Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 376
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 376

Leu Ala Cys Ala Lys Glu Ser Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 377
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 377

Leu Ala Cys Ala Lys Ser Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 378
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 378

Leu Ala Cys Ala Lys Ser Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
         35                  40                  45

<210> SEQ ID NO 379
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 379

Leu Ala Cys Ala Lys Glu Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
         35                  40                  45

<210> SEQ ID NO 380
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 380

Leu Ala Cys Ala Lys Glu Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
         35                  40                  45

<210> SEQ ID NO 381
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 381

Leu Ala Cys Ala Lys Glu Ser Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
         35                  40                  45

<210> SEQ ID NO 382
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 382

Leu Ala Cys Ala Lys Glu Ser Ala Asn Ala Glu Leu Asp Lys Tyr Gly
1               5                   10                  15

Val Ser Asp Phe Tyr Lys Arg Leu Ile Asp Lys Ala Lys Thr Val Glu

```
                     20                  25                  30

Gly Val Glu Ala Leu Lys Asp Ala Ile Leu Ala Ala Leu Pro
            35                  40                  45

<210> SEQ ID NO 383
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 383

Leu Ala Cys Ala Lys Ser Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 384
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 384

Leu Ala Cys Ala Lys Ser Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 385
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 385

Leu Ala Cys Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45

<210> SEQ ID NO 386
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 386

Leu Ala Cys Ala Lys Glu Ala Ala Asn Ser Glu Leu Asp Ser Tyr Gly
1               5                   10                  15
```

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 387
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 387

Leu Ala Cys Ala Lys Glu Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 388
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 388

Leu Ala Cys Ala Lys Glu Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 389
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 389

Leu Ala Cys Ala Lys Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 390
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 390

Leu Ala Cys Ala Lys Ser Ala Ala Asn Ser Glu Leu Asp Ser Tyr Gly
1               5                   10                  15

```
Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 391
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 391

Leu Ala Cys Ala Lys Glu Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 392
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 392

Leu Ala Cys Ala Lys Glu Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 393
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 393

Leu Ala Cys Ala Lys Glu Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 394
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 394

Leu Ala Cys Ala Lys Glu Ser Ala Asn Ala Glu Leu Asp Ala Tyr Gly
```

```
1               5                   10                  15
Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45
```

<210> SEQ ID NO 395
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 395

```
Leu Ala Cys Ala Lys Ser Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45
```

<210> SEQ ID NO 396
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 396

```
Leu Ala Cys Ala Lys Ser Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45
```

<210> SEQ ID NO 397
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 397

```
Leu Ala Gln Ala Lys Cys Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
            35                  40                  45
```

<210> SEQ ID NO 398
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 398

Leu Ala Gln Ala Lys Cys Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 399
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 399

Leu Ala Gln Ala Lys Cys Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 400
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Leu Ala Gln Ala Lys Cys Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 401
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Leu Ala Gln Ala Lys Cys Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 402
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Leu Ala Gln Ala Lys Cys Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 403
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Leu Ala Gln Ala Lys Cys Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 404
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Leu Ala Gln Ala Lys Cys Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 405
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Leu Ala Gln Ala Lys Cys Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 406
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 406

Leu Ala Gln Ala Lys Cys Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 407
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Leu Ala Gln Ala Lys Cys Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 408
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Leu Ala Gln Ala Lys Cys Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 409
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Leu Ala Ser Ala Lys Cys Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 410
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 410

Leu Ala Ser Ala Lys Cys Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 411
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Leu Ala Ser Ala Lys Cys Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 412
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Leu Ala Ser Ala Lys Cys Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 413
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Leu Ala Ser Ala Lys Cys Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 414
<211> LENGTH: 46
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 414

Leu Ala Ser Ala Lys Cys Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 415
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 415

Leu Ala Ser Ala Lys Cys Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 416
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 416

Leu Ala Ser Ala Lys Cys Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 417
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 417

Leu Ala Ser Ala Lys Cys Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 418
<211> LENGTH: 46
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 418

Leu Ala Ser Ala Lys Cys Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 419
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Leu Ala Ser Ala Lys Cys Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 420
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Leu Ala Ser Ala Lys Cys Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 421
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Leu Ala Glu Ala Lys Cys Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 422
<211> LENGTH: 46
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 422

Leu Ala Glu Ala Lys Cys Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 423
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Leu Ala Glu Ala Lys Cys Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 424
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Leu Ala Glu Ala Lys Cys Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 425
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Leu Ala Glu Ala Lys Cys Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 426
<211> LENGTH: 46
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 426

```
Leu Ala Glu Ala Lys Cys Ala Ala Asn Ser Glu Leu Asp Cys Tyr Gly
1               5                   10                  15
Val Ser Asp Phe Tyr Lys Arg Leu Ile Asp Lys Ala Lys Thr Val Glu
            20                  25                  30
Gly Val Glu Ala Leu Lys Asp Ala Ile Leu Ala Ala Leu Pro
        35                  40                  45
```

<210> SEQ ID NO 427
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

```
Leu Ala Glu Ala Lys Cys Ala Ala Asn Ala Glu Leu Asp Ser Tyr Gly
1               5                   10                  15
Val Ser Asp Phe Tyr Lys Arg Leu Ile Asp Lys Ala Lys Thr Val Glu
            20                  25                  30
Gly Val Glu Ala Leu Lys Asp Ala Ile Leu Ala Ala Leu Pro
        35                  40                  45
```

<210> SEQ ID NO 428
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

```
Leu Ala Glu Ala Lys Cys Ala Ala Asn Ser Glu Leu Asp Ser Tyr Gly
1               5                   10                  15
Val Ser Asp Phe Tyr Lys Arg Leu Ile Asp Lys Ala Lys Thr Val Glu
            20                  25                  30
Gly Val Glu Ala Leu Lys Asp Ala Ile Leu Ala Ala Leu Pro
        35                  40                  45
```

<210> SEQ ID NO 429
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

```
Leu Ala Glu Ala Lys Cys Ser Ala Asn Ser Glu Leu Asp Ser Tyr Gly
1               5                   10                  15
Val Ser Asp Phe Tyr Lys Arg Leu Ile Asp Lys Ala Lys Thr Val Glu
            20                  25                  30
Gly Val Glu Ala Leu Lys Asp Ala Ile Leu Ala Ala Leu Pro
        35                  40                  45
```

<210> SEQ ID NO 430
<211> LENGTH: 46

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Leu Ala Glu Ala Lys Cys Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 431
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 431

Leu Ala Glu Ala Lys Cys Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 432
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 432

Leu Ala Glu Ala Lys Cys Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 433
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 433

Leu Ala Cys Ala Lys Cys Ala Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 434

```
-continued

<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Leu Ala Cys Ala Lys Cys Ala Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 435
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Leu Ala Cys Ala Lys Cys Ser Ala Asn Ser Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 436
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Leu Ala Cys Ala Lys Cys Ser Ala Asn Ala Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 437
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Leu Ala Cys Ala Lys Cys Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

```
<210> SEQ ID NO 438
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Leu Ala Cys Ala Lys Cys Ala Ala Asn Ser Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 439
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Leu Ala Cys Ala Lys Cys Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 440
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Leu Ala Cys Ala Lys Cys Ala Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 441
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Leu Ala Cys Ala Lys Cys Ser Ala Asn Ser Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45
```

```
<210> SEQ ID NO 442
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 442

Leu Ala Cys Ala Lys Cys Ser Ala Asn Ala Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 443
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Leu Ala Cys Ala Lys Cys Ala Ala Asn Ala Glu Leu Asp Lys Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 444
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Leu Ala Cys Ala Lys Cys Ala Ala Asn Ser Glu Leu Asp Lys Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 445
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

Gly Ser Leu Ala Ser Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
                20                  25                  30

Val Glu Gly Val Glu Ala Leu Lys Asp Ala Ile Leu Ala Ala Leu Pro
            35                  40                  45
```

Gly

<210> SEQ ID NO 446
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Gly Ser Leu Ala Glu Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

Gly

<210> SEQ ID NO 447
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Gly Ser Leu Ala Ser Ala Lys Glu Ala Ala Asn Ala Glu Leu Asp Cys
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

Gly

<210> SEQ ID NO 448
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Gly Ser Leu Ala Glu Ala Lys Glu Ala Ala Asn Ala Glu Leu Asp Cys
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

Gly

<210> SEQ ID NO 449
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Gly Ser Leu Ala Ser Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
                20                  25                  30

Val Glu Gly Val Glu Ala Leu Lys Asp Ala Ile Leu Ala Ala Leu Pro
            35                  40                  45

Cys Gly
    50

<210> SEQ ID NO 450
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Gly Ser Leu Ala Glu Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
                20                  25                  30

Val Glu Gly Val Glu Ala Leu Lys Asp Ala Ile Leu Ala Ala Leu Pro
            35                  40                  45

Cys Gly
    50

<210> SEQ ID NO 451
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Gly Cys Ser Leu Ala Ser Ala Lys Glu Ala Ala Asn Ala Glu Leu Asp
1               5                   10                  15

Lys Tyr Gly Val Ser Asp Phe Tyr Lys Arg Leu Ile Asp Lys Ala Lys
                20                  25                  30

Thr Val Glu Gly Val Glu Ala Leu Lys Asp Ala Ile Leu Ala Ala Leu
            35                  40                  45

Pro Gly
    50

<210> SEQ ID NO 452
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Gly Cys Ser Leu Ala Glu Ala Lys Glu Ala Ala Asn Ala Glu Leu Asp
1               5                   10                  15

Lys Tyr Gly Val Ser Asp Phe Tyr Lys Arg Leu Ile Asp Lys Ala Lys
                20                  25                  30

Thr Val Glu Gly Val Glu Ala Leu Lys Asp Ala Ile Leu Ala Ala Leu
            35                  40                  45

Pro Gly
    50

<210> SEQ ID NO 453
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Gly Leu Ala Glu Ala Lys Val Leu Ala Asn Arg Glu Leu Asp Lys Tyr
1               5                   10                  15

Gly Val Ser Asp Tyr Tyr Lys Asn Leu Ile Asn Asn Ala Lys Thr Val
            20                  25                  30

Glu Gly Val Lys Ala Leu Ile Asp Glu Ile Leu Ala Ala Leu Pro
        35                  40                  45

<210> SEQ ID NO 454
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Gly Ser Ser Leu Ala Glu Ala Lys Val Leu Ala Asn Arg Glu Leu Asp
1               5                   10                  15

Lys Tyr Gly Val Ser Asp Phe Tyr Lys Arg Leu Ile Asn Lys Ala Lys
            20                  25                  30

Thr Val Glu Gly Val Glu Ala Leu Lys Leu His Ile Leu Ala Ala Leu
        35                  40                  45

Pro

<210> SEQ ID NO 455
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Gly Ser Ser Leu Ala Ser Ala Lys Glu Ala Ala Asn Ala Glu Leu Asp
1               5                   10                  15

Ala Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

Pro

<210> SEQ ID NO 456
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Gly Ser Ser Leu Ala Ser Ala Lys Glu Ala Ala Asn Ala Glu Leu Asp

```
                1               5                  10                  15
Ser Tyr Gly Val Ser Asp Phe Tyr Lys Arg Leu Ile Asp Lys Ala Lys
                20                  25                  30

Thr Val Glu Gly Val Glu Ala Leu Lys Asp Ala Ile Leu Ala Ala Leu
        35                  40                  45

Pro

<210> SEQ ID NO 457
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Gly Leu Ala Ser Ala Lys Glu Ala Ala Asn Ala Glu Leu Asp Ser Tyr
1               5                  10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ala Leu Pro
        35                  40                  45

<210> SEQ ID NO 458
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

Gly Leu Ala Glu Ala Lys Glu Ala Ala Asn Ala Glu Leu Asp Ser Tyr
1               5                  10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ala Leu Pro
        35                  40                  45

<210> SEQ ID NO 459
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

Gly Leu Ala Ser Ala Lys Glu Ala Ala Asn Ala Glu Leu Asp Cys Tyr
1               5                  10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ala Leu Pro
        35                  40                  45

<210> SEQ ID NO 460
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 460

Ala Leu Ala Ser Ala Lys Glu Ala Ala Asn Ala Glu Leu Asp Cys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 461
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 461

Gly Ser Ser Leu Ala Ser Ala Lys Glu Ala Ala Asn Ala Glu Leu Asp
1               5                   10                  15

Lys Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

Pro

<210> SEQ ID NO 462
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Gly Ser Leu Ala Ser Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 463
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Gly Ser Leu Ala Glu Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 464

<400> SEQUENCE: 464

000
```

<210> SEQ ID NO 465

<400> SEQUENCE: 465

000

<210> SEQ ID NO 466

<400> SEQUENCE: 466

000

<210> SEQ ID NO 467

<400> SEQUENCE: 467

000

<210> SEQ ID NO 468

<400> SEQUENCE: 468

000

<210> SEQ ID NO 469

<400> SEQUENCE: 469

000

<210> SEQ ID NO 470

<400> SEQUENCE: 470

000

<210> SEQ ID NO 471

<400> SEQUENCE: 471

000

<210> SEQ ID NO 472

<400> SEQUENCE: 472

000

<210> SEQ ID NO 473

<400> SEQUENCE: 473

000

<210> SEQ ID NO 474

<400> SEQUENCE: 474

000

<210> SEQ ID NO 475

<400> SEQUENCE: 475

000

```
<210> SEQ ID NO 476
<400> SEQUENCE: 476
000

<210> SEQ ID NO 477
<400> SEQUENCE: 477
000

<210> SEQ ID NO 478
<400> SEQUENCE: 478
000

<210> SEQ ID NO 479
<400> SEQUENCE: 479
000

<210> SEQ ID NO 480
<400> SEQUENCE: 480
000

<210> SEQ ID NO 481
<400> SEQUENCE: 481
000

<210> SEQ ID NO 482
<400> SEQUENCE: 482
000

<210> SEQ ID NO 483
<400> SEQUENCE: 483
000

<210> SEQ ID NO 484
<400> SEQUENCE: 484
000

<210> SEQ ID NO 485
<400> SEQUENCE: 485
000

<210> SEQ ID NO 486
<400> SEQUENCE: 486
000

<210> SEQ ID NO 487
```

```
<400> SEQUENCE: 487
000

<210> SEQ ID NO 488
<400> SEQUENCE: 488
000

<210> SEQ ID NO 489
<400> SEQUENCE: 489
000

<210> SEQ ID NO 490
<400> SEQUENCE: 490
000

<210> SEQ ID NO 491
<400> SEQUENCE: 491
000

<210> SEQ ID NO 492
<400> SEQUENCE: 492
000

<210> SEQ ID NO 493
<400> SEQUENCE: 493
000

<210> SEQ ID NO 494
<400> SEQUENCE: 494
000

<210> SEQ ID NO 495
<400> SEQUENCE: 495
000

<210> SEQ ID NO 496
<400> SEQUENCE: 496
000

<210> SEQ ID NO 497
<400> SEQUENCE: 497
000

<210> SEQ ID NO 498
<400> SEQUENCE: 498
```

000

<210> SEQ ID NO 499

<400> SEQUENCE: 499

000

<210> SEQ ID NO 500
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 500

Ser Leu Ala Glu Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 501
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 501

Leu Ala Glu Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro Gly
        35                  40                  45

<210> SEQ ID NO 502
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 502

Ser Leu Ala Glu Ala Lys Glu Ala Ala Asn Ala Glu Leu Asp Cys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro Gly
        35                  40                  45

<210> SEQ ID NO 503

<400> SEQUENCE: 503

000

<210> SEQ ID NO 504

```
<400> SEQUENCE: 504
000

<210> SEQ ID NO 505
<400> SEQUENCE: 505
000

<210> SEQ ID NO 506
<400> SEQUENCE: 506
000

<210> SEQ ID NO 507
<400> SEQUENCE: 507
000

<210> SEQ ID NO 508
<400> SEQUENCE: 508
000

<210> SEQ ID NO 509
<400> SEQUENCE: 509
000

<210> SEQ ID NO 510
<400> SEQUENCE: 510
000

<210> SEQ ID NO 511
<400> SEQUENCE: 511
000

<210> SEQ ID NO 512
<400> SEQUENCE: 512
000

<210> SEQ ID NO 513
<400> SEQUENCE: 513
000

<210> SEQ ID NO 514
<400> SEQUENCE: 514
000

<210> SEQ ID NO 515
<400> SEQUENCE: 515
```

000

<210> SEQ ID NO 516

<400> SEQUENCE: 516

000

<210> SEQ ID NO 517

<400> SEQUENCE: 517

000

<210> SEQ ID NO 518

<400> SEQUENCE: 518

000

<210> SEQ ID NO 519

<400> SEQUENCE: 519

000

<210> SEQ ID NO 520

<400> SEQUENCE: 520

000

<210> SEQ ID NO 521

<400> SEQUENCE: 521

000

<210> SEQ ID NO 522

<400> SEQUENCE: 522

000

<210> SEQ ID NO 523

<400> SEQUENCE: 523

000

<210> SEQ ID NO 524

<400> SEQUENCE: 524

000

<210> SEQ ID NO 525

<400> SEQUENCE: 525

000

<210> SEQ ID NO 526

<400> SEQUENCE: 526

000

-continued

<210> SEQ ID NO 527
<400> SEQUENCE: 527
000

<210> SEQ ID NO 528
<400> SEQUENCE: 528
000

<210> SEQ ID NO 529
<400> SEQUENCE: 529
000

<210> SEQ ID NO 530
<400> SEQUENCE: 530
000

<210> SEQ ID NO 531
<400> SEQUENCE: 531
000

<210> SEQ ID NO 532
<400> SEQUENCE: 532
000

<210> SEQ ID NO 533
<400> SEQUENCE: 533
000

<210> SEQ ID NO 534
<400> SEQUENCE: 534
000

<210> SEQ ID NO 535
<400> SEQUENCE: 535
000

<210> SEQ ID NO 536
<400> SEQUENCE: 536
000

<210> SEQ ID NO 537
<400> SEQUENCE: 537
000

<210> SEQ ID NO 538

<400> SEQUENCE: 538

000

<210> SEQ ID NO 539

<400> SEQUENCE: 539

000

<210> SEQ ID NO 540

<400> SEQUENCE: 540

000

<210> SEQ ID NO 541

<400> SEQUENCE: 541

000

<210> SEQ ID NO 542

<400> SEQUENCE: 542

000

<210> SEQ ID NO 543

<400> SEQUENCE: 543

000

<210> SEQ ID NO 544

<400> SEQUENCE: 544

000

<210> SEQ ID NO 545

<400> SEQUENCE: 545

000

<210> SEQ ID NO 546

<400> SEQUENCE: 546

000

<210> SEQ ID NO 547

<400> SEQUENCE: 547

000

<210> SEQ ID NO 548

<400> SEQUENCE: 548

000

<210> SEQ ID NO 549

<400> SEQUENCE: 549

000

<210> SEQ ID NO 550
<400> SEQUENCE: 550
000

<210> SEQ ID NO 551
<400> SEQUENCE: 551
000

<210> SEQ ID NO 552
<400> SEQUENCE: 552
000

<210> SEQ ID NO 553
<400> SEQUENCE: 553
000

<210> SEQ ID NO 554
<400> SEQUENCE: 554
000

<210> SEQ ID NO 555
<400> SEQUENCE: 555
000

<210> SEQ ID NO 556
<400> SEQUENCE: 556
000

<210> SEQ ID NO 557
<400> SEQUENCE: 557
000

<210> SEQ ID NO 558
<400> SEQUENCE: 558
000

<210> SEQ ID NO 559
<400> SEQUENCE: 559
000

<210> SEQ ID NO 560
<400> SEQUENCE: 560
000

<210> SEQ ID NO 561

<400> SEQUENCE: 561

000

<210> SEQ ID NO 562

<400> SEQUENCE: 562

000

<210> SEQ ID NO 563

<400> SEQUENCE: 563

000

<210> SEQ ID NO 564

<400> SEQUENCE: 564

000

<210> SEQ ID NO 565

<400> SEQUENCE: 565

000

<210> SEQ ID NO 566

<400> SEQUENCE: 566

000

<210> SEQ ID NO 567

<400> SEQUENCE: 567

000

<210> SEQ ID NO 568

<400> SEQUENCE: 568

000

<210> SEQ ID NO 569

<400> SEQUENCE: 569

000

<210> SEQ ID NO 570

<400> SEQUENCE: 570

000

<210> SEQ ID NO 571

<400> SEQUENCE: 571

000

<210> SEQ ID NO 572

<400> SEQUENCE: 572

000

<210> SEQ ID NO 573

<400> SEQUENCE: 573

000

<210> SEQ ID NO 574

<400> SEQUENCE: 574

000

<210> SEQ ID NO 575

<400> SEQUENCE: 575

000

<210> SEQ ID NO 576

<400> SEQUENCE: 576

000

<210> SEQ ID NO 577

<400> SEQUENCE: 577

000

<210> SEQ ID NO 578

<400> SEQUENCE: 578

000

<210> SEQ ID NO 579

<400> SEQUENCE: 579

000

<210> SEQ ID NO 580

<400> SEQUENCE: 580

000

<210> SEQ ID NO 581

<400> SEQUENCE: 581

000

<210> SEQ ID NO 582

<400> SEQUENCE: 582

000

<210> SEQ ID NO 583

<400> SEQUENCE: 583

000

<210> SEQ ID NO 584
<400> SEQUENCE: 584

000

<210> SEQ ID NO 585
<400> SEQUENCE: 585

000

<210> SEQ ID NO 586
<400> SEQUENCE: 586

000

<210> SEQ ID NO 587
<400> SEQUENCE: 587

000

<210> SEQ ID NO 588
<400> SEQUENCE: 588

000

<210> SEQ ID NO 589
<400> SEQUENCE: 589

000

<210> SEQ ID NO 590
<400> SEQUENCE: 590

000

<210> SEQ ID NO 591
<400> SEQUENCE: 591

000

<210> SEQ ID NO 592
<400> SEQUENCE: 592

000

<210> SEQ ID NO 593
<400> SEQUENCE: 593

000

<210> SEQ ID NO 594
<400> SEQUENCE: 594

```
000

<210> SEQ ID NO 595
<400> SEQUENCE: 595
000

<210> SEQ ID NO 596
<400> SEQUENCE: 596
000

<210> SEQ ID NO 597
<400> SEQUENCE: 597
000

<210> SEQ ID NO 598
<400> SEQUENCE: 598
000

<210> SEQ ID NO 599
<400> SEQUENCE: 599
000

<210> SEQ ID NO 600
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 600

Met Gly Ser Ser His His His His His His Leu Gln Ser Ser Gly Val
1               5                   10                  15

Asp Leu Gly Thr Glu Asn Leu Tyr Phe Gln Gly
            20                  25

<210> SEQ ID NO 601
<400> SEQUENCE: 601
000

<210> SEQ ID NO 602
<400> SEQUENCE: 602
000

<210> SEQ ID NO 603
<400> SEQUENCE: 603
000

<210> SEQ ID NO 604
<400> SEQUENCE: 604
```

000

<210> SEQ ID NO 605
<400> SEQUENCE: 605
000

<210> SEQ ID NO 606
<400> SEQUENCE: 606
000

<210> SEQ ID NO 607
<400> SEQUENCE: 607
000

<210> SEQ ID NO 608
<400> SEQUENCE: 608
000

<210> SEQ ID NO 609
<400> SEQUENCE: 609
000

<210> SEQ ID NO 610
<400> SEQUENCE: 610
000

<210> SEQ ID NO 611
<400> SEQUENCE: 611
000

<210> SEQ ID NO 612
<400> SEQUENCE: 612
000

<210> SEQ ID NO 613
<400> SEQUENCE: 613
000

<210> SEQ ID NO 614
<400> SEQUENCE: 614
000

<210> SEQ ID NO 615
<400> SEQUENCE: 615
000

<210> SEQ ID NO 616

<400> SEQUENCE: 616

000

<210> SEQ ID NO 617

<400> SEQUENCE: 617

000

<210> SEQ ID NO 618

<400> SEQUENCE: 618

000

<210> SEQ ID NO 619

<400> SEQUENCE: 619

000

<210> SEQ ID NO 620

<400> SEQUENCE: 620

000

<210> SEQ ID NO 621

<400> SEQUENCE: 621

000

<210> SEQ ID NO 622

<400> SEQUENCE: 622

000

<210> SEQ ID NO 623

<400> SEQUENCE: 623

000

<210> SEQ ID NO 624

<400> SEQUENCE: 624

000

<210> SEQ ID NO 625

<400> SEQUENCE: 625

000

<210> SEQ ID NO 626

<400> SEQUENCE: 626

000

<210> SEQ ID NO 627

<400> SEQUENCE: 627

000

<210> SEQ ID NO 628

<400> SEQUENCE: 628

000

<210> SEQ ID NO 629

<400> SEQUENCE: 629

000

<210> SEQ ID NO 630

<400> SEQUENCE: 630

000

<210> SEQ ID NO 631

<400> SEQUENCE: 631

000

<210> SEQ ID NO 632

<400> SEQUENCE: 632

000

<210> SEQ ID NO 633

<400> SEQUENCE: 633

000

<210> SEQ ID NO 634

<400> SEQUENCE: 634

000

<210> SEQ ID NO 635

<400> SEQUENCE: 635

000

<210> SEQ ID NO 636

<400> SEQUENCE: 636

000

<210> SEQ ID NO 637

<400> SEQUENCE: 637

000

<210> SEQ ID NO 638

```
<400> SEQUENCE: 638
000

<210> SEQ ID NO 639
<400> SEQUENCE: 639
000

<210> SEQ ID NO 640
<400> SEQUENCE: 640
000

<210> SEQ ID NO 641
<400> SEQUENCE: 641
000

<210> SEQ ID NO 642
<400> SEQUENCE: 642
000

<210> SEQ ID NO 643
<400> SEQUENCE: 643
000

<210> SEQ ID NO 644
<400> SEQUENCE: 644
000

<210> SEQ ID NO 645
<400> SEQUENCE: 645
000

<210> SEQ ID NO 646
<400> SEQUENCE: 646
000

<210> SEQ ID NO 647
<400> SEQUENCE: 647
000

<210> SEQ ID NO 648
<400> SEQUENCE: 648
000

<210> SEQ ID NO 649
<400> SEQUENCE: 649
```

-continued

000

<210> SEQ ID NO 650
<400> SEQUENCE: 650
000

<210> SEQ ID NO 651
<400> SEQUENCE: 651
000

<210> SEQ ID NO 652
<400> SEQUENCE: 652
000

<210> SEQ ID NO 653
<400> SEQUENCE: 653
000

<210> SEQ ID NO 654
<400> SEQUENCE: 654
000

<210> SEQ ID NO 655
<400> SEQUENCE: 655
000

<210> SEQ ID NO 656
<400> SEQUENCE: 656
000

<210> SEQ ID NO 657
<400> SEQUENCE: 657
000

<210> SEQ ID NO 658
<400> SEQUENCE: 658
000

<210> SEQ ID NO 659
<400> SEQUENCE: 659
000

<210> SEQ ID NO 660
<400> SEQUENCE: 660
000

<210> SEQ ID NO 661

<400> SEQUENCE: 661

000

<210> SEQ ID NO 662

<400> SEQUENCE: 662

000

<210> SEQ ID NO 663

<400> SEQUENCE: 663

000

<210> SEQ ID NO 664

<400> SEQUENCE: 664

000

<210> SEQ ID NO 665

<400> SEQUENCE: 665

000

<210> SEQ ID NO 666

<400> SEQUENCE: 666

000

<210> SEQ ID NO 667

<400> SEQUENCE: 667

000

<210> SEQ ID NO 668

<400> SEQUENCE: 668

000

<210> SEQ ID NO 669

<400> SEQUENCE: 669

000

<210> SEQ ID NO 670

<400> SEQUENCE: 670

000

<210> SEQ ID NO 671

<400> SEQUENCE: 671

000

<210> SEQ ID NO 672

<400> SEQUENCE: 672

000

<210> SEQ ID NO 673

<400> SEQUENCE: 673

000

<210> SEQ ID NO 674

<400> SEQUENCE: 674

000

<210> SEQ ID NO 675

<400> SEQUENCE: 675

000

<210> SEQ ID NO 676

<400> SEQUENCE: 676

000

<210> SEQ ID NO 677

<400> SEQUENCE: 677

000

<210> SEQ ID NO 678
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (45)..(46)
<223> OTHER INFORMATION: May or may not be present

<400> SEQUENCE: 678

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Asp Lys Ala Lys Thr Val Glu

```
                    20                  25                  30
Gly Val Glu Ala Leu Lys Asp Ala Ile Leu Ala Ala Leu Pro
            35                  40                  45

<210> SEQ ID NO 679
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Val or Glu
<220> FEATURE:
<221> NAME/KEY: MOD_RES
<222> LOCATION: (7)..(7)
<223> OTHER INFORMATION: Leu, Glu or Asp
<220> FEATURE:
<221> NAME/KEY: MOD_RES
<222> LOCATION: (9)..(9)
<223> OTHER INFORMATION: Asn, Leu or Ile
<220> FEATURE:
<221> NAME/KEY: MOD_RES
<222> LOCATION: (10)..(10)
<223> OTHER INFORMATION: Arg or Lys
<220> FEATURE:
<221> NAME/KEY: MOD_RES
<222> LOCATION: (13)..(13)
<223> OTHER INFORMATION: Asp or Lys
<220> FEATURE:
<221> NAME/KEY: MOD_RES
<222> LOCATION: (20)..(20)
<223> OTHER INFORMATION: Tyr or Phe
<220> FEATURE:
<221> NAME/KEY: MOD_RES
<222> LOCATION: (23)..(23)
<223> OTHER INFORMATION: Asn, Arg or Ser
<220> FEATURE:
<221> NAME/KEY: MOD_RES
<222> LOCATION: (24)..(24)
<223> OTHER INFORMATION: Val, Ile, Leu, Met, Phe or Tyr
<220> FEATURE:
<221> NAME/KEY: MOD_RES
<222> LOCATION: (26)..(26)
<223> OTHER INFORMATION: Asn, Ser, Glu or Asp
<220> FEATURE:
<221> NAME/KEY: MOD_RES
<222> LOCATION: (27)..(27)
<223> OTHER INFORMATION: Arg, Lys or Asn
<220> FEATURE:
<221> NAME/KEY: MOD_RES
<222> LOCATION: (29)..(29)
<223> OTHER INFORMATION: Lys or Arg
<220> FEATURE:
<221> NAME/KEY: MOD_RES
<222> LOCATION: (35)..(35)
<223> OTHER INFORMATION: Asp, Asn, Gln, Glu, His, Ser, Arg or Lys
<220> FEATURE:
<221> NAME/KEY: MOD_RES
<222> LOCATION: (38)..(38)
<223> OTHER INFORMATION: Lys, Ile or Thr
<220> FEATURE:
<221> NAME/KEY: MOD_RES
<222> LOCATION: (39)..(39)
<223> OTHER INFORMATION: Asn, Ser, Thr, Gly, His, Leu or Asp
<220> FEATURE:
<221> NAME/KEY: MOD_RES
<222> LOCATION: (40)..(40)
<223> OTHER INFORMATION: His, Glu or Asp

<400> SEQUENCE: 679

Leu Ala Glu Ala Lys Xaa Xaa Ala Xaa Xaa Glu Leu Xaa Lys Tyr Gly
1               5                   10                  15
```

```
Val Ser Asp Xaa Tyr Lys Xaa Xaa Ile Xaa Xaa Ala Xaa Thr Val Glu
            20                  25                  30

Gly Val Xaa Ala Leu Xaa Xaa Xaa Ile Leu Ala Ala Leu Pro
        35                  40                  45

<210> SEQ ID NO 680
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 680

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 681
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: May or may not be present
<220> FEATURE:
<223> OTHER INFORMATION: C-term OH or NH2

<400> SEQUENCE: 681

Gly Gly Pro Ser
1

<210> SEQ ID NO 682
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: May or may not be present
<220> FEATURE:
<223> OTHER INFORMATION: C-term OH or NH2

<400> SEQUENCE: 682

Gly Gly Pro Ser Ser
1               5

<210> SEQ ID NO 683
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: May or may not be present
<220> FEATURE:
<223> OTHER INFORMATION: C-term OH or NH2

<400> SEQUENCE: 683
```

Gly Gly Pro Ser Ser Gly
1               5

<210> SEQ ID NO 684
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: May or may not be present
<220> FEATURE:
<223> OTHER INFORMATION: C-term OH or NH2

<400> SEQUENCE: 684

Gly Gly Pro Ser Ser Gly Ala
1               5

<210> SEQ ID NO 685
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: May or may not be present
<220> FEATURE:
<221> NAME/KEY: MOD_RES
<222> LOCATION: (8)..(8)
<223> OTHER INFORMATION: May or may not be present
<220> FEATURE:
<223> OTHER INFORMATION: C-term OH or NH2

<400> SEQUENCE: 685

Gly Gly Pro Ser Ser Gly Ala Pro
1               5

<210> SEQ ID NO 686
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: May or may not be present
<220> FEATURE:
<221> NAME/KEY: MOD_RES
<222> LOCATION: (8)..(9)
<223> OTHER INFORMATION: May or may not be present
<220> FEATURE:
<223> OTHER INFORMATION: C-term OH or NH2

<400> SEQUENCE: 686

Gly Gly Pro Ser Ser Gly Ala Pro Pro
1               5

<210> SEQ ID NO 687
<211> LENGTH: 10
<212> TYPE: PRT
<213> ORGANISM: Artificial Sequence
<220> FEATURE:
<223> OTHER INFORMATION: Description of Artificial Sequence: Synthetic

```
      peptide
<220> FEATURE:
<221> NAME/KEY: MOD_RES
<222> LOCATION: (3)..(3)
<223> OTHER INFORMATION: May or may not be present
<220> FEATURE:
<221> NAME/KEY: MOD_RES
<222> LOCATION: (8)..(10)
<223> OTHER INFORMATION: May or may not be present
<220> FEATURE:
<223> OTHER INFORMATION: C-term OH or NH2

<400> SEQUENCE: 687

Gly Gly Pro Ser Ser Gly Ala Pro Pro Pro
1               5                   10

<210> SEQ ID NO 688
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H

<400> SEQUENCE: 688

Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asn Gly Gly Pro Ser Ser Gly Ala Pro Pro Ser Lys Lys Lys Lys
        35                  40                  45

Lys Lys
    50

<210> SEQ ID NO 689
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<223> OTHER INFORMATION: C-term NH2

<400> SEQUENCE: 689

His Gly Glu Gly Thr Phe Thr Ser Asp Leu Ser Lys Gln Met Glu Glu
1               5                   10                  15

Glu Ala Val Arg Leu Phe Ile Glu Trp Leu Trp Leu Lys Asn Gly Gly
            20                  25                  30

Pro Ser Ser Gly Ala Ser
        35

<210> SEQ ID NO 690
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H

<400> SEQUENCE: 690
```

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asn Gly Gly Pro Ser Ser Gly Ala Ser
        35                  40
```

<210> SEQ ID NO 691
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H

<400> SEQUENCE: 691

```
Asn Glu Glu Glu Glu Glu His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asn Gly Gly Pro Ser Ser Gly Ala Ser
        35                  40
```

<210> SEQ ID NO 692
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 692

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Ser Lys Lys Lys Lys Lys Lys
        35                  40
```

<210> SEQ ID NO 693
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H

<400> SEQUENCE: 693

```
Lys Lys Lys Lys Lys Lys His Gly Glu Gly Thr Phe Thr Ser Asp Leu
1               5                   10                  15

Ser Lys Gln Met Glu Glu Glu Ala Val Arg Leu Phe Ile Glu Trp Leu
            20                  25                  30

Lys Asn Gly Gly Pro Ser Ser Gly Ala Ser Lys Lys Lys Lys Lys Lys
        35                  40                  45
```

<210> SEQ ID NO 694
<211> LENGTH: 48
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 694

Asn Glu Glu Glu Glu His Gly Glu Gly Thr Phe Thr Ser Asp Leu
1               5                   10                  15

Ser Lys Gln Met Glu Glu Ala Val Arg Leu Phe Ile Glu Trp Leu
            20                  25                  30

Lys Asn Gly Gly Pro Ser Ser Gly Ala Ser Lys Lys Lys Lys Lys
        35                  40                  45

<210> SEQ ID NO 695
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 695

Lys Lys Lys Lys Lys Lys
1               5

<210> SEQ ID NO 696
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 696

Ser Gly Ser Leu Ala Glu Ala Lys Glu Ala Ala Asn Ala Glu Leu Asp
1               5                   10                  15

Ser Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

Pro

<210> SEQ ID NO 697
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 697

Ser Gly Ser Leu Ala Glu Ala Lys Glu Ala Ala Asn Ala Glu Leu Asp
1               5                   10                  15

Ser Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

<210> SEQ ID NO 698
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 698

Ser Gly Ser Leu Ala Glu Ala Lys Glu Ala Asn Ala Glu Leu Asp
1               5                   10                  15

Ser Tyr Gly Val Ser Asp Phe Tyr Lys Arg Leu Ile Asp Lys Ala Lys
                20                  25                  30

Thr Val Glu Gly Val Glu Ala Leu Lys Asp Ala Ile Leu Ala Ala Pro
            35                  40                  45

<210> SEQ ID NO 699
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 699

Ser Gly Ser Leu Ala Glu Ala Lys Glu Ala Asn Ala Glu Leu Asp
1               5                   10                  15

Ser Tyr Gly Val Ser Asp Phe Tyr Lys Arg Leu Ile Asp Lys Ala Lys
                20                  25                  30

Thr Val Glu Gly Val Glu Ala Leu Lys Asp Ala Ile Leu Ala Ala
            35                  40                  45

<210> SEQ ID NO 700
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 700

Gly Ser Leu Ala Glu Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
                20                  25                  30

Val Glu Gly Val Glu Ala Leu Lys Asp Ala Ile Leu Ala Ala Leu
            35                  40                  45

<210> SEQ ID NO 701
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 701

Gly Ser Leu Ala Glu Ala Lys Glu Ala Ala Asn Ala Glu Leu Asp Cys
1               5                   10                  15

Tyr Gly Val Ser Asp Phe Tyr Lys Arg Leu Ile Asp Lys Ala Lys Thr
                20                  25                  30

Val Glu Gly Val Glu Ala Leu Lys Asp Ala Ile Leu Ala Ala Leu
            35                  40                  45

<210> SEQ ID NO 702
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 702

Ser Leu Ala Glu Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu
        35                  40                  45

<210> SEQ ID NO 703
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 703

Ser Leu Ala Glu Ala Lys Glu Ala Ala Asn Ala Glu Leu Asp Cys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu
        35                  40                  45

<210> SEQ ID NO 704
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 704

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu
        35                  40                  45

<210> SEQ ID NO 705
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 705

Leu Ala Glu Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu
        35                  40                  45

<210> SEQ ID NO 706
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 706

Gly Ser Ser Leu Ala Ser Ala Lys Glu Ala Ala Asn Ala Glu Leu Asp
1               5                   10                  15

Ala Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala
        35                  40                  45

<210> SEQ ID NO 707
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 707

Gly Ser Ser Leu Ala Ser Ala Lys Glu Ala Ala Asn Ala Glu Leu Asp
1               5                   10                  15

Ser Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala
        35                  40                  45

<210> SEQ ID NO 708
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 708

Gly Leu Ala Ser Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala
        35                  40                  45

<210> SEQ ID NO 709
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 709

Gly Leu Ala Glu Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala
        35                  40                  45

<210> SEQ ID NO 710
<211> LENGTH: 45
<212> TYPE: PRT
<213> ORGANISM: Artificial Sequence
<220> FEATURE:

<210> SEQ ID NO 710
<211> LENGTH: 45 (not shown; continued from prior)
<223> OTHER INFORMATION: Description of Artificial Sequence: Synthetic
      polypeptide

<400> SEQUENCE: 710

Gly Leu Ala Ser Ala Lys Glu Ala Ala Asn Ala Glu Leu Asp Cys Tyr
1               5                   10                  15
Gly Val Ser Asp Phe Tyr Lys Arg Leu Ile Asp Lys Ala Lys Thr Val
            20                  25                  30
Glu Gly Val Glu Ala Leu Lys Asp Ala Ile Leu Ala Ala
        35                  40                  45

<210> SEQ ID NO 711
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 711

Ala Leu Ala Ser Ala Lys Glu Ala Ala Asn Ala Glu Leu Asp Cys Tyr
1               5                   10                  15
Gly Val Ser Asp Phe Tyr Lys Arg Leu Ile Asp Lys Ala Lys Thr Val
            20                  25                  30
Glu Gly Val Glu Ala Leu Lys Asp Ala Ile Leu Ala Ala
        35                  40                  45

<210> SEQ ID NO 712
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 712

Gly Ser Ser Leu Ala Ser Ala Lys Glu Ala Ala Asn Ala Glu Leu Asp
1               5                   10                  15
Lys Tyr Gly Val Ser Asp Phe Tyr Lys Arg Leu Ile Asp Lys Ala Lys
            20                  25                  30
Thr Val Glu Gly Val Glu Ala Leu Lys Asp Ala Ile Leu Ala Ala
        35                  40                  45

<210> SEQ ID NO 713
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 713

Gly Ser Leu Ala Ser Ala Lys Glu Ala Ala Asn Ala Glu Leu Asp Ser
1               5                   10                  15
Tyr Gly Val Ser Asp Phe Tyr Lys Arg Leu Ile Asp Lys Ala Lys Thr
            20                  25                  30
Val Glu Gly Val Glu Ala Leu Lys Asp Ala Ile Leu Ala Ala
        35                  40                  45

<210> SEQ ID NO 714
<211> LENGTH: 46
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 714

Gly Ser Leu Ala Glu Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala
        35                  40                  45

<210> SEQ ID NO 715
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 715

Gly Ser Leu Ala Glu Ala Lys Glu Ala Ala Asn Ala Glu Leu Asp Cys
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala
        35                  40                  45

<210> SEQ ID NO 716
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 716

Leu Ala Glu Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala
        35                  40

<210> SEQ ID NO 717
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 717

Ser Leu Ala Glu Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala
        35                  40                  45

<210> SEQ ID NO 718
<211> LENGTH: 44
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 718

Leu Ala Glu Ala Lys Glu Ala Ala Asn Ala Glu Leu Asp Cys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala
        35                  40

<210> SEQ ID NO 719
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 719

Ser Leu Ala Glu Ala Lys Glu Ala Ala Asn Ala Glu Leu Asp Cys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala
        35                  40                  45

<210> SEQ ID NO 720
<211> LENGTH: 49
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 720

Ala Gly Ser Leu Ala Glu Ala Lys Glu Ala Ala Asn Ala Glu Leu Asp
1               5                   10                  15

Ser Tyr Gly Val Ser Asp Phe Tyr Lys Arg Leu Ile Asp Lys Ala Lys
            20                  25                  30

Thr Val Glu Gly Val Glu Ala Leu Lys Asp Ala Ile Leu Ala Ala Leu
        35                  40                  45

Pro

<210> SEQ ID NO 721
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 721

Gly Gly Gly Gly Ser Gly Gly Gly Gly Ser Gly Gly Gly Gly Ser
1               5                   10                  15

<210> SEQ ID NO 722
<211> LENGTH: 18
<212> TYPE: PRT
<213> ORGANISM: Artificial Sequence
<220> FEATURE:
<223> OTHER INFORMATION: Description of Artificial Sequence: Synthetic

```
                              peptide

<400> SEQUENCE: 722

Gly Gly Glu Gly Gly Glu Gly Gly Glu Gly Gly Glu Gly Gly Glu Gly
1               5                   10                  15

Gly Glu

<210> SEQ ID NO 723
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 723

Gly Gly Lys Gly Gly Lys Gly Gly Lys Gly Gly Lys Gly Gly Lys Gly
1               5                   10                  15

Gly Lys

<210> SEQ ID NO 724
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 724

Glu Ala Ala Ala Lys Glu Ala Ala Ala Lys Glu Ala Ala Ala Lys
1               5                   10                  15

<210> SEQ ID NO 725
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 725

Glu Ala Ala Ala Lys Glu Ala Ala Ala Lys Glu Ala Ala Ala Lys Glu
1               5                   10                  15

Ala Ala Ala Lys
            20

<210> SEQ ID NO 726
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 726

Glu Ala Ala Ala Lys Glu Ala Ala Ala Lys Glu Ala Ala Ala Lys Glu
1               5                   10                  15

Ala Ala Ala Lys Glu Ala Ala Ala Lys
            20                  25

<210> SEQ ID NO 727
<211> LENGTH: 93
<212> TYPE: PRT
<213> ORGANISM: Artificial Sequence
<220> FEATURE:
```

<223> OTHER INFORMATION: Description of Artificial Sequence: Synthetic
polypeptide

<400> SEQUENCE: 727

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Thr Gly Gly Gly Ser Ala Ser Gly Ser Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu Pro
                85                  90

<210> SEQ ID NO 728
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 728

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Thr Gly Gly Gly Ser Ala Ser Gly
        35                  40                  45

Ser Leu Ala Glu Ala Lys Glu Ala Ala Asn Ala Glu Leu Asp Ser Tyr
    50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala Leu Pro
                85                  90                  95

<210> SEQ ID NO 729
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 729

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Thr Gly Gly Gly Ser Ala Ser Gly
        35                  40                  45

Ser Leu Ala Glu Ala Lys Glu Ala Ala Asn Ala Glu Leu Asp Ser Tyr
    50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala Leu

<210> SEQ ID NO 730
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 730

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Thr Gly Gly Gly Gly Ser Ala Ser Gly
        35                  40                  45

Ser Leu Ala Glu Ala Lys Glu Ala Ala Asn Ala Glu Leu Asp Ser Tyr
    50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala Leu Pro
                85                  90                  95

<210> SEQ ID NO 731
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 731

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Ser Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu Pro
                85

<210> SEQ ID NO 732
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 732

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Thr Gly Gly Gly Gly Ser Ala Ser Gly
        35                  40                  45

Ser Leu Ala Glu Ala Lys Glu Ala Ala Asn Ala Glu Leu Asp Ser Tyr
            50                  55                  60

Gly Val Ser Asp Phe Tyr Lys Arg Leu Ile Asp Lys Ala Lys Thr Val
 65                  70                  75                  80

Glu Gly Val Glu Ala Leu Lys Asp Ala Ile Leu Ala Ala Leu Pro
                 85                  90                  95

<210> SEQ ID NO 733
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 733

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Pro Ser Gly Gly Ser Leu Ala Glu Ala Lys Glu
            35                  40                  45

Ala Ala Asn Ala Glu Leu Asp Ser Tyr Gly Val Ser Asp Phe Tyr Lys
 50                  55                  60

Arg Leu Ile Asp Lys Ala Lys Thr Val Glu Gly Val Glu Ala Leu Lys
 65                  70                  75                  80

Asp Ala Ile Leu Ala Ala Leu Pro
                 85

<210> SEQ ID NO 734
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 734

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Gln Gly Gly Pro Ser
                 20                  25                  30

Lys Glu Ile Ile Ser Thr Gly Gly Gly Ser Ala Ser Gly Ser Leu
            35                  40                  45

Ala Glu Ala Lys Glu Ala Ala Asn Ala Glu Leu Asp Ser Tyr Gly Val
 50                  55                  60

Ser Asp Phe Tyr Lys Arg Leu Ile Asp Lys Ala Lys Thr Val Glu Gly
 65                  70                  75                  80

Val Glu Ala Leu Lys Asp Ala Ile Leu Ala Ala Leu
                 85                  90

<210> SEQ ID NO 735
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 735

His Gly Glu Gly Thr Phe Thr Ser Asp Leu Ser Lys Gln Leu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Thr Gly Gly Gly Ser Ala Ser Gly
        35                  40                  45

Ser Leu Ala Glu Ala Lys Glu Ala Asn Ala Glu Leu Asp Ser Tyr
    50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala Leu
                85                  90

<210> SEQ ID NO 736
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 736

His Gly Glu Gly Thr Phe Thr Ser Asp Leu Ser Lys Gln Leu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Thr Gly Gly Gly Ser Ala Ser Gly
        35                  40                  45

Ser Leu Ala Glu Ala Lys Glu Ala Asn Ala Glu Leu Asp Ser Tyr
    50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala
                85                  90

<210> SEQ ID NO 737
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 737

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Thr Gly Gly Gly Ser Ala Ser Gly
        35                  40                  45

Ser Leu Ala Glu Ala Lys Glu Ala Asn Ala Glu Leu Asp Ser Tyr
    50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala Leu
                85                  90

<210> SEQ ID NO 738
<211> LENGTH: 87

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 738

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Ser Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu
                85

<210> SEQ ID NO 739
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 739

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Ser Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu
                85

<210> SEQ ID NO 740
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 740

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Thr Gly Gly Gly Ser Ala Ser Gly Ser Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
```

```
                65                  70                  75                  80
Val Glu Ala Leu Lys Asp Ala Ile Leu Ala Ala
                85                  90

<210> SEQ ID NO 741
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 741

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Thr Gly Gly Gly Gly Ser Ala Ser Gly
            35                  40                  45

Ser Leu Ala Glu Ala Lys Glu Ala Ala Asn Ala Glu Leu Asp Ser Tyr
        50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala
                85                  90

<210> SEQ ID NO 742
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 742

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Pro Ser Thr Gly Gly Gly Gly Ser Ala Ser Gly
            35                  40                  45

Ser Leu Ala Glu Ala Lys Glu Ala Ala Asn Ala Glu Leu Asp Ser Tyr
        50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala
                85                  90

<210> SEQ ID NO 743
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 743

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30
```

Ser Gly Ala Pro Pro Ser Gly Gly Ser Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala
                85

<210> SEQ ID NO 744
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 744

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Thr Gly Gly Gly Ser Ala Ser Gly
        35                  40                  45

Ser Leu Ala Glu Ala Lys Glu Ala Ala Asn Ala Glu Leu Asp Ser Tyr
    50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala
                85                  90

<210> SEQ ID NO 745
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 745

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Gly Gly Ser Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala
                85

<210> SEQ ID NO 746
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 746

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Thr Gly Gly Gly Ser Ala Ser Ser Leu Ala
        35                  40                  45

Glu Ala Lys Glu Ala Ala Asn Ala Glu Leu Asp Ser Tyr Gly Val Ser
50                  55                  60

Asp Phe Tyr Lys Arg Leu Ile Asp Lys Ala Lys Thr Val Glu Gly Val
65                  70                  75                  80

Glu Ala Leu Lys Asp Ala Ile Leu Ala Ala Leu Pro
            85                  90

<210> SEQ ID NO 747
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 747

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Thr Gly Gly Gly Ser Ala Ser Ser Leu Ala
        35                  40                  45

Glu Ala Lys Glu Ala Ala Asn Ala Glu Leu Asp Ser Tyr Gly Val Ser
50                  55                  60

Asp Phe Tyr Lys Arg Leu Ile Asp Lys Ala Lys Thr Val Glu Gly Val
65                  70                  75                  80

Glu Ala Leu Lys Asp Ala Ile Leu Ala Ala Leu
            85                  90

<210> SEQ ID NO 748
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 748

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Thr Gly Gly Gly Ser Ala Ser Leu Ala Glu
        35                  40                  45

Ala Lys Glu Ala Ala Asn Ala Glu Leu Asp Ser Tyr Gly Val Ser Asp
50                  55                  60

Phe Tyr Lys Arg Leu Ile Asp Lys Ala Lys Thr Val Glu Gly Val Glu
65                  70                  75                  80

Ala Leu Lys Asp Ala Ile Leu Ala Ala Leu Pro
            85                  90

<210> SEQ ID NO 749
<211> LENGTH: 90
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 749

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Thr Gly Gly Gly Ser Ala Ser Leu Ala Glu
        35                  40                  45

Ala Lys Glu Ala Ala Asn Ala Glu Leu Asp Ser Tyr Gly Val Ser Asp
    50                  55                  60

Phe Tyr Lys Arg Leu Ile Asp Lys Ala Lys Thr Val Glu Gly Val Glu
65                  70                  75                  80

Ala Leu Lys Asp Ala Ile Leu Ala Ala Leu
                85                  90

<210> SEQ ID NO 750
<211> LENGTH: 88
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 750

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Gly Gly Gly Ser Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu Pro
                85

<210> SEQ ID NO 751
<211> LENGTH: 87
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 751

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Gly Gly Gly Ser Leu Ala Glu Ala Lys Glu
        35                  40                  45

Ala Ala Asn Ala Glu Leu Asp Ser Tyr Gly Val Ser Asp Phe Tyr Lys

```
                50                  55                  60
Arg Leu Ile Asp Lys Ala Lys Thr Val Glu Gly Val Glu Ala Leu Lys
 65                  70                  75                  80

Asp Ala Ile Leu Ala Ala Leu
                85

<210> SEQ ID NO 752
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 752

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Gln Gly Gly Pro Ser
                20                  25                  30

Lys Glu Ile Ile Ser Gly Gly Gly Ser Leu Ala Glu Ala Lys Glu Ala
                35                  40                  45

Ala Asn Ala Glu Leu Asp Ser Tyr Gly Val Ser Asp Phe Tyr Lys Arg
 50                  55                  60

Leu Ile Asp Lys Ala Lys Thr Val Glu Gly Val Glu Ala Leu Lys Asp
 65                  70                  75                  80

Ala Ile Leu Ala Ala Leu Pro
                85

<210> SEQ ID NO 753
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 753

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Gln Gly Gly Pro Ser
                20                  25                  30

Lys Glu Ile Ile Ser Gly Gly Gly Ser Leu Ala Glu Ala Lys Glu Ala
                35                  40                  45

Ala Asn Ala Glu Leu Asp Ser Tyr Gly Val Ser Asp Phe Tyr Lys Arg
 50                  55                  60

Leu Ile Asp Lys Ala Lys Thr Val Glu Gly Val Glu Ala Leu Lys Asp
 65                  70                  75                  80

Ala Ile Leu Ala Ala Leu
                85

<210> SEQ ID NO 754
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 754

His Gly Glu Gly Thr Phe Thr Ser Asp Leu Ser Lys Gln Leu Glu Glu
 1               5                  10                  15
```

```
Glu Ala Val Arg Leu Phe Ile Glu Trp Leu Lys Gln Gly Gly Pro Ser
             20                  25                  30

Lys Glu Ile Ile Ser Gly Gly Leu Ala Glu Ala Lys Glu Ala Ala
         35                  40                  45

Asn Ala Glu Leu Asp Ser Tyr Gly Val Ser Asp Phe Tyr Lys Arg Leu
 50                  55                  60

Ile Asp Lys Ala Lys Thr Val Glu Gly Val Glu Ala Leu Lys Asp Ala
 65                  70                  75                  80

Ile Leu Ala Ala Leu Pro
             85
```

<210> SEQ ID NO 755
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 755

```
His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Gln Gly Gly Pro Ser
             20                  25                  30

Lys Glu Ile Ile Ser Gly Gly Leu Ala Glu Ala Lys Glu Ala Ala
         35                  40                  45

Asn Ala Glu Leu Asp Ser Tyr Gly Val Ser Asp Phe Tyr Lys Arg Leu
 50                  55                  60

Ile Asp Lys Ala Lys Thr Val Glu Gly Val Glu Ala Leu Lys Asp Ala
 65                  70                  75                  80

Ile Leu Ala Ala Leu
             85
```

<210> SEQ ID NO 756
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 756

```
His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Gln Gly Gly Pro Ser
             20                  25                  30

Lys Glu Ile Ile Ser Gly Gly Ser Leu Ala Glu Ala Lys Glu Ala Ala
         35                  40                  45

Asn Ala Glu Leu Asp Ser Tyr Gly Val Ser Asp Phe Tyr Lys Arg Leu
 50                  55                  60

Ile Asp Lys Ala Lys Thr Val Glu Gly Val Glu Ala Leu Lys Asp Ala
 65                  70                  75                  80

Ile Leu Ala Ala Leu Pro
             85
```

<210> SEQ ID NO 757
<211> LENGTH: 85
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 757

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
                20                  25                  30

Lys Glu Ile Ile Ser Gly Gly Ser Leu Ala Glu Ala Lys Glu Ala Ala
            35                  40                  45

Asn Ala Glu Leu Asp Ser Tyr Gly Val Ser Asp Phe Tyr Lys Arg Leu
    50                  55                  60

Ile Asp Lys Ala Lys Thr Val Glu Gly Val Glu Ala Leu Lys Asp Ala
65                  70                  75                  80

Ile Leu Ala Ala Leu
                85

<210> SEQ ID NO 758
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 758

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Thr Gly Gly Gly Gly Ser Ala Ser Ser
            35                  40                  45

Leu Ala Glu Ala Lys Glu Ala Ala Asn Ala Glu Leu Asp Ser Tyr Gly
    50                  55                  60

Val Ser Asp Phe Tyr Lys Arg Leu Ile Asp Lys Ala Lys Thr Val Glu
65                  70                  75                  80

Gly Val Glu Ala Leu Lys Asp Ala Ile Leu Ala Ala Leu Pro
                85                  90

<210> SEQ ID NO 759
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 759

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Thr Gly Gly Gly Gly Ser Ala Ser Ser
            35                  40                  45

Leu Ala Glu Ala Lys Glu Ala Ala Asn Ala Glu Leu Asp Ser Tyr Gly
    50                  55                  60

Val Ser Asp Phe Tyr Lys Arg Leu Ile Asp Lys Ala Lys Thr Val Glu
65                  70                  75                  80
```

Gly Val Glu Ala Leu Lys Asp Ala Ile Leu Ala Ala Leu
                85                  90

<210> SEQ ID NO 760
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 760

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Thr Gly Gly Gly Ser Ala Ser Leu
            35                  40                  45

Ala Glu Ala Lys Glu Ala Ala Asn Ala Glu Leu Asp Ser Tyr Gly Val
        50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu Pro
                85                  90

<210> SEQ ID NO 761
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 761

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Thr Gly Gly Gly Ser Ala Ser Leu
            35                  40                  45

Ala Glu Ala Lys Glu Ala Ala Asn Ala Glu Leu Asp Ser Tyr Gly Val
        50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu
                85                  90

<210> SEQ ID NO 762
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 762

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Gly Gly Gly Gly Ser Leu Ala Glu Ala

```
                35                  40                  45
Lys Glu Ala Ala Asn Ala Glu Leu Asp Ser Tyr Gly Val Ser Asp Phe
            50                  55                  60
Tyr Lys Arg Leu Ile Asp Lys Ala Lys Thr Val Glu Gly Val Glu Ala
65                  70                  75                  80
Leu Lys Asp Ala Ile Leu Ala Ala Leu Pro
                85                  90
```

<210> SEQ ID NO 763
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 763

```
His Gly Glu Gly Thr Phe Thr Ser Asp Leu Ser Lys Gln Leu Glu Glu
1               5                   10                  15
Glu Ala Val Arg Leu Phe Ile Glu Trp Leu Lys Asn Gly Gly Pro Ser
                20                  25                  30
Ser Gly Ala Pro Pro Lys Ser Gly Gly Gly Ser Leu Ala Glu Ala
            35                  40                  45
Lys Glu Ala Ala Asn Ala Glu Leu Asp Ser Tyr Gly Val Ser Asp Phe
            50                  55                  60
Tyr Lys Arg Leu Ile Asp Lys Ala Lys Thr Val Glu Gly Val Glu Ala
65                  70                  75                  80
Leu Lys Asp Ala Ile Leu Ala Ala Leu
                85
```

<210> SEQ ID NO 764
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 764

```
His Gly Glu Gly Thr Phe Thr Ser Asp Leu Ser Lys Gln Leu Glu Glu
1               5                   10                  15
Glu Ala Val Arg Leu Phe Ile Glu Trp Leu Lys Asn Gly Gly Pro Ser
                20                  25                  30
Ser Gly Ala Pro Pro Lys Ser Gly Gly Gly Ser Leu Ala Glu Ala Lys
            35                  40                  45
Glu Ala Ala Asn Ala Glu Leu Asp Ser Tyr Gly Val Ser Asp Phe Tyr
            50                  55                  60
Lys Arg Leu Ile Asp Lys Ala Lys Thr Val Glu Gly Val Glu Ala Leu
65                  70                  75                  80
Lys Asp Ala Ile Leu Ala Ala Leu Pro
                85
```

<210> SEQ ID NO 765
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 765

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Gly Gly Ser Leu Ala Glu Ala Lys
        35                  40                  45

Glu Ala Ala Asn Ala Glu Leu Asp Ser Tyr Gly Val Ser Asp Phe Tyr
    50                  55                  60

Lys Arg Leu Ile Asp Lys Ala Lys Thr Val Glu Gly Val Glu Ala Leu
65                  70                  75                  80

Lys Asp Ala Ile Leu Ala Ala Leu
                85

<210> SEQ ID NO 766
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 766

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Gly Gly Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu Pro
                85

<210> SEQ ID NO 767
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 767

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Gly Gly Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu
                85

<210> SEQ ID NO 768

```
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 768

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Gly Ser Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu Pro
                85

<210> SEQ ID NO 769
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 769

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Gly Ser Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu
                85

<210> SEQ ID NO 770
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 770

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Ser Leu Ala Glu Ala Lys Glu Ala
        35                  40                  45

Ala Asn Ala Glu Leu Asp Ser Tyr Gly Val Ser Asp Phe Tyr Lys Arg
    50                  55                  60
```

Leu Ile Asp Lys Ala Lys Thr Val Glu Gly Val Glu Ala Leu Lys Asp
65                  70                  75                  80

Ala Ile Leu Ala Ala Leu Pro
                85

<210> SEQ ID NO 771
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 771

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Ser Leu Ala Glu Ala Lys Glu Ala
        35                  40                  45

Ala Asn Ala Glu Leu Asp Ser Tyr Gly Val Ser Asp Phe Tyr Lys Arg
    50                  55                  60

Leu Ile Asp Lys Ala Lys Thr Val Glu Gly Val Glu Ala Leu Lys Asp
65                  70                  75                  80

Ala Ile Leu Ala Ala Leu
                85

<210> SEQ ID NO 772
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 772

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Leu Ala Glu Ala Lys Glu Ala Ala
        35                  40                  45

Asn Ala Glu Leu Asp Ser Tyr Gly Val Ser Asp Phe Tyr Lys Arg Leu
    50                  55                  60

Ile Asp Lys Ala Lys Thr Val Glu Gly Val Glu Ala Leu Lys Asp Ala
65                  70                  75                  80

Ile Leu Ala Ala Leu Pro
                85

<210> SEQ ID NO 773
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 773

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser

```
                    20                  25                  30

Ser Gly Ala Pro Pro Lys Ser Gly Leu Ala Glu Ala Lys Glu Ala Ala
                35                  40                  45

Asn Ala Glu Leu Asp Ser Tyr Gly Val Ser Asp Phe Tyr Lys Arg Leu
            50                  55                  60

Ile Asp Lys Ala Lys Thr Val Glu Gly Val Glu Ala Leu Lys Asp Ala
65                  70                  75                  80

Ile Leu Ala Ala Leu
                85

<210> SEQ ID NO 774
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 774

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Thr Gly Gly Gly Ser Ala Ser Gly
                35                  40                  45

Ser Leu Ala Glu Ala Lys Glu Ala Ala Asn Ala Glu Leu Asp Ser Tyr
            50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala Leu Pro
                85                  90                  95

<210> SEQ ID NO 775
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 775

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Thr Gly Gly Gly Ser Ala Ser Gly
                35                  40                  45

Ser Leu Ala Glu Ala Lys Glu Ala Ala Asn Ala Glu Leu Asp Ser Tyr
            50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala Leu
                85                  90

<210> SEQ ID NO 776
<211> LENGTH: 94
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 776

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Thr Gly Gly Gly Gly Ser Ala Ser Ser
        35                  40                  45

Leu Ala Glu Ala Lys Glu Ala Ala Asn Ala Glu Leu Asp Ser Tyr Gly
    50                  55                  60

Val Ser Asp Phe Tyr Lys Arg Leu Ile Asp Lys Ala Lys Thr Val Glu
65                  70                  75                  80

Gly Val Glu Ala Leu Lys Asp Ala Ile Leu Ala Ala Leu Pro
                85                  90

<210> SEQ ID NO 777
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 777

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Thr Gly Gly Gly Gly Ser Ala Ser Ser
        35                  40                  45

Leu Ala Glu Ala Lys Glu Ala Ala Asn Ala Glu Leu Asp Ser Tyr Gly
    50                  55                  60

Val Ser Asp Phe Tyr Lys Arg Leu Ile Asp Lys Ala Lys Thr Val Glu
65                  70                  75                  80

Gly Val Glu Ala Leu Lys Asp Ala Ile Leu Ala Ala Leu
                85                  90

<210> SEQ ID NO 778
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 778

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Thr Gly Gly Gly Gly Ser Ala Ser Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu Pro
                85                  90

<210> SEQ ID NO 779
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 779

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Thr Gly Gly Gly Gly Ser Ala Ser Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu
                85                  90

<210> SEQ ID NO 780
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 780

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Gly Gly Gly Ser Leu Ala Glu Ala
        35                  40                  45

Lys Glu Ala Ala Asn Ala Glu Leu Asp Ser Tyr Gly Val Ser Asp Phe
    50                  55                  60

Tyr Lys Arg Leu Ile Asp Lys Ala Lys Thr Val Glu Gly Val Glu Ala
65                  70                  75                  80

Leu Lys Asp Ala Ile Leu Ala Ala Leu Pro
                85                  90

<210> SEQ ID NO 781
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 781

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Gly Gly Gly Ser Leu Ala Glu Ala
        35                  40                  45

```
Lys Glu Ala Ala Asn Ala Glu Leu Asp Ser Tyr Gly Val Ser Asp Phe
    50                  55                  60

Tyr Lys Arg Leu Ile Asp Lys Ala Lys Thr Val Glu Gly Val Glu Ala
65                  70                  75                  80

Leu Lys Asp Ala Ile Leu Ala Ala Leu
                85
```

<210> SEQ ID NO 782
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 782

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Gly Gly Gly Ser Leu Ala Glu Ala Lys
        35                  40                  45

Glu Ala Ala Asn Ala Glu Leu Asp Ser Tyr Gly Val Ser Asp Phe Tyr
    50                  55                  60

Lys Arg Leu Ile Asp Lys Ala Lys Thr Val Glu Gly Val Glu Ala Leu
65                  70                  75                  80

Lys Asp Ala Ile Leu Ala Ala Leu Pro
                85
```

<210> SEQ ID NO 783
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 783

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Lys Ser Gly Gly Gly Ser Leu Ala Glu Ala Lys
        35                  40                  45

Glu Ala Ala Asn Ala Glu Leu Asp Ser Tyr Gly Val Ser Asp Phe Tyr
    50                  55                  60

Lys Arg Leu Ile Asp Lys Ala Lys Thr Val Glu Gly Val Glu Ala Leu
65                  70                  75                  80

Lys Asp Ala Ile Leu Ala Ala Leu
                85
```

<210> SEQ ID NO 784
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 784

```
His Gly Glu Gly Thr Phe Thr Ser Asp Leu Ser Lys Gln Met Glu Glu
```

-continued

```
                 1               5                  10                  15
            Glu Ala Val Arg Leu Phe Ile Glu Trp Leu Lys Asn Gly Gly Pro Ser
                           20                  25                  30

Ser Gly Ala Pro Pro Lys Ser Gly Gly Leu Ala Glu Ala Lys Glu
                       35                  40                  45

Ala Ala Asn Ala Glu Leu Asp Ser Tyr Gly Val Ser Asp Phe Tyr Lys
                50                  55                  60

Arg Leu Ile Asp Lys Ala Lys Thr Val Glu Gly Val Glu Ala Leu Lys
             65                  70                  75                  80

Asp Ala Ile Leu Ala Ala Leu Pro
                            85

<210> SEQ ID NO 785
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 785

His Gly Glu Gly Thr Phe Thr Ser Asp Leu Ser Lys Gln Met Glu Glu
             1               5                  10                  15

Glu Ala Val Arg Leu Phe Ile Glu Trp Leu Lys Asn Gly Gly Pro Ser
                           20                  25                  30

Ser Gly Ala Pro Pro Lys Ser Gly Gly Leu Ala Glu Ala Lys Glu
                       35                  40                  45

Ala Ala Asn Ala Glu Leu Asp Ser Tyr Gly Val Ser Asp Phe Tyr Lys
                50                  55                  60

Arg Leu Ile Asp Lys Ala Lys Thr Val Glu Gly Val Glu Ala Leu Lys
             65                  70                  75                  80

Asp Ala Ile Leu Ala Ala Leu
                            85

<210> SEQ ID NO 786
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 786

His Gly Glu Gly Thr Phe Thr Ser Asp Leu Ser Lys Gln Met Glu Glu
             1               5                  10                  15

Glu Ala Val Arg Leu Phe Ile Glu Trp Leu Lys Asn Gly Gly Pro Ser
                           20                  25                  30

Ser Gly Ala Pro Pro Lys Ser Gly Gly Ser Leu Ala Glu Ala Lys Glu
                       35                  40                  45

Ala Ala Asn Ala Glu Leu Asp Ser Tyr Gly Val Ser Asp Phe Tyr Lys
                50                  55                  60

Arg Leu Ile Asp Lys Ala Lys Thr Val Glu Gly Val Glu Ala Leu Lys
             65                  70                  75                  80

Asp Ala Ile Leu Ala Ala Leu Pro
                            85

<210> SEQ ID NO 787
<211> LENGTH: 87
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 787

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Gly Ser Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu
                85

<210> SEQ ID NO 788
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 788

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Ser Leu Ala Glu Ala Lys Glu Ala
        35                  40                  45

Ala Asn Ala Glu Leu Asp Ser Tyr Gly Val Ser Asp Phe Tyr Lys Arg
    50                  55                  60

Leu Ile Asp Lys Ala Lys Thr Val Glu Gly Val Glu Ala Leu Lys Asp
65                  70                  75                  80

Ala Ile Leu Ala Ala Leu Pro
                85

<210> SEQ ID NO 789
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 789

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Ser Leu Ala Glu Ala Lys Glu Ala
        35                  40                  45

Ala Asn Ala Glu Leu Asp Ser Tyr Gly Val Ser Asp Phe Tyr Lys Arg
    50                  55                  60

Leu Ile Asp Lys Ala Lys Thr Val Glu Gly Val Glu Ala Leu Lys Asp
65                  70                  75                  80

```
Ala Ile Leu Ala Ala Leu
            85

<210> SEQ ID NO 790
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 790

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Leu Ala Glu Ala Lys Glu Ala Ala
        35                  40                  45

Asn Ala Glu Leu Asp Ser Tyr Gly Val Ser Asp Phe Tyr Lys Arg Leu
    50                  55                  60

Ile Asp Lys Ala Lys Thr Val Glu Gly Val Glu Ala Leu Lys Asp Ala
65                  70                  75                  80

Ile Leu Ala Ala Leu Pro
            85

<210> SEQ ID NO 791
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 791

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Lys Ser Gly Leu Ala Glu Ala Lys Glu Ala Ala
        35                  40                  45

Asn Ala Glu Leu Asp Ser Tyr Gly Val Ser Asp Phe Tyr Lys Arg Leu
    50                  55                  60

Ile Asp Lys Ala Lys Thr Val Glu Gly Val Glu Ala Leu Lys Asp Ala
65                  70                  75                  80

Ile Leu Ala Ala Leu
            85

<210> SEQ ID NO 792
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 792

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30
```

Ser Gly Ala Pro Pro Ser Thr Gly Gly Gly Ser Ala Ser Ser
            35                  40                  45

Leu Ala Glu Ala Lys Glu Ala Ala Asn Ala Glu Leu Asp Ser Tyr Gly
 50                  55                  60

Val Ser Asp Phe Tyr Lys Arg Leu Ile Asp Lys Ala Lys Thr Val Glu
 65                  70                  75                  80

Gly Val Glu Ala Leu Lys Asp Ala Ile Leu Ala Ala Leu Pro
                 85                  90

<210> SEQ ID NO 793
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 793

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Ser Thr Gly Gly Gly Ser Ala Ser Ser
            35                  40                  45

Leu Ala Glu Ala Lys Glu Ala Ala Asn Ala Glu Leu Asp Ser Tyr Gly
 50                  55                  60

Val Ser Asp Phe Tyr Lys Arg Leu Ile Asp Lys Ala Lys Thr Val Glu
 65                  70                  75                  80

Gly Val Glu Ala Leu Lys Asp Ala Ile Leu Ala Ala Leu
                 85                  90

<210> SEQ ID NO 794
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 794

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Ser Thr Gly Gly Gly Ser Ala Ser Leu
            35                  40                  45

Ala Glu Ala Lys Glu Ala Ala Asn Ala Glu Leu Asp Ser Tyr Gly Val
 50                  55                  60

Ser Asp Phe Tyr Lys Arg Leu Ile Asp Lys Ala Lys Thr Val Glu Gly
 65                  70                  75                  80

Val Glu Ala Leu Lys Asp Ala Ile Leu Ala Ala Leu Pro
                 85                  90

<210> SEQ ID NO 795
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 795

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Thr Gly Gly Gly Ser Ala Ser Leu
        35                  40                  45

Ala Glu Ala Lys Glu Ala Ala Asn Ala Glu Leu Asp Ser Tyr Gly Val
50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu
            85                  90

<210> SEQ ID NO 796
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 796

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Ser Leu Ala Glu Ala
        35                  40                  45

Lys Glu Ala Ala Asn Ala Glu Leu Asp Ser Tyr Gly Val Ser Asp Phe
    50                  55                  60

Tyr Lys Arg Leu Ile Asp Lys Ala Lys Thr Val Glu Gly Val Glu Ala
65                  70                  75                  80

Leu Lys Asp Ala Ile Leu Ala Ala Leu Pro
            85                  90

<210> SEQ ID NO 797
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 797

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Gly Ser Leu Ala Glu Ala
        35                  40                  45

Lys Glu Ala Ala Asn Ala Glu Leu Asp Ser Tyr Gly Val Ser Asp Phe
    50                  55                  60

Tyr Lys Arg Leu Ile Asp Lys Ala Lys Thr Val Glu Gly Val Glu Ala
65                  70                  75                  80

Leu Lys Asp Ala Ile Leu Ala Ala Leu
            85

```
<210> SEQ ID NO 798
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 798

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Gly Gly Gly Ser Leu Ala Glu Ala Lys
            35                  40                  45

Glu Ala Ala Asn Ala Glu Leu Asp Ser Tyr Gly Val Ser Asp Phe Tyr
50                  55                  60

Lys Arg Leu Ile Asp Lys Ala Lys Thr Val Glu Gly Val Glu Ala Leu
65                  70                  75                  80

Lys Asp Ala Ile Leu Ala Ala Leu Pro
                85

<210> SEQ ID NO 799
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 799

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Gly Gly Gly Ser Leu Ala Glu Ala Lys
            35                  40                  45

Glu Ala Ala Asn Ala Glu Leu Asp Ser Tyr Gly Val Ser Asp Phe Tyr
50                  55                  60

Lys Arg Leu Ile Asp Lys Ala Lys Thr Val Glu Gly Val Glu Ala Leu
65                  70                  75                  80

Lys Asp Ala Ile Leu Ala Ala Leu
                85

<210> SEQ ID NO 800
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 800

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Gly Gly Gly Leu Ala Glu Ala Lys Glu
            35                  40                  45

Ala Ala Asn Ala Glu Leu Asp Ser Tyr Gly Val Ser Asp Phe Tyr Lys
50                  55                  60
```

```
Arg Leu Ile Asp Lys Ala Lys Thr Val Glu Gly Val Glu Ala Leu Lys
 65                  70                  75                  80

Asp Ala Ile Leu Ala Ala Leu Pro
                 85
```

<210> SEQ ID NO 801
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 801

```
His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Ser Gly Gly Leu Ala Glu Ala Lys Glu
         35                  40                  45

Ala Ala Asn Ala Glu Leu Asp Ser Tyr Gly Val Ser Asp Phe Tyr Lys
 50                  55                  60

Arg Leu Ile Asp Lys Ala Lys Thr Val Glu Gly Val Glu Ala Leu Lys
 65                  70                  75                  80

Asp Ala Ile Leu Ala Ala Leu
                 85
```

<210> SEQ ID NO 802
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 802

```
His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
                20                  25                  30

Ser Gly Ala Pro Pro Ser Gly Ser Leu Ala Glu Ala Lys Glu Ala
         35                  40                  45

Ala Asn Ala Glu Leu Asp Ser Tyr Gly Val Ser Asp Phe Tyr Lys Arg
 50                  55                  60

Leu Ile Asp Lys Ala Lys Thr Val Glu Gly Val Glu Ala Leu Lys Asp
 65                  70                  75                  80

Ala Ile Leu Ala Ala Leu Pro
                 85
```

<210> SEQ ID NO 803
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 803

```
His Gly Glu Gly Thr Phe Thr Ser Asp Leu Ser Lys Gln Leu Glu Glu
 1               5                  10                  15
```

Glu Ala Val Arg Leu Phe Ile Glu Trp Leu Lys Asn Gly Gly Pro Ser
            20                  25                  30

Ser Gly Ala Pro Pro Ser Gly Ser Leu Ala Glu Ala Lys Glu Ala
        35                  40                  45

Ala Asn Ala Glu Leu Asp Ser Tyr Gly Val Ser Asp Phe Tyr Lys Arg
    50                  55                  60

Leu Ile Asp Lys Ala Lys Thr Val Glu Gly Val Glu Ala Leu Lys Asp
65                  70                  75                  80

Ala Ile Leu Ala Ala Leu
                85

<210> SEQ ID NO 804
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 804

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Leu Ala Glu Ala Lys Glu Ala Ala
        35                  40                  45

Asn Ala Glu Leu Asp Ser Tyr Gly Val Ser Asp Phe Tyr Lys Arg Leu
    50                  55                  60

Ile Asp Lys Ala Lys Thr Val Glu Gly Val Glu Ala Leu Lys Asp Ala
65                  70                  75                  80

Ile Leu Ala Ala Leu Pro
                85

<210> SEQ ID NO 805
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 805

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Leu Ala Glu Ala Lys Glu Ala Ala
        35                  40                  45

Asn Ala Glu Leu Asp Ser Tyr Gly Val Ser Asp Phe Tyr Lys Arg Leu
    50                  55                  60

Ile Asp Lys Ala Lys Thr Val Glu Gly Val Glu Ala Leu Lys Asp Ala
65                  70                  75                  80

Ile Leu Ala Ala Leu
                85

<210> SEQ ID NO 806
<211> LENGTH: 94
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 806

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Thr Gly Gly Gly Gly Ser Ala Ser Ser
        35                  40                  45

Leu Ala Glu Ala Lys Glu Ala Ala Asn Ala Glu Leu Asp Ser Tyr Gly
    50                  55                  60

Val Ser Asp Phe Tyr Lys Arg Leu Ile Asp Lys Ala Lys Thr Val Glu
65                  70                  75                  80

Gly Val Glu Ala Leu Lys Asp Ala Ile Leu Ala Ala Leu Pro
                85                  90

<210> SEQ ID NO 807
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 807

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Thr Gly Gly Gly Gly Ser Ala Ser Ser
        35                  40                  45

Leu Ala Glu Ala Lys Glu Ala Ala Asn Ala Glu Leu Asp Ser Tyr Gly
    50                  55                  60

Val Ser Asp Phe Tyr Lys Arg Leu Ile Asp Lys Ala Lys Thr Val Glu
65                  70                  75                  80

Gly Val Glu Ala Leu Lys Asp Ala Ile Leu Ala Ala Leu
                85                  90

<210> SEQ ID NO 808
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 808

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Thr Gly Gly Gly Gly Ser Ala Ser Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu Pro

```
                85                  90

<210> SEQ ID NO 809
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 809

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Thr Gly Gly Gly Gly Ser Ala Ser Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu
                85                  90

<210> SEQ ID NO 810
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 810

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Ser Leu Ala Glu Ala
        35                  40                  45

Lys Glu Ala Ala Asn Ala Glu Leu Asp Ser Tyr Gly Val Ser Asp Phe
    50                  55                  60

Tyr Lys Arg Leu Ile Asp Lys Ala Lys Thr Val Glu Gly Val Glu Ala
65                  70                  75                  80

Leu Lys Asp Ala Ile Leu Ala Ala Leu Pro
                85                  90

<210> SEQ ID NO 811
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 811

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Gly Gly Gly Gly Ser Leu Ala Glu Ala
        35                  40                  45
```

```
Lys Glu Ala Ala Asn Ala Glu Leu Asp Ser Tyr Gly Val Ser Asp Phe
 50                  55                  60

Tyr Lys Arg Leu Ile Asp Lys Ala Lys Thr Val Glu Gly Val Glu Ala
 65                  70                  75                  80

Leu Lys Asp Ala Ile Leu Ala Ala Leu
                 85
```

<210> SEQ ID NO 812
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 812

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Pro Ser Gly Gly Gly Ser Leu Ala Glu Ala Lys
             35                  40                  45

Glu Ala Ala Asn Ala Glu Leu Asp Ser Tyr Gly Val Ser Asp Phe Tyr
 50                  55                  60

Lys Arg Leu Ile Asp Lys Ala Lys Thr Val Glu Gly Val Glu Ala Leu
 65                  70                  75                  80

Lys Asp Ala Ile Leu Ala Ala Leu Pro
                 85
```

<210> SEQ ID NO 813
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 813

```
His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Pro Ser Gly Gly Gly Ser Leu Ala Glu Ala Lys
             35                  40                  45

Glu Ala Ala Asn Ala Glu Leu Asp Ser Tyr Gly Val Ser Asp Phe Tyr
 50                  55                  60

Lys Arg Leu Ile Asp Lys Ala Lys Thr Val Glu Gly Val Glu Ala Leu
 65                  70                  75                  80

Lys Asp Ala Ile Leu Ala Ala Leu
                 85
```

<210> SEQ ID NO 814
<211> LENGTH: 88
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 814

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu Pro
                85

<210> SEQ ID NO 815
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 815

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Gly Leu Ala Glu Ala Lys Glu
        35                  40                  45

Ala Ala Asn Ala Glu Leu Asp Ser Tyr Gly Val Ser Asp Phe Tyr Lys
    50                  55                  60

Arg Leu Ile Asp Lys Ala Lys Thr Val Glu Gly Val Glu Ala Leu Lys
65                  70                  75                  80

Asp Ala Ile Leu Ala Ala Leu
                85

<210> SEQ ID NO 816
<211> LENGTH: 87
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 816

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Ser Leu Ala Glu Ala Lys Glu Ala
        35                  40                  45

Ala Asn Ala Glu Leu Asp Ser Tyr Gly Val Ser Asp Phe Tyr Lys Arg
    50                  55                  60

Leu Ile Asp Lys Ala Lys Thr Val Glu Gly Val Glu Ala Leu Lys Asp
65                  70                  75                  80

Ala Ile Leu Ala Ala Leu Pro
                85

<210> SEQ ID NO 817
<211> LENGTH: 86

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 817

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Ser Leu Ala Glu Ala Lys Glu Ala
        35                  40                  45

Ala Asn Ala Glu Leu Asp Ser Tyr Gly Val Ser Asp Phe Tyr Lys Arg
50                  55                  60

Leu Ile Asp Lys Ala Lys Thr Val Glu Gly Val Glu Ala Leu Lys Asp
65                  70                  75                  80

Ala Ile Leu Ala Ala Leu
                85

<210> SEQ ID NO 818
<211> LENGTH: 86
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 818

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Leu Ala Glu Ala Lys Glu Ala Ala
        35                  40                  45

Asn Ala Glu Leu Asp Ser Tyr Gly Val Ser Asp Phe Tyr Lys Arg Leu
50                  55                  60

Ile Asp Lys Ala Lys Thr Val Glu Gly Val Glu Ala Leu Lys Asp Ala
65                  70                  75                  80

Ile Leu Ala Ala Leu Pro
                85

<210> SEQ ID NO 819
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 819

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Gly Leu Ala Glu Ala Lys Glu Ala Ala
        35                  40                  45

Asn Ala Glu Leu Asp Ser Tyr Gly Val Ser Asp Phe Tyr Lys Arg Leu
50                  55                  60

Ile Asp Lys Ala Lys Thr Val Glu Gly Val Glu Ala Leu Lys Asp Ala

```
                65                  70                  75                  80
Ile Leu Ala Ala Leu
                85

<210> SEQ ID NO 820
<211> LENGTH: 100
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 820

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Thr Gly Gly Gly
            35                  40                  45

Gly Ser Ala Ser Gly Ser Leu Ala Glu Ala Lys Glu Ala Ala Asn Ala
    50                  55                  60

Glu Leu Asp Ser Tyr Gly Val Ser Asp Phe Tyr Lys Arg Leu Ile Asp
65                  70                  75                  80

Lys Ala Lys Thr Val Glu Gly Val Glu Ala Leu Lys Asp Ala Ile Leu
                85                  90                  95

Ala Ala Leu Pro
            100

<210> SEQ ID NO 821
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 821

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Thr Gly Gly Gly
            35                  40                  45

Gly Ser Ala Ser Gly Ser Leu Ala Glu Ala Lys Glu Ala Ala Asn Ala
    50                  55                  60

Glu Leu Asp Ser Tyr Gly Val Ser Asp Phe Tyr Lys Arg Leu Ile Asp
65                  70                  75                  80

Lys Ala Lys Thr Val Glu Gly Val Glu Ala Leu Lys Asp Ala Ile Leu
                85                  90                  95

Ala Ala Leu

<210> SEQ ID NO 822
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 822
```

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Thr Gly Gly Gly
        35                  40                  45

Gly Ser Ala Ser Ser Leu Ala Glu Ala Lys Glu Ala Ala Asn Ala Glu
    50                  55                  60

Leu Asp Ser Tyr Gly Val Ser Asp Phe Tyr Arg Leu Ile Asp Lys
65                  70                  75                  80

Ala Lys Thr Val Glu Gly Val Glu Ala Leu Lys Asp Ala Ile Leu Ala
                85                  90                  95

Ala Leu Pro

<210> SEQ ID NO 823
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 823

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Thr Gly Gly Gly
        35                  40                  45

Gly Ser Ala Ser Ser Leu Ala Glu Ala Lys Glu Ala Ala Asn Ala Glu
    50                  55                  60

Leu Asp Ser Tyr Gly Val Ser Asp Phe Tyr Arg Leu Ile Asp Lys
65                  70                  75                  80

Ala Lys Thr Val Glu Gly Val Glu Ala Leu Lys Asp Ala Ile Leu Ala
                85                  90                  95

Ala Leu

<210> SEQ ID NO 824
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 824

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Thr Gly Gly Gly
        35                  40                  45

Gly Ser Ala Ser Leu Ala Glu Ala Lys Glu Ala Ala Asn Ala Glu Leu
    50                  55                  60

Asp Ser Tyr Gly Val Ser Asp Phe Tyr Arg Leu Ile Asp Lys Ala
65                  70                  75                  80

Lys Thr Val Glu Gly Val Glu Ala Leu Lys Asp Ala Ile Leu Ala Ala
                85                  90                  95

Leu Pro

<210> SEQ ID NO 825
<211> LENGTH: 97
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 825

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Thr Gly Gly Gly
            35                  40                  45

Gly Ser Ala Ser Leu Ala Glu Ala Lys Glu Ala Ala Asn Ala Glu Leu
    50                  55                  60

Asp Ser Tyr Gly Val Ser Asp Phe Tyr Lys Arg Leu Ile Asp Lys Ala
65                  70                  75                  80

Lys Thr Val Glu Gly Val Glu Ala Leu Lys Asp Ala Ile Leu Ala Ala
                85                  90                  95

Leu

<210> SEQ ID NO 826
<211> LENGTH: 95
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 826

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Gly Gly Gly Gly
            35                  40                  45

Ser Leu Ala Glu Ala Lys Glu Ala Ala Asn Ala Glu Leu Asp Ser Tyr
    50                  55                  60

Gly Val Ser Asp Phe Tyr Lys Arg Leu Ile Asp Lys Ala Lys Thr Val
65                  70                  75                  80

Glu Gly Val Glu Ala Leu Lys Asp Ala Ile Leu Ala Ala Leu Pro
                85                  90                  95

<210> SEQ ID NO 827
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 827

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
                20                  25                  30

Ser Gly Ala Pro Pro Ser Lys Lys Lys Lys Lys Gly Gly Gly
        35                  40                  45

Ser Leu Ala Glu Ala Lys Glu Ala Ala Asn Ala Glu Leu Asp Ser Tyr
 50                  55                  60

Gly Val Ser Asp Phe Tyr Lys Arg Leu Ile Asp Lys Ala Lys Thr Val
 65                  70                  75                  80

Glu Gly Val Glu Ala Leu Lys Asp Ala Ile Leu Ala Ala Leu
                 85                  90

<210> SEQ ID NO 828
<211> LENGTH: 94
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 828

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Ser Lys Lys Lys Lys Lys Gly Gly Gly Ser
        35                  40                  45

Leu Ala Glu Ala Lys Glu Ala Ala Asn Ala Glu Leu Asp Ser Tyr Gly
 50                  55                  60

Val Ser Asp Phe Tyr Lys Arg Leu Ile Asp Lys Ala Lys Thr Val Glu
 65                  70                  75                  80

Gly Val Glu Ala Leu Lys Asp Ala Ile Leu Ala Ala Leu Pro
                 85                  90

<210> SEQ ID NO 829
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 829

His Gly Glu Gly Thr Phe Thr Ser Asp Leu Ser Lys Gln Leu Glu Glu
 1               5                  10                  15

Glu Ala Val Arg Leu Phe Ile Glu Trp Leu Lys Asn Gly Gly Pro Ser
                 20                  25                  30

Ser Gly Ala Pro Pro Ser Lys Lys Lys Lys Lys Gly Gly Gly Ser
        35                  40                  45

Leu Ala Glu Ala Lys Glu Ala Ala Asn Ala Glu Leu Asp Ser Tyr Gly
 50                  55                  60

Val Ser Asp Phe Tyr Lys Arg Leu Ile Asp Lys Ala Lys Thr Val Glu
 65                  70                  75                  80

Gly Val Glu Ala Leu Lys Asp Ala Ile Leu Ala Ala Leu
                 85                  90

<210> SEQ ID NO 830
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 830

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Gly Gly Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu Pro
                85                  90

<210> SEQ ID NO 831
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 831

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Gly Gly Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu
                85                  90

<210> SEQ ID NO 832
<211> LENGTH: 93
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 832

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Gly Ser Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu Pro
                85                  90

<210> SEQ ID NO 833
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 833

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Gly Ser Leu
        35                  40                  45

Ala Glu Ala Lys Glu Ala Ala Asn Ala Glu Leu Asp Ser Tyr Gly Val
    50                  55                  60

Ser Asp Phe Tyr Lys Arg Leu Ile Asp Lys Ala Lys Thr Val Glu Gly
65                  70                  75                  80

Val Glu Ala Leu Lys Asp Ala Ile Leu Ala Ala Leu
                85                  90

<210> SEQ ID NO 834
<211> LENGTH: 92
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 834

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Ser Leu Ala
        35                  40                  45

Glu Ala Lys Glu Ala Ala Asn Ala Glu Leu Asp Ser Tyr Gly Val Ser
    50                  55                  60

Asp Phe Tyr Lys Arg Leu Ile Asp Lys Ala Lys Thr Val Glu Gly Val
65                  70                  75                  80

Glu Ala Leu Lys Asp Ala Ile Leu Ala Ala Leu Pro
                85                  90

<210> SEQ ID NO 835
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 835

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys Lys Lys Lys Lys Gly Ser Leu Ala
        35                  40                  45

Glu Ala Lys Glu Ala Ala Asn Ala Glu Leu Asp Ser Tyr Gly Val Ser

```
                    50                  55                  60

Asp Phe Tyr Lys Arg Leu Ile Asp Lys Ala Lys Thr Val Glu Gly Val
 65                  70                  75                  80

Glu Ala Leu Lys Asp Ala Ile Leu Ala Ala Leu
                 85                  90
```

<210> SEQ ID NO 836
<211> LENGTH: 91
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 836

```
His Gly Glu Gly Thr Phe Thr Ser Asp Leu Ser Lys Gln Leu Glu Glu
  1               5                  10                  15

Glu Ala Val Arg Leu Phe Ile Glu Trp Leu Lys Asn Gly Gly Pro Ser
                 20                  25                  30

Ser Gly Ala Pro Pro Ser Lys Lys Lys Lys Lys Gly Leu Ala Glu
             35                  40                  45

Ala Lys Glu Ala Ala Asn Ala Glu Leu Asp Ser Tyr Gly Val Ser Asp
 50                  55                  60

Phe Tyr Lys Arg Leu Ile Asp Lys Ala Lys Thr Val Glu Gly Val Glu
 65                  70                  75                  80

Ala Leu Lys Asp Ala Ile Leu Ala Ala Leu Pro
                 85                  90
```

<210> SEQ ID NO 837
<211> LENGTH: 90
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 837

```
His Gly Glu Gly Thr Phe Thr Ser Asp Leu Ser Lys Gln Leu Glu Glu
  1               5                  10                  15

Glu Ala Val Arg Leu Phe Ile Glu Trp Leu Lys Asn Gly Gly Pro Ser
                 20                  25                  30

Ser Gly Ala Pro Pro Ser Lys Lys Lys Lys Lys Gly Leu Ala Glu
             35                  40                  45

Ala Lys Glu Ala Ala Asn Ala Glu Leu Asp Ser Tyr Gly Val Ser Asp
 50                  55                  60

Phe Tyr Lys Arg Leu Ile Asp Lys Ala Lys Thr Val Glu Gly Val Glu
 65                  70                  75                  80

Ala Leu Lys Asp Ala Ile Leu Ala Ala Leu
                 85                  90
```

<210> SEQ ID NO 838
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 838

```
Met Ala His His His His His His Val Gly Thr Gly Ser Asn Glu Asn
  1               5                  10                  15
```

```
Leu Tyr Phe Gln His Gly Glu Gly Thr Phe Thr Ser Asp Leu Ser Lys
                 20                  25                  30

Gln Leu Glu Glu Glu Ala Val Arg Leu Phe Ile Glu Trp Leu Lys Gln
             35                  40                  45

Gly Gly Pro Ser Lys Glu Ile Ile Ser Thr Gly Gly Gly Ser Ala
     50                  55                  60

Ser Gly Ser Leu Ala Glu Ala Lys Glu Ala Asn Ala Glu Leu Asp
 65              70                  75                  80

Ser Tyr Gly Val Ser Asp Phe Tyr Lys Arg Leu Ile Asp Lys Ala Lys
                 85                  90                  95

Thr Val Glu Gly Val Glu Ala Leu Lys Asp Ala Ile Leu Ala Ala Leu
            100                 105                 110

Pro
```

<210> SEQ ID NO 839
<211> LENGTH: 252
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 839

```
Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65              70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
130                 135                 140

His Met Asp Ser Pro Asp Leu Gly Thr Glu Asn Leu Tyr Phe Gln His
145                 150                 155                 160

Gly Glu Gly Thr Phe Thr Ser Asp Leu Ser Lys Gln Leu Glu Glu Glu
                165                 170                 175

Ala Val Arg Leu Phe Ile Glu Trp Leu Lys Gln Gly Gly Pro Ser Lys
            180                 185                 190

Glu Ile Ile Ser Thr Gly Gly Gly Ser Ala Ser Gly Ser Leu Ala
        195                 200                 205

Glu Ala Lys Glu Ala Ala Asn Ala Glu Leu Asp Ser Tyr Gly Val Ser
    210                 215                 220

Asp Phe Tyr Lys Arg Leu Ile Asp Lys Ala Lys Thr Val Glu Gly Val
225                 230                 235                 240

Glu Ala Leu Lys Asp Ala Ile Leu Ala Ala Leu Pro
                245                 250
```

<210> SEQ ID NO 840
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 840

Met Ala His His His His His Val Gly Thr Gly Ser Asn Glu Asn
1               5                   10                  15

Leu Tyr Phe Gln His Gly Glu Gly Thr Phe Thr Ser Asp Leu Ser Lys
            20                  25                  30

Gln Leu Glu Glu Ala Val Arg Leu Phe Ile Glu Trp Leu Lys Asn
        35                  40                  45

Gly Gly Pro Ser Ser Gly Ala Pro Pro Ser Thr Gly Gly Gly
    50                  55                  60

Ser Ala Ser Gly Ser Leu Ala Glu Ala Lys Glu Ala Ala Asn Ala Glu
65                  70                  75                  80

Leu Asp Ser Tyr Gly Val Ser Asp Phe Tyr Lys Arg Leu Ile Asp Lys
                85                  90                  95

Ala Lys Thr Val Glu Gly Val Glu Ala Leu Lys Asp Ala Ile Leu Ala
            100                 105                 110

Ala Leu Pro
        115

<210> SEQ ID NO 841
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 841

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Glu Asn Leu Tyr Phe Gln His
145                 150                 155                 160

Gly Glu Gly Thr Phe Thr Ser Asp Leu Ser Lys Gln Leu Glu Glu Glu
                165                 170                 175

```
Ala Val Arg Leu Phe Ile Glu Trp Leu Lys Asn Gly Gly Pro Ser Ser
            180                 185                 190

Gly Ala Pro Pro Ser Thr Gly Gly Gly Ser Ala Ser Gly Ser
        195                 200                 205

Leu Ala Glu Ala Lys Glu Ala Ala Asn Ala Glu Leu Asp Ser Tyr Gly
210                 215                 220

Val Ser Asp Phe Tyr Lys Arg Leu Ile Asp Lys Ala Lys Thr Val Glu
225                 230                 235                 240

Gly Val Glu Ala Leu Lys Asp Ala Ile Leu Ala Ala Leu Pro
                245                 250

<210> SEQ ID NO 842
<211> LENGTH: 115
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 842

Met Ala His His His His His His Val Gly Thr Gly Ser Asn Glu Asn
1               5                   10                  15

Leu Tyr Phe Gln His Gly Glu Gly Thr Phe Thr Ser Asp Leu Ser Lys
            20                  25                  30

Gln Met Glu Glu Ala Val Arg Leu Phe Ile Glu Trp Leu Lys Asn
        35                  40                  45

Gly Gly Pro Ser Ser Gly Ala Pro Pro Ser Thr Gly Gly Gly Gly
    50                  55                  60

Ser Ala Ser Gly Ser Leu Ala Glu Ala Lys Glu Ala Ala Asn Ala Glu
65                  70                  75                  80

Leu Asp Ser Tyr Gly Val Ser Asp Phe Tyr Lys Arg Leu Ile Asp Lys
                85                  90                  95

Ala Lys Thr Val Glu Gly Val Glu Ala Leu Lys Asp Ala Ile Leu Ala
            100                 105                 110

Ala Leu Pro
        115

<210> SEQ ID NO 843
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 843

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95
```

```
Lys Gly Gln Leu Lys Glu Phe Leu Asp Ala Asn Leu Ala Gly Ser Gly
            100                 105                 110

Ser Gly His Met His His His His His Ser Ser Gly Leu Val Pro
            115                 120                 125

Arg Gly Ser Gly Met Lys Glu Thr Ala Ala Ala Lys Phe Glu Arg Gln
130                 135                 140

His Met Asp Ser Pro Asp Leu Gly Thr Glu Asn Leu Tyr Phe Gln His
145                 150                 155                 160

Gly Glu Gly Thr Phe Thr Ser Asp Leu Ser Lys Gln Met Glu Glu Glu
            165                 170                 175

Ala Val Arg Leu Phe Ile Glu Trp Leu Lys Asn Gly Gly Pro Ser Ser
            180                 185                 190

Gly Ala Pro Pro Pro Ser Thr Gly Gly Gly Ser Ala Ser Gly Ser
            195                 200                 205

Leu Ala Glu Ala Lys Glu Ala Ala Asn Ala Glu Leu Asp Ser Tyr Gly
            210                 215                 220

Val Ser Asp Phe Tyr Lys Arg Leu Ile Asp Lys Ala Lys Thr Val Glu
225                 230                 235                 240

Gly Val Glu Ala Leu Lys Asp Ala Ile Leu Ala Ala Leu Pro
            245                 250

<210> SEQ ID NO 844
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 844

Met Gly Ser Ser
1

<210> SEQ ID NO 845
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 845

Gly Ser Ser Leu
1

<210> SEQ ID NO 846
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 846

Met Ala His His His His His His Val Gly Thr Gly Ser Asn Glu Asn
1               5                   10                  15

Leu Tyr Phe Gln His Gly Glu Gly Thr Phe Thr Ser Asp Leu Ser Lys
            20                  25                  30

Gln Leu Glu Glu Glu Ala Val Arg Leu Phe Ile Glu Trp Leu Lys Gln
        35                  40                  45
```

```
Gly Gly Pro Ser Lys Glu Ile Ile Ser Thr Gly Gly Gly Ser Ala
 50                  55                  60

Ser Leu Ala Glu Ala Lys Val Leu Ala Asn Arg Glu Leu Asp Lys Tyr
 65                  70                  75                  80

Gly Val Ser Asp Phe Tyr Lys Arg Leu Ile Asn Lys Ala Lys Thr Val
                 85                  90                  95

Glu Gly Val Glu Ala Leu Lys Leu His Ile Leu Ala Ala Leu Pro
            100                 105                 110

<210> SEQ ID NO 847
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 847

His Gly Glu Gly Thr Phe Thr Ser Asp Leu Ser Lys Gln Leu Glu Glu
 1               5                   10                  15

Glu Ala Val Arg Leu Phe Ile Glu Trp Leu Lys Asn Thr Gly Gly Gly
             20                  25                  30

Gly Ser Ala Ser Gly Ser Leu Ala Glu Ala Lys Glu Ala Ala Asn Ala
         35                  40                  45

Glu Leu Asp Ser Tyr Gly Val Ser Asp Phe Tyr Lys Arg Leu Ile Asp
 50                  55                  60

Lys Ala Lys Thr Val Glu Gly Val Glu Ala Leu Lys Asp Ala Ile Leu
 65                  70                  75                  80

Ala Ala Leu Pro

<210> SEQ ID NO 848
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 848

Thr Gly Gly Gly Gly Ser
 1               5

<210> SEQ ID NO 849
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 849

Thr Gly Gly Gly Gly Ser Gly Gly Gly Ser
 1               5                   10

<210> SEQ ID NO 850
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 850
```

```
Thr Gly Gly Gly Gly Ser Gly Gly Gly Ser Gly Gly Gly Ser
1               5                   10
```

<210> SEQ ID NO 851
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 851

```
Thr Gly Gly Gly Gly Ser Gly Gly Gly Ser Gly Gly Gly Ser Gly Gly
1               5                   10                  15

Gly Ser
```

<210> SEQ ID NO 852
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 852

```
Thr Gly Gly Gly Gly Ser Gly Gly Gly Ser Gly Gly Gly Ser Gly Gly
1               5                   10                  15

Gly Ser Gly Gly Gly Ser
            20
```

<210> SEQ ID NO 853
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 853

```
Gly Gly Gly Ser Ala Ser
1               5
```

<210> SEQ ID NO 854
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 854

```
Gly Gly Gly Ser Gly Gly Gly Ser Ala Ser
1               5                   10
```

<210> SEQ ID NO 855
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 855

```
Gly Gly Gly Ser Gly Gly Gly Ser Gly Gly Gly Ser Ala Ser
1               5                   10
```

```
-continued

<210> SEQ ID NO 856
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 856

Gly Gly Gly Ser Gly Gly Gly Ser Gly Gly Gly Ser Gly Gly Gly Ser
1               5                   10                  15

Ala Ser

<210> SEQ ID NO 857
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 857

Gly Gly Gly Ser Gly Gly Gly Ser Gly Gly Gly Ser Gly Gly Gly Ser
1               5                   10                  15

Gly Gly Gly Ser Ala Ser
            20

<210> SEQ ID NO 858
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 858

Thr Gly Gly Gly Ser Gly Gly Gly Ser Ala Ser
1               5                   10

<210> SEQ ID NO 859
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 859

Thr Gly Gly Gly Gly Ser Gly Gly Gly Ser Gly Gly Gly Ser Ala Ser
1               5                   10                  15

<210> SEQ ID NO 860
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 860

Thr Gly Gly Gly Gly Ser Gly Gly Gly Ser Gly Gly Gly Ser Gly Gly
1               5                   10                  15

Gly Ser Ala Ser
        20

<210> SEQ ID NO 861
```

```
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 861

Thr Gly Gly Gly Gly Ser Gly Gly Gly Ser Gly Gly Gly Ser Gly Gly
1               5                   10                  15

Gly Ser Gly Gly Gly Ser Ala Ser
            20

<210> SEQ ID NO 862
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 862

Gly Ser Leu Ala Gln Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 863
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 863

Gly Ser Leu Ala Glu Ala Lys Glu Ala Ala Asn Arg Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 864
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 864

Gly Ser Leu Ala Gln Ala Lys Glu Ala Ala Asn Arg Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 865
<211> LENGTH: 48
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 865

Gly Ser Leu Ala Glu Ala Lys Glu Ala Ala Asn Arg Glu Leu Asp Ala
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 866
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 866

Gly Ser Leu Ala Glu Ala Lys Val Leu Ala Asn Arg Glu Leu Asp Lys
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 867
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 867

Ser Leu Ala Gln Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 868
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 868

Ser Leu Ala Glu Ala Lys Glu Ala Ala Asn Arg Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 869
<211> LENGTH: 47

<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 869

Ser Leu Ala Gln Ala Lys Glu Ala Ala Asn Arg Glu Leu Asp Ser Tyr
1               5                   10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ala Leu Pro
            35                  40                  45

<210> SEQ ID NO 870
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 870

Ser Leu Ala Glu Ala Lys Glu Ala Ala Asn Arg Glu Leu Asp Ala Tyr
1               5                   10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ala Leu Pro
            35                  40                  45

<210> SEQ ID NO 871
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 871

Ser Leu Ala Glu Ala Lys Val Leu Ala Asn Arg Glu Leu Asp Lys Tyr
1               5                   10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ala Leu Pro
            35                  40                  45

<210> SEQ ID NO 872
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 872

Leu Ala Glu Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Ala Ala Leu Pro
            35                  40                  45

<210> SEQ ID NO 873

```
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 873

Leu Ala Gln Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 874
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 874

Leu Ala Glu Ala Lys Glu Ala Ala Asn Arg Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 875
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 875

Leu Ala Glu Ala Lys Val Leu Ala Asn Arg Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 876
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 876

Gly Ser Leu Ala Gln Ala Lys Glu Ala Ala Asn Ala Glu Leu Asp Ser
1               5                   10                  15

Tyr Gly Val Ser Asp Phe Tyr Lys Arg Leu Ile Glu Lys Ala Lys Thr
            20                  25                  30

Val Glu Gly Val Glu Ala Leu Lys Asp Ala Ile Leu Ala Ala Leu Pro
        35                  40                  45
```

```
<210> SEQ ID NO 877
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 877

Gly Ser Leu Ala Glu Ala Lys Glu Ala Ala Asn Arg Glu Leu Asp Ser
1               5                   10                  15

Tyr Gly Val Ser Asp Phe Tyr Lys Arg Leu Ile Glu Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 878
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 878

Gly Ser Leu Ala Gln Ala Lys Glu Ala Ala Asn Arg Glu Leu Asp Ser
1               5                   10                  15

Tyr Gly Val Ser Asp Phe Tyr Lys Arg Leu Ile Glu Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 879
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 879

Gly Ser Leu Ala Glu Ala Lys Glu Ala Ala Asn Arg Glu Leu Asp Ala
1               5                   10                  15

Tyr Gly Val Ser Asp Phe Tyr Lys Arg Leu Ile Glu Lys Ala Lys Thr
            20                  25                  30

Val Glu Gly Val Glu Ala Leu Lys Asp Ala Ile Leu Ala Ala Leu Pro
        35                  40                  45

<210> SEQ ID NO 880
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 880

Gly Ser Leu Ala Glu Ala Lys Val Leu Ala Asn Arg Glu Leu Asp Lys
1               5                   10                  15

Tyr Gly Val Ser Asp Phe Tyr Lys Arg Leu Ile Glu Lys Ala Lys Thr
            20                  25                  30

Val Glu Gly Val Glu Ala Leu Lys Asp Ala Ile Leu Ala Ala Leu Pro
        35                  40                  45
```

<210> SEQ ID NO 881
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 881

Ser Leu Ala Gln Ala Lys Glu Ala Ala Asn Ala Glu Leu Asp Ser Tyr
1               5                   10                  15

Gly Val Ser Asp Phe Tyr Lys Arg Leu Ile Glu Lys Ala Lys Thr Val
                20                  25                  30

Glu Gly Val Glu Ala Leu Lys Asp Ala Ile Leu Ala Ala Leu Pro
            35                  40                  45

<210> SEQ ID NO 882
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 882

Ser Leu Ala Glu Ala Lys Glu Ala Ala Asn Arg Glu Leu Asp Ser Tyr
1               5                   10                  15

Gly Val Ser Asp Phe Tyr Lys Arg Leu Ile Glu Lys Ala Lys Thr Val
                20                  25                  30

Glu Gly Val Glu Ala Leu Lys Asp Ala Ile Leu Ala Ala Leu Pro
            35                  40                  45

<210> SEQ ID NO 883
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 883

Ser Leu Ala Gln Ala Lys Glu Ala Ala Asn Arg Glu Leu Asp Ser Tyr
1               5                   10                  15

Gly Val Ser Asp Phe Tyr Lys Arg Leu Ile Glu Lys Ala Lys Thr Val
                20                  25                  30

Glu Gly Val Glu Ala Leu Lys Asp Ala Ile Leu Ala Ala Leu Pro
            35                  40                  45

<210> SEQ ID NO 884
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 884

Ser Leu Ala Glu Ala Lys Glu Ala Ala Asn Arg Glu Leu Asp Ala Tyr
1               5                   10                  15

Gly Val Ser Asp Phe Tyr Lys Arg Leu Ile Glu Lys Ala Lys Thr Val
                20                  25                  30

Glu Gly Val Glu Ala Leu Lys Asp Ala Ile Leu Ala Ala Leu Pro
            35                  40                  45

<210> SEQ ID NO 885
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 885

Ser Leu Ala Glu Ala Lys Val Leu Ala Asn Arg Glu Leu Asp Lys Tyr
1               5                   10                  15

Gly Val Ser Asp Phe Tyr Lys Arg Leu Ile Glu Lys Ala Lys Thr Val
            20                  25                  30

Glu Gly Val Glu Ala Leu Lys Asp Ala Ile Leu Ala Ala Leu Pro
        35                  40                  45

<210> SEQ ID NO 886
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 886

Leu Ala Gln Ala Lys Glu Ala Ala Asn Ala Glu Leu Asp Ser Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 887
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 887

Leu Ala Glu Ala Lys Glu Ala Ala Asn Arg Glu Leu Asp Ser Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro
        35                  40                  45

<210> SEQ ID NO 888
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 888

Leu Ala Gln Ala Lys Glu Ala Ala Asn Arg Glu Leu Asp Ser Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro

-continued

```
            35                  40                  45
```

<210> SEQ ID NO 889
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 889

```
Leu Ala Glu Ala Lys Glu Ala Ala Asn Arg Glu Leu Asp Ala Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 890
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 890

```
Leu Ala Glu Ala Lys Val Leu Ala Asn Arg Glu Leu Asp Lys Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Asp Ala Ile Leu Ala Ala Leu Pro
        35                  40                  45
```

<210> SEQ ID NO 891
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 891

```
Gly Ser Leu Ala Gln Ala Lys Glu Ala Ala Asn Ala Glu Leu Asp Ser
1               5                   10                  15

Tyr Gly Val Ser Asp Phe Tyr Lys Arg Leu Ile Glu Lys Ala Lys Thr
            20                  25                  30

Val Glu Gly Val Glu Ala Leu Lys Glu Ala Ile Leu Ala Ala Leu Pro
        35                  40                  45
```

<210> SEQ ID NO 892
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 892

```
Gly Ser Leu Ala Glu Ala Lys Glu Ala Ala Asn Arg Glu Leu Asp Ser
1               5                   10                  15

Tyr Gly Val Ser Asp Phe Tyr Lys Arg Leu Ile Glu Lys Ala Lys Thr
            20                  25                  30
```

Val Glu Gly Val Glu Ala Leu Lys Glu Ala Ile Leu Ala Ala Leu Pro
            35                  40                  45

<210> SEQ ID NO 893
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 893

Gly Ser Leu Ala Gln Ala Lys Glu Ala Ala Asn Arg Glu Leu Asp Ser
1               5                   10                  15

Tyr Gly Val Ser Asp Phe Tyr Lys Arg Leu Ile Glu Lys Ala Lys Thr
            20                  25                  30

Val Glu Gly Val Glu Ala Leu Lys Glu Ala Ile Leu Ala Ala Leu Pro
            35                  40                  45

<210> SEQ ID NO 894
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 894

Gly Ser Leu Ala Glu Ala Lys Glu Ala Ala Asn Arg Glu Leu Asp Ala
1               5                   10                  15

Tyr Gly Val Ser Asp Phe Tyr Lys Arg Leu Ile Glu Lys Ala Lys Thr
            20                  25                  30

Val Glu Gly Val Glu Ala Leu Lys Glu Ala Ile Leu Ala Ala Leu Pro
            35                  40                  45

<210> SEQ ID NO 895
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 895

Gly Ser Leu Ala Glu Ala Lys Val Leu Ala Asn Arg Glu Leu Asp Lys
1               5                   10                  15

Tyr Gly Val Ser Asp Phe Tyr Lys Arg Leu Ile Glu Lys Ala Lys Thr
            20                  25                  30

Val Glu Gly Val Glu Ala Leu Lys Glu Ala Ile Leu Ala Ala Leu Pro
            35                  40                  45

<210> SEQ ID NO 896
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 896

Ser Leu Ala Gln Ala Lys Glu Ala Ala Asn Ala Glu Leu Asp Ser Tyr
1               5                   10                  15

Gly Val Ser Asp Phe Tyr Lys Arg Leu Ile Glu Lys Ala Lys Thr Val
            20                  25                  30

<210> SEQ ID NO 897
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 897

Ser Leu Ala Glu Ala Lys Glu Ala Ala Asn Arg Glu Leu Asp Ser Tyr
1               5                   10                  15

Gly Val Ser Asp Phe Tyr Lys Arg Leu Ile Glu Lys Ala Lys Thr Val
                20                  25                  30

Glu Gly Val Glu Ala Leu Lys Glu Ala Ile Leu Ala Ala Leu Pro
            35                  40                  45

<210> SEQ ID NO 898
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 898

Ser Leu Ala Gln Ala Lys Glu Ala Ala Asn Arg Glu Leu Asp Ser Tyr
1               5                   10                  15

Gly Val Ser Asp Phe Tyr Lys Arg Leu Ile Glu Lys Ala Lys Thr Val
                20                  25                  30

Glu Gly Val Glu Ala Leu Lys Glu Ala Ile Leu Ala Ala Leu Pro
            35                  40                  45

<210> SEQ ID NO 899
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 899

Ser Leu Ala Glu Ala Lys Glu Ala Ala Asn Arg Glu Leu Asp Ala Tyr
1               5                   10                  15

Gly Val Ser Asp Phe Tyr Lys Arg Leu Ile Glu Lys Ala Lys Thr Val
                20                  25                  30

Glu Gly Val Glu Ala Leu Lys Glu Ala Ile Leu Ala Ala Leu Pro
            35                  40                  45

<210> SEQ ID NO 900
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 900

Ser Leu Ala Glu Ala Lys Val Leu Ala Asn Arg Glu Leu Asp Lys Tyr
1               5                   10                  15

Gly Val Ser Asp Phe Tyr Lys Arg Leu Ile Glu Lys Ala Lys Thr Val

```
                20                  25                  30

Glu Gly Val Glu Ala Leu Lys Glu Ala Ile Leu Ala Ala Leu Pro
            35                  40                  45

<210> SEQ ID NO 901
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 901

Leu Ala Gln Ala Lys Glu Ala Ala Asn Ala Glu Leu Asp Ser Tyr Gly
1               5                   10                  15

Val Ser Asp Phe Tyr Lys Arg Leu Ile Glu Lys Ala Lys Thr Val Glu
                20                  25                  30

Gly Val Glu Ala Leu Lys Glu Ala Ile Leu Ala Ala Leu Pro
            35                  40                  45

<210> SEQ ID NO 902
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 902

Leu Ala Glu Ala Lys Glu Ala Ala Asn Arg Glu Leu Asp Ser Tyr Gly
1               5                   10                  15

Val Ser Asp Phe Tyr Lys Arg Leu Ile Glu Lys Ala Lys Thr Val Glu
                20                  25                  30

Gly Val Glu Ala Leu Lys Glu Ala Ile Leu Ala Ala Leu Pro
            35                  40                  45

<210> SEQ ID NO 903
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 903

Leu Ala Gln Ala Lys Glu Ala Ala Asn Arg Glu Leu Asp Ser Tyr Gly
1               5                   10                  15

Val Ser Asp Phe Tyr Lys Arg Leu Ile Glu Lys Ala Lys Thr Val Glu
                20                  25                  30

Gly Val Glu Ala Leu Lys Glu Ala Ile Leu Ala Ala Leu Pro
            35                  40                  45

<210> SEQ ID NO 904
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 904

Leu Ala Glu Ala Lys Glu Ala Ala Asn Arg Glu Leu Asp Ala Tyr Gly
1               5                   10                  15
```

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 905
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 905

Leu Ala Glu Ala Lys Val Leu Ala Asn Arg Glu Leu Asp Lys Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Glu Ala Ile Leu Ala Ala Leu Pro
        35                  40                  45

<210> SEQ ID NO 906
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 906

Gly Ser Leu Ala Gln Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ser Leu Pro
        35                  40                  45

<210> SEQ ID NO 907
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 907

Gly Ser Leu Ala Glu Ala Lys Glu Ala Ala Asn Arg Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ser Leu Pro
        35                  40                  45

<210> SEQ ID NO 908
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 908

Gly Ser Leu Ala Gln Ala Lys Glu Ala Ala Asn Arg Glu Leu Asp Ser
1               5                   10                  15

```
Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ser Leu Pro
        35                  40                  45

<210> SEQ ID NO 909
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 909

Gly Ser Leu Ala Glu Ala Lys Glu Ala Ala Asn Arg Glu Leu Asp Ala
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ser Leu Pro
        35                  40                  45

<210> SEQ ID NO 910
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 910

Gly Ser Leu Ala Glu Ala Lys Val Leu Ala Asn Arg Glu Leu Asp Lys
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Ser Leu Pro
        35                  40                  45

<210> SEQ ID NO 911
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 911

Ser Leu Ala Gln Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Ser Leu Pro
        35                  40                  45

<210> SEQ ID NO 912
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 912

Ser Leu Ala Glu Ala Lys Glu Ala Ala Asn Arg Glu Leu Asp Ser Tyr
```

```
                1               5                  10                  15
Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ser Leu Pro
                35                  40                  45
```

<210> SEQ ID NO 913
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 913

```
Ser Leu Ala Gln Ala Lys Glu Ala Ala Asn Arg Glu Leu Asp Ser Tyr
1               5                  10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ser Leu Pro
                35                  40                  45
```

<210> SEQ ID NO 914
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 914

```
Ser Leu Ala Glu Ala Lys Glu Ala Ala Asn Arg Glu Leu Asp Ala Tyr
1               5                  10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ser Leu Pro
                35                  40                  45
```

<210> SEQ ID NO 915
<211> LENGTH: 47
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 915

```
Ser Leu Ala Glu Ala Lys Val Leu Ala Asn Arg Glu Leu Asp Lys Tyr
1               5                  10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Ala Ser Leu Pro
                35                  40                  45
```

<210> SEQ ID NO 916
<211> LENGTH: 46
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 916

```
Leu Ala Gln Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45
```

<210> SEQ ID NO 917
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 917

```
Leu Ala Glu Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45
```

<210> SEQ ID NO 918
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 918

```
Leu Ala Gln Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45
```

<210> SEQ ID NO 919
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 919

```
Leu Ala Glu Ala Lys Glu Ala Ala Asn Arg Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45
```

<210> SEQ ID NO 920
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 920

-continued

Leu Ala Glu Ala Lys Val Leu Ala Asn Arg Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Ser Leu Pro
        35                  40                  45

<210> SEQ ID NO 921
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 921

Gly Ser Leu Ala Gln Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Glu Leu Pro
        35                  40                  45

<210> SEQ ID NO 922
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 922

Gly Ser Leu Ala Glu Ala Lys Glu Ala Ala Asn Arg Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Glu Leu Pro
        35                  40                  45

<210> SEQ ID NO 923
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 923

Gly Ser Leu Ala Gln Ala Lys Glu Ala Ala Asn Arg Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Glu Leu Pro
        35                  40                  45

<210> SEQ ID NO 924
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

```
<400> SEQUENCE: 924

Gly Ser Leu Ala Glu Ala Lys Glu Ala Ala Asn Arg Glu Leu Asp Ala
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Glu Leu Pro
        35                  40                  45

<210> SEQ ID NO 925
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 925

Gly Ser Leu Ala Glu Ala Lys Val Leu Ala Asn Arg Glu Leu Asp Lys
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Ala Glu Leu Pro
        35                  40                  45

<210> SEQ ID NO 926
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 926

Ser Leu Ala Gln Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Glu Leu Pro
        35                  40                  45

<210> SEQ ID NO 927
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 927

Ser Leu Ala Glu Ala Lys Glu Ala Ala Asn Arg Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Glu Leu Pro
        35                  40                  45

<210> SEQ ID NO 928
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
```

```
<400> SEQUENCE: 928

Ser Leu Ala Gln Ala Lys Glu Ala Ala Asn Arg Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Glu Leu Pro
        35                  40                  45

<210> SEQ ID NO 929
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 929

Ser Leu Ala Glu Ala Lys Glu Ala Ala Asn Arg Glu Leu Asp Ala Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Glu Leu Pro
        35                  40                  45

<210> SEQ ID NO 930
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 930

Ser Leu Ala Glu Ala Lys Val Leu Ala Asn Arg Glu Leu Asp Lys Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Ala Glu Leu Pro
        35                  40                  45

<210> SEQ ID NO 931
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 931

Leu Ala Gln Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Glu Leu Pro
        35                  40                  45

<210> SEQ ID NO 932
<211> LENGTH: 46
<212> TYPE: PRT
<213> ORGANISM: Artificial Sequence
<220> FEATURE:
<223> OTHER INFORMATION: Description of Artificial Sequence: Synthetic
```

-continued polypeptide

<400> SEQUENCE: 932

Leu Ala Glu Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Glu Leu Pro
        35                  40                  45

<210> SEQ ID NO 933
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 933

Leu Ala Gln Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Glu Leu Pro
        35                  40                  45

<210> SEQ ID NO 934
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 934

Leu Ala Glu Ala Lys Glu Ala Ala Asn Arg Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Glu Leu Pro
        35                  40                  45

<210> SEQ ID NO 935
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 935

Leu Ala Glu Ala Lys Val Leu Ala Asn Arg Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Ala Glu Leu Pro
        35                  40                  45

<210> SEQ ID NO 936
<211> LENGTH: 48
<212> TYPE: PRT
<213> ORGANISM: Artificial Sequence
<220> FEATURE:

-continued

<223> OTHER INFORMATION: Description of Artificial Sequence: Synthetic
      polypeptide

<400> SEQUENCE: 936

Gly Ser Leu Ala Gln Ala Lys Glu Ala Ala Asn Ala Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Lys Ala Leu Pro
        35                  40                  45

<210> SEQ ID NO 937
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 937

Gly Ser Leu Ala Glu Ala Lys Glu Ala Ala Asn Arg Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Lys Ala Leu Pro
        35                  40                  45

<210> SEQ ID NO 938
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 938

Gly Ser Leu Ala Gln Ala Lys Glu Ala Ala Asn Arg Glu Leu Asp Ser
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Lys Ala Leu Pro
        35                  40                  45

<210> SEQ ID NO 939
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 939

Gly Ser Leu Ala Glu Ala Lys Glu Ala Ala Asn Arg Glu Leu Asp Ala
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Lys Ala Leu Pro
        35                  40                  45

<210> SEQ ID NO 940
<211> LENGTH: 48
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 940

Gly Ser Leu Ala Glu Ala Lys Val Leu Ala Asn Arg Glu Leu Asp Lys
1               5                   10                  15

Tyr Gly Val Ser Asp Phe Tyr Lys Arg Leu Ile Asp Lys Ala Lys Thr
            20                  25                  30

Val Glu Gly Val Glu Ala Leu Lys Asp Ala Ile Leu Lys Ala Leu Pro
        35                  40                  45

<210> SEQ ID NO 941
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 941

Ser Leu Ala Gln Ala Lys Glu Ala Ala Asn Ala Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Lys Ala Leu Pro
        35                  40                  45

<210> SEQ ID NO 942
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 942

Ser Leu Ala Glu Ala Lys Glu Ala Ala Asn Arg Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Lys Ala Leu Pro
        35                  40                  45

<210> SEQ ID NO 943
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 943

Ser Leu Ala Gln Ala Lys Glu Ala Ala Asn Arg Glu Leu Asp Ser Tyr
1               5                   10                  15

Gly Val Ser Asp Phe Tyr Lys Arg Leu Ile Asp Lys Ala Lys Thr Val
            20                  25                  30

Glu Gly Val Glu Ala Leu Lys Asp Ala Ile Leu Lys Ala Leu Pro
        35                  40                  45

<210> SEQ ID NO 944
<211> LENGTH: 47
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 944

Ser Leu Ala Glu Ala Lys Glu Ala Ala Asn Arg Glu Leu Asp Ala Tyr
1               5                   10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Lys Ala Leu Pro
        35                  40                  45

<210> SEQ ID NO 945
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 945

Ser Leu Ala Glu Ala Lys Val Leu Ala Asn Arg Glu Leu Asp Lys Tyr
1               5                   10                  15

Gly Val Ser Asp Phe Tyr Lys Arg Leu Ile Asp Lys Ala Lys Thr Val
                20                  25                  30

Glu Gly Val Glu Ala Leu Lys Asp Ala Ile Leu Lys Ala Leu Pro
        35                  40                  45

<210> SEQ ID NO 946
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 946

Leu Ala Gln Ala Lys Glu Ala Ala Asn Ala Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Lys Ala Leu Pro
        35                  40                  45

<210> SEQ ID NO 947
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 947

Leu Ala Glu Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
                20                  25                  30

Gly Val Glu Ala Leu Lys Asp Ala Ile Leu Lys Ala Leu Pro
        35                  40                  45

<210> SEQ ID NO 948
<211> LENGTH: 46
```

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 948

Leu Ala Gln Ala Lys Glu Ala Ala Asn Arg Glu Leu Asp Ser Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Lys Ala Leu Pro
        35                  40                  45

<210> SEQ ID NO 949
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 949

Leu Ala Glu Ala Lys Glu Ala Ala Asn Arg Glu Leu Asp Ala Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Lys Ala Leu Pro
        35                  40                  45

<210> SEQ ID NO 950
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 950

Leu Ala Glu Ala Lys Val Leu Ala Asn Arg Glu Leu Asp Lys Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Asp Ala Ile Leu Lys Ala Leu Pro
        35                  40                  45

<210> SEQ ID NO 951
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
```

```
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 951

Leu Ala Xaa Ala Lys Ser Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 952
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
```

```
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 952

Leu Ala Xaa Ala Lys Glu Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 953
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 953

Leu Ala Ser Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45
```

```
<210> SEQ ID NO 954
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 954

Leu Ala Glu Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 955
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
```

```
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 955

Leu Ala Gln Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 956
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
```

```
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 956

Leu Ala Xaa Ala Lys Xaa Ala Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 957
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 957

Leu Ala Xaa Ala Lys Xaa Ser Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30
```

Gly Val Glu Ala Leu Lys Xaa Xaa Ile Leu Xaa Xaa Leu Pro
            35                  40                  45

<210> SEQ ID NO 958
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 958

Leu Ala Xaa Ala Lys Xaa Xaa Ala Asn Ala Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
            35                  40                  45

<210> SEQ ID NO 959
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys

```
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 959

Leu Ala Xaa Ala Lys Xaa Xaa Ala Asn Ser Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 960
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
```

```
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 960

Leu Ala Xaa Ala Lys Xaa Xaa Ala Asn Arg Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 961
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 961

Leu Ala Xaa Ala Lys Xaa Xaa Ala Asn Xaa Glu Leu Asp Ser Tyr Gly
1               5                   10                  15
```

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 962
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 962

Leu Ala Xaa Ala Lys Xaa Xaa Ala Asn Xaa Glu Leu Asp Cys Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 963
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:

```
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 963

Leu Ala Xaa Ala Lys Xaa Xaa Ala Asn Xaa Glu Leu Asp Lys Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 964
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
```

```
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 964

Leu Ala Xaa Ala Lys Xaa Xaa Ala Asn Xaa Glu Leu Asp Ala Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 965
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 965
```

```
Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Asp Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 966
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 966

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Glu Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 967
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
```

```
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 967

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Asp Xaa Ile Leu Xaa Xaa Leu Pro
        35                  40                  45

<210> SEQ ID NO 968
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
```

```
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 968

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Glu Xaa Ile Leu Xaa Xaa Leu Pro
        35                  40                  45

<210> SEQ ID NO 969
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present
```

<400> SEQUENCE: 969

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Ala Ile Leu Xaa Xaa Leu Pro
        35                  40                  45

<210> SEQ ID NO 970
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 970

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Glu Ile Leu Xaa Xaa Leu Pro
        35                  40                  45

<210> SEQ ID NO 971
<211> LENGTH: 46
<212> TYPE: PRT
<213> ORGANISM: Artificial Sequence
<220> FEATURE:
<223> OTHER INFORMATION: Description of Artificial Sequence: Synthetic

```
        polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 971

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Ala Xaa Leu Pro
        35                  40                  45

<210> SEQ ID NO 972
<211> LENGTH: 46
<212> TYPE: PRT
<213> ORGANISM: Artificial Sequence
<220> FEATURE:
<223> OTHER INFORMATION: Description of Artificial Sequence: Synthetic
        polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
```

```
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(46)
<223> OTHER INFORMATION: May or may not be present

<400> SEQUENCE: 972

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Lys Xaa Leu Pro
        35                  40                  45

<210> SEQ ID NO 973
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
```

-continued

```
<221> NAME/KEY: MOD_RES
<222> LOCATION: (45)..(46)
<223> OTHER INFORMATION: May or may not be present

<400> SEQUENCE: 973

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Ala Leu Pro
        35                  40                  45

<210> SEQ ID NO 974
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (45)..(46)
<223> OTHER INFORMATION: May or may not be present

<400> SEQUENCE: 974

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Ser Leu Pro
        35                  40                  45

<210> SEQ ID NO 975
<211> LENGTH: 46
<212> TYPE: PRT
```

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (45)..(46)
<223> OTHER INFORMATION: May or may not be present

<400> SEQUENCE: 975

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
                20                  25                  30

Gly Val Glu Ala Leu Lys Xaa Xaa Ile Leu Xaa Glu Leu Pro
            35                  40                  45

<210> SEQ ID NO 976
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
```

```
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (46)..(46)
<223> OTHER INFORMATION: May or may not be present

<400> SEQUENCE: 976

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 977
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
```

```
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(45)
<223> OTHER INFORMATION: May or may not be present

<400> SEQUENCE: 977

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Pro
        35                  40                  45

<210> SEQ ID NO 978
<211> LENGTH: 46
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(45)
<223> OTHER INFORMATION: May or may not be present
```

<400> SEQUENCE: 978

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu Pro
        35                  40                  45

<210> SEQ ID NO 979
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Glu, Ser, Gln or Cys
<220> FEATURE:
<221> NAME/KEY: MOD_RES
<222> LOCATION: (6)..(6)
<223> OTHER INFORMATION: Glu, Ser or Cys
<220> FEATURE:
<221> NAME/KEY: MOD_RES
<222> LOCATION: (7)..(7)
<223> OTHER INFORMATION: Ala or Ser
<220> FEATURE:
<221> NAME/KEY: MOD_RES
<222> LOCATION: (10)..(10)
<223> OTHER INFORMATION: Ala, Ser or Arg
<220> FEATURE:
<221> NAME/KEY: MOD_RES
<222> LOCATION: (14)..(14)
<223> OTHER INFORMATION: Ala, Ser, Cys or Lys
<220> FEATURE:
<221> NAME/KEY: MOD_RES
<222> LOCATION: (26)..(26)
<223> OTHER INFORMATION: Asp or Glu
<220> FEATURE:
<221> NAME/KEY: MOD_RES
<222> LOCATION: (39)..(39)
<223> OTHER INFORMATION: Asp or Glu
<220> FEATURE:
<221> NAME/KEY: MOD_RES
<222> LOCATION: (40)..(40)
<223> OTHER INFORMATION: Ala or Glu
<220> FEATURE:
<221> NAME/KEY: MOD_RES
<222> LOCATION: (43)..(43)
<223> OTHER INFORMATION: Ala or Lys
<220> FEATURE:
<221> NAME/KEY: MOD_RES
<222> LOCATION: (44)..(44)
<223> OTHER INFORMATION: Ala, Ser or Glu
<220> FEATURE:
<221> NAME/KEY: MOD_RES
<222> LOCATION: (45)..(45)
<223> OTHER INFORMATION: May or may not be present

<400> SEQUENCE: 979

Leu Ala Xaa Ala Lys Xaa Xaa Ala Asn Xaa Glu Leu Asp Xaa Tyr Gly
1               5                   10                  15

Val Ser Asp Phe Tyr Lys Arg Leu Ile Xaa Lys Ala Lys Thr Val Glu
            20                  25                  30

Gly Val Glu Ala Leu Lys Xaa Xaa Ile Leu Xaa Xaa Leu
        35                  40                  45

<210> SEQ ID NO 980
<211> LENGTH: 28
<212> TYPE: PRT

<213> ORGANISM: Heloderma suspectum

<400> SEQUENCE: 980

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 981
<211> LENGTH: 29
<212> TYPE: PRT
<213> ORGANISM: Heloderma suspectum

<400> SEQUENCE: 981

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly
            20                  25

<210> SEQ ID NO 982
<211> LENGTH: 31
<212> TYPE: PRT
<213> ORGANISM: Heloderma suspectum

<400> SEQUENCE: 982

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro
            20                  25                  30

<210> SEQ ID NO 983
<211> LENGTH: 32
<212> TYPE: PRT
<213> ORGANISM: Heloderma suspectum

<400> SEQUENCE: 983

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

<210> SEQ ID NO 984
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: This position may be 4-imidazoacetyl, des-
      amino-histidyl, imidazopropionyl, beta-hydroxy-imidazopropionyl,
      N-dimethyl-histidyl, or beta-carboxy-imidazopropionyl

<400> SEQUENCE: 984

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

-continued

<210> SEQ ID NO 985
<211> LENGTH: 85
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 985

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Ser Leu Ala Glu Ala Lys Glu Ala Ala Asn
        35                  40                  45

Ala Glu Leu Asp Ser Tyr Gly Val Ser Asp Phe Tyr Lys Arg Leu Ile
    50                  55                  60

Asp Lys Ala Lys Thr Val Glu Gly Val Glu Ala Leu Lys Asp Ala Ile
65                  70                  75                  80

Leu Ala Ala Leu Pro
                85

<210> SEQ ID NO 986
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 986

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Ser Leu Ala Glu Ala Lys Glu Ala Ala Asn
        35                  40                  45

Ala Glu Leu Asp Ser Tyr Gly Val Ser Asp Phe Tyr Lys Arg Leu Ile
    50                  55                  60

Asp Lys Ala Lys Thr Val Glu Gly Val Glu Ala Leu Lys Asp Ala Ile
65                  70                  75                  80

Leu Ala Ala Leu

<210> SEQ ID NO 987
<211> LENGTH: 84
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 987

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Leu Ala Glu Ala Lys Glu Ala Ala Asn Ala
        35                  40                  45

```
Glu Leu Asp Ser Tyr Gly Val Ser Asp Phe Tyr Lys Arg Leu Ile Asp
    50              55                  60

Lys Ala Lys Thr Val Glu Gly Val Glu Ala Leu Lys Asp Ala Ile Leu
65              70                  75                  80

Ala Ala Leu Pro

<210> SEQ ID NO 988
<211> LENGTH: 83
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 988

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser Gly Leu Ala Glu Ala Lys Glu Ala Ala Asn Ala
        35                  40                  45

Glu Leu Asp Ser Tyr Gly Val Ser Asp Phe Tyr Lys Arg Leu Ile Asp
    50              55                  60

Lys Ala Lys Thr Val Glu Gly Val Glu Ala Leu Lys Asp Ala Ile Leu
65              70                  75                  80

Ala Ala Leu
```

US 9,382,304 B2

ENGINEERED POLYPEPTIDES HAVING ENHANCED DURATION OF ACTION WITH REDUCED IMMUNOGENICITY

CROSS-REFERENCES TO RELATED APPLICATIONS

This application is a national phase of International Application No. PCT/US2012/045451, filed Jul. 3, 2012, which claims priority to U.S. Ser. No. 61/505,982 filed 8 Jul. 2011 and U.S. Ser. No. 61/585,577 filed 11 Jan. 2012; the disclosure of each of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Jun. 22, 2012, is named 0263WO1.txt and is 366,392 bytes in size.

BACKGROUND OF THE INVENTION

The present application relates to compounds having good duration of action, high potency and/or convenient dosing regimens, including oral administration, and method of use thereof. There are provided herein engineered polypeptides which incorporate an albumin binding domain in combination with a biologically active peptide. Without wishing to be bound by any theory, it is believed that because the engineered polypeptides described herein can bind albumin, the compounds can be sequestered (e.g., bound to albumin) while in the circulation leading to increased duration of action, due for example to decreased renal clearance and/or degradation. Diseases amendable to such treatment include obesity and overweight, diabetes, dyslipidemia, hyperlipidemia, short bowel syndrome, Alzheimer's disease, fatty liver disease, Parkinson's disease, cardiovascular disease, and other disorders of the central nervous system, or combinations thereof.

There remains a need to develop polypeptides useful in the above described metabolic diseases, conditions and disorders. Accordingly, it is an object of the present invention to provide engineered polypeptides with extended half-lives useful to treat the above conditions and methods for producing and using them.

Each patent, patent application, and publication cited herein is hereby incorporated herein by reference in its entirety and for all purposes.

BRIEF SUMMARY OF THE INVENTION

There are provided engineered polypeptide compounds having binding affinity for albumin and an additional therapeutic utility. The compounds are engineered polypeptides which include an albumin binding domain (ABD) polypeptide as defined herein capable of binding albumin and a hormone domain (HD) polypeptide, which HD polypeptides can be biologically active and can elicit a beneficial biological response, in covalent linkage with the ABD. Any of the ABD or HD polypeptides described herein can be optionally covalently bonded in the engineered polypeptide through a linker L, for example L1 as described herein. Without wishing to be bound by any theory, it is believed that because the engineered polypeptides described herein can bind albumin, the compounds can be sequestered in a subject leading to increased duration of action in the subject.

In a first aspect, there is provided an engineered polypeptide as described herein. The engineered polypeptide includes an albumin binding domain polypeptide (ABD) as described herein and a hormone domain (HD1). The hormone domain includes a polypeptide which is an exendin, a fragment of an exendin, or analog of an exendin.

In another aspect, there is provided a method for treating a disease or disorder in a subject in need of treatment. The method includes administering an engineered polypeptide as described herein to the subject.

In yet another aspect, there is provided a pharmaceutical composition which includes an engineered polypeptide compound described herein in combination with a pharmaceutically acceptable excipient.

In yet another aspect are polynucleotides encoding the engineered polypeptide and their intermediates, expression vectors bearing such polynucleotides, host cells expressing such polynucleotides, and means for their expression, synthesis, post-translational modification and isolation.

One advantage of the present invention is that the engineered polypeptides can be synthesized completely by recombinant methods, avoiding complex or additional synthetic or chemical steps and associated reactive reagents and catalysts. Consequently, the polypeptides of the present invention can be much less expensive to synthesize than chemically derivatized compounds of prolonged duration of action. In addition to a long duration of action (e.g., at least one week in a human subject, albeit once daily can also be achieved if desired), a further advantage is their relatively small size, which can allow for oral delivery to improve patient compliance.

The compounds disclosed herein demonstrate surprising efficacy in an OGTT DOA (oral glucose tolerance test for duration of action) test of at least 24 hours and even longer to two days in mice, which translates to five to seven days or longer in humans, a robust glycemic control, body weight loss, a dose-dependent reduction of food intake and body weight. In rats compound exposure upon a single administration lasts for as 4 to 7 days, which translates to at least once a week exposure in humans. Compounds are stable in plasma and to plasma proteases, are active while bound to serum albumin and can provide in vivo maximal efficacy similar to or greater than exendin-4. Even more surprisingly the compounds are suitable for oral delivery.

BRIEF DESCRIPTION OF THE DRAWINGS

FIG. 1A-F is a listing of the amino acid sequences of examples of albumin binding polypeptides (SEQ ID NO:301-452, SEQ ID NO:455-461) useful in the engineered polypeptides disclosed herein, the GA3 domain from protein G of *Streptococcus* strain G148 (SEQ ID NO:453) extended by a N-terminal glycine residue and an albumin binding polypeptide derived from G148-GA3 as previously described by Jonsson et al (Protein Eng. Design & Selection, 2008, 21:515-527); SEQ ID NO:454).

(SEQ ID NO:457), PEP07554 (SEQ ID NO:456), PEP07914 (SEQ ID NO:458), PEP07968 (i.e. DOTA conjugated to PEP07911 (SEQ ID NO:459)) and PEP07844 (SEQ ID NO:461), to IgG molecules present in 126 individual normal human sera, where A) shows the average OD-value, B) shows the percentage of negative sera (defined as OD<0.15), and C) shows the percentage of positive sera (defined as OD>1.0).

Figures 4A, 4B, 4C:
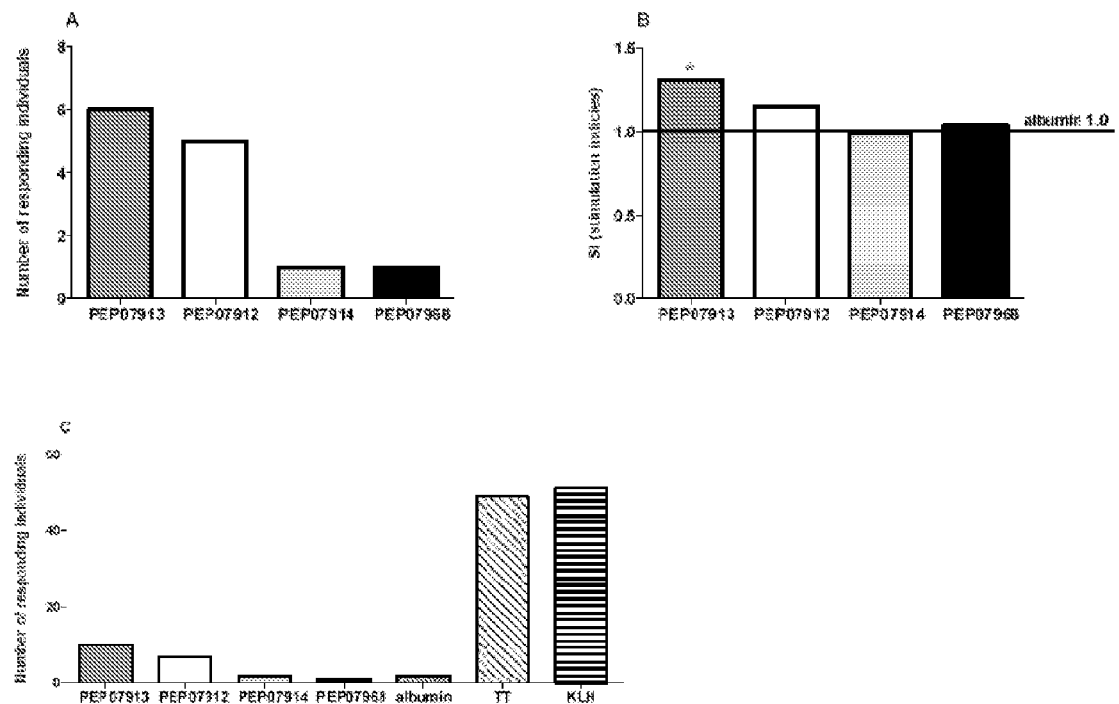

FIGS. 4A-C are diagrams showing an immunogenicity assessment of albumin binding polypeptides PEP07913 (SEQ ID NO:453), PEP07912 (SEQ ID NO:457), PEP07914 (SEQ ID NO:458) and PEP07968 (i.e. DOTA conjugated to PEP07911 (SEQ ID NO:459)) in a CD3+ CD4+ T cell proliferation assay. A) shows the number of individuals responding to the albumin binding polypeptides compared to recombinant human albumin in a cohort of 52 Caucasian donors. B) shows the average stimulation indices (SI) for PEP07913, PEP07912, PEP07914 and PEP07968 compared to the negative control containing recombinant human albumin. C) shows the number of responding individuals against all proteins in the study as compared to the buffer control.

Figure 5A:
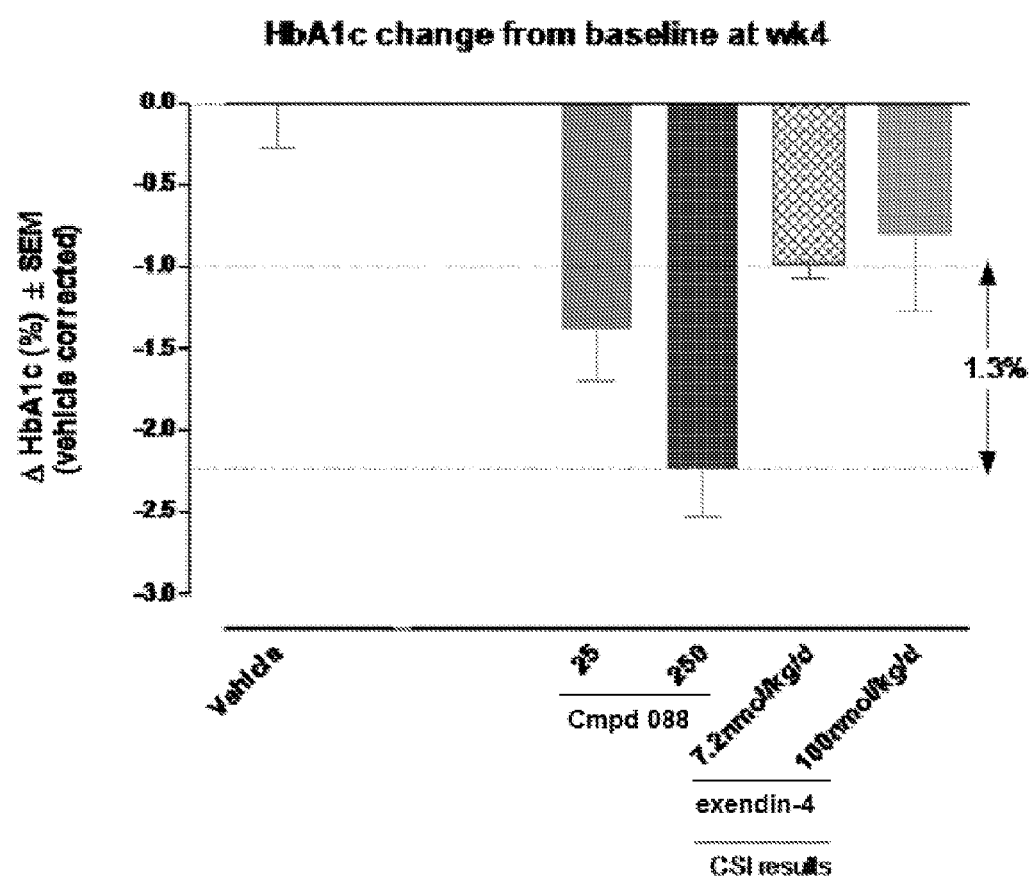
Figure 5B:
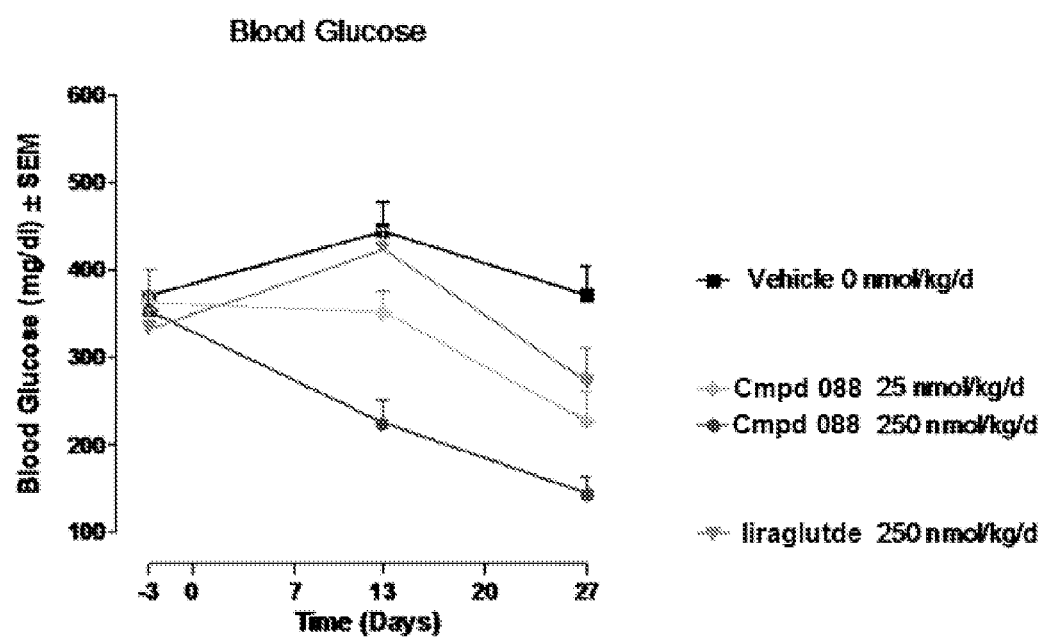
Figure 5C:
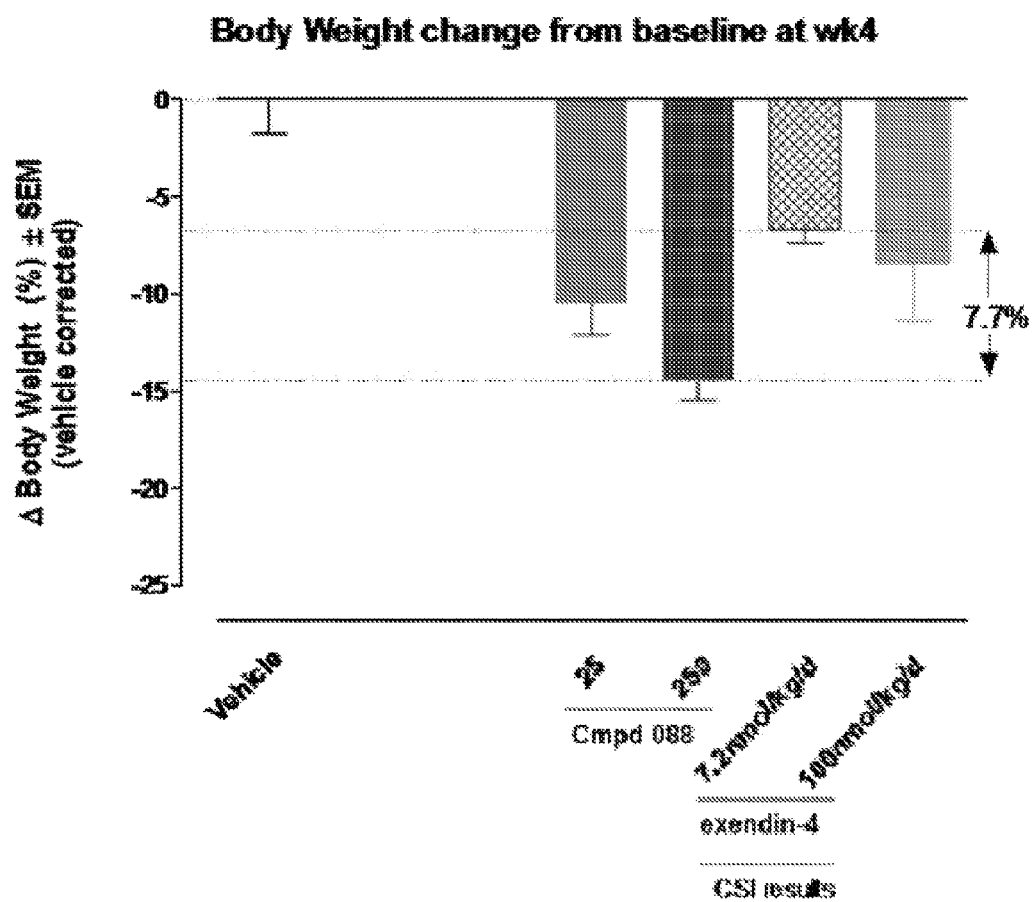

FIGS. 5A-5C. Effect of albumin-binding engineered polypeptides in ob/ob mice after four weeks of administration. FIG. 5A: change in HbA1c (hemoglobin A1c) at the indicated day after twice per week injection of Cmpd 088 at 25 or 250 nmol/kg compared to continuously infused (CSI) exendin-4 at 7.2 or 100 nanomoles/kg/day. FIG. 5B: change in blood glucose after dosage as described for FIG. 5A. FIG. 5C: change in body weight after dosage as described for FIG. 5A. * p<0.5 vs. Vehicle control; Anova, Dunnett's test.

Figure 6A:
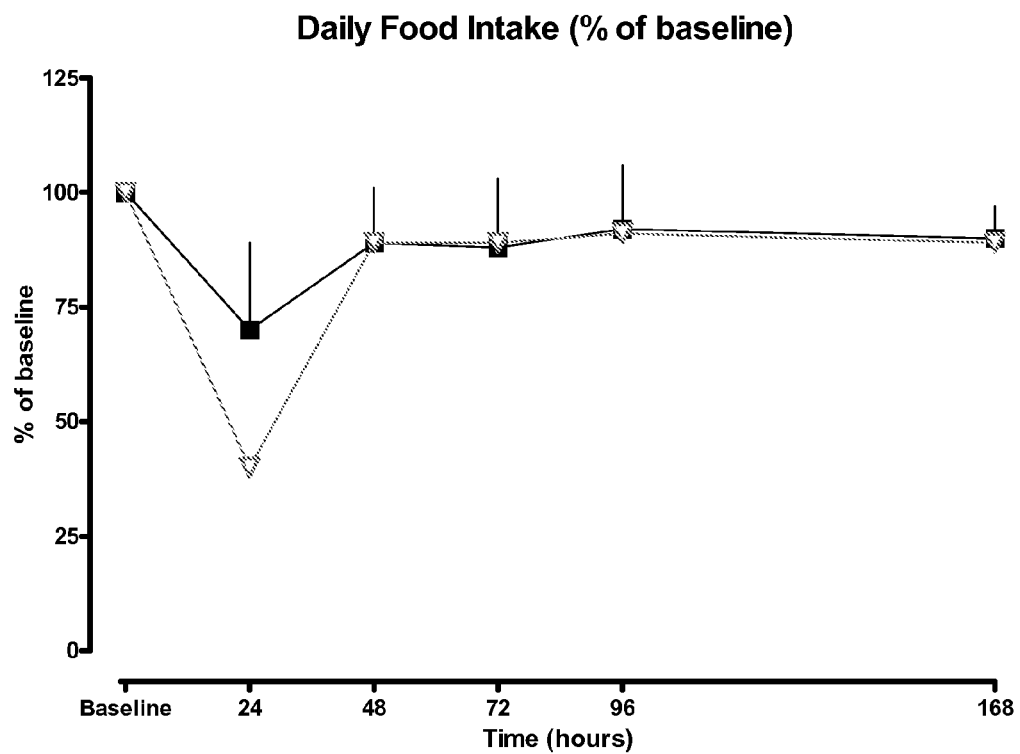
Figure 6B:
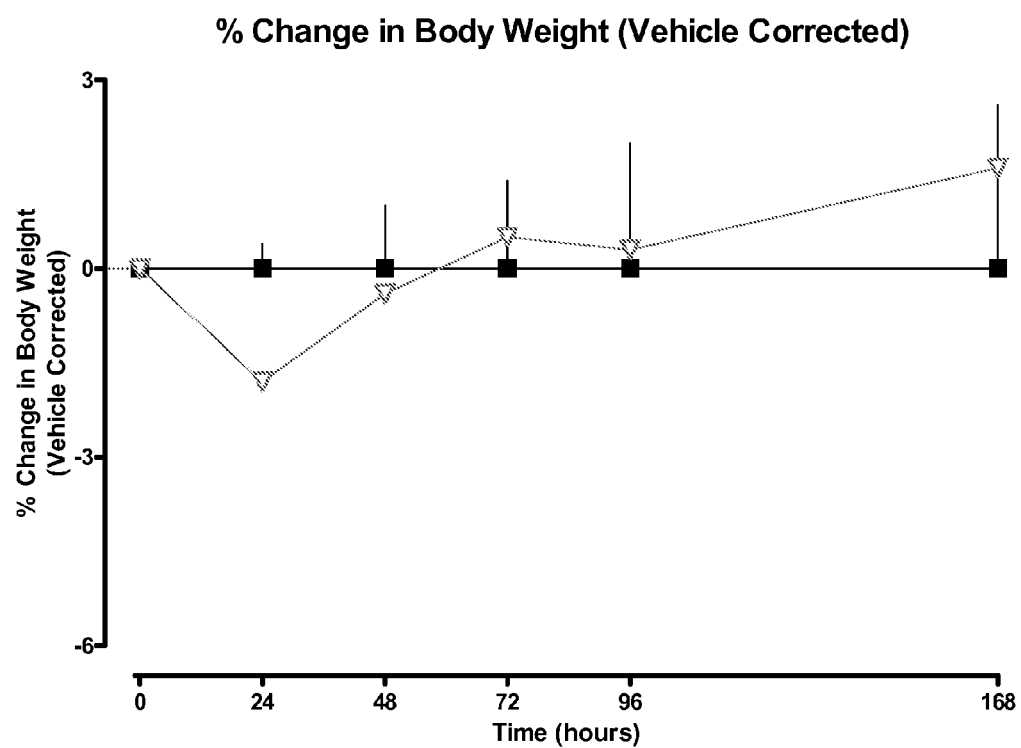
Figure 6C:
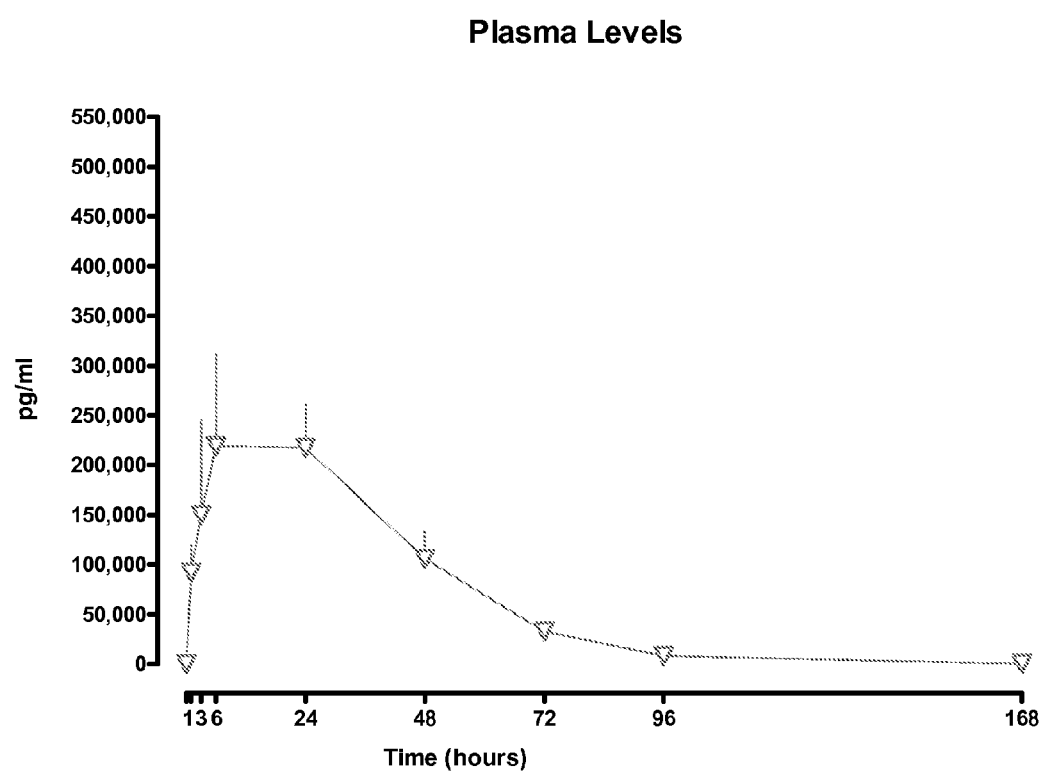

FIGS. 6A-6C. Pharmacokinetic (PK) profile and biological activity of an exemplary engineered polypeptide Cmpd 11 dosed in normal Harlan Sprague-Dawley (HSD) rats. FIG. 6A depicts effect of compounds to reduce food intake. FIG. 6B depicts effect of compounds to reduce body weight. FIG. 6C depicts a PK profile of the compound after a single dose. In the figures, vehicle is solid square and engineered polypeptide is open inverted triangle.

Figure 7A:
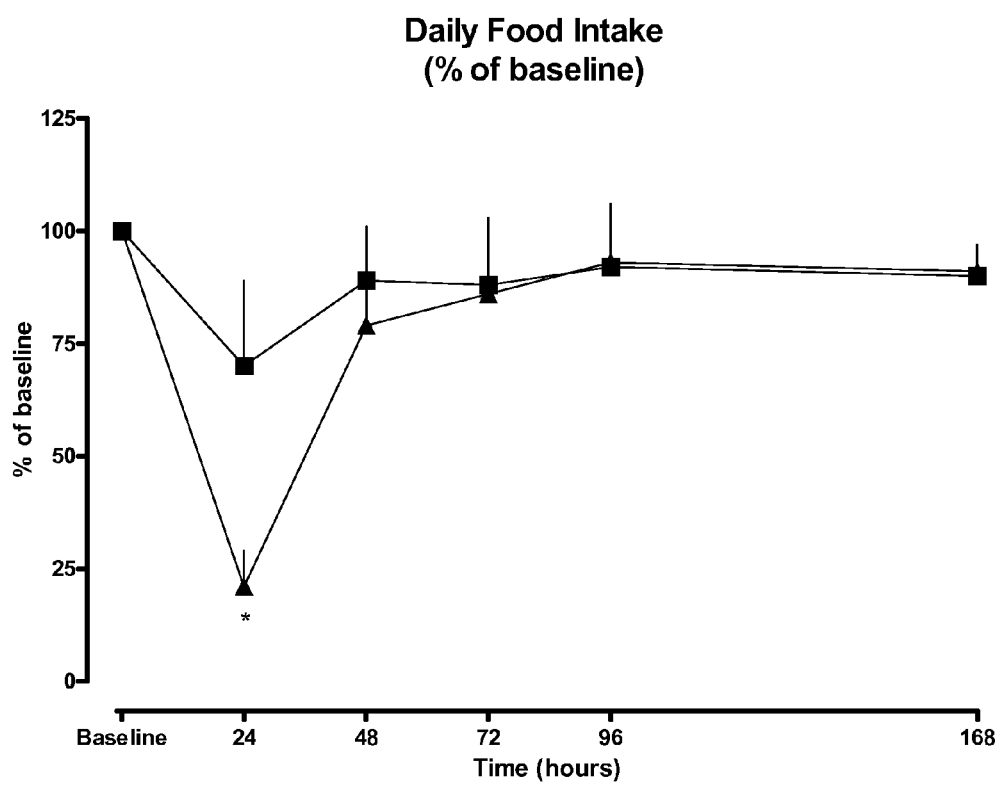
Figure 7B:
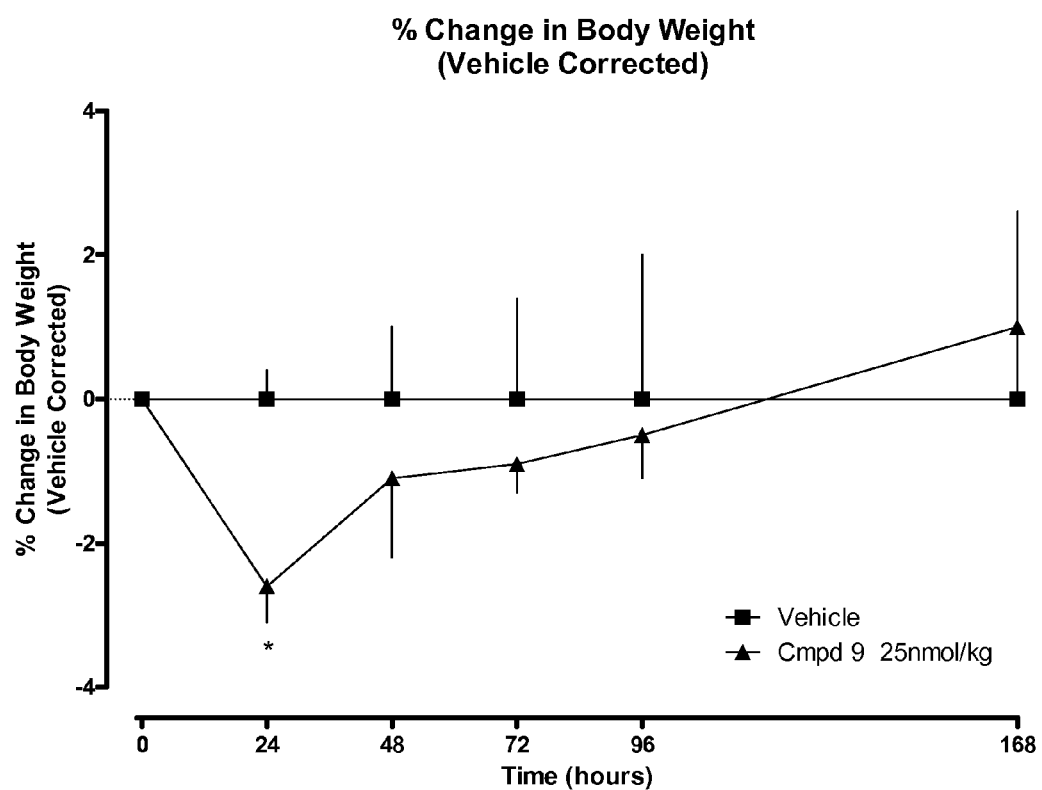
Figure 7C:
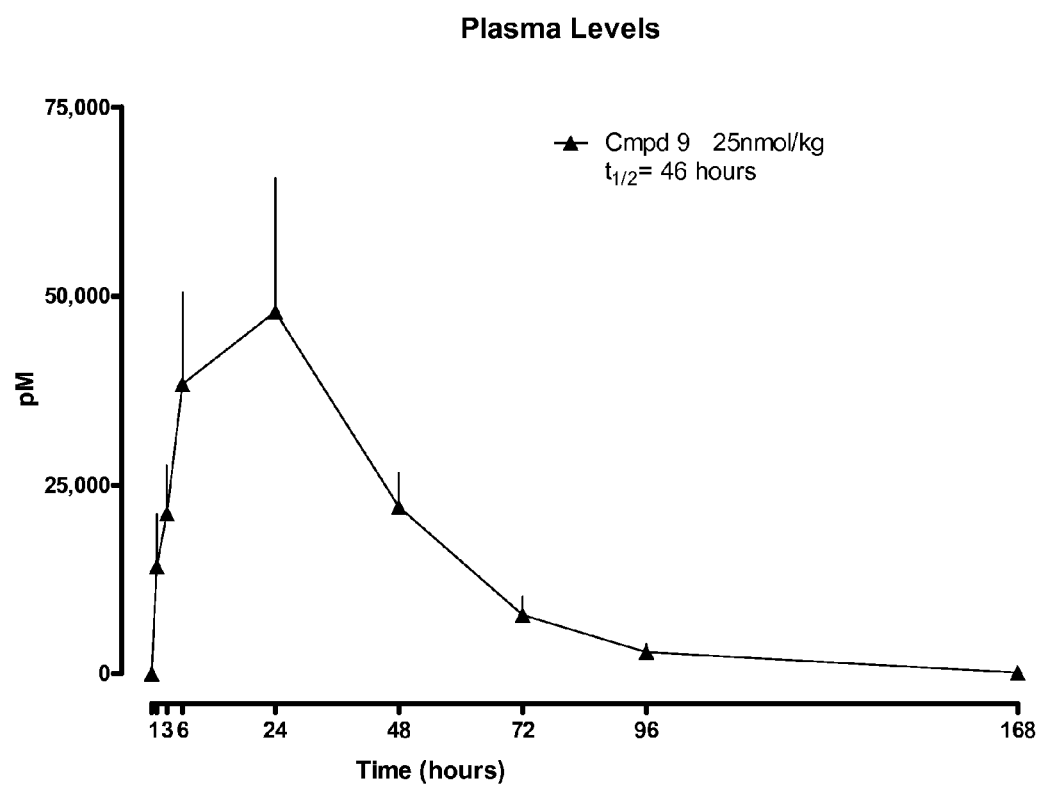

FIGS. 7A-7C. Pharmacokinetic (PK) profile and biological activity of an exemplary engineered polypeptide Cmpd 9 dosed in normal Harlan Sprague-Dawley (HSD) rats. FIG. 7A depicts effect of compounds to reduce food intake. FIG. 7B depicts effect of compounds to reduce body weight. FIG. 7C depicts a PK profile of the compound after a single dose. In the figures, vehicle is solid square and engineered polypeptide is closed triangle.

Figure 8A:
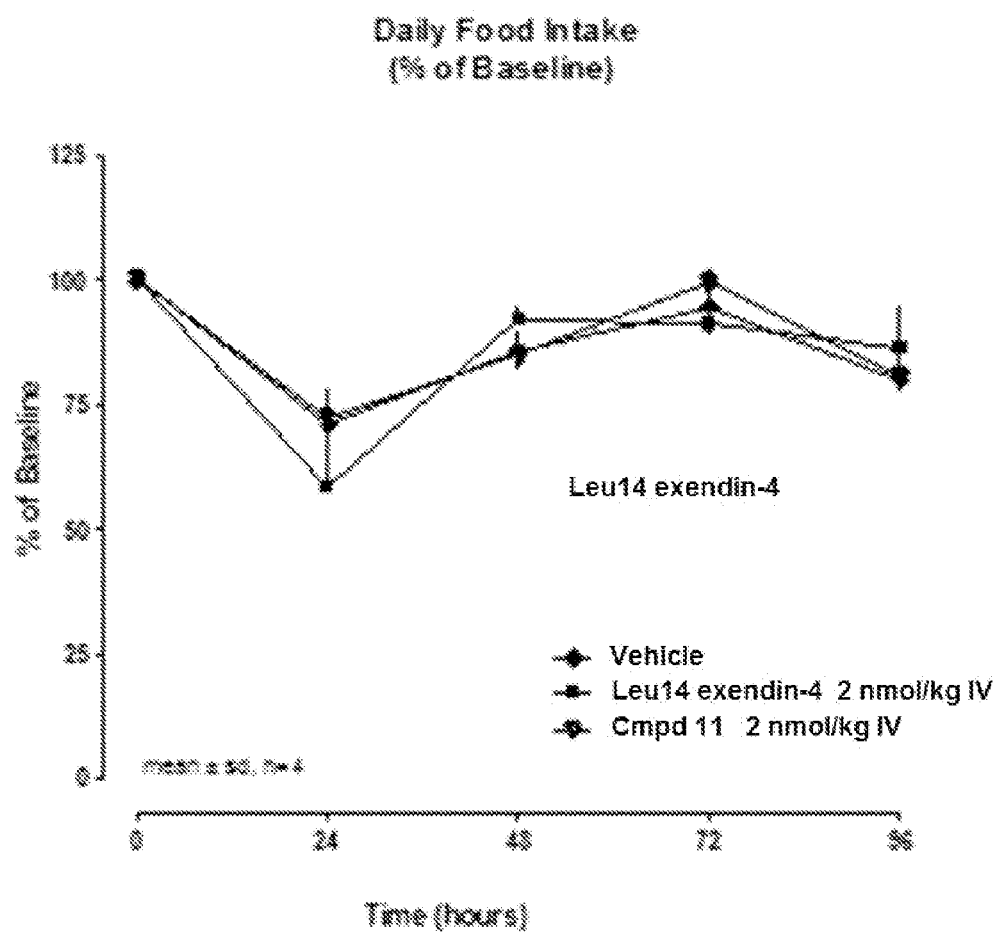
Figure 8B:
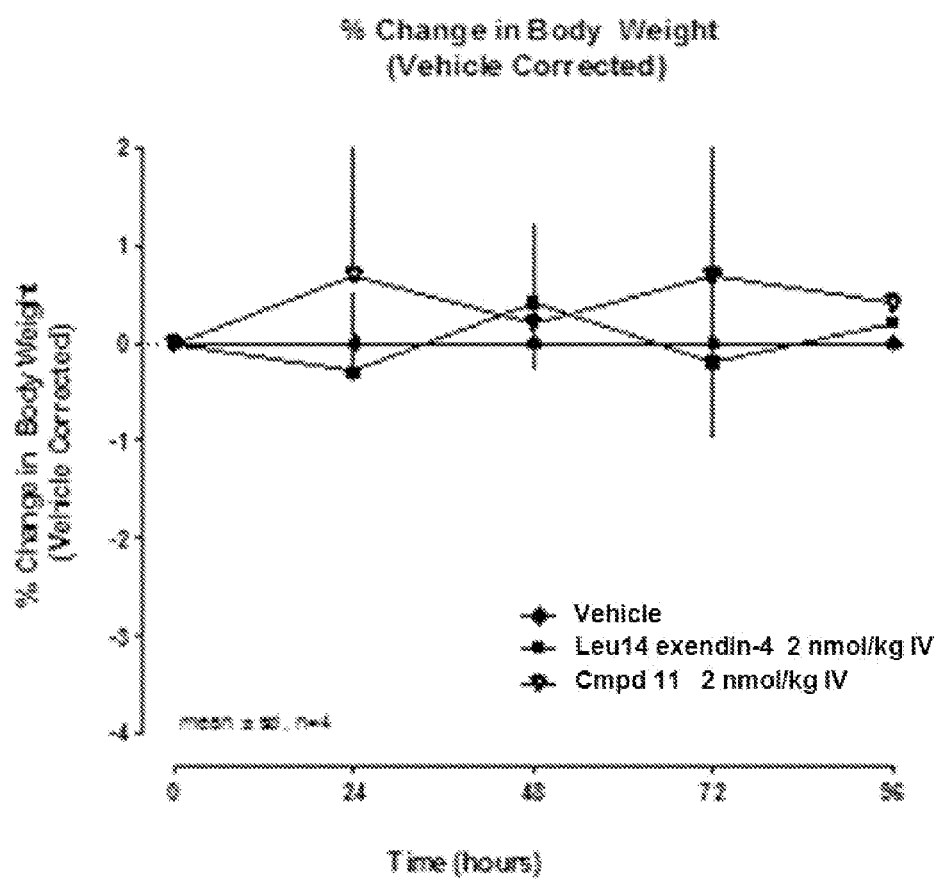
Figure 8C:
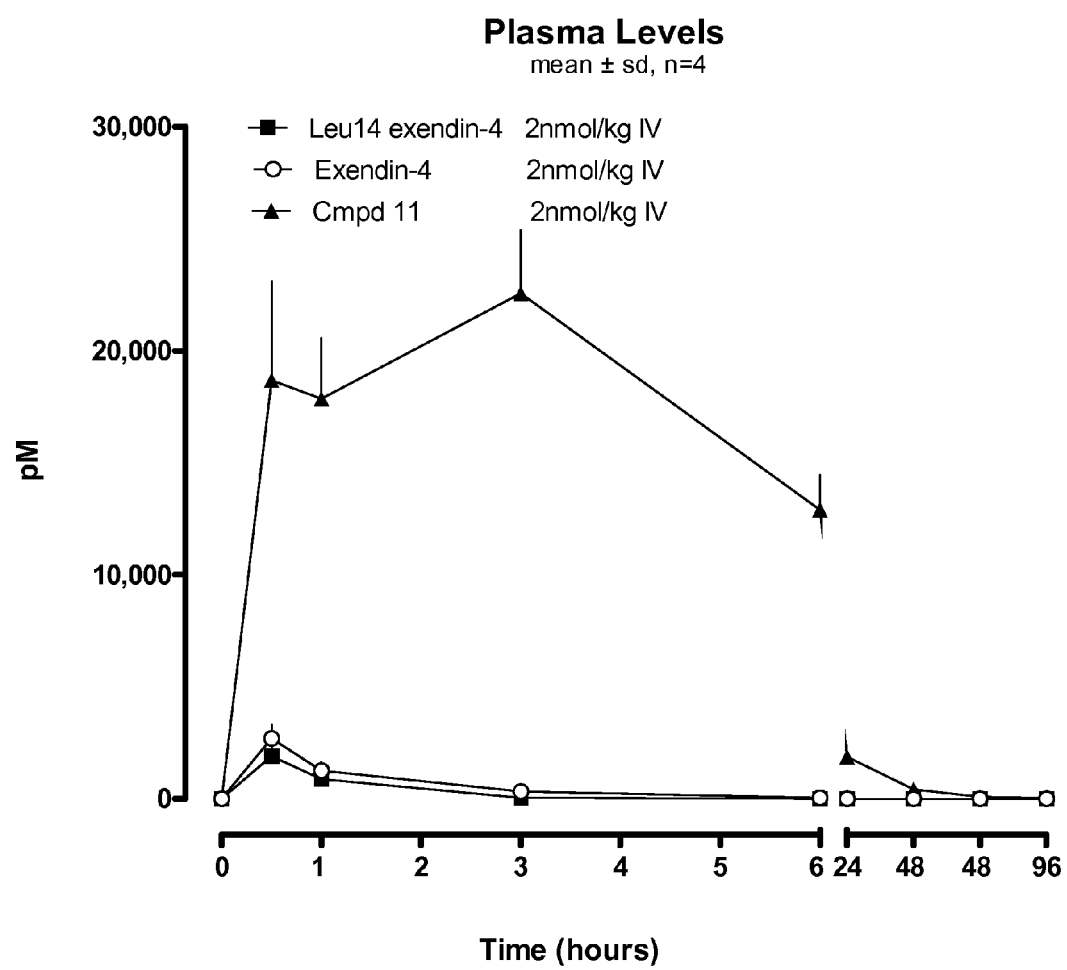

FIGS. 8A-8C. FIGS. 8A-8C depict pharmacokinetic (PK) profile and biological activity of an exemplary engineered polypeptide Cmpd 11 compared to an unconjugated exendin analog dosed intravenously in normal Harlan Sprague-Dawley (HSD) rats. FIG. 8A depicts effect of compound to reduce food intake. FIG. 8B depicts effect of compound to reduce body weight. FIG. 8C depicts a PK profile of the exemplary compound after a single intravenous dose. Results presented as picomolar plasma levels. Legend: vehicle (diamond); [$^{14}$Leu]exendin-4 at 2 nmol/kg IV (box); exendin-4 at 2 nmol/kg IV (circle); Cmpd 11 at 2 nmol/kg IV (open and closed triangle).

Figure 9A:
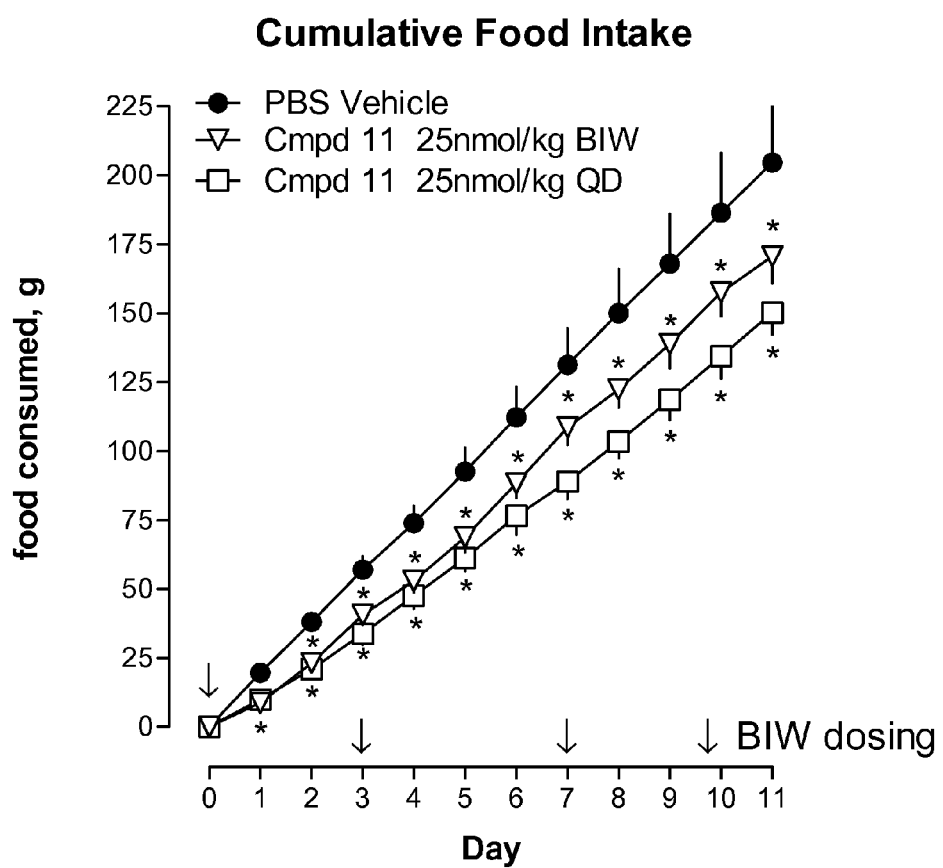
Figure 9B:
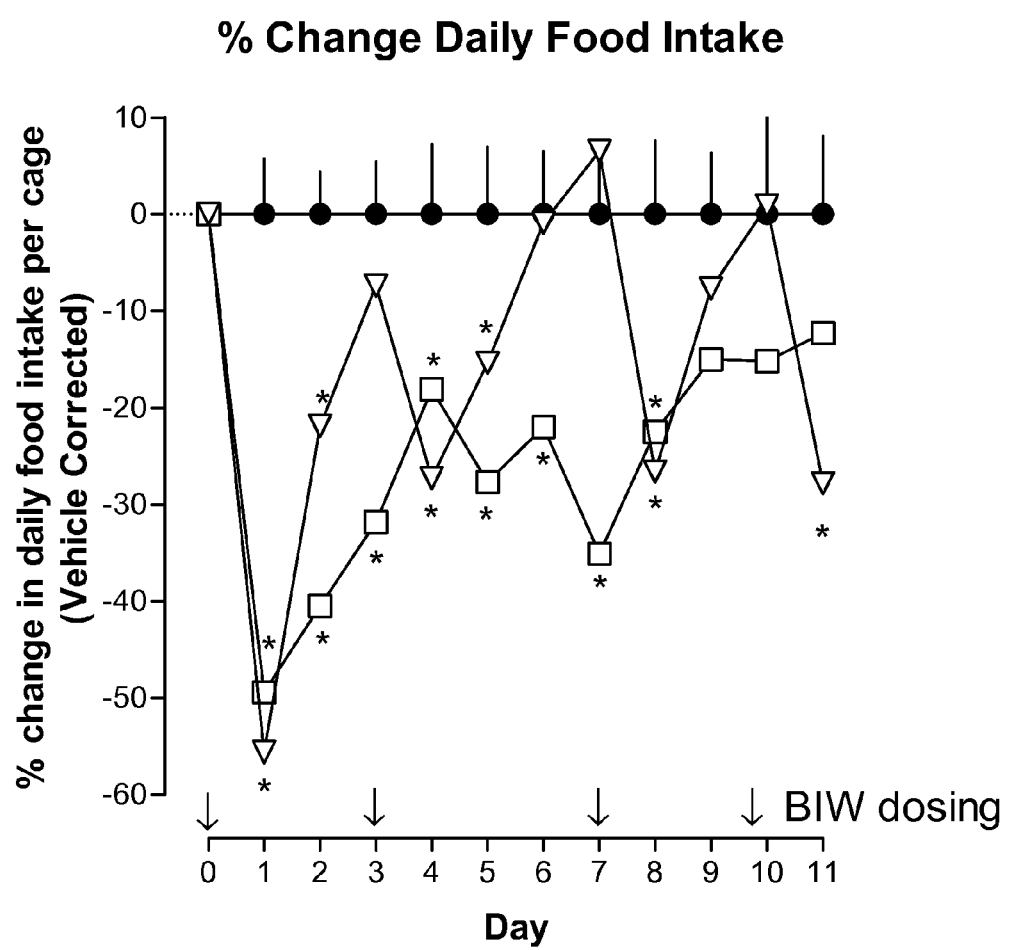
Figure 9C:
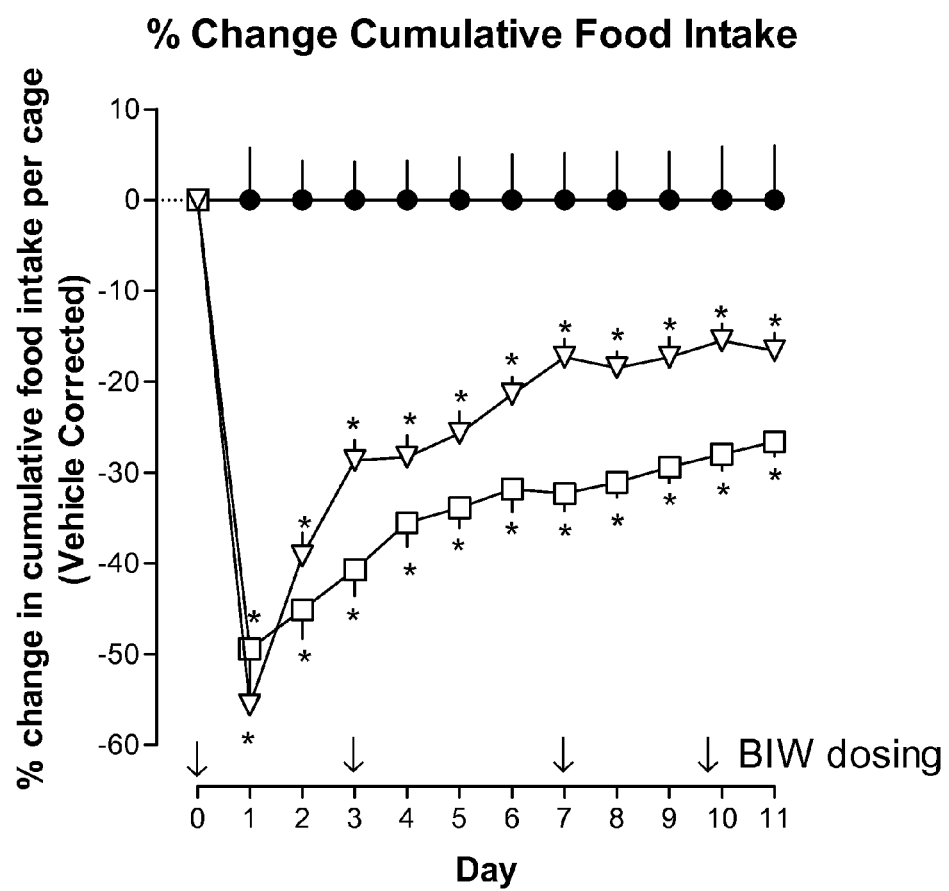
Figure 9D:
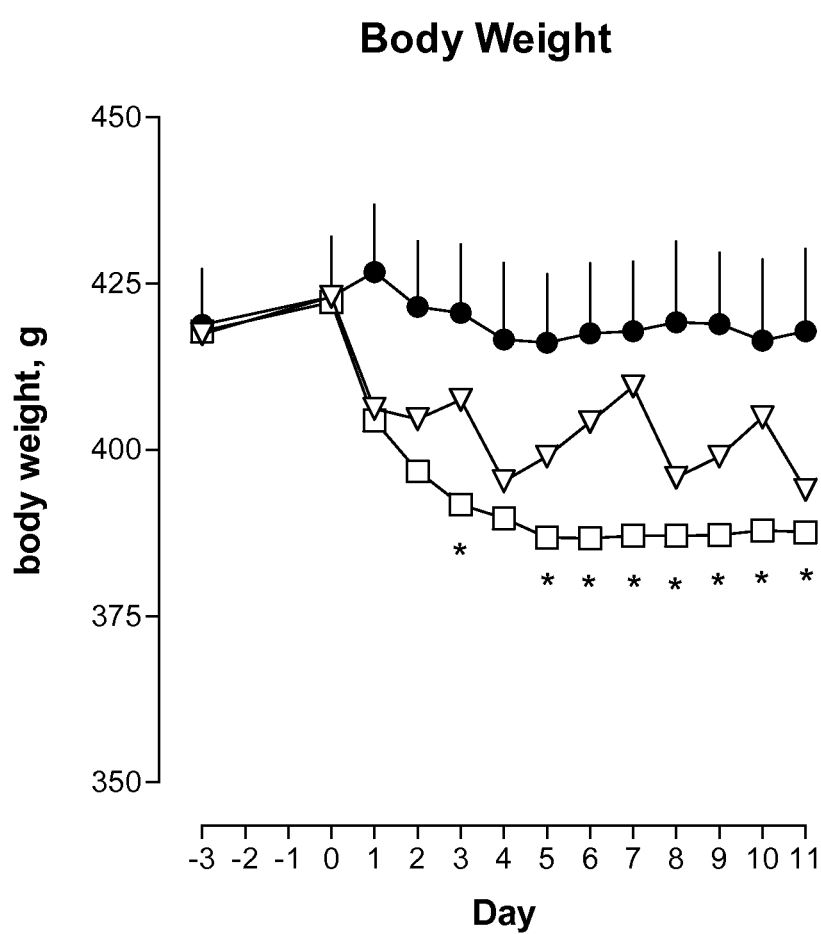
Figure 9E:
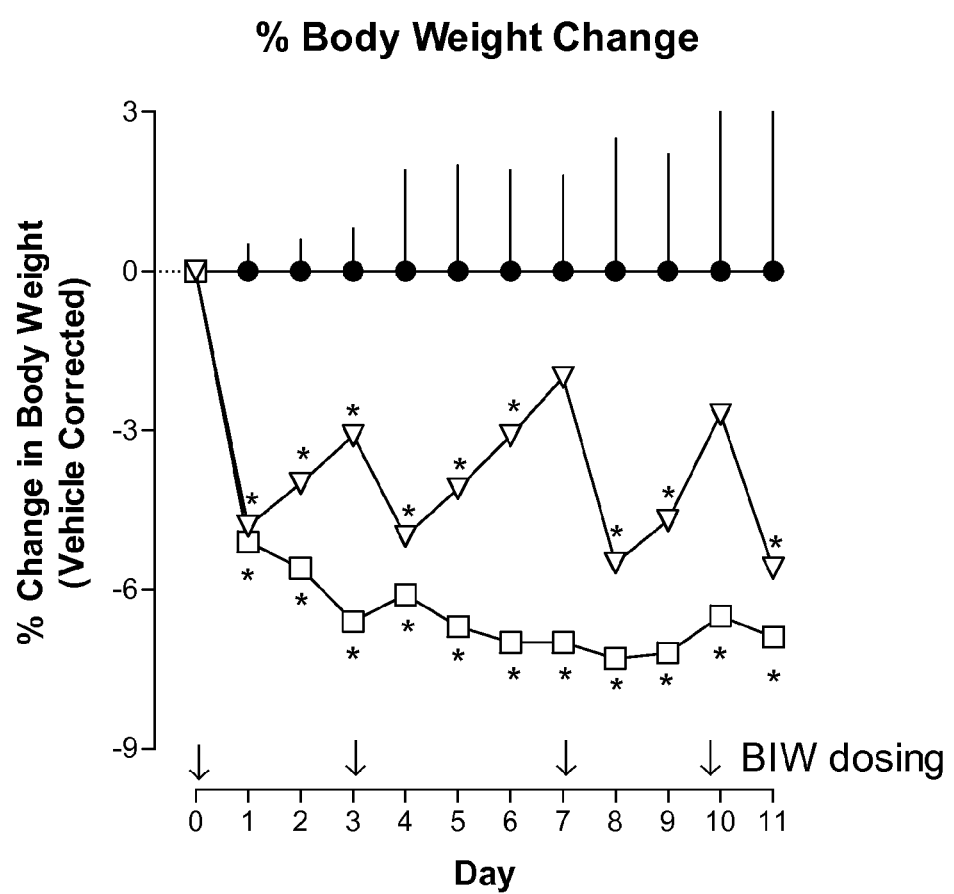
Figure 9F:
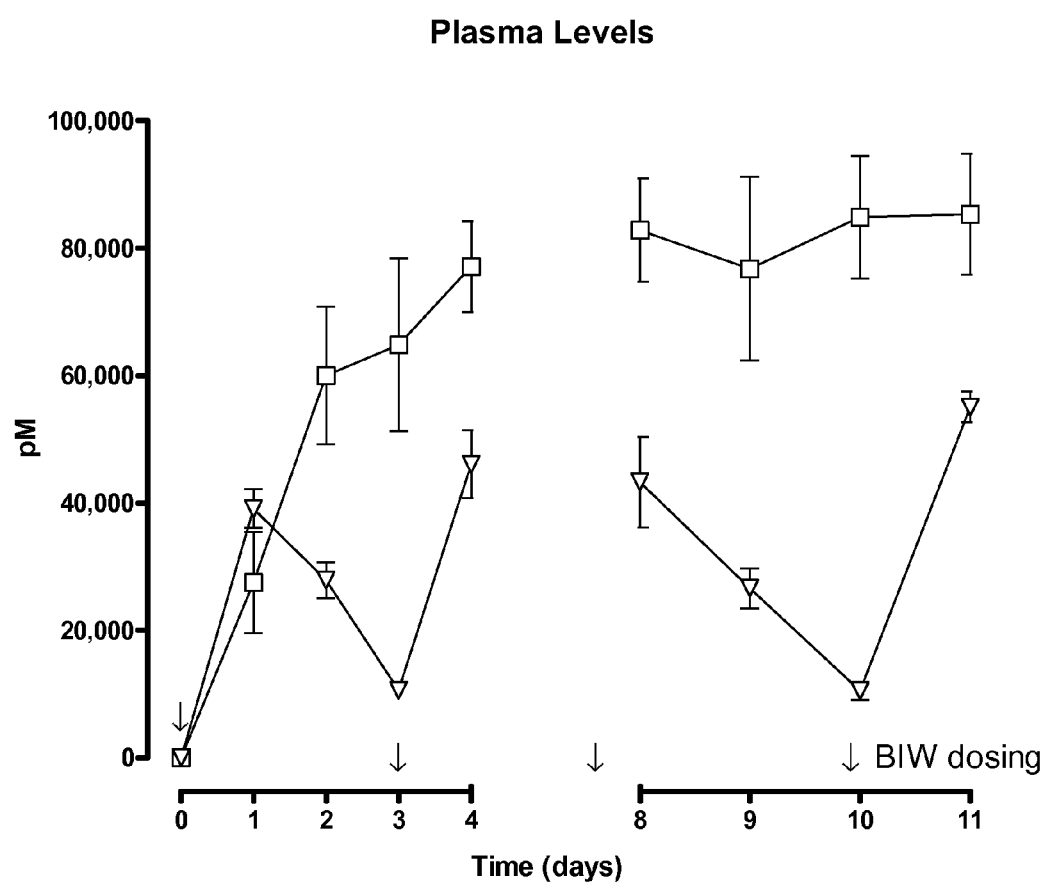

FIGS. 9A-9F. FIGS. 9A-9F depict pharmacokinetic (PK) profile and biological activity of an exemplary engineered polypeptide Cmpd 11 administered sub-chronically either daily or twice weekly. Cmpd 11 was subcutaneously administered at 25 nmol/kg over 14 days, either twice weekly (BIW; open inverted trangles) as indicated by the down arrows or daily (QD; open square) and compared to vehicle (closed circle). FIG. 9A depicts cumulative food intake. FIG. 9B depicts percent change in daily food intake. FIG. 9C depicts percent change in cumulative food intake. FIG. 9D depicts total body weight. FIG. 9E depicts percent change in body weight. FIG. 9F depicts a PK profile of Cmpd 11 given BIW or QD.

Figure 10:
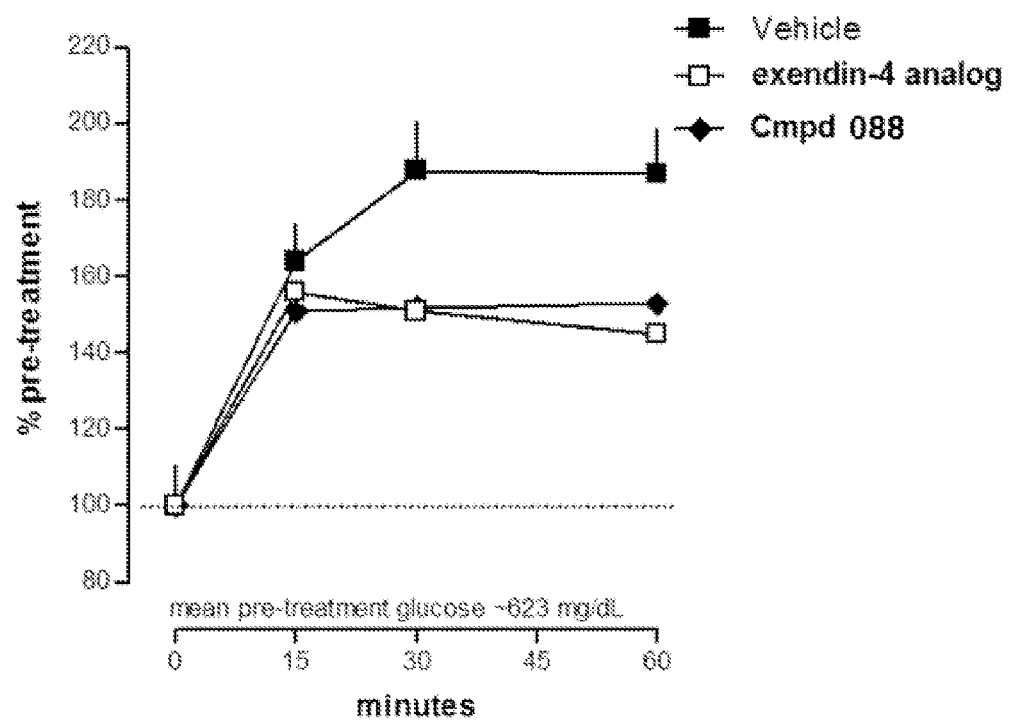

FIG. 10. This figure depicts a biological activity time course of polypeptide (Cmpd 088) compared to unconjugated exendin analog to lower blood glucose after oral delivery. See Examples. Mean pre-treatment glucose: ~623 mg/dL. Legend: vehicle (closed box); exendin-4 analog (open box); Cmpd 088 (diamond).

DETAILED DESCRIPTION OF THE INVENTION

I. Definitions

"Obesity" and "overweight" refer to mammals having a weight greater than normally expected, and may be determined by, e.g., physical appearance, body mass index (BMI) as known in the art, waist-to-hip circumference ratios, skinfold thickness, waist circumference, and the like. The Centers for Disease Control and Prevention (CDC) define overweight as an adult human having a BMI of 25 to 29.9; and define obese as an adult human having a BMI of 30 or higher. Additional metrics for the determination of obesity exist. For example, the CDC states that a person with a waist-to-hip ratio greater than 1.0 is overweight.

"Lean body mass" refers to the fat-free mass of the body, i.e., total body weight minus body fat weight is lean body mass. Lean body mass can be measured by methods such as hydrostatic weighing, computerized chambers, dual-energy X-ray absorptiometry, skin calipers, magnetic resonance imaging (MRI) and bioelectric impedance analysis (BIA) as known in the art.

"Mammal" refers to warm-blooded animals that generally have fur or hair, that give live birth to their progeny, and that feed their progeny with milk. Mammals include humans; companion animals (e.g., dogs, cats); farm animals (e.g., cows, horses, sheep, pigs, goats); wild animals; and the like. In one embodiment, the mammal is a female. In one embodiment, the mammal is a female human. In one embodiment, the mammal is a cat or dog. In one embodiment, the mammal is a diabetic mammal, e.g., a human having type 2 diabetes. In one embodiment, the mammal is an obese diabetic mammal, e.g., an obese mammal having type 2 diabetes. The term "subject" in the context of methods described herein refers to a mammal.

"Fragment" in the context of polypeptides refers herein in the customary chemical sense to a portion of a polypeptide. For example, a fragment can result from N-terminal deletion or C-terminal deletion of one or more residues of a parent polypeptide, and/or a fragment can result from internal deletion of one or more residues of a parent polypeptide. "Fragment" in the context of an antibody refers to a portion of an antibody which can be linked to a biologically active molecule to modulate solubility, distribution within a subject, and the like. For example, exendin-4(1-30) describes a biologically active fragment of exendin-4 where the exendin C-terminal "tail" of amino acids 31-39 is deleted. The term "parent" in the context of polypeptides refers, in the customary sense, to a polypeptide which serves as a reference structure prior to modification, e.g., insertion, deletion and/or substitution. The term "conjugate" in the context of engineered polypeptides described herein refers to covalent linkage between component polypeptides, e.g., ABD, HD1 and the like. The term "fusion" in the context of engineered polypeptides described herein refers to covalent linkage between component polypeptides, e.g., ABD, HD1 and the like, via either or both terminal amino or carboxy functional group of the peptide backbone. Engineered polypeptides can be synthetically or recombinantly made. Typically, fusions are made using recombinant biotechnology, however, can also be made by chemical synthesis and conjugation methods.

"Analog" as used herein in the context of polypeptides refers to a compound that has insertions, deletions and/or substitutions of amino acids relative to a parent compound. "Analog sequence" as used herein in the context of polypeptides refers to an amino acid sequence that has insertions, deletions and/or substitutions of amino acids relative to a parent amino acid sequence (e.g., wild-type sequence, native sequence). An analog may have superior stability, solubility, efficacy, half-life, and the like. In some embodiments, an analog is a compound having at least 50%, for example 50%, 55%, 60%, 65%, 70%, 75%, 80%, 85%, 90%, 95%, 98%, or even higher, sequence identity to the parent compound. In a preferred embodiment the analog has from 1 to 5 amino acid modifications selected independently from any one or combination of an insertion, deletion, addition and substitution. In any of the embodiments herein, the exendin analog can have from 1 to 5 amino acid modifications selected independently from any one or combination of an insertion, deletion, addition and substitution, and preferably retains at least 50%, for example 50%, 55%, 60%, 65%, 70%, 75%, 80%, 85%, 90%, 95%, 98%, or even higher, sequence identity to the parent compound, and even more preferably at least 80%, 85%, 90%, 95%, 98%, or even higher, sequence identity to the parent compound, and preferably the parent compound is exendin-4, exendin-4(1-38), exendin-4(1-37), exendin-4(1-36), exendin-4(1-35), exendin-4(1-34), exendin-4(1-33), exendin-4(1-32), exendin-4(1-31), exendin-4(1-30), exendin-4(1-29) or exendin-4(1-28), or their Leu-14 substitution counterparts, e.g Leu14 exendin-4(1-38), Leu14 exendin-4(1-38), Leu14 exendin-4(1-37), Leu14 exendin-4(1-36), Leu14 exendin-4(1-35), Leu14 exendin-4(1-34), Leu14 exendin-4(1-33), Leu14 exendin-4(1-32), Leu14 exendin-4(1-31), Leu14 exendin-4(1-30), Leu14 exendin-4(1-29) or Leu14 exendin-4(1-28), and most preferably the parent compound has the sequence of exendin-4 or Leu14 exendin-4. In a preferred embodiment the exendin analog fragment is not an exendin-4(1-28) or its amino acid substitution analog such as Leu14 exendin-4(1-28). Preferably the exendin analog fragment is at least 29 amino acids in length. In one embodiment at least amino acids corresponding to positions 1, 4, 6, 7 and 9 of exendin-4 are those as in native exendin-4, and further the one to five modifications are conservative amino acid substitutions at positions other than positions 1, 4, 6, 7 and 9 of exendin-4. For example, in yet a further embodiment of the embodiments herein, an exendin analog retains the amino acid at least as found in position 3, 4, 6, 5, 7, 8, 9, 10, 11, 13, 15, 18, 19, 22, 23, 25, 26, and/or 30 of exendin-4, and further preferably has no more than 1 to 5 of the remaining positions substituted with another amino acid, most preferably a chemically conservative amino acid. In all of the analogs herein, any substitution or modification at positions 1 and/or 2 will retain resistance to DPP-IV cleavage while retaining or improving insulinotropic activity as is known in the art for exendin-4 analogs, such as desamino-histidyl-exendin-4. As customary in the art, the term "conservative" in the context of amino acid substitutions refers to substitution which maintains properties of charge type (e.g., anionic, cationic, neutral, polar and the like), hydrophobicity or hydrophilicity, bulk (e.g., van der Waals contacts and the like), and/or functionality (e.g., hydroxy, amine, sulfhydryl and the like). The term "non-conservative" refers to an amino acid substitution which is not conservative.

"Identity," "sequence identity" and the like in the context of comparing two or more nucleic acids or polypeptide sequences, refer to two or more sequences or subsequences that are the same or have a specified percentage of amino acid residues or nucleotides that are the same (i.e., about 50% identity, preferably 50%, 55%, 60%, 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a sequence comparison algorithms as known in the art, for example BLAST or BLAST 2.0. This definition includes sequences that have deletions and/or additions, as well as those that have substitutions, as well as naturally occurring, e.g., polymorphic or allelic variants, and man-made variants. In preferred algorithms, account is made for gaps and the like, as known in the art. For sequence comparison, typically one sequence acts as a reference sequence, to which test sequences are compared. When using a sequence comparison algorithm, test and reference sequences are entered into a computer, subsequence coordinates are designated if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters. Optimal alignment of sequences for comparison can be conducted, e.g., by the local homology algorithm of Smith & Waterman, 1981, *Adv. Appl. Math.* 2:482, by the homology alignment algorithm of Needleman & Wunsch, 1970, *J. Mol. Biol.* 48:443, by the search for similarity method of Pearson & Lipman, 1988, *Proc. Nat'l. Acad. Sci. USA* 85:2444, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection. See e.g., *Current Protocols in Molecular Biology* (Ausubel et al., eds. 1995 supplement)). Preferred examples of algorithms that are suitable for determining percent sequence identity and sequence similarity include the BLAST and BLAST 2.0 algorithms, which are described in Altschul et al., 1977, *Nucl. Acids Res.* 25:3389-3402 and Altschul et al., 1990, *J. Mol. Biol.* 215:403-410. BLAST and BLAST 2.0 are used, as known in the art, to determine percent sequence identity for the nucleic acids and proteins of the invention. Software for performing BLAST analyses is publicly available through the web site of the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., Id.). These initial neighborhood word hits act as seeds for initiating searches to find longer HSPs containing them. The word hits are extended in both directions along each sequence for as far as the cumulative alignment score can be increased. Cumulative scores are calculated using, e.g., for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, 1989, *Proc. Natl. Acad. Sci. USA* 89:10915) alignments (B) of 50, expectation (E) of 10, M=5, N=−4, and a comparison of both strands.

The term "about" in the context of a numeric value refers to +/−10% of the numeric value.

The terms "peptide" and "polypeptide" in the context of components of the engineered polypeptides described herein are synonymous.

II. Compounds

In a first aspect, engineered polypeptide compounds are provided with a sequence which includes an albumin binding domain (ABD) polypeptide sequence and at least one polypeptide hormone domain (HD1) sequence. The terms "albumin binding domain," "ABD" and the like refer to polypeptides capable of binding albumin as described herein. The terms "hormone domain," "hormone domain polypeptide" and the like refer to a GLP-1 receptor agonist polypeptide capable of eliciting a biological response in a subject. Exemplary hormone domains include, but are not limited to, an exendin, an exendin fragment, or an exendin analog.

It was surprisingly found that an exendin, exendin analog or active fragment can be fused to an very-high-affinity albumin binding domain (ABD) derived from and having substantial amino acid sequence identity to the albumin-binding domains of bacterial protein G of *Streptococcus* strain G148, while retaining sufficient exendin-4 biological activity and having an extended duration of action, for example of at least 3 days and even 5 days in a rodent, which translates to at least a one week duration or longer in a human subject. "Duration of action" refers in the customary sense to allowing for more infrequent dosing in a therapeutical regimen. Thus, a prolonged duration of action will allowed for less frequent and/or more convenient dosing schedules. This was surprising in part because such ABD peptides have not been extensively demonstrated to be a robust platform as a therapeutic protein carrier, they are relatively hydrophobic which could interact adversely with an attached therapeutic peptide, and were not able to act as a carrier for at least one family of peptide hormones. Specifically, rat amylin when conjugated or fused to the ABDs described herein did not display any significant or long-acting in vivo activity in the same rodent models in which various exendin-ABD constructs were found to be active and with long duration of action.

Furthermore, the therapeutic conjugate or fusion compounds herein surprisingly have retained albumin binding affinity and specificity while having lower immunogenicity and exendin-4 therapeutic activity. The compounds are surprisingly active despite the absence of a plasma-protease cleavage site between the exendin and the ABD. Further surprising, the therapeutic compounds are believed active even when bound to albumin. The ABD compounds described herein provide albumin binding affinity and specificity while having lower immunogenicity than previously described ABD compounds, which were based on the albumin binding region of Streptococcal protein G strain 148 (G148) and in Jonsson et al. (Protein Eng. Design & Selection, 2008, 21:515-527). Recently, a few T- and B-cell epitopes were experimentally identified within the albumin binding region of Streptococcal protein G strain 148 (G148) (Goetsch et al, Clin. Diagn. Lab. Immunol. 10:125-32, 2003). The authors were interested in utilizing the T-cell epitopes of G148 in vaccines, i.e. to utilize the inherent immune-stimulatory property of the albumin binding region. Goetsch et al. additionally found a B-cell epitope, i.e. a region bound by antibodies after immunization, in the sequence of G148. In pharmaceutical compositions for human administration no immune-response is desired. Therefore, the albumin binding domain G148 is as such not preferred for use in such compositions due to its abovementioned immune-stimulatory properties.

Biologically Active Components.

Biologically active compound components contemplated for use in the compounds and methods described herein include the exendins. The terms "biologically active compound" and the like refer in the customary sense to compounds, e.g., polypeptides and the like, which can elicit a biological response.

Exendins.

The exendins are peptides that are found in the salivary secretions of the Gila monster and the Mexican Bearded Lizard, reptiles that are endogenous to Arizona and Northern Mexico. Exendin-3 is present in the salivary secretions of *Heloderma horridum* (Mexican Beaded Lizard), and exendin-4 is present in the salivary secretions of *Heloderma suspectum* (Gila monster). See Eng et al, 1990, *J. Biol. Chem.*, 265:20259-62; Eng et al, 1992, *J. Biol. Chem.*, 267:7402-7405. The sequences of exendin-3 and exendin-4, respectively, follow:

(SEQ ID NO: 1)
HSDGTFTSDLSKQMEEEAVRLFIEWLKNGGPSSGAPPPS-NH$_2$;

(SEQ ID NO: 2)
HGEGTFTSDLSKQMEEEAVRLFIEWLKNGGPSSGAPPPS-NH$_2$.

Hargrove et al. (*Regulatory Peptides*, 2007, 141:113-119) reported an exendin-4 peptide analog that is a full-length C-terminally amidated exendin-4 peptide analog with a single nucleotide difference at position 14 compared to native exendin-4. The sequence of [$^{14}$Leu]Exendin-4 is as follows: HGEGTFTSDLSKQLEEEAVR-LFIEWLKNGGPSSGAPPPS—NH$_2$ (SEQ ID NO:3). The Leu14 exendin-4 is a preferred analog for use in the engineered polypeptides and their uses described herein. Another exendin-4 peptide analog is a chimera of the first 32 amino acids of exendin-4 having amino acid substitutions at positions 14 and 28 followed by a 5 amino acid sequence from the C-terminus of a non-mammalian (frog) GLP1: [Leu$^{14}$,Gln$^{28}$] Exendin-4(1-32)-fGLP-1(33-37). This compound has the following sequence: HGEGTFTSDLSKQLEEEAVR-LFIEWLKQGGPSKEIIS (SEQ ID NO:4). Also known in the art are C-terminally truncated, biologically active forms of exendin-4, such as exendin-4(1-28), exendin-4(1-29), exendin-4(1-30), exendin-4(1-31), exendin-4(1-32) and their amidated forms. All of these exendin analogs are suitable as components of the engineered polypeptides of the present invention. As is customary in the art, square brackets (i.e., "[ ]") in a peptidic compound name indicates substitution of the residue or chemical feature within the square brackets. For example, [$^{14}$Leu]Exendin-4, [$^{14}$Leu]Ex-4, and the like refer to exendin-4 having leucine at position 14. The numeric position of an amino acid can be indicated by prepended or postpended numbers in a variety of ways routinely employed in the art. For example, the terms $^{14}$Leu, Leu14, 14Leu, Leu$^{14}$ and the like, are synonymous in referring to leucine at position 14.

It is understood that in some embodiments a C-terminal amide, or other C-terminal capping moiety can be present in compounds described herein.

Although the exendins have some sequence similarity to several members of the glucagon-like peptide family, with the highest homology, 53%, being to GLP-1(7-36)NH$_2$ (Goke et al, 1993, *J. Biol. Chem.*, 268:19650-55) [sequence of GLP-1 (7-37)NH$_2$: HAEGTFTSDVSSYLEGQAAKEFI-AWLVKGRG (SEQ ID NO:5], also sometimes referred to as "GLP-1") which has an insulinotropic effect stimulating insulin secretion from pancreatic beta-cells, exendins are not GLP-1 homologs.

Pharmacological studies have led to reports that exendin-4 can act at GLP-1 receptors in vitro on certain insulin-secreting cells, however, it has also been reported that exendin-4 may act at receptors not acted upon by GLP-1. Further, exendin-4 shares some but not all biological properties in vivo with GLP-1, and it has a significantly longer duration of action than GLP-1. Based on their insulinotropic activities, the use of exendin-3 and exendin-4 for the treatment of diabetes mellitus and the prevention of hyperglycemia has been proposed (Eng, U.S. Pat. No. 5,424,286, incorporated herein by reference in its entirety and for all purposes), and in fact, exendin-4 has been approved in the United States and in Europe for use as a therapeutic for treating type 2 diabetes.

Indeed, it is believed that exendins are not the species homolog of mammalian GLP-1 as was reported by Chen and Drucker who cloned the exendin gene from the Gila monster (*J. Biol. Chem.* 272:4108-15 (1997)). The observation that the Gila monster also has separate genes for proglucagons (from which GLP-1 is processed), that are more similar to mammalian proglucagon than exendin, indicated that exendins are not merely species homologs of GLP-1.

Methods for regulating gastrointestinal motility using exendin agonists are described in U.S. Pat. No. 6,858,576 (i.e., based on U.S. application Ser. No. 08/908,867 filed Aug. 8, 1997, which is a continuation-in-part of U.S. application Ser. No. 08/694,954 filed Aug. 8, 1996). Methods for reducing food intake using exendin agonists are described in U.S. Pat. No. 6,956,026 (i.e., based on U.S. application Ser. No. 09/003,869, filed Jan. 7, 1998, which claims the benefit of U.S. Application Nos. 60/034,905 filed Jan. 7, 1997, 60/055,404 filed Aug. 7, 1997, 60/065,442 filed Nov. 14, 1997, and 60/066,029 filed Nov. 14, 1997.

Novel exendin agonist compound sequences useful in the engineered polypeptides described herein are described in WO 99/07404 (i.e., PCT/US98/16387 filed Aug. 6, 1998), in WO 99/25727 (i.e., PCT/US98/24210, filed Nov. 13, 1998), in WO 99/25728 (i.e., PCT/US98/24273, filed Nov. 13, 1998), in WO 99/40788, in WO 00/41546, and in WO 00/41548, which are incorporated herein by reference and for all purposes along with their granted U.S. patent counterparts. Methods to assay for exendin activities in vitro and in vivo, as known in the art, including insulinotropic, food intake inhibition activity and weight loss activity, are described herein and also in the above references and other references recited herein.

Certain exemplary exendins, exendin agonists, and exendin analog agonists include: exendin fragments exendin-4 (1-30) (His Gly Glu Gly Thr Phe Thr Ser Asp Leu Ser Lys Gln Met Glu Glu Glu Ala Val Arg Leu Phe Ile Glu Trp Leu Lys Asn Gly Gly) (SEQ ID NO: 680); exendin-4(1-28), exendin-4(1-29), exendin-4(1-30), exendin-4(1-31) and exendin-4(1-32). Analogs include substitution at the $^{14}$Met position (i.e., $^{14}$Met) with a non-oxidizing amino acid such as leucine. Examples include [$^{14}$Leu]exendin-4, [$^{14}$Leu]exendin-4(1-30), [$^{14}$Leu]exendin-4(1-28) and [$^{14}$Leu,$^{25}$Phe]exendin-4.

Exendin analog agonists for use in the engineered polypeptides described herein include those described in U.S. Pat. No. 7,223,725 (incorporated herein by reference and for all purposes), such as compounds of the formula: Xaa$_1$ Xaa$_2$ Xaa$_3$ Gly Xaa$_5$ Xaa$_6$ Xaa$_7$ Xaa$_8$ Xaa$_9$ Xaa$_{10}$ Xaa$_{11}$ Xaa$_{12}$ Xaa$_{13}$ Xaa$_{14}$ Xaa$_{15}$ Xaa$_{16}$ Xaa$_{17}$ Ala Xaa$_{19}$ Xaa$_{20}$ Xaa$_{21}$ Xaa$_{22}$ Xaa$_{23}$ Xaa$_{24}$ Xaa$_{25}$ Xaa$_{26}$ Xaa$_{27}$ Xaa$_{28}$-Z$_1$; wherein Xaa$_1$ is His, Arg or Tyr; Xaa$_2$ is Ser, Gly, Ala or Thr; Xaa$_3$ is Ala, Asp or Glu; Xaa$_5$ is Ala or Thr; Xaa$_6$ is Ala, Phe, Tyr; Xaa$_7$ is Thr or Ser; Xaa$_8$ is Ala, Ser or Thr; Xaa$_9$ is Asp or Glu; Xaa$_{10}$ is Ala, Leu, Ile, Val, or Met; Xaa$_{11}$ is Ala or Ser; Xaa$_{12}$ is Ala or Lys; Xaa$_{13}$ is Ala or Gln; Xaa$_{14}$ is Ala, Leu, Ile, Val or Met; Xaa$_{15}$ is Ala or Glu; Xaa$_{16}$ is Ala or Glu; Xaa$_{17}$ is Ala or Glu; Xaa$_{19}$ is Ala or Val; Xaa$_{20}$ is Ala or Arg; Xaa$_{21}$ is Ala or Leu; Xaa$_{22}$ is Ala, Phe, Tyr; Xaa$_{23}$ is Ile, Val, Leu, or Met; Xaa$_{24}$ is Ala, Glu or Asp; Xaa$_{25}$ is Ala, Trp, Phe, Tyr; Xaa$_{26}$ is Ala or Leu; Xaa$_{27}$ is Ala or Lys; Xaa$_{28}$ is Ala or Asn; Z$_1$ is —OH, —NH$_2$, Gly-Z$_2$, Gly Gly-Z$_2$, Gly Gly Xaa$_{31}$-Z$_2$, Gly Gly Xaa$_{31}$ Ser-Z$_2$ (SEQ ID NO: 681), Gly Gly Xaa$_{31}$ Ser Ser-Z$_2$ (SEQ ID NO: 682), Gly Gly Xaa$_{31}$ Ser Ser Gly-Z$_2$ (SEQ ID NO: 683), Gly Gly Xaa$_{31}$ Ser Ser Gly Ala-Z$_2$ (SEQ ID NO: 684), Gly Gly Xaa$_{31}$ Ser Ser Gly Ala Xaa$_{36}$-Z$_2$ (SEQ ID NO: 685), Gly Gly Xaa$_{31}$ Ser Ser Gly Ala Xaa$_{36}$ Xaa$_{37}$-Z$_2$ (SEQ ID NO: 686) or Gly Gly Xaa$_{31}$ Ser Ser Gly Ala Xaa$_{36}$ Xaa$_{37}$ Xaa$_{38}$-Z$_2$ (SEQ ID NO: 687); Xaa$_{31}$, Xaa$_{36}$, Xaa$_{37}$ and Xaa$_{38}$ are independently Pro or are absent; and Z$_2$ is —OH or —NH$_2$. In any and each of the exendin analogs described above, also specifically contemplated are those wherein a replacement for the histidine corresponding to Xaa1 is made with any of D-histidine, desamino-histidine, 2-amino-histidine, beta-hydroxy-histidine, homohistidine. N-alpha-acetyl-histidine, alpha-fluoromethyl-histidine, alpha-methyl-histidine, 3-pyridylalanine, 2-pyridylalanine, 4-pyridylalanine, 4-imidazoacetyl, des-amino-histidyl (imidazopropionyl), beta-hydroxy-imidazopropionyl, N-dimethyl-histidyl or beta-carboxy-imidazopropionyl. Further specifically contemplated herein are exendin analogs described herein wherein a replacement for the glycine at Xaa2 is made with any of D-Ala, Val, Leu, Lys, Aib, (1-amino cyclopropyl) carboxylic acid, (1-aminocyclobutyl)carboxylic acid, 1-aminocyclopentyl)carboxylic acid, (1-aminocyclohexyl)carboxylic acid, (1-aminocycloheptyl)carboxylic acid, or (1-amino cyclooctyl)carboxylic acid.

According to one embodiment, exemplary compounds include those of the above formula wherein: Xaa$_1$ is H is or Arg; Xaa$_2$ is Gly or Ala; Xaa$_3$ is Asp or Glu; Xaa$_5$ is Ala or Thr; Xaa$_6$ is Ala or Phe; Xaa$_7$ is Thr or Ser; Xaa$_8$ is Ala, Ser or Thr; Xaa$_9$ is Asp or Glu; Xaa$_{10}$ is Ala, or Leu; Xaa$_{11}$ is Ala or Ser; Xaa$_{12}$ is Ala or Lys; Xaa$_{13}$ is Ala or Gln; Xaa$_{14}$ is Ala or Leu; Xaa$_{15}$ is Ala or Glu; Xaa$_{16}$ is Ala or Glu; Xaa$_{12}$ is Ala or Glu; Xaa$_{19}$ is Ala or Val; Xaa$_{20}$ is Ala or Arg; Xaa$_{21}$ is Ala or Leu; Xaa$_{22}$ is Phe; Xaa$_{23}$ is Ile, Val; Xaa$_{24}$ is Ala, Glu or Asp; Xaa$_{25}$ is Ala, Trp or Phe; Xaa$_{26}$ is Ala or Leu; Xaa$_{27}$ is Ala or Lys; Xaa$_{28}$ is Ala or Asn; Z$_1$ is —OH, —NH$_2$, Gly-Z$_2$, Gly Gly-Z$_2$, Gly Gly Xaa$_{31}$-Z$_2$, Gly Gly Xaa$_{31}$ Ser-Z$_2$ (SEQ ID NO: 681), Gly Gly Xaa$_{31}$ Ser Ser-Z$_2$ (SEQ ID NO: 682), Gly Gly Xaa$_{31}$ Ser Ser Gly-Z$_2$ (SEQ ID NO: 683), Gly Gly Xaa$_{31}$ Ser Ser Gly Ala-Z$_2$ (SEQ ID NO: 684), Gly Gly Xaa$_{31}$ Ser Ser Gly Ala Xaa$_{36}$-Z$_2$ (SEQ ID NO: 685), Gly Gly Xaa$_{31}$ Ser Ser Gly Ala Xaa$_{36}$ Xaa$_{37}$-Z$_2$ (SEQ ID NO: 686), Gly Gly Xaa$_{31}$ Ser Ser Gly Ala Xaa$_{36}$ Xaa$_{37}$ Xaa$_{38}$-Z$_2$ (SEQ ID NO: 687); Xaa$_{31}$; Xaa$_{36}$, Xaa$_{37}$ and Xaa$_{38}$ being independently Pro or is absent and Z$_2$ being —OH or —NH$_2$; provided that no more than three of Xaa$_3$, Xaa$_5$, Xaa$_6$, Xaa$_8$, Xaa$_{10}$, Xaa$_{11}$, Xaa$_{12}$, Xaa$_{13}$, Xaa$_{14}$, Xaa$_{15}$, Xaa$_{16}$, Xaa$_{17}$, Xaa$_{19}$, Xaa$_{20}$, Xaa$_{21}$, Xaa$_{24}$, Xaa$_{25}$, Xaa$_{26}$, Xaa$_{27}$ and Xaa$_{28}$ are Ala. In any and each of the exendin analogs described above, also specifically contemplated are those wherein a replacement for the histidine corresponding to position Xaa1 is made with any of D-histidine, desamino-histidine, 2-amino-histidine, beta-hydroxy-histidine, homohistidine. N-alpha-acetyl-histidine, alpha-fluoromethyl-histidine, alpha-methyl-histidine, 3-pyridylalanine, 2-pyridylalanine, 4-pyridylalanine, 4-imidazoacetyl, des-amino-histidyl (imidazopropionyl), beta-hydroxy-imidazopropionyl, N-dimethyl-histidyl or beta-carboxy-imidazopropionyl. Further specifically contemplated herein are exendin analogs described herein wherein a replacement for the glycine at Xaa 2 is made with any of D-Ala, Val, Leu, Lys, Aib, (1-aminocyclopropyl) carboxylic acid, (1-amino cyclobutyl)carboxylic acid, 1-aminocyclopentyl)carboxylic acid, (1-aminocyclohexyl)carboxylic acid, (1-amino cycloheptyl)carboxylic acid, or (1-aminocyclooctyl)carboxylic acid.

Other exemplary compounds include those set forth in WO 99/25727 identified therein as compounds 2-23. According to another embodiment, provided are compounds where Xaa$_{14}$ is Leu, Ile, or Val more preferably Leu, and/or Xaa$_{25}$ is Trp, Phe or Tyr, more preferably Trp or Phe. These compounds will be less susceptive to oxidative degradation, both in vitro and in vivo, as well as during synthesis of the compound.

Additional examples of exendin analogs suitable for use in the present fusion polypeptides include those described in U.S. Pat. No. 6,528,486 published Mar. 4, 2003 (incorporated herein by reference and for all purposes). Specifically, exendin analogs include those consisting of an exendin or exendin analog having at least 90% homology to exendin-4 having optionally between one and five deletions at positions 34-39, and a C-terminal extension of a peptide sequence of 4-20 amino acid units covalently bound to said exendin wherein each amino acid unit in said peptide extension sequence is selected from the group consisting of Ala, Leu, Ser, Thr, Tyr, Asn, Gln, Asp, Glu, Lys, Arg, His, and Met. More preferably the extension is a peptide sequence of 4-20 amino acid residues, e.g., in the range of 4-15, more preferably in the range of 4-10 in particular in the range of 4-7 amino acid residues, e.g., of 4, 5, 6, 7, 8 or 10 amino acid residues, where 6 amino acid residues are preferred. Most preferably, according to U.S. Pat. No. 6,528,486 the extension peptide contains at least one Lys residue, and is even more preferably from 3 to 7 lysines and even most preferably 6 lysines.

For example, one analog is HGEGTFTSDLSKQMEEE-AVRLFIEWLKNGG PSSGAPPSKKKKKK (SEQ ID NO:118) (also designated ([des-$^{36}$Pro]exendin-4(1-39)-Lys$_6$). Additional exemplary analogs include Lys$_6$-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-(Lys)$_6$ (H-Lys$_6$-des Pro $^{36}$exendin-4(1-39)-Lys$_6$) (SEQ ID NO: 688); His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Trp-Leu-Lys-Asn-Gly-Gly-Pro-Ser-Ser-Gly-Ala-Ser (H-[des $^{36}$Pro, $^{37,38}$Pro]exendin-4(1-39)-NH$_2$) (SEQ ID NO: 689); Lys-Lys-Lys-Lys-Lys-Lys-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser (H-(Lys)$_6$-[des $^{36}$Pro, $^{37,38}$Pro]exendin-4(1-39) (SEQ ID NO: 690); Asn-Glu-Glu-Glu-Glu-Glu-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly- Pro-Ser-Ser-Gly-Ala-Ser (H-Asn-(Glu)$_5$-[des $^{36}$Pro, $^{37,38}$Pro]exendin-4(1-39) (SEQ ID NO: 691); His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser- (Lys)$_6$ ([des $^{36}$Pro, $^{37,38}$Pro]exendin-4(1-39)-(Lys)$_6$) (SEQ ID NO: 692); (Lys)-6-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Ser-(Lys)$_6$ (H-(Lys)$_6$-[des $^{36}$Pro, $^{37,38}$Pro]exendin-4(1-39)-(Lys)$_6$) (SEQ ID NO: 693); and Asn-Glu-Glu-Glu-Glu-Glu-His-Gly-Glu-Gly-Thr-Phe-Thr-Ser-Asp-Leu-Ser-Lys-Gln-Met-Glu-Glu- Glu-Ala-Val-Arg-Leu-Phe-Ile-Glu-Trp-Leu-Lys-Asn-Gly-Gly-Pro-Ser-Ser-Gly-Ala-Ser-(Lys)$_6$ (Asn-(Glu)$_5$-[des $^{36}$Pro, $^{37,38}$Pro]exendin-4(1-39)-(Lys)$_6$) (SEQ ID NO: 694). As customary in the art, repetition of an amino acid can be indicated by a subscripted number setting forth the number of repetitions; i.e., Lys$_6$ (SEQ ID NO: 695), (Lys)$_6$ (SEQ ID NO: 695) and the like refer to hexalysyl (SEQ ID NO: 695) In any and each of the exendin analogs described above, specifically contemplated are those wherein a replacement for the histidine corresponding to position 1 is made with any of D-histidine, desamino-histidine, 2-amino-histidine, beta-hydroxy-histidine, homohistidine. N-alpha-acetyl-histidine, alpha-fluoromethyl-histidine, alpha-methyl-histidine, 3-pyridylalanine, 2-pyridylalanine, 4-pyridylalanine, 4-imidazoacetyl, des-amino-histidyl (or imidazopropionyl), beta-hydroxy-imidazopropionyl, N-dimethyl-histidyl or beta-carboxy-imidazopropionyl. Further specifically contemplated herein are exendin analogs described herein wherein a replacement for the glycine at position 2 is made with any of D-Ala, Val, Leu, Lys, Aib, (1-aminocyclopropyl)carboxylic acid, (1-aminocyclobutyl)carboxylic acid, 1-aminocyclopentyl)carboxylic acid, (1-amino cyclohexyl)carboxylic acid, (1-aminocycloheptyl) carboxylic acid, or (1-aminocyclooctyl) carboxylic acid.

Further examples of exendin analogs suitable for use in the engineered polypeptide constructs are those described in published PCT application WO2004035623 (incorporated herein by reference and for all purposes), particularly those comprised of naturally-occurring amino acids, which describes exendin analogs having at least one modified amino acid residue particularly at positions $^{13}$Gln, $^{14}$Met, $^{25}$Trp or $^{28}$Asn with reference to the corresponding positions of exendin-4(1-39). According to that publication are additional such analogs further comprising a 1-7 amino acid C-terminal extension that comprises at least one Lys amino acid and more preferably at least five Lys amino acid units such as six or seven Lys amino acid units.

Yet further examples of exendin analogs suitable for use in the engineered polypeptide constructs are those described in published PCT application WO/2010/120476, entitled "N-Terminus Conformationally Constrained GLP-1 Receptor Agonist Compounds" (incorporated herein by reference and for all purposes), which describes exendin analogs having modified amino acid residues in the N-terminal portion of an exendin or exendin analog to create a high beta-turn characteristic in that region. For example, analogs are designed to mimic amino acid residues His1 Gly2 Glu3 by creating a conformationally constrained region, include exendin analogs containing a thiazolidine-proline peptide mimetic at His1 Gly2 Glu3 (see for example compounds described in FIGS. 17A-F therein), which can be used as a modification in exendin-4, lixisenatide, or other analogs described herein.

In any and each of the exendins, e.g. exendin-4, analogs and formulas described herein, specifically contemplated are those wherein a replacement for the histidine corresponding to position 1 is made with any of L-histidine, D-histidine, desamino-histidine, 2-amino-histidine, beta-hydroxy-histidine, homohistidine. N-alpha-acetyl-histidine, alpha-fluoromethyl-histidine, alpha-methyl-histidine, 3-pyridylalanine, 2-pyridylalanine, 4-pyridylalanine, 4-imidazoacetyl, des-amino-histidyl (imidazopropionyl), beta-hydroxy-imidazopropionyl, N-dimethyl-histidyl or beta-carboxy-imidazopionyl. For example, preferred exendin analogs for use in engineered polypeptide conjugates as described herein wherein the His1 position is modified are (4-imidazoacetyl) exendin-4, (des-amino-histidyl) exendin-4 (or (imidazopropionyl) exendin-4), (beta-hydroxy-imidazopropionyl) exendin-4, (N-dimethyl-histidyl) exendin-4 and (beta-carboxy-imidazopropionyl) exendin-4. Further specifically contemplated herein are exendins or exendin analogs described herein wherein a replacement for the glycine at position 2 is made with any of D-Ala, Val, Leu, Lys, Aib, (1-aminocyclopropyl)carboxylic acid, (1-aminocyclobutyl) carboxylic acid, 1-aminocyclopentyl)carboxylic acid, (1-amino cyclohexyl)carboxylic acid, (1-aminocycloheptyl) carboxylic acid, or (1-aminocyclooctyl) carboxylic acid. Thus for example, such an engineered polypeptide would include (4-imidazoacetyl)exendin-4-Gly-PEP07986, where the exendin-4 analog is linked via a peptide bound at its C-terminal alpha carboxy group to a glycine as linker via a peptide bond to the N-terminus of the PEP07986 sequence.

Any of the above exendin analogs or their active fragments are suitable for use in the present engineered polypeptides, with or without a linker to the ABD.

Albumin Binding Domain (ABD) Peptides.

For previously disclosed albumin binding domains derived from Streptococcal protein G strain 148 (G148) and for some variants having a high affinity to albumin, e.g. WO09/016, 043, the higher affinity was achieved at the cost of reduced thermal stability. In addition, it has been reported that T- and B-cell epitopes were experimentally identified within the albumin binding region of G148 (Goetsch et al, Clin Diagn Lab Immunol 10:125-32, 2003). The authors behind the study were interested in utilizing the T-cell epitopes of G148 in vaccines, i.e. to utilize the inherent immune-stimulatory property of the albumin binding region. Goetsch et al. additionally found a B-cell epitope, i.e. a region bound by antibodies after immunization, in the sequence of G148. Therefore, the albumin binding domain G148 and polypeptides derived from G148, and thus fusion/conjugates containing them, risk the abovementioned immune-stimulatory properties. In pharmaceutical compositions for human administration no (or reduced) immune-response is desired.

The above drawbacks and deficiencies of such fusions and/or conjugates are overcome or reduced by the use of the improved albumin binding domain (ABD) peptides disclosed herein for use in the engineered polypeptides of the invention. Such ABDs are those with comparably high affinity for albumin and derive from albumin-binding domain of bacterial protein G of *Streptococcus* strain G148 and have substantial amino acid sequence identity thereto, yet are modified as described herein to further provide desirable immunological properties, e.g. reduced immunogenicity. Accordingly, the albumin binding domain polypeptide comprising the long-duration engineered polypeptide conjugate or fusion described herein is a three-helix bundle protein domain, which comprises an albumin binding motif and additional sequences comprising the three-helix configuration. The ABD peptides described herein and contemplated for the engineered polypeptides described herein are superior to those having the albumin binding sequence as described by Jonsson et al. (*Protein Eng. Design & Selection*, 2008, 21:515-527) as well as the ABD peptides described therein, and those ABD peptides further described in PCT Published Appl. No. WO2009/016043. To the ABD polypeptide described herein is fused an exendin or analog or active fragment thereof to create the engineered polypeptide described herein. An albumin binding domain polypeptide suitable for conjugation or fusion to an exendin compound can comprise the improved ABD amino acid sequence which comprises a sequence selected from:

```
formula (i)
                                          (SEQ ID NO: 300)
LA X3 AK X6 X7 AN X10 ELD X14 YGVSDF YKRLI X26

KAKTVEGVEALK X39 X40 IL X43 X44 LP
``` wherein independently of each other
X3 is selected from E, S, Q and C;
X6 is selected from E, S and C;
X7 is selected from A and S;
X14 is selected from A, S, C and K;
X10 is selected from A, S and R;
X26 is selected from D and E;
X39 is selected from D and E;
X40 is selected from A and E;
X43 is selected from A and K;
X44 is selected from A, S and E;
the leucine at position 45 is present or absent; and
the proline at position 46 is present or absent; and
formula (ii) an amino acid sequence which has at least 95% identity to the sequence defined in (i),
with the proviso that $X_7$ is not L, E or D;
or alternatively,
with the proviso that the amino acid sequence is not defined by the following sequence, as defined in PCT Published Application No. WO 2009/016043: LAEAK $X_a X_b$ A $X_c X_d$ EL $X_e$ KY GVSD $X_5$ YK $X_8 X_9$ I $X_{11} X_{12}$ A $X_{14}$ TVEGV $X_{20}$ AL $X_{23} X_{24} X_{25}$ ILAALP (SEQ ID NO: 679) wherein independently of each other,
$X_a$ is selected from V and E;
$X_b$ is selected from L, E and D;
$X_c$ is selected from N, L and I;
$X_d$ is selected from R and K;
$X_e$ is selected from D and K; and
$X_5$ is selected from Y and F;
$X_8$ is selected from N, R and S;
$X_9$ is selected from V, I, L, M, F and Y;
$X_{11}$ is selected from N, S, E and D;
$X_{12}$ is selected from R, K and N;
$X_{14}$ is selected from K and R;
$X_{20}$ is selected from D, N, Q, E, H, S, R and K;
$X_{23}$ is selected from K, I and T;
$X_{24}$ is selected from A, S, T, G, H, L and D; and
$X_{25}$ is selected from H, E and D.

In a further embodiment of the albumin binding polypeptide according to the first aspect above—the formula (i) or (ii), X6 is E. In another embodiment of the albumin binding polypeptide according to this aspect, X6 is S. In another embodiment of the albumin binding polypeptide according to this aspect, X3 is S. In another embodiment of the albumin binding polypeptide according to this aspect, X3 is E. In another embodiment of the albumin binding polypeptide according to this aspect, X7 is A. In another embodiment of the albumin binding polypeptide according to this aspect, X7 is S. In another embodiment of the albumin binding polypeptide according to this aspect, X14 is S. In another embodiment of the albumin binding polypeptide according to this aspect, X14 is C. In another embodiment of the albumin binding polypeptide according to this aspect, X14 is A. In another embodiment of the albumin binding polypeptide according to this aspect, X14 is K. In another embodiment of the albumin binding polypeptide according to this aspect, X10 is A. In another embodiment of the albumin binding polypeptide according to this aspect, X10 is S. In another embodiment of the albumin binding polypeptide according to this aspect, X26 is D. In another embodiment of the albumin binding polypeptide according to this aspect, X26 is E. In another embodiment of the albumin binding polypeptide according to this aspect X39 is D. In another embodiment of the albumin binding polypeptide according to this aspect X39 is E. In another embodiment of the albumin binding polypeptide according to this aspect X40 is A. In another embodiment of the albumin binding polypeptide according to this aspect X40 is E. In another embodiment of the albumin binding polypeptide according to this aspect X43 is A. In another embodiment of the albumin binding polypeptide according to this aspect X43 is K. In another embodiment of the albumin binding polypeptide according to this aspect X44 is A. In another embodiment of the albumin binding polypeptide according to this aspect X44 is S. In another embodiment of the albumin binding polypeptide according to this aspect X44 is E. In another embodiment of the albumin binding polypeptide according to this aspect leucine at position 45 is present. In another embodiment of the albumin binding polypeptide according to this aspect leucine at position 45 is absent. In a further embodiment the proline at position 46 is present. In a further embodiment the proline at position 46 at is absent.

In a further preferred embodiment albumin binding domain polypeptide suitable for conjugation or fusion to an exendin compound can comprise the improved ABD amino acid sequence selected from:

```
formula (iii)
                                          (SEQ ID NO: 678)
LA X3 AK X6 X7 AN X10 ELD X14 YGVSDF YKRLIDKAKT

VEGVEALKDA ILAALP
``` wherein independently of each other
    X3 is selected from E, S, Q and C;
    X6 is selected from E, S and C;
    X7 is selected from A and S;
    X10 is selected from A, S and R;
    X14 is selected from A, S, C and K;
    the leucine at position 45 is present or absent; and
    the proline at position 46 is present or absent; and
formula (iv) an amino acid sequence which has at least 95% identity to the sequence defined in (iii),
    with the proviso that $X_7$ is not L, E or D;
    or alternatively,
    with the proviso that the amino acid sequence is not defined by the following sequence, as defined in PCT Published Application No. WO 2009/016043: LAEAK $X_a$ $X_b$ A $X_c$ $X_d$ EL $X_e$ KY GVSD $X_5$ YK $X_8$ $X_9$ I $X_{11}$ $X_{12}$ A $X_{14}$ TVEGV $X_{20}$ AL $X_{23}$ $X_{24}$ $X_{25}$ ILAALP (SEQ ID NO: 679) wherein independently of each other,
    $X_a$ is selected from V and E;
    $X_b$ is selected from L, E and D;
    $X_c$ is selected from N, L and I;
    $X_d$ is selected from R and K;
    $X_e$ is selected from D and K; and
    $X_5$ is selected from Y and F;
    $X_8$ is selected from N, R and S;
    $X_9$ is selected from V, I, L, M, F and Y;
    $X_{11}$ is selected from N, S, E and D;
    $X_{12}$ is selected from R, K and N;
    $X_{14}$ is selected from K and R;
    $X_{20}$ is selected from D, N, Q, E, H, S, R and K;
    $X_{23}$ is selected from K, I and T;
    $X_{24}$ is selected from A, S, T, G, H, L and D; and
    $X_{25}$ is selected from H, E and D.

In a further embodiment of the albumin binding polypeptide according to this aspect—formula (iii) or (iv), X6 is E. In another embodiment of the albumin binding polypeptide according to this aspect, X6 is S. In another embodiment of the albumin binding polypeptide according to this aspect, X3 is S. In another embodiment of the albumin binding polypeptide according to this aspect, X3 is E. In another embodiment of the albumin binding polypeptide according to this aspect, X7 is A. In another embodiment of the albumin binding polypeptide according to this aspect, X7 is S. In another embodiment of the albumin binding polypeptide according to this aspect, X14 is S. In another embodiment of the albumin binding polypeptide according to this aspect, X14 is C. In another embodiment of the albumin binding polypeptide according to this aspect, X14 is A. In another embodiment of the albumin binding polypeptide according to this aspect, X14 is K. In another embodiment of the albumin binding polypeptide according to this aspect, X10 is A. In another embodiment of the albumin binding polypeptide according to this aspect, X10 is S. In another embodiment of the albumin binding polypeptide according to this aspect leucine at position 45 is present. In another embodiment of the albumin binding polypeptide according to this aspect leucine at position 45 is absent. In a further embodiment the proline at position 46 is present. In a further embodiment the proline at position 46 at is absent.

In a further embodiment of any one of the formulas (i) to (iv) the ABD comprises a one or more N-terminal helix-capping amino acids, and in a further embodiment the helix-capping amino acid may be serine, or may be glycine-serine. Accordingly for each albumin binding domain sequence disclosed herein, including those in the figures and sequenced listing, also specifically contemplated for all aspects as disclosed herein in the engineered polypeptide, are albumin binding domains corresponding to the ABD of any one of the formulas (i) to (iv) contained therein, their Ser-ABD, Gly-Ser-ABD, Gly-ABD, Ala-ABD and their des-C-terminal-proline sequences.

Thus, modified variants of (i) or (iii), which are such that the resulting sequence is at least 95% identical to a sequence belonging to the class defined by (i) or (iii), are also encompassed. For example, it is possible that an amino acid residue belonging to a certain functional grouping of amino acid residues (e.g. hydrophobic, hydrophilic, polar etc) could be exchanged for another amino acid residue from the same functional group.

The above defined class of sequence related ABD polypeptides having a binding affinity for albumin is derived from a common parent polypeptide sequence, which folds into a three alpha helix bundle domain. More specifically, the polypeptides as described above are derived from a model building based on a structure of a complex between serum albumin and the albumin binding domain G148-GA3 (Lejon et al, J. Biol. Chem. 279:42924-8, 2004), as well as analyses of binding and structural properties of a number of mutational variants of the common parent polypeptide sequence. The above defined amino acid sequence of any one of formulas (i) to (iv) comprises amino acid substitutions, as compared to the parent polypeptide sequence, that result in a class of polypeptides which are expected to fold into an almost identical three helix bundle domain. While the parent polypeptide sequence already comprises a binding surface for interaction with albumin, that binding surface is modified by some of the substitutions according to the above definition. The substitutions according to the above definition provide an improved albumin binding ability as compared to the parent polypeptide sequence. Importantly and surprisingly, the substitutions according to the above definition provide enhanced immunological properties, in addition to retaining and/or improving strong affinity for albumin.

Accordingly, the improved ABD polypeptides according to the first aspect of the disclosure exhibit a set of characteristics, which, for example, make them suitable for use as fusion or conjugate partners for therapeutic molecules for human administration. Importantly and surprisingly, the improved ABD according to the present disclosure demonstrate, for example in comparison with related albumin binding polypeptides such as the albumin binding domain G148-GA3 and the albumin binding polypeptides disclosed in WO09/016,043, at least five of the following six characteristics:

(1) The ABD polypeptides display a different surface compared to, for example, G148-GA3 and other bacterially derived albumin binding domains. The difference may decrease or eliminate any risk for antibody reactions in a subject, such as a human, which has been previously exposed to such bacterial proteins.

(2) The ABD polypeptides comprise fewer potential T-epitopes than, for example, G148-GA3 and other related, but different, mutational variants of the common parent polypeptide sequence, and hence exhibit low and/or lower immunogenicity when administered to a subject, such as a human.

(3) The polypeptides display lower reactivity with circulating antibodies when administered to a subject, such as a human. Thus, by amino acid substitutions in the surface of the polypeptides exposed to circulating antibodies, i.e. in the polypeptide surface not involved in the binding interaction with albumin, antibody cross-reactivity is reduced as compared to, for example, antibody cross-reactivity caused by G148-GA3 as measured in a test set of human sera.

(4) The polypeptides have a high albumin binding ability, both in terms of a higher binding affinity, as defined by a $K_D$ value, and in terms of a slower off-rate, as defined by a koff value, than, for example, known naturally occurring albumin binding polypeptides, such as the albumin binding domains derived from bacterial proteins.

(5) The polypeptides comprise fewer amino acid residues that are associated with stability problems of polypeptides than, for example, known naturally occurring albumin binding polypeptides, such as the albumin binding domains derived from bacterial proteins. Thus, the polypeptides comprise, for example, no oxidation-prone methionines or tryptophans and only one asparagine.

(6) The polypeptides have a higher structural stability, as defined by a melting point of above 55° C., than previous albumin binding polypeptides, such as those disclosed in WO09/016,043.

In one embodiment, the albumin binding polypeptide of the conjugate/fusions according to the first aspect display all six of the above listed characteristics. In another embodiment, the albumin binding polypeptide according to the first aspect displays, when bound to albumin, a more hydrophilic profile than, for example, previous albumin binding polypeptides, such as those disclosed in WO09/016,043. The surface of the albumin binding polypeptide which is exposed to the surroundings when the polypeptide interacts with albumin comprises fewer amino acid residues that confer surface hydrophobicity.

Further for each of the embodiments herein of the ABD sequence, the C-terminal proline (corresponding to position 46 above) can be optionally absent. Even further for each embodiment of the ABD sequence, the leucine at position 45 can be optionally present or absent. "ABD sequence" is a sequence of an ABD compound that is monovalent or divalent, as appropriate, that forms part of an engineered polypeptide disclosed herein. "Peptide hormone domain (HD1) sequence" is a sequence of a peptide hormone domain (HD1) compound that is monovalent or divalent, as appropriate, that forms part of an engineered polypeptide disclosed herein. "Exendin sequence" is a sequence of an exendin compound that is monovalent or divalent, as appropriate, that forms part of an engineered polypeptide disclosed herein. "Exendin analog sequence" is a sequence of an exendin analog compound that is monovalent or divalent, as appropriate, that forms part of an engineered polypeptide disclosed herein. "Exendin active fragment sequence" is a sequence of an exendin active fragment compound that is monovalent or divalent, as appropriate, that forms part of an engineered polypeptide disclosed herein. "Exendin analog active fragment sequence" is a sequence of an exendin analog active fragment compound that is monovalent or divalent, as appropriate, that forms part of an engineered polypeptide disclosed herein. "Albumin binding motif (ABM) sequence" is a sequence of an ABM that is monovalent or divalent, as appropriate, that forms part of an engineered polypeptide disclosed herein. Unless stated otherwise, it is understood that where an engineered polypeptide "comprises" a compound (e.g., an ABD or HD1), the sequence of the engineered polypeptide includes the sequence of the compound (e.g. an ABD sequence or an HD1 sequence).

Because of the presence of an albumin binding motif, the ABD peptide binds to albumin with a $K_D$ value of the interaction that is at most $1 \times 10^{-6}$ M and even more preferably at most $1 \times 10^{-9}$ M (even tighter affinity). More preferably the $K_D$ value of the interaction that is at most $1 \times 10^{-10}$ M, even more preferably is at most $1 \times 10^{-11}$ M, yet even more preferably is at most $1 \times 10^{-12}$ M, and even further is at most $1 \times 10^{-13}$ M. The values are most preferably for affinity to human serum albumin ("HSA").

The terms "albumin binding" and "binding affinity for albumin" as used herein refer to a property of a polypeptide which may be tested for example by the use of surface plasmon resonance technology, such as in a Biacore instrument as known in the art. For example, as described in the examples below, albumin binding affinity may be tested in an experiment in which albumin, or a fragment thereof, is immobilized on a sensor chip of the instrument, and the sample containing the polypeptide to be tested is passed over the chip. Alternatively, the polypeptide to be tested is immobilized on a sensor chip of the instrument, and a sample containing albumin, or a fragment thereof, is passed over the chip. Albumin may, in this regard, be a serum albumin from a mammal, such as human serum albumin. The skilled person may then interpret the results obtained by such experiments to establish at least a qualitative measure of the binding affinity of the polypeptide for albumin. If a quantitative measure is desired, for example to determine a $K_D$ value for the interaction, surface plasmon resonance methods may also be used. Binding values may for example be defined in a Biacore2000 instrument (GE Healthcare). Albumin is suitably immobilized on a sensor chip of the measurement, and samples of the polypeptide whose affinity is to be determined are prepared by serial dilution and injected. $K_D$ values may then be calculated from the results using for example the 1:1 Langmuir binding model of the BIAevaluation 4.1 software provided by the instrument manufacturer (GE Healthcare).

In one embodiment, the albumin binding polypeptide according to this aspect binds to albumin such that the $k_{off}$ value of the interaction is at most $5\times10^{-5}$ s$^{-1}$, such as at most $5\times10^{-6}$ s$^{-1}$.

In another embodiment, the amino acid sequence of the albumin binding polypeptide is selected from any one of SEQ ID NO:301-344. More specifically, the amino acid sequence is selected from SEQ ID NO:304-305, SEQ ID NO:307-308, SEQ ID NO:310-311, SEQ ID NO:313-314, SEQ ID NO:316-317, SEQ ID NO:319-320, SEQ ID NO:322-323, SEQ ID NO:325-326, SEQ ID NO:328-329, SEQ ID NO:331-332, SEQ ID NO:334-335, SEQ ID NO:337-338, SEQ ID NO:341-342 and SEQ ID NO:349-350.

In another preferred embodiment of the ABD used in the engineered polypeptides described herein, the amino acid sequence of the albumin binding polypeptide portion of an engineered polypeptide includes an ABD selected from any one of the sequences described herein, including those from Table 1 or FIG. 1, the sequence listing herein and further including their des-Pro46 and/or des-Leu45 forms.

In one embodiment, the albumin binding polypeptide according to this aspect further includes one or more additional amino acid residues positioned at the N- and/or the C-terminal of the ABD sequence defined in (i) or (iii). These additional amino acid residues may play a role in further enhancing the binding of albumin by the polypeptide, and improving the conformational stability of the folded albumin binding domain, but may equally well serve other purposes, related for example to one or more of production, purification, stabilization in vivo or in vitro, coupling, labeling or detection of the polypeptide, as well as any combination thereof. Such additional amino acid residues may include one or more amino acid residue(s) added for purposes of chemical coupling, e.g. to the HD1.

For example, the amino acids directly preceding or following the alpha helix at the N- or C-terminus of the ABD amino acid sequence (i) or (iii) may thus in one embodiment affect the conformational stability. One example of an amino acid residue which may contribute to improved conformational stability is a serine residue positioned at the N-terminal of the ABD amino acid sequence (i) or (iii) as defined above. The N-terminal serine residue may in some cases form a canonical S—X—X-E capping box, by involving hydrogen bonding between the gamma oxygen of the serine side chain and the polypeptide backbone NH of the glutamic acid residue. This N-terminal capping may contribute to stabilization of the first alpha helix of the three helix domain constituting the albumin binding polypeptide according to the first aspect of the disclosure.

Thus, in one embodiment, the additional amino acids include at least one serine residue at the N-terminal of the polypeptide. The ABD amino acid sequence is in other words preceded by one or more serine residue(s). In another embodiment of the albumin binding polypeptide, the additional amino acids include a glycine residue at the N-terminal of the ABD sequence. It is understood that the ABD amino acid sequence (i) or (iii) may be preceded by one, two, three, four or any suitable number of amino acid residues. Thus, the ABD amino acid sequence may be preceded by a single serine residue, a single glycine residue or a combination of the two, such as a glycine-serine (GS) combination or a glycine-serine-serine (GSS) combination. Examples of albumin binding polypeptides comprising additional amino residues at the N-terminal are set out in SEQ ID NO:445-463, such as in SEQ ID NO:445-448 and SEQ ID NO:462-463, and in Table 1 and FIG. 1. In yet another embodiment, the additional amino acid residues comprise a serine at the N-terminal of the polypeptide as defined by the sequence formula (i) or (iii). An example of one such ABD having a N-terminal serine is SGSLAEAKEAANAELDSYGVSD-FYKRLIDKAKTVEGVEALKDAILAALP (SEQ ID NO. 696). The corresponding des-proline form is SGSLAE-AKEAANAELDSYGVSDFYKRLIDKAK-TVEGVEALKDAILAAL (SEQ ID NO: 697). The corresponding des-Leu form is SGSLAEAKEAANAELDSYGVSD-FYKRLIDKAKTVEGVEALKDAILAAP (SEQ ID NO: 698). The corresponding des-Pro des-Leu form is SGSLAE-AKEAANAELDSYGVSDFYKRLIDKAK-TVEGVEALKDAILAA (SEQ ID NO: 699).

In yet another embodiment, the additional amino acid residue or residues include an alanine acid at the N-terminal of the ABD polypeptide defined herein, or in combination with serine as an alanine-serine sequence at the N-terminal of the ABD sequences above. In yet another embodiment, the additional amino acid residue or residues include a glutamic acid at the N-terminal of the ABD polypeptide defined herein. In yet another embodiment, the additional amino acid residue or residues includes a cysteine at the N-terminal of the ABD polypeptide defined herein. Such additional residues when present are preferably from 1 to 5 amino acids.

Similarly, C-terminal capping may be exploited to improve stability of the third alpha helix of the three helix domain constituting the albumin binding polypeptide. The C-terminal proline residue present at the C-terminal of the ABD amino acid sequence defined in (i) or (iii) may at least partly function as a capping residue. A lysine residue following the proline residue at the C-terminal may contribute to further stabilization of the third helix of the albumin binding polypeptide, by hydrogen bonding between the epsilon amino group of the lysine residue and the carbonyl groups of the amino acids located two and three residues before the lysine in the polypeptide backbone, e.g. the carbonyl groups of the leucine and alanine residues of the ABD amino acid sequence defined in (i) or (iii). Thus, in one embodiment, the additional amino acids include a lysine residue at the C-terminal of the polypeptide. Such additional residues when present are preferably from 1 to 5 amino acids.

As discussed above, the additional amino acids may be related to the production of the albumin binding polypeptide. In particular, one or more optional amino acid residues following the C-terminal proline may provide advantages when the albumin binding polypeptide according to the first aspect is produced by chemical peptide synthesis. Such additional amino acid residues may for example prevent formation of undesired substances, such as diketopiperazine at the dipeptide stage of the synthesis. One example of such an amino acid residue is glycine. Thus, in one embodiment, the additional amino acids include a glycine residue at the C-terminal of the polypeptide, directly following the proline residue or following an additional lysine and/or glycine residue as accounted for above. Alternatively, polypeptide production may benefit from amidation of the C-terminal proline residue of the ABD amino acid sequence (i) or (iii). In this case, the C-terminal proline includes an additional amine group at the carboxyl carbon.

Examples of albumin binding polypeptides comprising additional amino acid residues at the C-terminal are set out in SEQ ID NO:445-452, such as in SEQ ID NO:449-450, and in Table 1 and FIG. 1. The skilled person is aware of methods for accomplishing C-terminal modification, such as by different types of pre-made matrices for peptide synthesis.

In another embodiment, the additional amino acid residues includes a cysteine residue at the N- and/or C-terminal of the polypeptide. Such a cysteine residue may directly precede and/or follow the ABD amino acid sequence as defined in (i) or (iii) or may precede and/or follow any other additional amino acid residues as described above. Examples of albumin binding polypeptides comprising a cysteine residue at the N- and/or C-terminal of the polypeptide chain are set out in SEQ ID NO:449-450 (C-terminal) and SEQ ID NO:451-452 (N-terminal), and in Table 1 and FIG. 1. By the addition of a cysteine residue to the polypeptide chain, a thiol group for site directed conjugation of the albumin binding polypeptide may be obtained. Alternatively, a selenocysteine residue may be introduced at the C-terminal of the polypeptide chain, in a similar fashion as for the introduction of a cysteine residue, to facilitate site-specific conjugation (Cheng et al, Nat Prot 1:2, 2006).

In one embodiment, the albumin binding polypeptide includes no more than two cysteine residues. In another embodiment, the albumin binding polypeptide includes no more than one cysteine residue.

In another embodiment, the additional amino acid residues of the albumin binding polypeptide includes a "tag" for purification or detection of the polypeptide, such as a hexahistidyl ($His_6$) tag (SEQ ID NO: 49), or a "myc" ("c-Myc") tag or a "FLAG" tag for interaction with antibodies specific to the tag and/or to be used in purification. The skilled person is aware of other alternatives.

Exemplary ABD species include, but are not limited to, the compounds set forth in Table 1 following and the Examples.

TABLE 1

Selected ABD peptides

| Designation | ABD peptide sequence | SEQ ID NO: |
|---|---|---|
| PEP07271 | GSSLASAKEAANAELDAYGVSDFYKRLIDKAKTVEGVEALKDAILAALP | 455 |
| PEP07554 | GSSLASAKEAANAELDSYGVSDFYKRLIDKAKTVEGVEALKDAILAALP | 456 |
| PEP07912 | GLASAKEAANAELDSYGVSDFYKRLIDKAKTVEGVEALKDAILAALP | 457 |
| PEP07914 | GLAEAKEAANAELDSYGVSDFYKRLIDKAKTVEGVEALKDAILAALP | 458 |
| PEP07911 | GLASAKEAANAELDCYGVSDFYKRLIDKAKTVEGVEALKDAILAALP | 459 |
| PEP07834 | ALASAKEAANAELDCYGVSDFYKRLIDKAKTVEGVEALKDAILAALP | 460 |
| PEP07844 | GSSLASAKEAANAELDKYGVSDFYKRLIDKAKTVEGVEALKDAILAALP | 461 |
| PEP07983 | GSLASAKEAANAELDSYGVSDFYKRLIDKAKTVEGVEALKDAILAALP | 462 |
| PEP07986 | GSLAEAKEAANAELDSYGVSDFYKRLIDKAKTVEGVEALKDAILAALP | 463 |
| PEP08185 | GSLAEAKEAANAELDCYGVSDFYKRLIDKAKTVEGVEALKDAILAALPG | 448 |
|  | LAEAKEAANAELDSYGVSDFYKRLIDKAKTVEGVEALKDAILAALP | 313 |
|  | SLAEAKEAANAELDSYGVSDFYKRLIDKAKTVEGVEALKDAILAALP | 500 |
|  | LAEAKEAANAELDCYGVSDFYKRLIDKAKTVEGVEALKDAILAALPG | 501 |
|  | SLAEAKEAANAELDCYGVSDFYKRLIDKAKTVEGVEALKDAILAALPG | 502 |
| (des C-terminal Pro) PEP07986 | GSLAEAKEAANAELDSYGVSDFYKRLIDKAKTVEGVEALKDAILAAL | 700 |
| (des C-terminal Pro-Gly) PEP08185 | GSLAEAKEAANAELDCYGVSDFYKRLIDKAKTVEGVEALKDAILAAL | 701 |
|  | SLAEAKEAANAELDSYGVSDFYKRLIDKAKTVEGVEALKDAILAAL | 702 |
|  | SLAEAKEAANAELDCYGVSDFYKRLIDKAKTVEGVEALKDAILAAL | 703 |
|  | LAEAKEAANAELDSYGVSDFYKRLIDKAKTVEGVEALKDAILAAL | 704 |
|  | LAEAKEAANAELDCYGVSDFYKRLIDKAKTVEGVEALKDAILAAL | 705 |
|  | GSSLASAKEAANAELDAYGVSDFYKRLIDKAKTVEGVEALKDAILAALP | 455 |
|  | GSSLASAKEAANAELDSYGVSDFYKRLIDKAKTVEGVEALKDAILAALP | 456 |
|  | GLASAKEAANAELDSYGVSDFYKRLIDKAKTVEGVEALKDAILAALP | 457 |
|  | GLAEAKEAANAELDSYGVSDFYKRLIDKAKTVEGVEALKDAILAALP | 458 |
|  | GLASAKEAANAELDCYGVSDFYKRLIDKAKTVEGVEALKDAILAALP | 459 |
|  | ALASAKEAANAELDCYGVSDFYKRLIDKAKTVEGVEALKDAILAALP | 460 |

TABLE 1-continued

Selected ABD peptides

| Designation | ABD peptide sequence | SEQ ID NO: |
|---|---|---|
| | GSSLASAKEAANAELDKYGVSDFYKRLIDKAKTVEGVEALKDAILAALP | 461 |
| | GSLASAKEAANAELDSYGVSDFYKRLIDKAKTVEGVEALKDAILAALP | 462 |
| | GSLAEAKEAANAELDSYGVSDFYKRLIDKAKTVEGVEALKDAILAALP | 463 |
| | GSLAEAKEAANAELDCYGVSDFYKRLIDKAKTVEGVEALKDAILAALPG | 448 |
| | LAEAKEAANAELDSYGVSDFYKRLIDKAKTVEGVEALKDAILAALP | 313 |
| | SLAEAKEAANAELDSYGVSDFYKRLIDKAKTVEGVEALKDAILAALP | 500 |
| | LAEAKEAANAELDCYGVSDFYKRLIDKAKTVEGVEALKDAILAALPG | 501 |
| | SLAEAKEAANAELDCYGVSDFYKRLIDKAKTVEGVEALKDAILAALPG | 502 |
| | GSLAEAKEAANAELDSYGVSDFYKRLIDKAKTVEGVEALKDAILAAL | 700 |
| | GSLAEAKEAANAELDCYGVSDFYKRLIDKAKTVEGVEALKDAILAAL | 701 |
| | SLAEAKEAANAELDSYGVSDFYKRLIDKAKTVEGVEALKDAILAAL | 702 |
| | SLAEAKEAANAELDCYGVSDFYKRLIDKAKTVEGVEALKDAILAAL | 703 |
| | LAEAKEAANAELDSYGVSDFYKRLIDKAKTVEGVEALKDAILAAL | 704 |
| | LAEAKEAANAELDCYGVSDFYKRLIDKAKTVEGVEALKDAILAAL | 705 |
| | GSSLASAKEAANAELDAYGVSDFYKRLIDKAKTVEGVEALKDAILAA | 706 |
| | GSSLASAKEAANAELDSYGVSDFYKRLIDKAKTVEGVEALKDAILAA | 707 |
| | GLASAKEAANAELDSYGVSDFYKRLIDKAKTVEGVEALKDAILAA | 708 |
| | GLAEAKEAANAELDSYGVSDFYKRLIDKAKTVEGVEALKDAILAA | 709 |
| | GLASAKEAANAELDCYGVSDFYKRLIDKAKTVEGVEALKDAILAA | 710 |
| | ALASAKEAANAELDCYGVSDFYKRLIDKAKTVEGVEALKDAILAA | 711 |
| | GSSLASAKEAANAELDKYGVSDFYKRLIDKAKTVEGVEALKDAILAA | 712 |
| | GSLASAKEAANAELDSYGVSDFYKRLIDKAKTVEGVEALKDAILAA | 713 |
| | GSLAEAKEAANAELDSYGVSDFYKRLIDKAKTVEGVEALKDAILAA | 714 |
| | GSLAEAKEAANAELDCYGVSDFYKRLIDKAKTVEGVEALKDAILAA | 715 |
| | LAEAKEAANAELDSYGVSDFYKRLIDKAKTVEGVEALKDAILAA | 716 |
| | SLAEAKEAANAELDSYGVSDFYKRLIDKAKTVEGVEALKDAILAA | 717 |
| | LAEAKEAANAELDCYGVSDFYKRLIDKAKTVEGVEALKDAILAA | 718 |
| | SLAEAKEAANAELDCYGVSDFYKRLIDKAKTVEGVEALKDAILAA | 719 |
| | GSLAEAKEAANAELDSYGVSDFYKRLIDKAKTVEGVEALKDAILAA | 714 |
| | GSLAEAKEAANAELDCYGVSDFYKRLIDKAKTVEGVEALKDAILAA | 715 |
| | SLAEAKEAANAELDSYGVSDFYKRLIDKAKTVEGVEALKDAILAA | 717 |
| | SLAEAKEAANAELDCYGVSDFYKRLIDKAKTVEGVEALKDAILAA | 719 |
| | LAEAKEAANAELDSYGVSDFYKRLIDKAKTVEGVEALKDAILAA | 716 |
| | LAEAKEAANAELDCYGVSDFYKRLIDKAKTVEGVEALKDAILAA | 718 |
| | GSSLASAKEAANAELDAYGVSDFYKRLIDKAKTVEGVEALKDAILAA | 706 |
| | GSSLASAKEAANAELDSYGVSDFYKRLIDKAKTVEGVEALKDAILAA | 707 |
| | GLASAKEAANAELDSYGVSDFYKRLIDKAKTVEGVEALKDAILAA | 708 |

TABLE 1-continued

Selected ABD peptides

| Designation | ABD peptide sequence | SEQ ID NO: |
|---|---|---|
| | GLAEAKEAANAELDSYGVSDFYKRLIDKAKTVEGVEALKDAILAA | 709 |
| | GLASAKEAANAELDCYGVSDFYKRLIDKAKTVEGVEALKDAILAA | 710 |
| | ALASAKEAANAELDCYGVSDFYKRLIDKAKTVEGVEALKDAILAA | 711 |
| | GSSLASAKEAANAELDKYGVSDFYKRLIDKAKTVEGVEALKDAILAA | 712 |
| | GSLASAKEAANAELDSYGVSDFYKRLIDKAKTVEGVEALKDAILAA | 713 |
| | GSLAEAKEAANAELDSYGVSDFYKRLIDKAKTVEGVEALKDAILAA | 714 |
| | GSLAEAKEAANAELDCYGVSDFYKRLIDKAKTVEGVEALKDAILAA | 715 |
| | LAEAKEAANAELDSYGVSDFYKRLIDKAKTVEGVEALKDAILAAL | 704 |
| | SLAEAKEAANAELDSYGVSDFYKRLIDKAKTVEGVEALKDAILAA | 717 |
| | LAEAKEAANAELDCYGVSDFYKRLIDKAKTVEGVEALKDAILAA | 718 |
| | SLAEAKEAANAELDCYGVSDFYKRLIDKAKTVEGVEALKDAILAA | 719 |
| | GSLAEAKEAANAELDSYGVSDFYKRLIDKAKTVEGVEALKDAILAA | 714 |
| | GSLAEAKEAANAELDCYGVSDFYKRLIDKAKTVEGVEALKDAILAA | 715 |
| | SLAEAKEAANAELDSYGVSDFYKRLIDKAKTVEGVEALKDAILAA | 717 |
| | SLAEAKEAANAELDCYGVSDFYKRLIDKAKTVEGVEALKDAILAA | 719 |
| | LAEAKEAANAELDSYGVSDFYKRLIDKAKTVEGVEALKDAILAA | 716 |
| | LAEAKEAANAELDCYGVSDFYKRLIDKAKTVEGVEALKDAILAA | 718 |

For example, in preferred engineered polypeptide embodiments the ABD comprises LAEAKEAANAELDSYGVSDFYKRLIDKAKTVEGVEALKDAILAALP (SEQ ID NO: 313), and its N-terminally extended ABD sequence forms including SLAEAKEAANAELDSYGVSDFYKRLIDKAKTVEGVEALKDAILAALP (SEQ ID NO: 500) and GSLAEAKEAANAELDSYGVSDFYKRLIDKAKTVEGVEALKDAILAALP (SEQ ID NO:463; PEP07986). The serine in position 2 is capping the sequence, raising Tm approximately 2° C. compared to having a glycine or an alanine in this position. An alanine can also immediately precede the serine as in AGSLAEAKEAANAELDSYGVSDFYKRLIDKAKTVEGVEALKDAILAALP (SEQ ID NO. 720). Also preferred are the corresponding polypeptides where the C-terminal proline, glycine or both is absent in each of the above ABD sequences. Accordingly, also preferred are sequences where the ABD includes the des-proline forms, which can improve yields compared to the parent forms: LAEAKEAANAELDSYGVSDFYKRLIDKAKTVEGVEALKDAILAAL (SEQ ID NO: 704), and its N-terminally extended ABD sequence forms including SLAEAKEAANAELDSYGVSDFYKRLIDKAKTVEGVEALKDAILAAL (SEQ ID NO:702) and GSLAEAKEAANAELDSYGVSDFYKRLIDKAKTVEGVEALKDAILAAL (SEQ ID NO:700). Also preferred is the des-Leu45 form of each ABD.

In preferred engineered polypeptide embodiments where Cys-conjugation is desired the preferred ABD can comprise LAEAKEAANAELDCYGVSDFYKRLIDKAKTVEGVEALKDAILAALPG (SEQ ID 501) and its N-terminally extended ABD sequence forms including SLAEAKEAANAELDCYGVSDFYKRLIDKAKTVEGVEALKDAILAALPG (SEQ ID 502) and GSLAEAKEAANAELDCYGVSDFYKRLIDKAKTVEGVEALKDAILAALPG (SEQ ID NO: 448; PEP08185). Also preferred are the polypeptides where the C-terminal proline or glycine or both are absent in each of the above ABD sequences.

In one aspect with any of the ABD sequences disclosed herein, the linker to exendin-4 or exendin analog sequence is a glycine including linker as disclosed herein, for example G, GGG, GGS, GGGS (SEQ ID NO:192), TGGGGAS (SEQ ID NO:193), TGGGGGAS (SEQ ID NO:194), or TGGGGSAS (SEQ ID NO:195).

In one embodiment of the engineered polypeptides described herein, particularly those ending at its C-terminus with proline or other amino acid known to racemize during peptide synthesis, a glycine can be added to the C-terminus to counter potential problems with racemization of the C-terminal amino acid residue. Alternatively the C-terminal amino acid can in its (alpha-amino group) amidated form, e.g. proline versus proline amide, rather than ending with a glycine. However, if the amidated polypeptide is desired to be produced by recombinant rather than chemical synthesis, then amidation of the C-terminal amino acid can be performed by several methods known in the art, e.g. use of amidating PAM enzyme. An engineered polypeptide obtainable by recombinant production is preferred.

The ABD herein fold completely reversibly, that is they can be denatured and will refold spontaneously to the desired active tertiary structure. This was assessed by circular dichroism spectra analysis, for example of ABD SEQ ID NO:463, where one compares spectrum taken at 20° C. (folded state) and a second spectrum taken after heating to 90° C. (heat denaturation) a third spectrum taken following return to 20° C. (refolded state). During this procedure the Tm can be determined Another aspect of the engineered polypeptides is that the ABD can provide an increase in the solubility in aqueous solution of a poor or low soluble exendin variant. This property can be imparted by the ABD itself or because of the ensuing complex of the engineered polypeptide bound to highly soluble albumin in vivo or in vitro, which association increases the solubility of the engineered polypeptide in aqueous solution. Thus, in an embodiment of this further aspect, there is provided a composition, including an exendin compound which per se has a solubility in water of no more than 1 mg/ml, or no more than 2 mg/ml or no more than 5 mg/ml, covalently coupled to an albumin binding domain as a fusion protein or conjugate as described herein, wherein the compound and the albumin binding polypeptide, fusion protein or conjugate are covalently coupled and the solubility of the engineered polypeptide is greater than that of the unfused (or not conjugated) native exendin compound.

Binding to Albumin.

Serum albumin is the most abundant protein in mammalian sera (40 g/L; approximately 0.7 mM in humans) where it binds a variety of molecules including but not limited to lipids and bilirubin (Peters T, 1985, *Advances in Protein Chemistry* 37:161). It has been observed that the half-life of serum albumin is directly proportional to the size of the animal, where for example human serum albumin (HSA) has a half-life of 19 days and rabbit serum albumin has a half-life of about 5 days (McCurdy T R et al., *J. Lab. Clin. Med.* 143:115, 2004). Human serum albumin is widely distributed throughout the body, in particular in the intestinal and blood compartments, where it is mainly involved in the maintenance of osmolarity. Structurally, albumins are single-chain proteins including three homologous domains and totaling 584 or 585 amino acids (Dugaiczyk L et al., 1982, *Proc. Natl. Acad. Sci. USA* 79:71). Albumins contain 17 disulfide bridges and a single reactive thiol, C34, but lack N-linked and O-linked carbohydrate moieties (Peters, 1985, Id.; Nicholson J P et al., 2000, *Br J Anaesth* 85:599). The lack of glycosylation simplifies recombinant expression of albumin. This property of albumin, together with the fact that its three-dimensional structure is known (He, X M and Carter, D C, *Nature* 358:209 1992), has made it an attractive candidate for use in recombinant fusion proteins. Such fusion proteins generally combine a therapeutic protein (which would be rapidly cleared from the body upon administration of the protein per se) and a plasma protein (which exhibits a natural slow clearance) in a single polypeptide chain (Sheffield W P, *Curr. Drug Targets Cardiovacs. Haematol. Disord.* 1:1 2001). Such fusion proteins may provide clinical benefits in requiring less frequent injection and higher levels of therapeutic protein in vivo. However, the engineered polypeptides herein are not conjugated to albumin, but instead contain motifs that allow non-covalent binding to albumin.

Albumin Half-Life.

It has been observed that the half-life of albumin in different species generally adheres to allometric scaling based on animal weight. For example, the albumin half-life in mouse, rat, rabbit and human has been estimated as 1, 1.9, 5.6 and 19 days, respectively. Indeed, power fitting analysis (Davies & Morris, 1993, *Pharm. Res.* (N.Y.) 10:1093-1095) provides the equation:

$$\text{Albumin half-life (days)} = 3.75 \times \text{body weight(kg)}^{0.368}.$$

Further Embodiments.

It is understood that each of the polypeptides disclosed herein are also contemplated to include a methionine at the N-terminus in frame with the naturally-occurring first amino acid thereof, e.g., Met-exendin-4, which is exendin-4 with an added N-terminal methionine. It is further understood that where a C-terminal Gly appears in a engineered polypeptide sequence set forth herein, the residue may be lost during subsequent amidation. Some embodiments are intermediates in synthesis, for example, such as those having a "His tag" which is used for affinity purification as is known in the art, and that can optionally be subsequently removed to yield a mature engineered polypeptide suitable for therapeutic use.

In some embodiments of any of the engineered polypeptides described herein, an exendin analog can have at least 70%, for example 70%, 75%, 80%, 85%, 90%, 95%, 98% or even higher, sequence identity relative to a parent exendin sequence. In some embodiments, the parent exendin is exendin-4, and the exendin analog may have at least 70%, for example 70%, 75%, 80%, 85%, 90%, 95%, 98% or even higher, sequence identity relative to exendin-4. As known the art, GLP-1 (glucagon-like peptide 1) is not an exendin; and the sequence of GLP-1 is specifically excluded from exendin sequences suitable for the engineered polypeptides described herein.

In some embodiments, compounds are provided having a linker, for example L1, as described herein, covalently linking a polypeptide hormone domain with an ABD peptide. In some embodiments, a first linker (L1) covalently links HD1 within the engineered polypeptide. In some embodiments, L1 is a bond. In some embodiments, the polypeptide hormone domain (e.g., HD1 as described herein) can be covalently linked to the ABD peptide via a peptide linker. Any linker is optional; i.e., any linker may simply be a bond. When present the chemical structure of a linker is not critical because it serves mainly a spacer function. In one embodiment the linker includes from 1 to 30 or less amino acids linked by peptide bonds. The amino acids can be selected from the 20 naturally occurring (i.e., physiological) amino acids. Alternatively, non-natural amino acids can be incorporated either by chemical synthesis, post-translational chemical modification or by in vivo incorporation by recombinant expression in a host cell. Some of these amino acids may be glycosylated. In another embodiment the 1 to 30 or less amino acids are selected from glycine, alanine, proline, asparagine, glutamine, and lysine, and further from aspartate and glutamate. In a further embodiment the linker is made up of a majority of amino acids that are sterically unhindered, such as glycine, alanine and/or serine. "Sterically unhindered" refers, in the customary sense, to a amino acid having a small side chain, e.g., 0-2 non-hydrogen atoms, such that steric hinderance is minimized relative to amino acids having larger side chains, e.g., Leu, Trp, Tyr, Phe, and the like. Polyglycines are particularly useful, e.g. $(Gly)_3$, $(Gly)_4$ (SEQ ID NO:125), $(Gly)_5$ (SEQ ID NO:126), as are polyalanines, poly(Gly-Ala) and poly(Gly-Ser). Charged polyglycines can be useful, and include e.g., poly $(Gly_n\text{-Glu})$ (SEQ ID NO:127), poly$(Gly_n\text{-Lys})$ (SEQ ID NO:128), poly$(Gly_n\text{-Asp})$ (SEQ ID NO:129), and poly$(Gly_n\text{-Arg})$ (SEQ ID NO:130) motifs (where n can be 1 to 6). Other specific examples of linkers are $(Gly)_3$Lys $(Gly)_4$ (SEQ ID NO:131); $(Gly)_3$AsnGlySer$(Gly)_2$ (SEQ ID NO:132); $(Gly)_3$Cys$(Gly)_4$ (SEQ ID NO:133); and GlyProAsnGlyGly (SEQ ID NO:134). Combinations of Gly and Ala are particularly useful as are combination of Gly and Ser. Thus, in a further embodiment the peptide linker is selected from the group consisting of a glycine rich peptide, e.g., Gly-Gly-Gly; the sequences $[Gly\text{-}Ser]_n$(SEQ ID NO:135), [Gly-Gly-Ser]$_n$(SEQ ID NO:136), [Gly-Gly-Gly-Ser]$_n$ (SEQ ID NO:137) and [Gly-Gly-Gly-Gly-Ser]$_n$ (SEQ ID NO:138), where n is 1, 2, 3, 4, 5 or 6, for example [Gly-Gly-Gly-Gly Ser]$_3$ (SEQ ID NO: 721). "Glycine rich peptide" refers to a polypeptide which includes a plurality of glycine residues, preferably a majority of glycine residues, more preferably a preponderance of glycine residues.

In certain embodiments, charged linkers may be used. Such charges linkers may be contain a significant number of acidic residues (e.g., Asp, Glu, and the like), or may contain a significant number of basic residues (e.g., Lys, Arg, and the like), such that the linker has a pI lower than 7 or greater than 7, respectively. As understood by the artisan, and all other things being equal, the greater the relative amount of acidic or basic residues in a given linker, the lower or higher, respectively, the pI of that linker will be. Such linkers may impart advantageous properties to the engineered polypeptides disclosed herein, such as modifying the peptides pI (isoelectric point) which can in turn improve solubility and/or stability characteristics of such polypeptides at a particular pH, such as at physiological pH (e.g., between pH 7.2 and pH 7.6, inclusive), or in a pharmaceutical composition including such polypeptides. As is known in the art, solubility for a peptide can be improved by formulation in a composition having a pH that is at least or more than plus or minus one pH unit from the pI of the peptide.

For example, an "acidic linker" is a linker that has a pI of less than 7; between 6 and 7, inclusive; between 5 and 6, inclusive; between 4 and 5, inclusive; between 3 and 4, inclusive; between 2 and 3, inclusive; or between 1 and 2, inclusive. Similarly, a "basic linker" is a linker that has a pI of greater than 7; between 7 and 8, inclusive; between 8 and 9, inclusive; between 9 and 10, inclusive; between 10 and 11, inclusive; between 11 and 12 inclusive, or between 12 and 13, inclusive. In certain embodiments, an acidic linker will contain a sequence that is selected from the group of [Gly-Glu]$_n$ (SEQ ID NO:139); [Gly-Gly-Glu]$_n$ (SEQ ID NO:140); [Gly-Gly-Gly-Glu]$_n$ (SEQ ID NO:141); [Gly-Gly-Gly-Gly-Glu]$_n$ (SEQ ID NO:142), [Gly-Asp]$_n$ (SEQ ID NO:143); [Gly-Gly-Asp]$_n$ (SEQ ID NO:144); [Gly-Gly-Gly-Asp]$_n$ (SEQ ID NO:145); [Gly-Gly-Gly-Gly-Asp]$_n$ (SEQ ID NO:146), where n is 1, 2, 3, 4, 5, 6, 7, 8, 9, 10, or more; for example, [Gly-Gly-Glu]$_6$ (SEQ ID NO: 722). In certain embodiments, a basic linker will contain a sequence that is selected from the group of [Gly-Lys]$_n$ (SEQ ID NO:147); [Gly-Gly-Lys]$_n$ (SEQ ID NO:148); [Gly-Gly-Gly-Lys]$_n$ (SEQ ID NO:149); [Gly-Gly-Gly-Gly-Lys]$_n$ (SEQ ID NO:150), [Gly-Arg]$_n$ (SEQ ID NO:151); [Gly-Gly-Arg]$_n$ (SEQ ID NO:152); [Gly-Gly-Gly-Arg]$_n$ (SEQ ID NO:153); [Gly-Gly-Gly-Gly-Arg]$_n$ (SEQ ID NO:154) where n is 1, 2, 3, 4, 5, 6, 7, 8, 9, 10, or more; for example, [Gly-Gly-Lys]$_6$ (SEQ ID NO: 723).

Additionally, linkers may be prepared which possess certain structural motifs or characteristics, such as an alpha helix. For example, such a linker may contain a sequence that is selected from the group of [Glu-Ala-Ala-Ala-Lys]$_n$ (SEQ ID NO:155), where n is 1, 2, 3, 4, 5, 6, 7, 8, 9, 10, or more; for example, [Glu-Ala-Ala-Ala-Lys]$_3$ (SEQ ID NO: 724), [Glu-Ala-Ala-Ala-Lys]$_4$ (SEQ ID NO: 725), or [Glu-Ala-Ala-Ala-Lys]$_5$ (SEQ ID NO: 726). One in the art can readily determine helix content of any particular linker sequence.

A biocompatible linker other than a peptide linker may be used to covalently attach the C-terminus of an exendin to the N-terminus of the ABD sequence. The linker can be a biocompatible polymer, preferably water soluble, and more preferably about 50 kD to about 5000 kD, or about 50 KD to 500 kD, or about 100 kD to 500 kD. An exemplary biocompatible, water soluble polymer linker is a PEG linker, such as —(CH$_2$—CH$_2$—O)$_n$— where n is such that the PEG linker can have a molecular weight of 100 to 5000 kD, preferably 100 to 500 kD. Such a linker may be —NH—CH$_2$—CH$_2$—(O—CH$_2$—CH$_2$)$_n$—O—CH$_2$—CO—, where n is such that the PEG linker molecular weight is 100 kD to 5000 kD, preferably 10 kD to 500 kD. Other biocompatible polymers can be used, such as including but not limited to polysaccharides, polypropylene glycol, and co-polymers of propylene and ethylene glycols. Typically such a linker will include a reactive group at each end that can be the same or different reactive group. Such linkers with reactive groups are known and available. Preferably the reactive group is reactive with either an N-terminal amino or C-terminal carboxy group of a peptide. For example, a reactive group can be an a butylaldehyde, a propionaldehyde, an aldehyde, a succinimide or a maleimide moiety, as is known in the art. Less preferred are alkyl linkers such as —NH—(CH$_2$)$_n$—C(O)—, wherein n=2-20, and which can be further substituted by any group that does not sterically-hinder peptide function, such as a lower alkyl (e.g., $C_1$-$C_6$), lower acyl, halogen, CN, and NH$_2$.

It is also to be understood that linkers suitable for use in accordance with the invention may possess one or more of the characteristics and motifs described above and herein. For example, a linker may include an acidic linker as well as a structural motif, such as an alpha helix. Similarly, a linker may include a basic linker and a structural motif, such as an alpha helix. A linker may include an acidic linker, a basic linker, and a structural motif, such as an alpha helix. Additionally, it is also to be understood that engineered polypeptides in accordance with the invention may possess more than one linker, and each such linker may possess one or more of the characteristics described herein.

The linkers described herein are exemplary, and linkers within the scope of this invention may be much longer and may include other residues. In one embodiment, expressly excluded are engineered polypeptides in which the exendin sequence is linked directly to the ABD sequence without a linker.

In some embodiments, the engineered polypeptide includes an ABD sequence at the C-terminal, and a HD1 sequence at the N-terminal. In certain preferred embodiments, the N-terminal is an exendin sequence, an exendin fragment sequence or an exendin analog sequence. Further to embodiments which include an ABD and a HD1, the engineered polypeptide can have the structure HD1-ABD.

It is understood that absent an express indication of the N-terminus and/or C-terminus of a engineered polypeptide set forth herein, the engineered polypeptide is to be read in the N-terminus to C-terminus orientation. For example, where HD1 has the sequence of an exendin compound or analog thereof, the terms HD1-ABD, HD1-L1-ABD, HD1-ABD, and the like mean, in the absence of an express indication of the N-terminus and/or the C-terminus, that the exendin sequence or analog thereof resides at the N-terminus of the engineered polypeptide, and the ABD resides at the C-terminus Conversely, if the N-terminus and/or C-terminus is expressly indicated, then the engineered polypeptide is to be read according to the express indication of the termini. For example, the terms HD1$_{C\text{-}term}$-ABD, HD1-L1-ABD$_{N\text{-}term}$ and the like mean that the ABD resides at the N-terminus of the engineered polypeptide, and HD1 resides at the C-terminus.

In some embodiments, the engineered polypeptide described herein has an affinity for serum albumin which is different than the affinity of the ABD polypeptide alone, i.e., in the absence of a fused hormone domain. In order to obtain effective association, the engineered polypeptide can have a binding affinity for serum albumin such that the dissociation constant $K_D$ is, for example, less than about $10^{-6}$ M, $10^{-7}$ M, $10^{-8}$ M, $10^{-9}$ M, $10^{-10}$ M, $10^{-11}$ M, $10^{-12}$ M, $10^{-13}$ M, $10^{-14}$ M or even $10^{-15}$ M. In some embodiments, the affinity is not excessively tight such that the engineered polypeptide can dissociate from the albumin and elicit a biological response, for example binding to a receptor, for example, a GLP-1 receptor. The affinity can be measured as described in PCT Published Appl. No. WO2009/016043, preferably to human serum albumin, which is incorporated herein by reference in its entirety and for all purposes, including without limitation assays and synthesis methods.

In some embodiments, a engineered polypeptide described herein is superior to a corresponding compound having a different moiety that can extend plasma half-life (e.g., PEG or of Fc or albumin) conjugated with a hormone domain(s). In this context, the term "superior" refers to a variety of functional properties which could be weighed in the evaluation of a treatment for a disease or disorder. For example, the engineered polypeptide described herein could require less biologically active (hormone domain) component, for example 1×, 2×, 3×, 4×, 5×, or even less, than the corresponding compound having a different moiety conjugated with the hormone domain(s). For further example, the engineered polypeptide described herein could have higher potency, for example, 1.5×, 2×, 3×, 4×, 5×, 10×, 20×, 50×, or even higher potency.

Engineered polypeptide compounds contemplated herein include the compounds as set forth in Table 2 following. Preferred compounds are Cmpd 5, Cmpd 9 and Cmpd 11.

TABLE 2

Selected exemplary engineered polypeptides

| Cmpd | Sequence | SEQ ID NO: |
|---|---|---|
| 5 | HGEGTFTSDLSKQLEEEAVRLFIEWLKQGGPSKEIISTGGGGSASGSLAEAKEAANAELDSYGVSDFYKRLIDKAKTVEGVEALKDAILAALP | 727 |
| 6 | HGEGTFTSDLSKQLEEEAVRLFIEWLKNGGPSSGAPPKSTGGGGSASGSLAEAKEAANAELDSYGVSDFYKRLIDKAKTVEGVEALKDAILAALP | 728 |
| 7 | HGEGTFTSDLSKQLEEEAVRLFIEWLKNGGPSSGAPPPSTGGGGSASGSLAEAKEAANAELDSYGVSDFYKRLIDKAKTVEGVEALKDAILAAL | 729 |
| 8 | HGEGTFTSDLSKQMEEEAVRLFIEWLKNGGPSSGAPPPSTGGGGSASGSLAEAKEAANAELDSYGVSDFYKRLIDKAKTVEGVEALKDAILAALP | 730 |
| 9 | HGEGTFTSDLSKQMEEEAVRLFIEWLKNGGPSSGAPPPSGGSLAEAKEAANAELDSYGVSDFYKRLIDKAKTVEGVEALKDAILAALP | 731 |
| 10 | HGEGTFTSDLSKQLEEEAVRLFIEWLKNGGPSSGAPPPSTGGGGSASGSLAEAKEAANAELDSYGVSDFYKRLIDKAKTVEGVEALKDAILAALP | 732 |
| 11 | HGEGTFTSDLSKQLEEEAVRLFIEWLKNGGPSSGAPPPSGGSLAEAKEAANAELDSYGVSDFYKRLIDKAKTVEGVEALKDAILAALP | 733 |
|  | HGEGTFTSDLSKQLEEEAVRLFIEWLKQGGPSKEIISTGGGGSASGSLAEAKEAANAELDSYGVSDFYKRLIDKAKTVEGVEALKDAILAAL | 734 |
|  | HGEGTFTSDLSKQLEEEAVRLFIEWLKNGGPSSGAPPKSTGGGGSASGSLAEAKEAANAELDSYGVSDFYKRLIDKAKTVEGVEALKDAILAAL | 735 |
|  | HGEGTFTSDLSKQLEEEAVRLFIEWLKNGGPSSGAPPPSTGGGGSASGSLAEAKEAANAELDSYGVSDFYKRLIDKAKTVEGVEALKDAILAA | 736 |
|  | HGEGTFTSDLSKQMEEEAVRLFIEWLKNGGPSSGAPPPSTGGGGSASGSLAEAKEAANAELDSYGVSDFYKRLIDKAKTVEGVEALKDAILAAL | 737 |
|  | HGEGTFTSDLSKQMEEEAVRLFIEWLKNGGPSSGAPPPSGGSLAEAKEAANAELDSYGVSDFYKRLIDKAKTVEGVEALKDAILAAL | 738 |
|  | HGEGTFTSDLSKQLEEEAVRLFIEWLKNGGPSSGAPPPSGGSLAEAKEAANAELDSYGVSDFYKRLIDKAKTVEGVEALKDAILAAL | 739 |
|  | HGEGTFTSDLSKQLEEEAVRLFIEWLKQGGPSKEIISTGGGGSASGSLAEAKEAANAELDSYGVSDFYKRLIDKAKTVEGVEALKDAILAA | 740 |
|  | HGEGTFTSDLSKQLEEEAVRLFIEWLKNGGPSSGAPPKSTGGGGSASGSLAEAKEAANAELDSYGVSDFYKRLIDKAKTVEGVEALKDAILAA | 741 |
|  | HGEGTFTSDLSKQMEEEAVRLFIEWLKNGGPSSGAPPPSTGGGGSASGSLAEAKEAANAELDSYGVSDFYKRLIDKAKTVEGVEALKDAILAA | 742 |
|  | HGEGTFTSDLSKQMEEEAVRLFIEWLKNGGPSSGAPPPSGGSLAEAKEAANAELDSYGVSDFYKRLIDKAKTVEGVEALKDAILAA | 743 |
|  | HGEGTFTSDLSKQLEEEAVRLFIEWLKNGGPSSGAPPPSTGGGGSASGSLAEAKEAANAELDSYGVSDFYKRLIDKAKTVEGVEALKDAILAA | 744 |
|  | HGEGTFTSDLSKQLEEEAVRLFIEWLKNGGPSSGAPPPSGGSLAEAKEAANAELDSYGVSDFYKRLIDKAKTVEGVEALKDAILAA | 745 |

Additional engineered polypeptide compounds specifically contemplated herein as if set forth specifically, have any on an HD1 and an ABD component, optionally with any of the L1 sequences disclosed herein, and include the compounds having the structure of any of the engineered polypeptides of the tables and listing herein, including those disclosed in Table 3 following:

TABLE 3

Selected exemplary engineered polypeptides

| Cmpd | Sequence | SEQ ID NO: |
|---|---|---|
| 5 | HGEGTFTSDLSKQLEEEAVRLFIEWLKQGGPSKEIISTGGGGSASGSLAEAKEAANAELDSYGVSDFYKRLIDKAKTVEGVEALKDAILAALP | 727 |
|  | HGEGTFTSDLSKQLEEEAVRLFIEWLKQGGPSKEIISTGGGGSASGSLAEAKEAANAELDSYGVSDFYKRLIDKAKTVEGVEALKDAILAAL | 734 |
|  | HGEGTFTSDLSKQLEEEAVRLFIEWLKQGGPSKEIISTGGGGSASSLAEAKEAANAELDSYGVSDFYKRLIDKAKTVEGVEALKDAILAALP | 746 |
|  | HGEGTFTSDLSKQLEEEAVRLFIEWLKQGGPSKEIISTGGGGSASGSLAEAKEAANAELDSYGVSDFYKRLIDKAKTVEGVEALKDAILAA | 740 |
|  | HGEGTFTSDLSKQLEEEAVRLFIEWLKQGGPSKEIISTGGGGSASSLAEAKEAANAELDSYGVSDFYKRLIDKAKTVEGVEALKDAILAAL | 747 |
|  | HGEGTFTSDLSKQLEEEAVRLFIEWLKQGGPSKEIISTGGGGSASLAEAKEAANAELDSYGVSDFYKRLIDKAKTVEGVEALKDAILAALP | 748 |
|  | HGEGTFTSDLSKQLEEEAVRLFIEWLKQGGPSKEIISTGGGGSASLAEAKEAANAELDSYGVSDFYKRLIDKAKTVEGVEALKDAILAAL | 749 |
|  | HGEGTFTSDLSKQLEEEAVRLFIEWLKQGGPSKEIISGGGGSLAEAKEAANAELDSYGVSDFYKRLIDKAKTVEGVEALKDAILAALP | 750 |
|  | HGEGTFTSDLSKQLEEEAVRLFIEWLKQGGPSKEIISGGGGSLAEAKEAANAELDSYGVSDFYKRLIDKAKTVEGVEALKDAILAAL | 751 |
|  | HGEGTFTSDLSKQLEEEAVRLFIEWLKQGGPSKEIISGGGSLAEAKEAANAELDSYGVSDFYKRLIDKAKTVEGVEALKDAILAALP | 752 |
|  | HGEGTFTSDLSKQLEEEAVRLFIEWLKQGGPSKEIISGGGSLAEAKEAANAELDSYGVSDFYKRLIDKAKTVEGVEALKDAILAAL | 753 |
|  | HGEGTFTSDLSKQLEEEAVRLFIEWLKQGGPSKEIISGGGLAEAKEAANAELDSYGVSDFYKRLIDKAKTVEGVEALKDAILAALP | 754 |
|  | HGEGTFTSDLSKQLEEEAVRLFIEWLKQGGPSKEIISGGGLAEAKEAANAELDSYGVSDFYKRLIDKAKTVEGVEALKDAILAAL | 755 |
|  | HGEGTFTSDLSKQLEEEAVRLFIEWLKQGGPSKEIISGGSLAEAKEAANAELDSYGVSDFYKRLIDKAKTVEGVEALKDAILAALP | 756 |
|  | HGEGTFTSDLSKQLEEEAVRLFIEWLKQGGPSKEIISGGSLAEAKEAANAELDSYGVSDFYKRLIDKAKTVEGVEALKDAILAAL | 757 |
|  | HGEGTFTSDLSKQLEEEAVRLFIEWLKQGGPSKEIISGSLAEAKEAANAELDSYGVSDFYKRLIDKAKTVEGVEALKDAILAALP | 985 |
|  | HGEGTFTSDLSKQLEEEAVRLFIEWLKQGGPSKEIISGSLAEAKEAANAELDSYGVSDFYKRLIDKAKTVEGVEALKDAILAAL | 986 |
|  | HGEGTFTSDLSKQLEEEAVRLFIEWLKQGGPSKEIISGLAEAKEAANAELDSYGVSDFYKRLIDKAKTVEGVEALKDAILAALP | 987 |
|  | HGEGTFTSDLSKQLEEEAVRLFIEWLKQGGPSKEIISGLAEAKEAANAELDSYGVSDFYKRLIDKAKTVEGVEALKDAILAAL | 988 |
| 6 | HGEGTFTSDLSKQLEEEAVRLFIEWLKNGGPSSGAPPKSTGGGGSASGSLAEAKEAANAELDSYGVSDFYKRLIDKAKTVEGVEALKDAILAALP | 728 |
|  | HGEGTFTSDLSKQLEEEAVRLFIEWLKNGGPSSGAPPKSTGGGGSASGSLAEAKEAANAELDSYGVSDFYKRLIDKAKTVEGVEALKDAILAAL | 735 |
|  | HGEGTFTSDLSKQLEEEAVRLFIEWLKNGGPSSGAPPKSTGGGGSASSLAEAKEAANAELDSYGVSDFYKRLIDKAKTVEGVEALKDAILAALP | 758 |
|  | HGEGTFTSDLSKQLEEEAVRLFIEWLKNGGPSSGAPPKSTGGGGSASSLAEAKEAANAELDSYGVSDFYKRLIDKAKTVEGVEALKDAILAAL | 759 |

TABLE 3-continued

Selected exemplary engineered polypeptides

| Cmpd Sequence | SEQ ID NO: |
|---|---|
| HGEGTFTSDLSKQLEEEAVRLFIEWLKNGGPSSGAPPKSTGGGGSASLAEAK EAANAELDSYGVSDFYKRLIDKAKTVEGVEALKDAILAALP | 760 |
| HGEGTFTSDLSKQLEEEAVRLFIEWLKNGGPSSGAPPKSTGGGGSASLAEAK EAANAELDSYGVSDFYKRLIDKAKTVEGVEALKDAILAAL | 761 |
| HGEGTFTSDLSKQLEEEAVRLFIEWLKNGGPSSGAPPKSGGGGSLAEAKEAA NAELDSYGVSDFYKRLIDKAKTVEGVEALKDAILAALP | 762 |
| HGEGTFTSDLSKQLEEEAVRLFIEWLKNGGPSSGAPPKSGGGGSLAEAKEAA NAELDSYGVSDFYKRLIDKAKTVEGVEALKDAILAAL | 763 |
| HGEGTFTSDLSKQLEEEAVRLFIEWLKNGGPSSGAPPKSGGGSLAEAKEAAN AELDSYGVSDFYKRLIDKAKTVEGVEALKDAILAALP | 764 |
| HGEGTFTSDLSKQLEEEAVRLFIEWLKNGGPSSGAPPKSGGGSLAEAKEAAN AELDSYGVSDFYKRLIDKAKTVEGVEALKDAILAAL | 765 |
| HGEGTFTSDLSKQLEEEAVRLFIEWLKNGGPSSGAPPKSGGGLAEAKEAANA ELDSYGVSDFYKRLIDKAKTVEGVEALKDAILAALP | 766 |
| HGEGTFTSDLSKQLEEEAVRLFIEWLKNGGPSSGAPPKSGGGLAEAKEAANA ELDSYGVSDFYKRLIDKAKTVEGVEALKDAILAAL | 767 |
| HGEGTFTSDLSKQLEEEAVRLFIEWLKNGGPSSGAPPKSGGSLAEAKEAANA ELDSYGVSDFYKRLIDKAKTVEGVEALKDAILAALP | 768 |
| HGEGTFTSDLSKQLEEEAVRLFIEWLKNGGPSSGAPPKSGGSLAEAKEAANA ELDSYGVSDFYKRLIDKAKTVEGVEALKDAILAAL | 769 |
| HGEGTFTSDLSKQLEEEAVRLFIEWLKNGGPSSGAPPKSGSLAEAKEAANAE LDSYGVSDFYKRLIDKAKTVEGVEALKDAILAALP | 770 |
| HGEGTFTSDLSKQLEEEAVRLFIEWLKNGGPSSGAPPKSGSLAEAKEAANAE LDSYGVSDFYKRLIDKAKTVEGVEALKDAILAAL | 771 |
| HGEGTFTSDLSKQLEEEAVRLFIEWLKNGGPSSGAPPKSGLAEAKEAANAEL DSYGVSDFYKRLIDKAKTVEGVEALKDAILAALP | 772 |
| HGEGTFTSDLSKQLEEEAVRLFIEWLKNGGPSSGAPPKSGLAEAKEAANAEL DSYGVSDFYKRLIDKAKTVEGVEALKDAILAAL | 773 |
| HGEGTFTSDLSKQMEEEAVRLFIEWLKNGGPSSGAPPKSTGGGGSASGSLAE AKEAANAELDSYGVSDFYKRLIDKAKTVEGVEALKDAILAALP | 774 |
| HGEGTFTSDLSKQMEEEAVRLFIEWLKNGGPSSGAPPKSTGGGGSASGSLAE AKEAANAELDSYGVSDFYKRLIDKAKTVEGVEALKDAILAAL | 775 |
| HGEGTFTSDLSKQMEEEAVRLFIEWLKNGGPSSGAPPKSTGGGGSASSLAEA KEAANAELDSYGVSDFYKRLIDKAKTVEGVEALKDAILAALP | 776 |
| HGEGTFTSDLSKQMEEEAVRLFIEWLKNGGPSSGAPPKSTGGGGSASSLAEA KEAANAELDSYGVSDFYKRLIDKAKTVEGVEALKDAILAAL | 777 |
| HGEGTFTSDLSKQMEEEAVRLFIEWLKNGGPSSGAPPKSTGGGGSASLAEAK EAANAELDSYGVSDFYKRLIDKAKTVEGVEALKDAILAALP | 778 |
| HGEGTFTSDLSKQMEEEAVRLFIEWLKNGGPSSGAPPKSTGGGGSASLAEAK EAANAELDSYGVSDFYKRLIDKAKTVEGVEALKDAILAAL | 779 |
| HGEGTFTSDLSKQMEEEAVRLFIEWLKNGGPSSGAPPKSGGGGSLAEAKEAA NAELDSYGVSDFYKRLIDKAKTVEGVEALKDAILAALP | 780 |
| HGEGTFTSDLSKQMEEEAVRLFIEWLKNGGPSSGAPPKSGGGGSLAEAKEAA NAELDSYGVSDFYKRLIDKAKTVEGVEALKDAILAAL | 781 |
| HGEGTFTSDLSKQMEEEAVRLFIEWLKNGGPSSGAPPKSGGGSLAEAKEAAN AELDSYGVSDFYKRLIDKAKTVEGVEALKDAILAALP | 782 |
| HGEGTFTSDLSKQMEEEAVRLFIEWLKNGGPSSGAPPKSGGGSLAEAKEAAN AELDSYGVSDFYKRLIDKAKTVEGVEALKDAILAAL | 783 |
| HGEGTFTSDLSKQMEEEAVRLFIEWLKNGGPSSGAPPKSGGGLAEAKEAANA ELDSYGVSDFYKRLIDKAKTVEGVEALKDAILAALP | 784 |

TABLE 3-continued

Selected exemplary engineered polypeptides

| Cmpd | Sequence | SEQ ID NO: |
|---|---|---|
| | HGEGTFTSDLSKQMEEEAVRLFIEWLKNGGPSSGAPPKSGGGLAEAKEAAN AELDSYGVSDFYKRLIDKAKTVEGVEALKDAILAAL | 785 |
| | HGEGTFTSDLSKQMEEEAVRLFIEWLKNGGPSSGAPPKSGGSLAEAKEAANA ELDSYGVSDFYKRLIDKAKTVEGVEALKDAILAALP | 786 |
| | HGEGTFTSDLSKQMEEEAVRLFIEWLKNGGPSSGAPPKSGGSLAEAKEAANA ELDSYGVSDFYKRLIDKAKTVEGVEALKDAILAAL | 787 |
| | HGEGTFTSDLSKQMEEEAVRLFIEWLKNGGPSSGAPPKSGSLAEAKEAANAE LDSYGVSDFYKRLIDKAKTVEGVEALKDAILAALP | 788 |
| | HGEGTFTSDLSKQMEEEAVRLFIEWLKNGGPSSGAPPKSGSLAEAKEAANAE LDSYGVSDFYKRLIDKAKTVEGVEALKDAILAAL | 789 |
| | HGEGTFTSDLSKQMEEEAVRLFIEWLKNGGPSSGAPPKSGLAEAKEAANAEL DSYGVSDFYKRLIDKAKTVEGVEALKDAILAALP | 790 |
| | HGEGTFTSDLSKQMEEEAVRLFIEWLKNGGPSSGAPPKSGLAEAKEAANAEL DSYGVSDFYKRLIDKAKTVEGVEALKDAILAAL | 791 |
| 10 | HGEGTFTSDLSKQLEEEAVRLFIEWLKNGGPSSGAPPPSTGGGGSASGSLAEA KEAANAELDSYGVSDFYKRLIDKAKTVEGVEALKDAILAALP | 732 |
| | HGEGTFTSDLSKQLEEEAVRLFIEWLKNGGPSSGAPPPSTGGGGSASSLAEAK EAANAELDSYGVSDFYKRLIDKAKTVEGVEALKDAILAALP | 792 |
| | HGEGTFTSDLSKQLEEEAVRLFIEWLKNGGPSSGAPPPSTGGGGSASGSLAEA KEAANAELDSYGVSDFYKRLIDKAKTVEGVEALKDAILAA | 736 |
| | HGEGTFTSDLSKQLEEEAVRLFIEWLKNGGPSSGAPPPSTGGGGSASSLAEAK EAANAELDSYGVSDFYKRLIDKAKTVEGVEALKDAILAAL | 793 |
| | HGEGTFTSDLSKQLEEEAVRLFIEWLKNGGPSSGAPPPSTGGGGSASLAEAKE AANAELDSYGVSDFYKRLIDKAKTVEGVEALKDAILAALP | 794 |
| | HGEGTFTSDLSKQLEEEAVRLFIEWLKNGGPSSGAPPPSTGGGGSASLAEAKE AANAELDSYGVSDFYKRLIDKAKTVEGVEALKDAILAAL | 795 |
| | HGEGTFTSDLSKQLEEEAVRLFIEWLKNGGPSSGAPPPSGGGGSLAEAKEAA NAELDSYGVSDFYKRLIDKAKTVEGVEALKDAILAALP | 796 |
| | HGEGTFTSDLSKQLEEEAVRLFIEWLKNGGPSSGAPPPSGGGGSLAEAKEAA NAELDSYGVSDFYKRLIDKAKTVEGVEALKDAILAAL | 797 |
| | HGEGTFTSDLSKQLEEEAVRLFIEWLKNGGPSSGAPPPSGGGSLAEAKEAAN AELDSYGVSDFYKRLIDKAKTVEGVEALKDAILAALP | 798 |
| | HGEGTFTSDLSKQLEEEAVRLFIEWLKNGGPSSGAPPPSGGGSLAEAKEAAN AELDSYGVSDFYKRLIDKAKTVEGVEALKDAILAAL | 799 |
| | HGEGTFTSDLSKQLEEEAVRLFIEWLKNGGPSSGAPPPSGGGLAEAKEAANA ELDSYGVSDFYKRLIDKAKTVEGVEALKDAILAALP | 800 |
| | HGEGTFTSDLSKQLEEEAVRLFIEWLKNGGPSSGAPPPSGGGLAEAKEAANA ELDSYGVSDFYKRLIDKAKTVEGVEALKDAILAAL | 801 |
| 11 | HGEGTFTSDLSKQLEEEAVRLFIEWLKNGGPSSGAPPPSGGSLAEAKEAANA ELDSYGVSDFYKRLIDKAKTVEGVEALKDAILAALP | 733 |
| | HGEGTFTSDLSKQLEEEAVRLFIEWLKNGGPSSGAPPPSGGSLAEAKEAANA ELDSYGVSDFYKRLIDKAKTVEGVEALKDAILAAL | 739 |
| | HGEGTFTSDLSKQLEEEAVRLFIEWLKNGGPSSGAPPPSGSLAEAKEAANAE LDSYGVSDFYKRLIDKAKTVEGVEALKDAILAALP | 802 |
| | HGEGTFTSDLSKQLEEEAVRLFIEWLKNGGPSSGAPPPSGSLAEAKEAANAE LDSYGVSDFYKRLIDKAKTVEGVEALKDAILAAL | 803 |
| | HGEGTFTSDLSKQLEEEAVRLFIEWLKNGGPSSGAPPPSGLAEAKEAANAEL DSYGVSDFYKRLIDKAKTVEGVEALKDAILAALP | 804 |
| | HGEGTFTSDLSKQLEEEAVRLFIEWLKNGGPSSGAPPPSGGSLAEAKEAANA ELDSYGVSDFYKRLIDKAKTVEGVEALKDAILAA | 745 |

TABLE 3-continued

Selected exemplary engineered polypeptides

| Cmpd | Sequence | SEQ ID NO: |
|---|---|---|
| | HGEGTFTSDLSKQLEEEAVRLFIEWLKNGGPSSGAPPPSGLAEAKEAANAEL DSYGVSDFYKRLIDKAKTVEGVEALKDAILAAL | 805 |
| 8 | HGEGTFTSDLSKQMEEEAVRLFIEWLKNGGPSSGAPPPSTGGGGSASGSLAE AKEAANAELDSYGVSDFYKRLIDKAKTVEGVEALKDAILAALP | 730 |
| | HGEGTFTSDLSKQMEEEAVRLFIEWLKNGGPSSGAPPPSTGGGGSASGSLAE AKEAANAELDSYGVSDFYKRLIDKAKTVEGVEALKDAILAAL | 737 |
| | HGEGTFTSDLSKQMEEEAVRLFIEWLKNGGPSSGAPPPSTGGGGSASSLAEA KEAANAELDSYGVSDFYKRLIDKAKTVEGVEALKDAILAALP | 806 |
| | HGEGTFTSDLSKQMEEEAVRLFIEWLKNGGPSSGAPPPSTGGGGSASSLAEA KEAANAELDSYGVSDFYKRLIDKAKTVEGVEALKDAILAAL | 807 |
| | HGEGTFTSDLSKQMEEEAVRLFIEWLKNGGPSSGAPPPSTGGGGSASLAEAK EAANAELDSYGVSDFYKRLIDKAKTVEGVEALKDAILAALP | 808 |
| | HGEGTFTSDLSKQMEEEAVRLFIEWLKNGGPSSGAPPPSTGGGGSASLAEAK EAANAELDSYGVSDFYKRLIDKAKTVEGVEALKDAILAAL | 809 |
| | HGEGTFTSDLSKQMEEEAVRLFIEWLKNGGPSSGAPPPSGGGGSLAEAKEAA NAELDSYGVSDFYKRLIDKAKTVEGVEALKDAILAALP | 810 |
| | HGEGTFTSDLSKQMEEEAVRLFIEWLKNGGPSSGAPPPSGGGGSLAEAKEAA NAELDSYGVSDFYKRLIDKAKTVEGVEALKDAILAAL | 811 |
| | HGEGTFTSDLSKQMEEEAVRLFIEWLKNGGPSSGAPPPSGGGSLAEAKEAAN AELDSYGVSDFYKRLIDKAKTVEGVEALKDAILAALP | 812 |
| | HGEGTFTSDLSKQMEEEAVRLFIEWLKNGGPSSGAPPPSGGGSLAEAKEAAN AELDSYGVSDFYKRLIDKAKTVEGVEALKDAILAAL | 813 |
| | HGEGTFTSDLSKQMEEEAVRLFIEWLKNGGPSSGAPPPSGGGLAEAKEAANA ELDSYGVSDFYKRLIDKAKTVEGVEALKDAILAALP | 814 |
| | HGEGTFTSDLSKQMEEEAVRLFIEWLKNGGPSSGAPPPSGGGLAEAKEAANA ELDSYGVSDFYKRLIDKAKTVEGVEALKDAILAAL | 815 |
| 9 | HGEGTFTSDLSKQMEEEAVRLFIEWLKNGGPSSGAPPPSGGSLAEAKEAANA ELDSYGVSDFYKRLIDKAKTVEGVEALKDAILAALP | 731 |
| | HGEGTFTSDLSKQMEEEAVRLFIEWLKNGGPSSGAPPPSGGSLAEAKEAANA ELDSYGVSDFYKRLIDKAKTVEGVEALKDAILAAL | 738 |
| | HGEGTFTSDLSKQMEEEAVRLFIEWLKNGGPSSGAPPPSGGSLAEAKEAANA ELDSYGVSDFYKRLIDKAKTVEGVEALKDAILAA | 743 |
| | HGEGTFTSDLSKQMEEEAVRLFIEWLKNGGPSSGAPPPSGSLAEAKEAANAE LDSYGVSDFYKRLIDKAKTVEGVEALKDAILAALP | 816 |
| | HGEGTFTSDLSKQMEEEAVRLFIEWLKNGGPSSGAPPPSGSLAEAKEAANAE LDSYGVSDFYKRLIDKAKTVEGVEALKDAILAAL | 817 |
| | HGEGTFTSDLSKQMEEEAVRLFIEWLKNGGPSSGAPPPSGLAEAKEAANAEL DSYGVSDFYKRLIDKAKTVEGVEALKDAILAALP | 818 |
| | HGEGTFTSDLSKQMEEEAVRLFIEWLKNGGPSSGAPPPSGLAEAKEAANAEL DSYGVSDFYKRLIDKAKTVEGVEALKDAILAAL | 819 |
| | HGEGTFTSDLSKQLEEEAVRLFIEWLKNGGPSSGAPPSKKKKKKTGGGGSAS GSLAEAKEAANAELDSYGVSDFYKRLIDKAKTVEGVEALKDAILAALP | 820 |
| | HGEGTFTSDLSKQLEEEAVRLFIEWLKNGGPSSGAPPSKKKKKKTGGGGSAS GSLAEAKEAANAELDSYGVSDFYKRLIDKAKTVEGVEALKDAILAAL | 821 |
| | HGEGTFTSDLSKQLEEEAVRLFIEWLKNGGPSSGAPPSKKKKKKTGGGGSAS SLAEAKEAANAELDSYGVSDFYKRLIDKAKTVEGVEALKDAILAALP | 822 |
| | HGEGTFTSDLSKQLEEEAVRLFIEWLKNGGPSSGAPPSKKKKKKTGGGGSAS SLAEAKEAANAELDSYGVSDFYKRLIDKAKTVEGVEALKDAILAAL | 823 |
| | HGEGTFTSDLSKQLEEEAVRLFIEWLKNGGPSSGAPPSKKKKKKTGGGGSAS LAEAKEAANAELDSYGVSDFYKRLIDKAKTVEGVEALKDAILAALP | 824 |

TABLE 3-continued

Selected exemplary engineered polypeptides

| Cmpd Sequence | SEQ ID NO: |
|---|---|
| HGEGTFTSDLSKQLEEEAVRLFIEWLKNGGPSSGAPPSKKKKKKTGGGGSAS<br>LAEAKEAANAELDSYGVSDFYKRLIDKAKTVEGVEALKDAILAAL | 825 |
| HGEGTFTSDLSKQLEEEAVRLFIEWLKNGGPSSGAPPSKKKKKKGGGGSLAE<br>AKEAANAELDSYGVSDFYKRLIDKAKTVEGVEALKDAILAALP | 826 |
| HGEGTFTSDLSKQLEEEAVRLFIEWLKNGGPSSGAPPSKKKKKKGGGGSLAE<br>AKEAANAELDSYGVSDFYKRLIDKAKTVEGVEALKDAILAAL | 827 |
| HGEGTFTSDLSKQLEEEAVRLFIEWLKNGGPSSGAPPSKKKKKKGGGSLAEA<br>KEAANAELDSYGVSDFYKRLIDKAKTVEGVEALKDAILAALP | 828 |
| HGEGTFTSDLSKQLEEEAVRLFIEWLKNGGPSSGAPPSKKKKKKGGGSLAEA<br>KEAANAELDSYGVSDFYKRLIDKAKTVEGVEALKDAILAAL | 829 |
| HGEGTFTSDLSKQLEEEAVRLFIEWLKNGGPSSGAPPSKKKKKKGGGLAEAK<br>EAANAELDSYGVSDFYKRLIDKAKTVEGVEALKDAILAALP | 830 |
| HGEGTFTSDLSKQLEEEAVRLFIEWLKNGGPSSGAPPSKKKKKKGGGLAEAK<br>EAANAELDSYGVSDFYKRLIDKAKTVEGVEALKDAILAAL | 831 |
| HGEGTFTSDLSKQLEEEAVRLFIEWLKNGGPSSGAPPSKKKKKKGGSLAEAK<br>EAANAELDSYGVSDFYKRLIDKAKTVEGVEALKDAILAALP | 832 |
| HGEGTFTSDLSKQLEEEAVRLFIEWLKNGGPSSGAPPSKKKKKKGGSLAEAK<br>EAANAELDSYGVSDFYKRLIDKAKTVEGVEALKDAILAAL | 833 |
| HGEGTFTSDLSKQLEEEAVRLFIEWLKNGGPSSGAPPSKKKKKKGSLAEAKE<br>AANAELDSYGVSDFYKRLIDKAKTVEGVEALKDAILAALP | 834 |
| HGEGTFTSDLSKQLEEEAVRLFIEWLKNGGPSSGAPPSKKKKKKGSLAEAKE<br>AANAELDSYGVSDFYKRLIDKAKTVEGVEALKDAILAAL | 835 |
| HGEGTFTSDLSKQLEEEAVRLFIEWLKNGGPSSGAPPSKKKKKKGLAEAKEA<br>ANAELDSYGVSDFYKRLIDKAKTVEGVEALKDAILAALP | 836 |
| HGEGTFTSDLSKQLEEEAVRLFIEWLKNGGPSSGAPPSKKKKKKGLAEAKEA<br>ANAELDSYGVSDFYKRLIDKAKTVEGVEALKDAILAAL | 837 |

Specifically contemplated are compounds of the above sequences in which any N-terminal methionine is absent. The N-terminal methionine can be present primarily as a convenience for bacterial expression. However, engineered peptides of the present invention can be expressed in a eukaryotic host cell (e.g. yeast (e.g. *Pichia*), mammalian, baculovirus) or other host cell having post-translational N-terminal proteolytic processing to yield an N-terminal amino acid as found in a naturally occurring mature peptide counterpart of the desired hormone or ABD sequence, i.e. without the added methionine or other leader sequence. Alternatively, an N-terminal sequence used for expression and/or secretion (and even purification) can be one that can be removed post-translationally, e.g. as by use of a protease such as TEV.

III. Methods of Design and Production

Design of Constructs.

The engineered polypeptides described herein can be designed at the amino acid level. These sequences can then be back translated using a variety of software products known in the art such that the nucleotide sequence is optimized for the desired expression host, e.g. based protein expression, codon optimization, restriction site content. For example, the nucleotide sequence can be optimized for *E. coli* based protein expression and for restriction site content. Based on the nucleotide sequence of interest, overlapping oligonucleotides can be provided for multistep PCR, as known in the art. These oligonucleotides can be used in multiple PCR reactions under conditions well known in the art to build the cDNA encoding the protein of interest. For one example is 1×Amplitaq Buffer, 1.3 mM $MgCl_2$, 200 uM dNTPs, 4 U Amplitaq Gold, 0.2 uM of each primer (AmpliTaq Gold, ABI), with cycling parameters: (94C:30s, 58C:1 min, 72C:1 min), 35 cycles.

Restriction sites can be added to the ends of the PCR products for use in vector ligation as known in the art. Specific sites can include Nde1 and Xho1, such that the cDNA can then be in the proper reading frame in a pET45b expression vector (Novagen). By using these sites, any N-terminal His Tag that are in this vector can be removed as the translation start site would then be downstream of the tag. Once expression constructs are completed, verification can be conduct by sequencing using e.g., T7 promoter primer, T7 terminator primer and standard ABI BigDye Term v3.1 protocols as known in the art. Sequence information can be obtained from e.g., an ABI 3730 DNA Analyzer and can be analyzed using Vector NTI v.10 software (Invitrogen). Expression constructs can be designed in a modular manner such that linker sequences can be easily cut out and changed, as known in the art.

Protease recognition sites, known in the art or described herein, can be incorporated into constructs useful for the design, construction, manipulation and production of recombinant engineering polypeptides described herein.

Exemplary Constructs.

Constructs useful in the production of engineered polypeptides contemplated herein include constructs encoding the polypeptides set forth in Table 4 following.

TABLE 4

Selected exemplary constructs for recombinant production of engineered polypeptides MAHHHHHHVGTGSNENLYFQ
HGEGTFTSDLSKQLEEEAVRLFIEWLKQGGPSKEIISTGGGGSASGSLAEAKEAANAE
LDSYGVSDFYKRLIDKAKTVEGVEALKDAILAALP (SEQ ID NO: 838)

MSDKIIHLTDDSFDTDVLKADGAILVDFWAEWCGPCKMIAPILDEIADEYQGKLTVA
KLNIDQNPGTAPKYGIRGIPTLLLFKNGEVAATKVGALSKGQLKEFLDANLAGSGSG
HMHHHHHHSSGLVPRGSGMKETAAAKFERQHMDSPDLGTENLYFQ
HGEGTFTSDLSKQLEEEAVRLFIEWLKQGGPSKEIISTGGGGSASGSLAEAKEAANAE
LDSYGVSDFYKRLIDKAKTVEGVEALKDAILAALP (SEQ ID NO: 839)

MAHHHHHHVGTGSNENLYFQ
HGEGTFTSDLSKQLEEEAVRLFIEWLKNGGPSSGAPPPSTGGGGSASGSLAEAKEAA
NAELDSYGVSDFYKRLIDKAKTVEGVEALKDAILAALP (SEQ ID NO: 840)

MSDKIIHLTDDSFDTDVLKADGAILVDFWAEWCGPCKMIAPILDEIADEYQGKLTVA
KLNIDQNPGTAPKYGIRGIPTLLLFKNGEVAATKVGALSKGQLKEFLDANLAGSGSG
HMHHHHHHSSGLVPRGSGMKETAAAKFERQHMDSPDLGTENLYFQ
HGEGTFTSDLSKQLEEEAVRLFIEWLKNGGPSSGAPPPSTGGGGSASGSLAEAKEAA
NAELDSYGVSDFYKRLIDKAKTVEGVEALKDAILAALP (SEQ ID NO: 841)

MAHHHHHHVGTGSNENLYFQ
HGEGTFTSDLSKQMEEEAVRLFIEWLKNGGPSSGAPPPSTGGGGSASGSLAEAKEAA
NAELDSYGVSDFYKRLIDKAKTVEGVEALKDAILAALP (SEQ ID NO: 842)

MSDKIIHLTDDSFDTDVLKADGAILVDFWAEWCGPCKMIAPILDEIADEYQGKLTVA
KLNIDQNPGTAPKYGIRGIPTLLLFKNGEVAATKVGALSKGQLKEFLDANLAGSGSG
HMHHHHHHSSGLVPRGSGMKETAAAKFERQHMDSPDLGTENLYFQ
HGEGTFTSDLSKQMEEEAVRLFIEWLKNGGPSSGAPPPSTGGGGSASGSLAEAKEAA
NAELDSYGVSDFYKRLIDKAKTVEGVEALKDAILAALP (SEQ ID NO: 843)

General Methods of Production.

The engineered polypeptide compounds described herein may be prepared using biological, chemical, and/or recombinant DNA techniques that are known in the art. Exemplary methods are described herein and in U.S. Pat. No. 6,872,700; WO 2007/139941; WO 2007/140284; WO 2008/082274; WO 2009/011544; and US Publication No. 2007/0238669, the disclosures of which are incorporated herein by reference in their entireties and for all purposes. Other methods for preparing the compounds are set forth herein.

The engineered polypeptides compounds described herein may be prepared using standard solid-phase peptide synthesis techniques, such as an automated or semiautomated peptide synthesizer. Briefly and generally, the ABD and therapeutic hormonal peptide can be made separately and then conjugated together or can be made as a single polypeptide. Thus, the albumin binding polypeptide, therapeutic hormone or engineered polypeptide may alternatively be produced by non-biological peptide synthesis using amino acids and/or amino acid derivatives having reactive side-chains protected, the non-biological peptide synthesis including step-wise coupling of the amino acids and/or the amino acid derivatives to form a polypeptide according to the first aspect having reactive side-chains protected, removing the protecting groups from the reactive side-chains of the polypeptide, and folding of the polypeptide in aqueous solution. Thus, normal amino acids (e.g. glycine, alanine, phenylalanine, isoleucine, leucine and valine) and pre-protected amino acid derivatives are used to sequentially build a polypeptide sequence, in solution or on a solid support in an organic solvent. When a complete polypeptide sequence is built, the protecting groups are removed and the polypeptide is allowed to fold in an aqueous solution.

Each polypeptide according to the present disclosure reversibly folds, with the ABD domain reversibly folding into a three helix bundle domain without added factors, and hence folds spontaneously. The engineered conjugate may be produced by a method including producing an albumin binding polypeptide according to any method, e.g. as described herein, such as by non-biological peptide synthesis, and conjugating the produced ABD polypeptide with the therapeutic hormone defined herein. The ABDs herein fold completely reversibly. This was assessed by circular dichroism spectra analysis; one spectrum taken at 20° C. and a second spectrum after heating to 90° C. followed by return to 20° C. During this procedure the Tm, as known in the art, was determined and found to be unchanged after the folding of the denatured polypeptide.

Typically, using such techniques, an alpha-N-carbamoyl protected amino acid and an amino acid attached to the growing peptide chain on a resin are coupled at RT in an inert solvent (e.g., dimethylformamide, N-methylpyrrolidinone, methylene chloride, and the like) in the presence of coupling agents (e.g., dicyclohexylcarbodiimide, 1-hydroxybenzotriazole, and the like) in the presence of a base (e.g., diisopropylethylamine, and the like). The alpha-N-carbamoyl protecting group is removed from the resulting peptide-resin using a reagent (e.g., trifluoroacetic acid, piperidine, and the like) and the coupling reaction repeated with the next desired N-protected amino acid to be added to the peptide chain. Suitable N-protecting groups are well known in the art, such as t-butyloxycarbonyl (tBoc) fluorenylmethoxycarbonyl (Fmoc), and the like. The solvents, amino acid derivatives and 4-methylbenzhydryl-amine resin used in the peptide synthesizer may be purchased from Applied Biosystems Inc. (Foster City, Calif.).

For chemical synthesis solid phase peptide synthesis can be used for the engineered polypeptides, since in general solid phase synthesis is a straightforward approach with excellent scalability to commercial scale, and is generally compatible with relatively long engineered polypeptides. Solid phase peptide synthesis may be carried out with an automatic peptide synthesizer (Model 430A, Applied Biosystems Inc., Foster City, Calif.) using the NMP/HOBt (Option 1) system and tBoc or Fmoc chemistry (See APPLIED BIOSYSTEMS USER'S MANUAL FOR THE ABI 430A PEPTIDE SYNTHESIZER, Version 1.3B Jul. 1, 1988, section 6, pp. 49-70, Applied Biosystems, Inc., Foster City, Calif.) with capping. Boc-peptide-resins may be cleaved with HF (−5° C. to 0° C., 1 hour). The peptide may be extracted from the resin with alternating water and acetic acid, and the filtrates lyophilized. The Fmoc-peptide resins may be cleaved according to standard methods (e.g., Introduction to Cleavage Techniques, Applied Biosystems, Inc., 1990, pp. 6-12). Peptides may also be assembled using an Advanced Chem Tech Synthesizer (Model MPS 350, Louisville, Ky.).

A chemical synthesis method that provided better yields is exemplified as follows for Cmpd 11. Solid phase synthesis was performed using a Prelude 6 channel peptide synthesizer (Protein Technologies, Inc., Tucson, Ariz., USA) using Fomc-Pro-Novasyn TGT resin (0.2 mmole/g) using default "double coupling" settings. However for VS (amino acid positions 59-60) and KT (amino acid positions 71-72) sequences pseudoproline double coupling was used, and for amino acids V19, R20, I23, and P37 triple coupling was used. For the exendin portion from His1 to Ser39, HATU/DIEA double or triple coupling (~60 min each, 6× excess of reagents) was performed unless otherwise indicated with deblocking with 20% piperidine 2×15 min. For the linker and ABD portion, HATU/DIEA double coupling was performed unless otherwise indicated (~60 min each, 3× excess of reagents) with deblocking with 20% piperidine 2×15 min. Polypeptide purification was performed using RP-HPLC purification on a C5 column using acetonitrile as solvent, with eluted samples identified by analysis on an analytical RP-HPLC on a C18 column using acetonitrile as solvent, followed by preparative RP-HPLC on a C18 column using a more narrow gradient than in the first RP-HPLC and acetonitrile as solvent. Fractions containing desired engineered polypeptide were pooled and lyophilized.

The compounds (exendins, ABDs, linkers, engineered polypeptides) described herein may also be prepared using recombinant DNA techniques using methods known in the art, such as Sambrook et al., 1989, MOLECULAR CLONING: A LABORATORY MANUAL, 2d Ed., Cold Spring Harbor. Non-peptide compounds may be prepared by art-known methods. For example, phosphate-containing amino acids and peptides containing such amino acids, may be prepared using methods known in the art, such as described in Bartlett et al, 1986, Biorg. Chem., 14:356-377. Compounds can be conjugated using art methods or as described herein The engineered polypeptides may alternatively be produced by recombinant techniques well known in the art. See, e.g., Sambrook et al., 1989 (Id.). These engineered polypeptides produced by recombinant technologies may be expressed from a polynucleotide. One skilled in the art will appreciate that the polynucleotides, including DNA and RNA, that encode such engineered polypeptides may be obtained from the wild-type cDNA, e.g. exendin-4, taking into consideration the degeneracy of codon usage, and may further engineered as desired to incorporate the indicated substitutions. These polynucleotide sequences may incorporate codons facilitating transcription and translation of mRNA in microbial hosts. Such manufacturing sequences may readily be constructed according to the methods well known in the art. See, e.g., WO 83/04053, incorporated herein by reference in its entirety and for all purposes. The polynucleotides above may also optionally encode an N-terminal methionyl residue. Non-peptide compounds useful in the present invention may be prepared by art-known methods. For example, phosphate-containing amino acids and peptides containing such amino acids may be prepared using methods known in the art. See, e.g., Bartlett and Landen, 1986, Bioorg. Chem. 14: 356-77.

A variety of expression vector/host systems may be utilized to contain and express a engineered polypeptide coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (e.g., baculovirus); plant cell systems transfected with virus expression vectors (e.g., cauliflower mosaic virus, CaMV; tobacco mosaic virus, TMV) or transformed with bacterial expression vectors (e.g., Ti or pBR322 plasmid); or animal cell systems. Mammalian cells that are useful in recombinant protein productions include but are not limited to VERO cells, HeLa cells, Chinese hamster ovary (CHO) cell lines, COS cells (such as COS-7), WI 38, BHK, HepG2, 3T3, RIN, MDCK, A549, PC12, K562 and 293 cells. Exemplary protocols for the recombinant expression of the protein are described herein and/or are known in the art.

As such, polynucleotide sequences are useful in generating new and useful viral and plasmid DNA vectors, new and useful transformed and transfected procaryotic and eucaryotic host cells (including bacterial, yeast, and mammalian cells grown in culture), and new and useful methods for cultured growth of such host cells capable of expression of the present engineered polypeptides. The polynucleotide sequences encoding engineered polypeptides herein may be useful for gene therapy in instances where underproduction of engineered polypeptides would be alleviated, or the need for increased levels of such would be met.

The present invention also provides for processes for recombinant DNA production of the present engineered polypeptides. Provided is a process for producing the engineered polypeptides from a host cell containing nucleic acids encoding the engineered polypeptide including: (a) culturing the host cell containing polynucleotides encoding the engineered polypeptide under conditions facilitating the expression of the DNA molecule; and (b) obtaining the engineered polypeptides.

Host cells may be prokaryotic or eukaryotic and include bacteria, mammalian cells (such as Chinese Hamster Ovary (CHO) cells, monkey cells, baby hamster kidney cells, cancer cells or other cells), yeast cells, and insect cells.

Mammalian host systems for the expression of the recombinant protein also are well known to those of skill in the art. Host cell strains may be chosen for a particular ability to process the expressed protein or produce certain post-translation modifications that will be useful in providing protein activity. Such modifications of the polypeptide include, but are not limited to, acetylation, carboxylation, glycosylation, phosphorylation, lipidation and acylation. Post-translational processing, which cleaves a "prepro" form of the protein, may also be important for correct insertion, folding and/or function. Different host cells, such as CHO, HeLa, MDCK, 293, W138, and the like, have specific cellular machinery and characteristic mechanisms for such post-translational activities, and may be chosen to ensure the correct modification and processing of the introduced foreign protein.

Alternatively, a yeast system may be employed to generate the engineered polypeptides of the present invention. The coding region of the engineered polypeptides DNA is amplified by PCR. A DNA encoding the yeast pre-pro-alpha leader sequence is amplified from yeast genomic DNA in a PCR reaction using one primer containing nucleotides 1-20 of the alpha mating factor gene and another primer complementary to nucleotides 255-235 of this gene (Kurjan and Herskowitz, 1982, *Cell*, 30: 933-43). The pre-pro-alpha leader coding sequence and engineered polypeptide coding sequence fragments are ligated into a plasmid containing the yeast alcohol dehydrogenase (ADH2) promoter, such that the promoter directs expression of a fusion protein consisting of the pre-pro-alpha factor fused to the mature engineered polypeptide. As taught by Rose and Broach, (Rose & Broach, 1990, *Meth. Enz.*, 185: 234-79, Goeddel ed., Academic Press, Inc., San Diego, Calif.), the vector further includes an ADH2 transcription terminator downstream of the cloning site, the yeast "2-micron" replication origin, the yeast leu-2d gene, the yeast REP1 and REP2 genes, the *E. coli* beta-lactamase gene, and an *E. coli* origin of replication. The beta-lactamase and leu-2d genes provide for selection in bacteria and yeast, respectively. The leu-2d gene also facilitates increased copy number of the plasmid in yeast to induce higher levels of expression. The REP1 and REP2 genes encode proteins involved in regulation of the plasmid copy number.

The DNA construct described in the preceding paragraph is transformed into yeast cells using a known method, e.g., lithium acetate treatment (Steams et al., 1990, *Meth. Enz.* 185: 280-297). The ADH2 promoter is induced upon exhaustion of glucose in the growth media (Price et al., 1987, *Gene* 55:287). The pre-pro-alpha sequence effects secretion of the fusion protein from the cells. Concomitantly, the yeast KEX2 protein cleaves the pre-pro sequence from the mature engineered polypeptides (Bitter et al., 1984, *Proc. Natl. Acad. Sci. USA* 81:5330-5334).

Engineered polypeptides of the invention may also be recombinantly expressed in yeast, e.g. *Pichia*, using a commercially available expression system, e.g., the *Pichia* Expression System (Invitrogen, San Diego, Calif.), following the manufacturer's instructions. This system also relies on the pre-pro-alpha sequence to direct secretion, but transcription of the insert is driven by the alcohol oxidase (AOX1) promoter upon induction by methanol. The secreted engineered polypeptide is purified from the yeast growth medium by, e.g., the methods used to purify said engineered polypeptide from bacterial and mammalian cell supernatants.

Alternatively, the DNA encoding a engineered polypeptide may be cloned into a baculovirus expression vector, e.g. pVL1393 (PharMingen, San Diego, Calif.). This engineered-polypeptide-encoding vector is then used according to the manufacturer's directions (PharMingen) or known techniques to infect *Spodoptera frugiperda* cells, grown for example in sF9 protein-free media, and to produce recombinant protein. The protein is purified and concentrated from the media using methods known in the art, e.g. a heparin-Sepharose column (Pharmacia, Piscataway, N.J.) and sequential molecular sizing columns (Amicon, Beverly, Mass.), and resuspended in appropriate solution, e.g. PBS. SDS-PAGE analysis can be used to characterize the protein, for example by showing a single band that confirms the size of the desired engineered polypeptide, as can full amino acid amino acid sequence analysis, e.g. Edman sequencing on a Proton 2090 Peptide Sequencer, or confirmation of its N-terminal sequence.

For example, the DNA sequence encoding the predicted mature engineered polypeptide may be cloned into a plasmid containing a desired promoter and, optionally, a leader sequence (see, e.g., Better et al., 1988, *Science* 240:1041-1043). The sequence of this construct may be confirmed by automated sequencing. The plasmid is then transformed into *E. coli*, strain MC1061, using standard procedures employing $CaCl_2$ incubation and heat shock treatment of the bacteria (Sambrook et al., Id.). The transformed bacteria are grown in LB medium supplemented with carbenicillin, and production of the expressed protein is induced by growth in a suitable medium. If present, the leader sequence will affect secretion of the mature engineered polypeptide and be cleaved during secretion. The secreted recombinant engineered polypeptide is purified from the bacterial culture media by the method described herein.

Alternatively, the engineered polypeptides may be expressed in an insect system. Insect systems for protein expression are well known to those of skill in the art. In one such system, *Autographa californica* nuclear polyhedrosis virus (AcNPV) is used as a vector to express foreign genes in *Spodoptera frugiperda* cells or in *Trichoplusia larvae*. The engineered polypeptide coding sequence is cloned into a non-essential region of the virus, such as the polyhedrin gene, and placed under control of the polyhedrin promoter. Successful insertion of a engineered polypeptide will render the polyhedrin gene inactive and produce recombinant virus lacking coat protein coat. The recombinant viruses are then used to infect *S. frugiperda* cells or *Trichoplusia larvae* in which engineered polypeptide of the present invention is expressed (Smith et al., 1983, *J. Virol.* 46:584; Engelhard et al., 1994, *Proc. Natl. Acad. Sci. USA* 91:3224-3227).

In another example, the DNA sequence encoding the engineered polypeptides may be amplified by PCR and cloned into an appropriate vector, for example, pGEX-3× (Pharmacia, Piscataway, N.J.). The pGEX vector is designed to produce a fusion protein including glutathione-S-transferase (GST), encoded by the vector, and a protein encoded by a DNA fragment inserted into the vector's cloning site. The primers for the PCR may be generated to include, for example, an appropriate cleavage site. The recombinant fusion protein may then be cleaved from the GST portion of the fusion protein. The pGEX-3×/engineered polypeptide construct is transformed into *E. coli* XL-1 Blue cells (Stratagene, La Jolla, Calif.), and individual transformants are isolated and grown at 37 degrees C. in LB medium (supplemented with carbenicillin) to an optical density at wavelength 600 nm of 0.4, followed by further incubation for 4 hours in the presence of 0.5 mM Isopropyl beta-D-Thiogalactopyranoside (Sigma Chemical Co., St. Louis, Mo.). Plasmid DNA from individual transformants is purified and partially sequenced using an automated sequencer to confirm the presence of the desired engineered polypeptide-encoding gene insert in the proper orientation.

The fusion protein, when expected to be produced as an insoluble inclusion body in the bacteria, may be purified as described above or as follows. Cells are harvested by centrifugation; washed in 0.15 M NaCl, 10 mM Tris, pH 8, 1 mM EDTA; and treated with 0.1 mg/mL lysozyme (Sigma Chemical Co.) for 15 min. at RT. The lysate is cleared by sonication, and cell debris is pelleted by centrifugation for 10 min. at 12,000×g. The fusion protein-containing pellet is resuspended in 50 mM Tris, pH 8, and 10 mM EDTA, layered over 50% glycerol, and centrifuged for 30 min. at 6000×g. The pellet is resuspended in standard phosphate buffered saline solution (PBS) free of $Mg^{++}$ and $Ca^{++}$. The fusion protein is further purified by fractionating the resuspended pellet in a denaturing SDS polyacrylamide gel (Sambrook et al., supra). The gel is soaked in 0.4 M KCl to visualize the protein, which is excised and electroeluted in gel-running buffer lacking SDS. If the GST/engineered polypeptide fusion protein is produced in bacteria as a soluble protein, it may be purified using the GST Purification Module (Pharmacia Biotech).

The fusion protein may be subjected to digestion to cleave the GST from the mature engineered polypeptide. The digestion reaction (20-40 ng fusion protein, 20-30 units human thrombin (4000 U/mg (Sigma) in 0.5 mL PBS) is incubated 16-48 hrs. at RT and loaded on a denaturing SDS-PAGE gel to fractionate the reaction products. The gel is soaked in 0.4 M KCl to visualize the protein bands. The identity of the protein band corresponding to the expected molecular weight of the engineered polypeptide may be confirmed by partial amino acid sequence analysis using an automated sequencer (Applied Biosystems Model 473A, Foster City, Calif.).

In a particularly exemplary method of recombinant expression of the engineered polypeptides of the present invention, mammalian 293 cells may be co-transfected with plasmids containing the engineered polypeptides cDNA in the pCMV vector (5' CMV promoter, 3' HGH poly A sequence) and pSV2neo (containing the neo resistance gene) by the calcium phosphate method. In one embodiment, the vectors should be linearized with ScaI prior to transfection. Similarly, an alternative construct using a similar pCMV vector with the neo gene incorporated can be used. Stable cell lines are selected from single cell clones by limiting dilution in growth media containing 0.5 mg/mL G418 (neomycin-like antibiotic) for 10-14 days. Cell lines are screened for engineered polypeptides expression by ELISA or Western blot, and high-expressing cell lines are expanded for large scale growth.

It is preferable that the transformed cells are used for long-term, high-yield protein production and as such stable expression is desirable. Once such cells are transformed with vectors that contain selectable markers along with the desired expression cassette, the cells may be allowed to grow for 1-2 days in an enriched media before they are switched to selective media. The selectable marker is designed to confer resistance to selection, and its presence allows growth and recovery of cells that successfully express the introduced sequences. Resistant clumps of stably transformed cells can be proliferated using tissue culture techniques appropriate to the cell.

A number of selection systems may be used to recover the cells that have been transformed for recombinant protein production. Such selection systems include, but are not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to methotrexate; gpt, that confers resistance to mycophenolic acid; neo, that confers resistance to the aminoglycoside, G418; also, that confers resistance to chlorsulfuron; and hygro, that confers resistance to hygromycin. Additional selectable genes that may be useful include trpB, which allows cells to utilize indole in place of tryptophan, or hisD, which allows cells to utilize histinol in place of histidine. Markers that give a visual indication for identification of transformants include anthocyanins, beta-glucuronidase and its substrate, GUS, and luciferase and its substrate, luciferin.

The engineered polypeptides of the present invention may be produced using a combination of both automated peptide synthesis and recombinant techniques. For example, either or both the exendin compound and the ABD, and optionally a linker, can be made synthetically or recombinantly and then ligated together using methods known in the art, such as "native chemical ligation" and known variations thereof in which an amide bond is formed joining the parent compounds. See, e.g., U.S. Pat. No. 6,326,468, which is incorporated herein by reference and for all purposes. Alternatively, for example, an engineered polypeptide of the present invention may contain a combination of modifications including deletion, substitution, insertion and derivatization by PEGylation (or other moiety, e.g. polymer, fatty acyl chain, C-terminal amidation). Such an engineered polypeptide may be produced in stages. In the first stage, an intermediate engineered polypeptide containing the modifications of deletion, substitution, insertion, and any combination thereof, may be produced by recombinant techniques as described. Then after an optional purification step as described herein, the intermediate engineered polypeptide is PEGylated (or subjected to other chemical derivatization, e.g., acylation, C-terminal amidation) through chemical modification with an appropriate PEGylating reagent (e.g., from NeKtar Transforming Therapeutics, San Carlos, Calif.) to yield the desired engineered polypeptide derivative. One skilled in the art will appreciate that the above-described procedure may be generalized to apply to a engineered polypeptide containing a combination of modifications selected from deletion, substitution, insertion, derivation, and other means of modification well known in the art and contemplated by the present invention.

C-terminal amidation can be achieved by use of a glycine amino acid-C-terminally extended precursor, synthesized for example in yeast (e.g. *Pichia*) as alpha-factor fusion protein that will be secreted into culture medium. After purification, the C-terminal glycine of the engineered polypeptide precursor can be converted to amide by enzymatic amidation, e.g. peptidylglycine alpha-amidating monooxygenase (PAM). See e.g., Cooper et al., 1989, *Biochem. Biophys. Acta,* 1014: 247-258. See also U.S. Pat. No. 6,319,685, which is incorporated herein by reference in its entirety and for all purposes, which teaches methods for enzymatic amidation, including an alpha-amidating enzyme from rat being sufficiently pure in alpha-amidating enzyme to exhibit a specific activity of at least about 25 mU per mg of protein, and being sufficiently free of proteolytic impurities to be suitable for use with substrates purified from natural sources or produced by recombinant DNA techniques.

Peptides may be purified by any number of methods known in the art, including as described herein In one method peptides are purified by RP-HPLC (preparative and analytical) using a Waters Delta Prep 3000 system. A C4, C8 or C18 preparative column (10 micron, 2.2×25 cm; Vydac, Hesperia, Calif.) may be used to isolate peptides, and purity may be determined using a C4, C8 or C18 analytical column (5 micron, 0.46×25 cm; Vydac). Solvents (A=0.1% TFA/water and B=0.1% TFA/CH$_3$CN) may be delivered to the analytical column at a flow rate of 1.0 ml/min and to the preparative column at 15 ml/min Amino acid analyses may be performed on the Waters Pico Tag system and processed using the Maxima program. Peptides may be hydrolyzed by vapor-phase acid hydrolysis (115° C., 20-24 h). Hydrolysates may be derivatized and analyzed by standard methods (Cohen et al, THE PICO TAG METHOD: A MANUAL OF ADVANCED TECHNIQUES FOR AMINO ACID ANALYSIS, pp. 11-52, Millipore Corporation, Milford, Mass. (1989)). Fast atom bombardment analysis may be carried out by M-Scan, Incorporated (West Chester, Pa.). Mass calibration may be performed using cesium iodide or cesium iodide/glycerol. Plasma desorption ionization analysis using time of flight detection may be carried out on an Applied Biosystems Bio-Ion 20 mass spectrometer.

Engineered Polypeptide Expression Assay.

Methods are available for assaying the level of protein expression by a host cell. Procedures useful for assaying the level of protein expression by a host cell are exemplified in the following typical protocol. About 25 ul BL21 *E. coli* cells are transformed with 2 ul plasmid DNA (expression vector for the engineered polynucleotide). Cells can be plated and incubated overnight at 37 degrees C. or at room temperature (RT) over a 48-hr period. A single colony can be selected and used to grow starter culture in 4 ml LB media with appropriate antibiotic for ~6 hrs. Glycerol stocks can be prepared by adding 100 ul 80% sterile glycerol to 900 ul stock, which can then be mixed gently and stored at −80 C. A 250 ul sample can be removed for TCP uninduced sample. An aliquot, for example, 2 ml of Magic media containing appropriate antibiotic can be inoculated with 5 ul starter culture, which can then be incubated overnight (up to 24 hrs) at 37 C, 300 rpm. As known in the art, Magic Media is autoinducing. Alternatively, 60 ml Magic Media containing appropriate antibiotic can be inoculated with 60 ul starter culture in a 250 ml or 125 ml Thompson flask, which can then be incubated overnight (up to 24 hrs) at 30 C, 300 rpm. After incubation, 250 ul culture can be removed from each tube and the cells pelleted. The cell can be resuspended in 1 ml 50 mM Tris pH 8, 150 mM NaCl, to which can be added 0.1 volumes (100 ul) POP culture reagent and 1 ul r-lysozyme (1:750 dilution in r-lysozyme buffer). The mixture can be mixed well and incubated at least 10 min at RT. The preparation can then be centrifuge 10 min at 14000×G. The supernatant (soluble fraction) can be removed and retained, and samples can be prepared for gel analysis (15 ul+5 ul LDS). The remaining inclusion body pellet can be resuspended in 1 ml 1% SDS with sonication. The sample can be prepared for gel analysis (15 ul+5 ul LDS). For uninduced samples, 1.0 volumes POP culture reagent and 1 ul r-lysozyme (1:750 dilution in r-lysozyme buffer) can be added. The mixture can be mixed well and incubated at least 10 min at RT. These samples may not need to be centrifuged. The sample can then be prepared for gel analysis (15 ul+5 ul LDS). NU-PAGE gels (4-12%) non-reduced in 1×MES buffer can be run and stained with SimplyBlue microwave protocol. Destaining can be conducted overnight, as known in the art. A gel image can be retained, and analyzed to determine protein expression levels.

Engineered polypeptides can be and were expressed and isolated as follows. A protein sequence of the desired engineered polypeptide was designed and back translated using commercial software to a DNA sequence for cloning into an *E. coli* expression vector. Nucleic acid sequences were either obtained as oligonucleotides and ligated using standard PCR amplification techniques, or were digested from existing expression constructs using standard restriction enzymes and then ligated together. Sequences expressing the protein of interest were placed in plasmid pET45 with a T7 promoter for inducible expression. After constructs were verified by sequencing, the vector DNA was purified and transformed into an expression host, typically BL21(DE3). A single colony was selected to grow a starter culture in 4 ml LB media for ~6 hrs. Glycerol stocks were prepared by adding 100 ul 80% glycerol to 900 ul stock and stored at −80 C. Optionally, 500 ul of un-induced sample was retained for gel analysis. A 60 ml culture (e.g. MagicMedia™ *E. coli* Expression Medium; Invitrogen, USA; see Glenn et al., *J. Biol. Chem.* 2008, 283(19):12717-29) was inoculated using 60 ul starter culture in a 125 ml Thompson flask and incubated at 30 degrees C. overnight. Removed 250 ul sample for analysis. The cells were collected as a pellet by centrifuging, and frozen for later processing. Preparation of cell extract and first pass purification with Nickel resin was performed as follows. *E. coli* cell pellets were completely resuspended in a volume of lysis buffer (50 mM TrisHCl, 150 mM NaCl, pH 8.0) equal to the starting culture volume. Cells were then subjected to a microfluidizer (Microfluidics, MA) at 100 psi for three times. Cell extracts were centrifuged for 30 minutes at 16,000×g to remove debris. EGTA (150 mM stock) was added to the cell extract to a final concentration of 3 mM EGTA. The lysate was then applied to a Ni-NTA Superflow column that had been washed and pre-equilibrated. Protein bound to the column was then washed with lysis buffer plus EGTA (50 mM TrisHCl, 150 mM NaCl, pH8.0, 3 mM EGTA) before the bound protein was eluted with 50 mL of elution buffer (25 mM TrisHCl, 50 mM NaCl, 250 mM Imidazol, pH8.0). Cleavage of His-Tag and subsequent purification was as follows. The eluted protein was concentrated with Amicon-Ultra15 centrifugal filter unit (Millipore, USA) and then diluted with 25 mM TrisHCl, pH8.0, 50 mM NaCl to prepare for protease digestion which removes the HisTag from the N-terminus of the desired protein. Added was 0.1% of β-mercaptoethanol and 1% of Turbo TEV protease (2 mg/mL, 10,000 units/mg; Excellgen, USA) to the protein solution, which was mixed and incubated at room temperature for 4 hours and then at 4° C. over night. An Ni-NTA Superflow column (Qiagen, USA) was pre-equilabrated with 50 mM TrisHCl, 100 mM NaCl, 45 mM imidazole, pH8.0. The TEV digest reaction was diluted 2-fold with 50 mM TrisHCl, 150 mM NaCl, pH8.0. The diluted digest reaction was carefully applied to the top of Ni-NTA column and flow-through was collected. To the column was added 10 mL of 50 mM trisHCl, 100 mM NaCl, 45 mM imidazole, pH8.0 to elute any unbound protein. The eluted proteins from the column were collected and combined, and then polished using size exclusion chromatography (2× with Superdex 75 HiLoad 26/60 column; GE Healthcare Biosciences, USA). Any remaining bacterial endotoxin was removed using EndoTrap Red (Lonza, Switzerland) according to manufacturer's instructions.

Inclusion Body Preparation.

For engineered polypeptides that are found in the inclusion body fraction, the following procedure can be beneficial. The cell pellet can be resuspended in a minimum of 100 ml Lysis buffer for each 50 ml culture. Upon the addition of 30 ml, a 10 ml pipette can be used to resuspend, then the tube can be washed out with an additional 70 ml. The resuspended cell solution can be multiply run, e.g., 4 passes, through a microfluidizer@ 100 PSI (min) taking care to keep chamber in ice water through the entire process. The fluidized slurry can be centrifuged at 14000×g, 20 min (e.g., JLA 10.5, 10,000 rpm, using 250 ml nalgene bottles). The inclusion body pellet can be resuspended on ice in chilled lysis buffer with stir bar and stir plate for 1 hour at 4 C after disruption with pipette tip. The pellet can be resuspended a second time in distilled $H_2O$ with stir bar and stir plate for 1 hour at 4 C after disruption with pipette tip, followed by centrifugation at 14000×g, 15 min. The supernatant can be removed and discarded. The resultant can be stored at −80 C.

Protein Purification.

As described herein, numerous methods are known for isolation of expressed polypeptides. Preferred are secreted engineered polypeptides. However, the following is one example if inclusion bodies are formed. Inclusion body pellets can be solubilized in appropriate volume of solubilization buffer (8M urea or 8M guanidine, 50 mM Tris, 10 mM DTT, pH 7.75) for 1 hour at RT. The solubilized pellets can be centrifuged for 20 min at 27 000 g. Filtered (e.g., 0.4 um) supernatant can be transferred drop by drop into appropriate volume of refolding buffer (50 mM Tris-HCl, 1 M urea, 0.8 M arginine, 4 mM cysteine, 1 mM cystamine; pH 8) at RT. The result can then be placed at 4° C. overnight or longer with gentle mixing. Samples can be concentrated and run on a gel filtration column (Superdex75 26/60) at 1-2 ml/min in 4 C environment using a GE Healthsciences AKTA FPLC. Appropriate protein containing fractions can be identified via SDS-PAGE, pooled and run through a second gel filtration column. Pooled protein can then be concentrated in Amicon filter to appropriate concentration and assayed for endotoxin levels using, e.g., Endosafe PTS Reader (Charles River), as known in the art. Once a protein sample has passed the endotoxin criteria, it can be sterile filtered, dispensed into aliquots and run through quality control assays. Quality control assays can include analytical HPLC-SEC, non reducing SDS PAGE and RP HPLC-MS to obtain approximate mass. Proteins can be obtained in 1×PBS (137 mM sodium chloride, 2.7 mM potassium chloride, 4.3 mM disodium phosphate, 1.4 mM monopotassium phosphate, pH7.2), distributed into aliquots and flash frozen for storage at −70 to −80° C.

IV. Methods of Use and Treating Disease

Indications.

A variety of diseases and disorders are contemplated to be beneficially treated by the polypeptide compounds and methods described herein, primarily based upon those amenable to treatment by interaction with the GLP-1 receptor, such as by exendin-4.

Obesity and Overweight.

Obesity and its associated disorders including overweight are common and serious public health problems in the United States and throughout the world. Upper body obesity is the strongest risk factor known for type 2 diabetes mellitus and is a strong risk factor for cardiovascular disease. Obesity is a recognized risk factor for hypertension, atherosclerosis, congestive heart failure, stroke, gallbladder disease, osteoarthritis, sleep apnea, reproductive disorders such as polycystic ovarian syndrome, cancers of the breast, prostate, and colon, and increased incidence of complications of general anesthesia. See, e.g., Kopelman, 2000, *Nature* 404:635-43.

Obesity reduces life-span and carries a serious risk of the co-morbidities listed above, as well disorders such as infections, varicose veins, acanthosis nigricans, eczema, exercise intolerance, insulin resistance, hypertension hypercholesterolemia, cholelithiasis, orthopedic injury, and thromboembolic disease. See e.g., Rissanen et al, 1990, *Br. Med. J.*, 301: 835-7. Obesity is also a risk factor for the group of conditions called insulin resistance syndrome, or "Syndrome X" and metabolic syndrome. The worldwide medical cost of obesity and associated disorders is enormous.

The pathogenesis of obesity is believed to be multi-factoral. A problem is that, in obese subjects, nutrient availability and energy expenditure do not come into balance until there is excess adipose tissue. The central nervous system (CNS) controls energy balance and coordinates a variety of behavioral, autonomic and endocrine activities appropriate to the metabolic status of the animal. The mechanisms or systems that control these activities are broadly distributed across the forebrain (e.g., hypothalamus), hindbrain (e.g., brainstem), and spinal cord. Ultimately, metabolic (i.e., fuel availability) and cognitive (i.e., learned preferences) information from these systems is integrated and the decision to engage in appetitive (food seeking) and consummatory (ingestion) behaviors is either turned on (meal procurement and initiation) or turned off (meal termination). The hypothalamus is thought to be principally responsible for integrating these signals and then issuing commands to the brainstem. Brainstem nuclei that control the elements of the consummatory motor control system (e.g., muscles responsible for chewing and swallowing). As such, these CNS nuclei have literally been referred to as constituting the "final common pathway" for ingestive behavior.

Neuroanatomical and pharmacological evidence support that signals of energy and nutritional homeostasis integrate in forebrain nuclei and that the consummatory motor control system resides in brainstem nuclei, probably in regions surrounding the trigeminal motor nucleus. There are extensive reciprocal connection between the hypothalamus and brainstem. A variety of CNS-directed anti-obesity therapeutics (e.g., small molecules and peptides) focus predominantly upon forebrain substrates residing in the hypothalamus and/or upon hindbrain substrates residing in the brainstem.

Obesity remains a poorly treatable, chronic, essentially intractable metabolic disorder. Accordingly, a need exists for new therapies useful in weight reduction and/or weight maintenance in a subject. Such therapies would lead to a profound beneficial effect on the subject's health.

Diabetes and Cardiovascular Disease.

Diabetes mellitus is recognized as a complex, chronic disease in which 60% to 70% of all case fatalities among diabetic patients are a result of cardiovascular complications. Diabetes is not only considered a coronary heart disease risk equivalent but is also identified as an independent predictor of adverse events, including recurrent myocardial infarction, congestive heart failure, and death following a cardiovascular incident. The adoption of tighter glucose control and aggressive treatment for cardiovascular risk factors would be expected to reduce the risk of coronary heart disease complications and improve overall survival among diabetic patients. Yet, diabetic patients are two to three times more likely to experience an acute myocardial infarction than non-diabetic patients, and diabetic patients live eight to thirteen years less than non-diabetic patients.

Understanding the high risk nature of diabetic/acute myocardial infarction patients, the American College of Cardiology/American Heart Association ("ACC/AHA") clinical practice guidelines for the management of hospitalized patients with unstable angina or non-ST-elevation myocardial infarction (collectively referred to as "ACS") recently recognized that hospitalized diabetic patients are a special population requiring aggressive management of hyperglycemia. Specifically, the guidelines state that glucose-lowering therapy for hospitalized diabetic/ACS patients should be targeted to achieve preprandial glucose less than 10 mg/dL, a maximum daily target than 180 mg/dL, and a post-discharge hemoglobin A1c less than 7%.

In a nationwide sample of elderly ACS patients, it was demonstrated that an increase in 30-day mortality in diabetic patients corresponded with the patients having higher glucose values upon admission to the hospital. See "Diabetic Coronary Artery Disease & Intervention," *Coronary Therapeutics* 2002, Oak Brook, Ill., Sep. 20, 2002. There is increasing evidence that sustained hyperglycemia rather than transient elevated glucose upon hospital admission is related to serious adverse events. Although the ideal metric for hyperglycemia and vascular risk in patients is not readily known, it appears that the mean glucose value during hospitalization is most predictive of mortality. In a separate study of ACS patients form over forty hospitals in the United States, it was found that persistent hyperglycemia, as opposed to random glucose values upon admission to the hospital, was more predictive of in-hospital mortality. See *Acute Coronary Syndrome Summit: A State of the Art Approach*, Kansas City, Mo., Sep. 21, 2002. Compared with glucose values upon admission, a logistic regression model of glucose control over the entire hospitalization was most predictive of mortality. There was nearly a two-fold increased risk of mortality during hospitalization for each 10 mg/dL increase in glucose over 120 mg/dL. In a smaller cohort of consecutive diabetic/ACS patients, there was a graded increase in mortality at one year with increasing glucose levels upon hospital admission. In the hospital setting, the ACC/AHA guidelines suggest initiation of aggressive insulin therapy to achieve lower blood glucose during hospitalization.

Lipid Regulation Diseases.

Dyslipidemia is a disruption in the normal lipid component in the blood. It is believed that prolonged elevation of insulin levels can lead to dyslipidemia. Hyperlipidemia is the presence of raised or abnormal levels of lipids and/or lipoproteins in the blood. Fatty liver disease, e.g., nonalcoholic fatty liver disease (NAFLD) refers to a wide spectrum of liver disease ranging from simple fatty liver (steatosis), to nonalcoholic steatohepatitis (NASH), to cirrhosis (irreversible, advanced scarring of the liver). All of the stages of NAFLD have in common the accumulation of fat (fatty infiltration) in the liver cells (hepatocytes).

Additionally, without wishing to be bound by any theory, it is believed that relative insulin deficiency in type 2 diabetes, glucose toxicity, and increased hepatic free fatty acid burden through elevated delivery from intra-abdominal adipose tissue via the portal vein, are implicated as possible causes in fatty liver disorders. Indeed, it has been hypothesized that eating behavior is the key factor driving the metabolic syndrome of obesity with its many corollaries, including NASH. Accordingly, treatments aimed at decreasing food intake and increasing the number of small meals, as has already been demonstrated in type 2 diabetes, may effectively treat and prevent NASH. Drugs that promote insulin secretion and weight loss, and delay gastric emptying are also effective at improving glucose tolerance and thus may improve fatty liver with its attendant hyperinsulinemia. Thus, use of exendins, exendin analog agonists, exendin derivative agonists, particularly exendin-4, can be well suited as a treatment modality for this condition. Accordingly, engineered polypeptides described herein which include an exendin or biologically active (hormone domain) peptide component, or fragment or analog thereof, can be useful in the treatment of fatty liver disorders.

Alzheimer's Disease.

Alzheimer's disease (AD), as known in the art, is associated with plaques and tangles in the brain which include dysregulation of the A-beta protein. Stimulation of neuronal GLP-1 receptors has been reported to play an important role in regulating neuronal plasticity and cell survival. Stimulation of GLP-1 receptor has been reported to induce neurite outgrowth and to protect against excitotoxic cell death and oxidative injury in cultured neuronal cells. GLP-1 and exendin-4 were reported to reduce endogenous levels of amyloid-beta peptide (A-beta protein) in mouse brain and to reduce levels of beta-amyloid precursor protein (beta-APP) in neurons. See, e.g., Perry et al., 2004, *Curr. Drug Targets* 5(6): 565-571. Treatment with the engineered compounds disclosed herein can provide benefit to the therapeutic targets associated with Alzheimer's disease.

Parkinson's Disease.

Parkinson's disease (PD) is the synonym of "primary parkinsonism", i.e. isolated parkinsonism due to a neurodegenerative process without any secondary systemic cause. Parkinsonism is characterized by symptoms of tremor, stiffness, and slowing of movement caused by loss of dopamine. Without wishing to be bound by any theory, it is believed that exendin-4 may act as a survival factor for dopaminergic neurons by functioning as a microglia-deactivating factor and suggest that exendin-4 may be a valuable therapeutic agent for neurodegenerative diseases such as PD.

Metabolic Syndrome X.

Metabolic Syndrome X is characterized by insulin resistance, dyslipidemia, hypertension, and visceral distribution of adipose tissue, and plays a pivotal role in the pathophysiology of type 2 diabetes. It has also been found to be strongly correlated with NASH, fibrosis, and cirrhosis of the liver. Accordingly, engineered polypeptides described herein can be useful in the treatment of metabolic syndrome X.

Steroid Induced Diabetes.

Glucocorticoids are well known to affect carbohydrate metabolism. In response to exogenous glucocorticoid administration, increased hepatic glucose production and reduced insulin secretion and insulin-stimulated glucose uptake in peripheral tissues is observed. Furthermore, glucocorticoid treatment alters the proinsulin(P1)/immunoreactive insulin (IRI) ratio, as known in the art. Typical characteristics of the hyperglycemia induced by glucocorticoids in subjects without diabetes include a minimal elevation of fasting blood glucose, exaggerated postprandial hyperglycemia, insensitivity to exogenous insulin, and non-responsiveness to metformin or sulfonylurea therapy. Accordingly, engineered polypeptides described herein which include an exendin biologically active (hormone domain) peptide component, or fragment or analog thereof, can be useful in the treatment of steroid induced diabetes.

Human Immunodeficiency Virus (HIV) Treatment-Induced Diabetes.

Shortly after the introduction of human immunodeficiency virus (HIV)-1 protease inhibitors (PIs) into routine clinical use, reports linking PT use with the development of hyperglycemia began to appear. While approximately 1% to 6% of HIV-infected subjects who are treated with PIs will develop diabetes mellitus, a considerably larger proportion will develop insulin resistance and impaired glucose tolerance. Accordingly, engineered polypeptides described herein which include an exendin biologically active (hormone domain) peptide component, or fragment or analog thereof, can be useful in the treatment of HIV treatment-induced diabetes.

Latent Autoimmune Diabetes in Adults (LADA).

Progressive autoimmune diabetes, also known as latent autoimmune diabetes in adults (LADA), is thought to be present in approximately 10% of patients diagnosed with type 2 diabetes. LADA patients have circulating antibodies to either islet cell cytoplasmic antigen or, more frequently, glutamic acid decarboxylase. These subjects exhibit clinical features characteristic of both type 1 and type 2 diabetes. Although insulin secretion is better preserved in the slowly progressing than in the rapidly progressing form of autoimmune diabetes, insulin secretion tends to deteriorate with time in LADA subjects. Accordingly, engineered polypeptides described herein which include an exendin biologically active (hormone domain) peptide component, or fragment or analog thereof, can be useful in the treatment of LADA.

Hypoglycemia Unawareness (HU).

Defective glucose counterregulation can occur even after only a single recent episode of hypoglycemia. Subjects who experience repeated episodes of hypoglycemia often lose their capacity to recognize the symptoms typically associated with hypoglycemia or impending insulin shock, a condition called "hypoglycemia unawareness". Because the-patient doesn't appreciate his or her own status, blood glucose levels can then fall so low that serious neurological problems ensue, including coma and seizure. Accordingly, engineered polypeptides described herein which include an exendin biologically active (hormone domain) peptide component, or fragment or analog thereof, can be useful in the treatment of HU.

Restrictive Lung Disease.

GLP 1 receptor has been localized in the lung. Exendins can elicit a biological response via GLP-1 receptor. In particular, sarcoidosis is a systemic granulomatous disease that frequently involves the lung. Although classically thought of as a restrictive lung disease, airway obstruction has become a recognized feature of the disease in the past years. Sarcoidosis can affect the airway at any level and when the involvement includes small airways, it can resemble more common obstructive airway diseases, such as asthma and chronic bronchitis. Accordingly, engineered polypeptides described herein which include an exendin biologically active (hormone domain) peptide component, or fragment or analog thereof, can be useful in the treatment of restrictive lung disease because such hormone domain peptide can improve elasticity of lung or delay rigidity.

Short Bowel Syndrome (SBS).

Exendin-4 has been reported as effective for the treatment of short bowel syndrome. See Kunkel et al. Neurogastroenterol. Motil. (2011). SBS is a serious clinical disorder characterized by diarrhea and nutritional deprivation. Glucagon-like peptide-1 (GLP-1), produced by L-cells in the ileum, regulates proximal gut transit. When extensive ileal resection occurs, as in SBS, GLP-1 levels may be deficient. Exenatide improved the nutritional state and intestinal symptoms of patients with SBS. Accordingly, SBS patients are amenable to treatment with the engineered polypeptides described herein. Improvement in bowel frequency and form and obtaining bowel movements that are no longer meal-related can be achieved. An additional benefit is that total parenteral nutrition can be stopped. These compounds herein will provide substantial improvement in the bowel habits, nutritional status and quality of life of SBS patients, and further may reduce the need for parenteral nutrition and small bowel transplant.

Accordingly, in one aspect, there is provided a method for treating a disease or disorder in a subject. The subject is in need of treatment for the disease or disorder. In some embodiments, the subject is need of treatment is obese. The disease or disorder is diabetes, overweight, obesity, Alzheimer's disease, fatty liver disease, dyslipidemia, coronary artery disease, stroke, SBS or hyperlipidemia, or other diseases discussed herein. Diabetes can include type I, type II, gestational or pre-diabetes as well as HIV or steroid induced diabetes. The method of treatment includes administration to the subject of a engineered polypeptide as described herein in an amount effective to treatment the disease or disorder. Particularly useful for these diseases are compounds described herein having glucose lowering activity (e.g. exendin-4 or its fragments or analogs linked to an ABD), having reduction of body weight or reduction of food intake activity, lowering of HbA1c, delaying of gastric emptying, lowering of plasma glucagon, and/or intestinal motility benefit.

In some embodiments, the disease or disorder is diabetes, overweight or obesity, or dyslipidemia or hyperlipidemia. The engineered polypeptide can include ABD and HD1 polypeptides, and optionally a linker K1, where HD1 is an exendin or fragment or analog thereof. Accordingly, the engineered polypeptide can have one of the following structures: HD1-ABD or HD1-L1-ABD. In some embodiments, the exendin is preferably exendin-4 or Leu14 exendin-4.

In some embodiments, the disease or disorder is diabetes, overweight, obesity, dyslipidemia, Alzheimer's disease, fatty liver disease, SBS or hyperlipidemia. The engineered polypeptide may include an exendin or fragment or analog thereof. Accordingly, the engineered polypeptide can have one of the following structures: HD1-ABD or HD1-L1-ABD. In some embodiments, the exendin in the engineered polypeptide is preferably exendin-4 or its analog Leu14 exendin-4. In some embodiments, the exendin fragment is a fragment of exendin-4. In some embodiments, the exendin analog has at least 70%, for example 70%, 75%, 80%, 85%, 90%, 95% or even higher, identity with exendin-4. Particularly useful for these diseases are compounds described herein having glucose lowering activity (e.g. exendin-4 or its fragments or analogs linked to an ABD), having reduction of body weight or reduction of food intake activity, lowering of HbA1c, delaying of gastric emptying, lowering of plasma glucagon, or intestinal motility benefit.

In some embodiments, the disease or disorder is diabetes, overweight, obesity, dyslipidemia, Alzheimer's disease, fatty liver disease, SBS or hyperlipidemia. The engineered polypeptide may include an exendin or fragment or analog thereof. Accordingly, the engineered polypeptide can have one of the following structures: HD1 ABD or HD1 L1 ABD. In some embodiments, the exendin is preferably exendin-4 or its analog Leu14 exendin-4. In some embodiments, the exendin fragment is a fragment of exendin-4. In some embodiments, the exendin analog has at least 70%, for example 70%, 75%, 80%, 85%, 90%, 95% or even higher, identity with exendin-4. Particularly useful for these diseases are compounds described herein having glucose lowering activity (e.g. exendin-4 or its fragments or analogs linked to an ABD), having reduction of body weight or reduction of food intake activity, delaying of gastric emptying, lowering of plasma glucagon, or intestinal motility benefit.

The disease or disorder can be diabetes, overweight, obesity, dyslipidemia, Alzheimer's disease, fatty liver disease, SBS, hyperlipidemia, Parkinson's disease or cardiovascular disease or other diseases described herein. The engineered polypeptide may include an exendin or fragment or analog thereof. Accordingly, the engineered polypeptide can have one of the following structures: HD1 ABD or HD1 µl ABD. In some embodiments, the exendin preferably is exendin-4 or its analog Leu14 exendin-4. In some embodiments, the exendin fragment is a fragment of exendin-4. In some embodiments, the exendin analog has at least 70%, for example 70%, 75%, 80%, 85%, 90%, 95% or even higher, identity with exendin-4. Particularly useful for these diseases are compounds described herein having glucose lowering activity (e.g. exendin-4 or its fragments or analogs linked to an ABD), having reduction of body weight or reduction of food intake activity, a lowering of HbA1c, delaying of gastric emptying, lowering of plasma glucagon, or intestinal motility benefit.

Additional diseases and disorders which can be treated by the compounds and methods described herein include steroid-induced diabetes, HIV treatment-induced diabetes, latent autoimmune diabetes in adults (LADA), Nonalcoholic steatohepatitis (NASH) and nonalcoholic fatty liver disease (NAFLD), hypoglycemia unawareness (HU), restrictive lung disease including sarcoidosis, and metabolic syndrome X. The engineered polypeptide may include an exendin or fragment or analog thereof. Accordingly, the engineered polypeptide can have one of the following structures: HD1-ABD or HD1-L1-ABD. In some embodiments, the exendin is preferably exendin-4 or its analog Leu14 exendin-4. In some embodiments, the exendin fragment is a fragment of exendin-4. In some embodiments, the exendin analog has at least 70%, for example 70%, 75%, 80%, 85%, 90%, 95% or even higher, identity with exendin-4. Particularly useful for these diseases are compounds described herein having glucose lowering activity (e.g. exendin-4 or its fragments or analogs linked to an ABD), having reduction of body weight or reduction of food intake activity, delaying of gastric emptying, lowering of HbA1c, lowering of plasma glucagon, or intestinal motility benefit. The engineered polypeptide can include only exendin, or analog or fragment thereof, as a hormone domain. The disease or disorder can be diabetes, overweight, obesity, dyslipidemia, Alzheimer's disease, fatty liver disease, SBS, hyperlipidemia, Parkinson's disease or cardiovascular disease or other diseases described herein. The engineered polypeptide may include an exendin or fragment or analog thereof. Accordingly, the engineered polypeptide can have one of the following structures: HD1-ABD or HD1-L1-ABD. exendin-4 or its fragments or analogs linked to an ABD), having reduction of body weight or reduction of food intake activity, delaying of gastric emptying, lowering of plasma glucagon, or intestinal motility benefit.

Additional diseases and disorders which can be treated by the compounds and methods described herein include steroid-induced diabetes, HIV treatment-induced diabetes, latent autoimmune diabetes in adults (LADA), Nonalcoholic steatohepatitis (NASH) and nonalcoholic fatty liver disease (NAFLD), hypoglycemia unawareness (HU), restrictive lung disease including sarcoidosis, and metabolic syndrome X. The engineered polypeptide preferably has one of the following structures: HD1-analogs linked to an ABD or HD1-L1-ABD. In some embodiments, the exendin is preferably exendin-4 or its analog Leu14 exendin-4. In some embodiments, the exendin fragment is a fragment of exendin-4. In some embodiments, the exendin analog has at least 70%, for example 70%, 75%, 80%, 85%, 90%, 95% or even higher, identity with exendin-4.

V. Assays

Methods for production and assay of engineered polypeptides described herein are generally available to the skilled artisan. Further, specific methods are described herein as well as in the patent publications and other references cited herein, which are incorporated by reference for this additional purpose.

GLP-1 Receptor Binding and Functional Assays:

GLP-1 receptor binding activity and affinity may be measured in any number of known methods. For example, in one method binding activity is measured using a binding displacement assay in which the receptor source is RINm5F cell membranes, and the ligand is [$^{125}$I]GLP-1 or iodinated exendin(1-39) or iodinated exendin(9-39). Homogenized RINm5F cell membranes are incubated in 20 mM HEPES buffer with 40,000 cpm [$^{125}$I]GLP-1 (or exendin) tracer, and varying concentrations of test compound for 2 hours at 23° C. with constant mixing. Reaction mixtures are filtered through glass filter pads presoaked with 0.3% PEI solution and rinsed with ice-cold phosphate buffered saline. Bound counts are determined using a scintillation counter. Binding affinities are calculated using GraphPad Prism® software (GraphPad Software, Inc., San Diego, Calif.).

In vitro assays for functional GLP-1 receptor activation can be performed using known methods and cells and tissues. For example, exendin-4 stimulation of GLP-1 receptor bearing cells can induce an increase in adenylate cyclase activation, cAMP synthesis, membrane depolarization, rise in intracellular calcium and increase in glucose-induced insulin secretion. See e.g., Holz et al., 1995, *J. Biol. Chem.* 270(30): 17749-57. Cell-based assays using the rMTC 6-23 (clone 6) cell line can be used to determine GLP-1 receptor agonist activity of a compound based on the cAMP generated. In one embodiment of the bioassay the GLP-1 receptor agonist activity of a compound is quantitatively determined by correlations to cAMP production in cell-based assays with 6-23 (clone 6) cells. The cell-based assay uses living 6-23 (clone 6) cells. The 6-23 (clone 6) cells are available from the American Type Culture Collection as ATCC® No. CRL-1607™ and the European Collection of Cell Cultures as ECACC No. 87042206. In another embodiment the cell-based assay is a homogeneous time-resolved fluorescence assay (HTRF®). HTRF® kits are commercially available from Cisbio International (Bedford, Mass.). Methods for using HTRF® kits are known in the art and the kits generally include instruction manuals, e.g., on how to prepare samples, standards, calibration curves, and conduct experiments. Homogeneous time-resolved fluorescence cell-based assays are described in U.S. Pat. No. 5,527,684, the disclosure of which is incorporated by reference herein, and Document Reference No. 62AM4PEB rev02 (August 2007) available from Cisbio HTRF® Product Center. See worldwideweb.htrf.com/products/gper/camp/, the disclosure of which is incorporated by reference herein. In a preferred method the bioassay uses the rat thyroid carcinoma 6-23 (clone 6) cells in a cell-based assay using the HTRF® cAMP dynamic 2 1,000 assay kit, available from Cisbio as Catalog No. 62AM4PEB. The HTRF® standards and calibrations are prepared following the instructions in the kit. Assays may be performed with or without the presence of albumin.

In vivo assays for activity and duration of action and pharmacokinetics can be done using known methods. For example, duration can be performed using an oral glucose tolerance test (OGTT) in which the drug is administered to the subject at a desired time point before the glucose is administered orally(to measure drug duration of action; OGTT DOA) and glucose blood levels are measured (e.g. readily done in mice). Activity and duration can also be measured using an intravenous glucose tolerance test (IVGTT) in which the drug is administered to the subject at a desired time point before the glucose is administered IV (IVGTT DOA) and blood glucose levels are measured (e.g. can readily be done in rats). Preferred engineered compounds have a desired effect on blood glucose of at least 24 hours duration after a single dose of drug, preferably at least 3 days, at least 4 days, at least 5 days, at least 6 days, and at least 1 week after the single dose of drug is given.

For example, test polypeptide is injected subcutaneously at t=0 immediately following a baseline sample into NIH/Swiss female mice. Blood samples are taken at desired time periods such as t=2, 4, and 8 hours during day 1 and then daily through day 5 or through to day 7 or longer. Blood glucose is measured with a OneTouch® Ultra® (LifeScan, Inc., a Johnson & Johnson Company, Milpitas, Calif.). For a duration of activity (DOA) determination, such as for glucose control activity of a drug, an OGTT or IVGTT can be performed at the desired point after drug administration. Body weight can also be measured, as well as food intake, or other pharmacological or pharmacokinetic parameter. For example, female NIH/Swiss mice (8-20 weeks old) are group housed with a 12:12 hour light:dark cycle with lights on at 0600. Water and a standard pelleted mouse chow diet were available ad libitum, except as noted. The morning of the experiment, animals are divided into experimental groups and fasted starting at approximately 0630 hrs. In a typical study, n=2 cages with 3 mice/cage. At time=0 min, a blood glucose sample is taken and immediately followed by an intraperitoneal injection of vehicle or compound in an amount ranging from about 1 nmol/kg to 25 nmol/kg. Blood glucose can be measured at 30, 60, 120, 180, and 240 min and daily for a week or longer after the single dose. In a variation of the experiment, doses are provided daily or even weekly over a longer period such as 14 or 28 days. Percent pre-treatment is calculated by dividing the blood glucose at the measured time point, e.g. 60 minutes or 1 day, by the blood glucose at time=0 min. Significant treatment effects were identified by ANOVA (p<0.05). Where a significant difference exists, test means are compared to the control mean using Dunnett's test (Prism® v. 4.01, GraphPad Software Inc., San Diego, Calif.). Blood glucose can measured with a OneTouch® Ultra® (LifeScan, Inc., a Johnson & Johnson Company, Milpitas, Calif.). * p<0.05 vs. vehicle control; ANOVA, Dunnett's test. Other parameters can also be measured.

In Vivo Assay for Food Intake Inhibition:

The engineered polypeptides may be tested for their duration and extent of appetite suppression and for their duration and extent of effect on body weight loss in various known methods. For example, the polypeptides may be tested for appetite suppression in the mouse food intake assay and for their effect on body weight gain in diet-induced obesity (DIO) mice. An experimental protocol for such assays are described below.

For example, female NIH/Swiss mice (8-24 weeks old) are group housed with a 12:12 hour light:dark cycle with lights on at 0600. Water and a standard pelleted mouse chow diet are available ad libitum, except as noted. Animals are fasted starting at approximately 1500 hrs, 1 day prior to experiment. The morning of the experiment, animals are divided into experimental groups. In a typical study, n=4 cages with 3 mice/cage. At time=0 min, all animals are given an intraperitoneal injection of vehicle or test compound, typically in an amount ranging from about 2 nmol/kg to 75 nmol/kg, and immediately given a pre-weighed amount (10-15 g) of standard chow. Food is removed and weighed at various times, typically 30, 60, and 120 minutes or longer, such as daily, to determine the amount of food consumed (Morley, Flood et al., 1994, *Am. J. Physiol.* 267: R178-R184). Food intake is calculated by subtracting the weight of the food remaining at the e.g., 30 or 60 minute time point, from the weight of the food provided initially at time=0. Significant treatment effects are identified by ANOVA (p<0.05). Where a significant difference exists, test means are compared to the control mean using Dunnett's test (Prism® v. 2.01, GraphPad Software Inc., San Diego, Calif.). Body weight can also be measured.

Body Weight, Fat Redistribution, and Lean Body Mass Assays:

Assays for body weight and related effects can also be performed as follows. Diet-induced obesity (DIO) in the in the Sprague-Dawley rat is a valuable model for the study of obesity and regulation of energy homeostasis. These rats were developed from a line of (Crl:CD® (SD)BR) rats that are prone to become obese on a diet relatively high in fat and energy. See, for example, Levin, 1994, *Am. J. Physiol.* 267: R527-R535, Levin et al., 1997, *Am. J. Physiol.* 273:R725-R730. DIO male rats are obtained from Charles River Laboratories, Inc. (Wilmington, Mass.). The rats are housed individually in shoebox cages at 22° C. in a 12/12-hour light dark cycle. Rats are maintained ad-libitum on a moderately high fat diet (32% kcal from fat; Research Diets D1226B). The animals typically achieve a mean body weight of about 500 g. Levin DIO rats are habituated to caging environment for 7 days. During the 3 nights of habituation, animals receive a single intraperitoneal (IP) injection of vehicle. On test day, rats are administered a single IP injection of compound or vehicle (e.g. 10% DMSO) at the onset of the dark cycle. Food intake is measured by an automated food intake measuring system (BioDAQ, Research Diets) at 5 sec intervals throughout the course of the study. Body weight is recorded nightly.

Body composition can be measured prior to and after drug treatment using NMR (Echo Medical Systems, Houston, Tex.). For body composition measurements, rats are briefly placed (~1 min) in a well-ventilated plexiglass tube that was then inserted into a specialized rodent NMR machine. This enabled the calculation of changes in actual grams of fat and dry lean tissue (e.g., grams of body fat after treatment−grams of body fat at baseline=change in grams of body fat) and changes in % body composition for fat and dry lean tissue (e.g., % body fat after treatment−% body fat at baseline=change in % body fat). All data are represented as mean±SEM. Analysis of variance (ANOVA) and post-hoc tests are used to test for group difference. A P-value <0.05 is considered significant. Statistical analysis and graphing are performed using PRISM® 4 for Windows (GraphPad Software, Inc., San Diego, Calif.). Graphs and results are typically presented as vehicle-corrected changes in percent body weight, body fat and changes in body protein

VI. Pharmaceutical Compositions

In one aspect, there are provided pharmaceutical compositions including compounds described herein in combination with a pharmaceutically acceptable excipient (e.g., carrier). The term "pharmaceutically acceptable carrier," as used herein refers to pharmaceutical excipients, for example, pharmaceutically, physiologically, acceptable organic or inorganic carrier substances suitable for enteral or parenteral application that do not deleteriously react with the active agent. Suitable pharmaceutically acceptable carriers include water, salt solutions (e.g., Ringer's solution and the like), alcohols, oils, gelatins, and carbohydrates such as lactose, amylose or starch, fatty acid esters, hydroxymethycellulose, and polyvinyl pyrrolidine. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention.

In a further aspect, there is provided a pharmaceutical composition which includes a engineered polypeptide as described herein in combination with a pharmaceutically acceptable excipient. In one embodiment, the pharmaceutical composition is an oral pharmaceutical composition, as described herein. In some embodiments, the pharmaceutical composition is a long lasting pharmaceutical composition. The term "long lasting" in the context of administration of a pharmaceutical composition refers to duration of action. Accordingly, a long lasting pharmaceutical composition may be administered at intervals of, for example, 1 hr, 2 hr, 4 hr, 8 hr, 12 hr, 1 day, 2 days, 3 days, 4 days, 5 days, 6 days, 1 week, 2 weeks, 3 weeks, 1 month or even longer. In one embodiment, administration is twice a day (i.e., "twice daily"). In a preferred embodiment, administration is once a day (i.e., "once daily"). In a more preferred embodiments, administration is once a week (i.e., "once weekly"). In some embodiments, the engineered polypeptide is selected from the engineered polypeptides set forth in Tables 2 and 3 herein. In some embodiments, the engineered polypeptide is selected from the engineered polypeptides set forth in Table 2 herein. Preferably the compound is Cmpd 5, 9 or 11, or has at least 95% amino acid sequence identity thereto.

A. Formulations

The engineered polypeptides described herein can be administered alone or can be co-administered to a subject.

Co-administration is meant to include simultaneous or sequential administration of the compounds individually or in combination (more than one compound). For example, it has been found that obesity can be beneficially treated with a combination therapy including leptin (e.g., meterleptin) and an amylin (e.g., pramlintide). See e.g., U.S. Published Appl. No. 2008/0207512. Accordingly, an engineered polypeptide described herein including an ABD and an exendin compound useful for treatment of e.g., obesity and overweight, can be administered alone to achieve such treatment or co-administered with either a leptin or leptin agonist, e.g. meterleptin, and/or an amylin or amylin agonist, e.g. pramlintide.

In some embodiments, the formulations and methods described herein further provide that the exendin, exendin analog or exendin analog agonist engineered polypeptide is co-administered with one or more anti-diabetic agents, such as anti-hyperglycemia agents, e.g. insulin (including regular, short acting, long-acting, and basal insulins), amylins, pramlintide, metformin and thiazolidinediones (including rosiglitazone and pioglitazone).

In some embodiments, the formulations and methods described herein further provide that the exendin, exendin analog or exendin analog agonist engineered polypeptide is co-administered with one or more cholesterol and/or triglyceride lowering agents. Exemplary agents include HMG CoA reductase inhibitors (e.g., atorvastatin, fluvastatin, lovastatin, pravastatin, rosuvastatin, simvastatin); bile ace sequestrants (e.g., colesevelam, cholestyramine, colestipol); fibrates (e.g., fenofibrate, clofibrate, gemfibrozil); ezetimibe, nicotinic acid, probucol, a lovastatin/niacin combination; an atorvastatin/amlodipine combination; and a simvastatin/ezetimibe combination.

The present disclosure provides the composition for use as a medicament, i.e. for use in therapy, since the exendin compound is a therapeutically active compound, and surprisingly retains activity when fused to ABD. Compositions including an engineered polypeptide, either liquid or dry form, and optionally at least one pharmaceutically acceptable carrier and/or excipient are also specifically contemplated and are exemplified herein.

The composition has an ability to associate with albumin in vivo or in vitro. In certain cases, it may be of benefit to form a complex of the composition with albumin outside of a living organism, i.e. to add exogenous albumin to the composition. Such a composition may be lyophilized, providing a formulation that is suitable for storage at ambient temperature. Thus, the present disclosure also provides a composition as defined above which further includes albumin, such as human serum albumin, and which may optionally be in dry form.

Co-administration can be achieved by separately administering the exendin, exendin agonist, or exendin analog agonist engineered polypeptide with the second agent, or by administering a single pharmaceutical formulation including the exendin, exendin agonist, or exendin analog agonist engineered polypeptide and the second agent. Appropriate dosage regimens for the second agents are generally known in the art.

The preparations can also be co-administered, when desired, with other active substances (e.g. to reduce metabolic degradation) as known in the art or other therapeutically active agents. An exendin engineered polypeptide described herein can be administered with other active anti-diabetes or anti-obesity agents, such as leptin or leptin agonists and amylin or amylin agonist compounds, e.g. the amylins, including davalintide and their analogs.

Amylins.

Amylin is a peptide hormone synthesized by pancreatic β-cells that is co-secreted with insulin in response to nutrient intake. The sequence of amylin is highly preserved across mammalian species, with structural similarities to calcitonin gene-related peptide (CGRP), the calcitonins, the intermedins, and adrenomedullin, as known in the art. The glucoregulatory actions of amylin complement those of insulin by regulating the rate of glucose appearance in the circulation via suppression of nutrient-stimulated glucagon secretion and slowing gastric emptying. In insulin-treated patients with diabetes, pramlintide, a synthetic and equipotent analogue of human amylin, reduces postprandial glucose excursions by suppressing inappropriately elevated postprandial glucagon secretion and slowing gastric emptying. The sequences of rat amylin, human amylin and pramlintide follow:

```
                                              (SEQ ID NO: 6)
    KCNTATCATQRLANFLVRSSNNLGPVLPPTNVGSNTY;

(SEQ ID NO: 7)
    KCNTATCATQRLANFLVHSSNNFGAILSSTNVGSNTY;

(SEQ ID NO: 8)
    KCNTATCATQRLANFLVHSSNNFGPILPPTNVGSNTY.
```

Davalintide.

Davalintide, also known as "AC-2307" is a potent amylin agonist useful in the treatment of a variety of disease indications. See WO 2006/083254 and WO 2007/114838, each of which is incorporated by reference herein in its entirety and for all purposes. Davalintide is a chimeric peptide, having an N-terminal loop region of amylin or calcitonin and analogs thereof, an alpha-helical region of at least a portion of an alpha-helical region of calcitonin or analogs thereof or an alpha-helical region having a portion of an amylin alpha-helical region and a calcitonin alpha-helical region or analog thereof, and a C-terminal tail region of amylin or calcitonin. The sequences of human calcitonin, salmon calcitonin and davalintide follow:

```
                                              (SEQ ID NO: 9)
    CGNLSTCMLGTYTQDFNKFHTFPQTAIGVGAP;

(SEQ ID NO: 10)
    CSNLSTCVLGKLSQELHKLQTYPRTNTGSGTP;

(SEQ ID NO: 11)
    KCNTATCVLGRLSQELHRLQTYPRTNTGSNTY.
```

Without wishing to be bound by any theory, it is believed that amylins and davalintide, and fragment and analogs thereof, can require C-terminal amidation to elicit a full biological response. It is understood that amylin compounds such as those described herein which include amylins and/or davalintide, and fragment and analogs thereof, can be amidated at the C-terminal.

"Amylin agonist compounds" include native amylin peptides, amylin analog peptides, and other compounds (e.g., small molecules) that have amylin agonist activity. The "amylin agonist compounds" can be derived from natural sources, can be synthetic, or can be derived from recombinant DNA techniques. Amylin agonist compounds have amylin agonist receptor binding activity and may include amino acids (e.g., natural, unnatural, or a combination thereof), peptide mimetics, chemical moieties, and the like. The skilled artisan will recognize amylin agonist compounds using amylin receptor binding assays or by measuring amylin agonist activity in soleus muscle assays. In one embodiment, amylin agonist compounds will have an $IC_{50}$ of about 200 nM or less, about 100 nM or less, or about 50 nM or less, in an amylin receptor binding assay, such as that described herein, in U.S. Pat. No.

5,686,411, and US Publication No. 2008/0176804, the disclosures of which are incorporated by reference herein in their entireties and for all purposes. In one embodiment, amylin agonist compounds will have an $EC_{50}$ of about 20 nM or less, about nM 15 or less, about nM 10 or less, or about nM 5 or less in a soleus muscle assay, such as that described herein and in U.S. Pat. No. 5,686,411. In one embodiment, the amylin agonist compound has at least 90% or 100% sequence identity to $^{25,28,29}$Pro-human-amylin. In one embodiment, the amylin agonist compound is a peptide chimera of amylin (e.g., human amylin, rat amylin, and the like) and calcitonin (e.g., human calcitonin, salmon calcitonin, and the like). Suitable and exemplary amylin agonist compounds are also described in US Publication No. 2008/0274952, the disclosure of which is incorporated by reference herein in its entirety and for all purposes.

When co-administered with another active agent, the compounds can be administered simultaneously or sequentially, together or separately formulated. Since the engineered compounds herein are inherently long-acting, they are suitable for once daily, once weekly or longer administration. Accordingly, the other agent may be administered either in one or multiple doses, e.g. once daily, twice daily, three times daily, once weekly, as needed, during the period of dosing for the exendin engineered polypeptide, e.g. once weekly.

Single and multiple-use formulations of other agents such as amylin compounds have been reported. For example, pramlintide has been formulated for and successfully administered for once, twice and three times daily administration for treating diabetes and for treating obesity.

These pharmaceutical compounds may be formulated with pharmaceutically acceptable carriers or diluents as well as any other known adjuvants and excipients in accordance with conventional techniques such as those disclosed in *Remington's Pharmaceutical Sciences* by E. W. Martin. See also Wang et al. (1988) *J. of Parenteral Sci.* and Tech., Technical Report No. 10, Supp. 42:2 S.

In general, the engineered polypeptides may be formulated into a stable, safe pharmaceutical composition for administration to a patient. Pharmaceutical formulations contemplated for use in the methods of the invention may include approximately 0.01 to 1.0% (w/v), in certain cases 0.05 to 1.0%, of the engineered polypeptide, approximately 0.02 to 0.5% (w/v) of an acetate, phosphate, citrate or glutamate buffer allowing a pH of the final composition of from about 3.0 to about 7.0; approximately 1.0 to 10% (w/v) of a carbohydrate or polyhydric alcohol tonicifier and, optionally, approximately 0.005 to 1.0% (w/v) of a preservative selected from the group of m-cresol, benzyl alcohol, methyl, ethyl, propyl and butyl parabens and phenol. Such a preservative is generally included if the formulated peptide is to be included in a multiple use product.

In particular embodiments, a pharmaceutical formulation of the present engineered polypeptides may contain a range of concentrations of the compound(s), e.g., between about 0.01% to about 98% w/w, or between about 1 to about 98% w/w, or preferably between 80% and 90% w/w, or preferably between about 0.01% to about 50% w/w, or more preferably between about 10% to about 25% w/w in these embodiments. A sufficient amount of water for injection may be used to obtain the desired concentration of solution.

Additional tonicifying agents such as sodium chloride, as well as other known excipients, may also be present, if desired. In some cases, such excipients are useful in maintenance of the overall tonicity of the compound. An excipient may be included in the presently described formulations at various concentrations. For example, an excipient may be included in the concentration range from about 0.02% to about 20% w/w, preferably between about 0.02% and 0.5% w/w, about 0.02% to about 10% w/v, or about 1% to about 20% w/w. In addition, similar to the present formulations themselves, an excipient may be included in solid (including powdered), liquid, semi-solid or gel form.

The pharmaceutical formulations may be composed in various forms, e.g., solid, liquid, semisolid or liquid. The term "solid", as used herein, is meant to encompass all normal uses of this term including, for example, powders and lyophilized formulations. The presently described formulations may be lyophilized.

The terms buffer, buffer solution and buffered solution, when used with reference to hydrogen-ion concentration or pH, refer to the ability of a system, particularly an aqueous solution, to resist a change of pH on adding acid or alkali, or on dilution with a solvent. Characteristic of buffered solutions, which undergo small changes of pH on addition of acid or base, is the presence either of a weak acid and a salt of the weak acid, or a weak base and a salt of the weak base. An example of the former system is acetic acid and sodium acetate. The change of pH is slight as long as the amount of hydronium or hydroxyl ion added does not exceed the capacity of the buffer system to neutralize it.

As described herein, a variety of liquid vehicles are suitable for use in the formulations of engineered polypeptides, for example, water or an aqueous/organic solvent mixture or suspension.

The stability of a engineered polypeptide formulation for use as described herein is enhanced by maintaining the pH of the formulation in a range determined by methods known in the art. In certain embodiments, the pH of the formulation is maintained in the range of about 3.5 to 5.0, or about 3.5 to 6.5, in some embodiments from about 3.7 to 4.3, or about 3.8 to 4.2. In some embodiments, pH may be about 4.0, about 5.0, about 6.0, about 7.0, about 8.0, about 9.0, or even higher. In some embodiments, pH may be in the physiological range, pH 6-8, preferably pH 7-7.6.

In certain embodiments, the buffer with the engineered polypeptide is an acetate buffer (preferably at a final formulation concentration of from about 1-5 to about 60 mM), phosphate buffer (preferably at a final formulation concentration of from about 1-5 to about to about 30 mM) or glutamate buffer (preferably at a final formulation concentration of from about 1-5 to about to about 60 mM). In some embodiments, the buffer is acetate (preferably at a final formulation concentration of from about 5 to about 30 mM).

A stabilizer may be included in the formulations but is not necessarily needed. If included, however, a stabilizer useful in the practice of the present invention is a carbohydrate or a polyhydric alcohol. A suitable stabilizer useful in the practice of the present invention is approximately 1.0 to 10% (w/v) of a carbohydrate or polyhydric alcohol. The polyhydric alcohols and carbohydrates share the same feature in their backbones, i.e., —CHOH—CHOH—, which is responsible for stabilizing the proteins. The polyhydric alcohols include such compounds as sorbitol, mannitol, glycerol, and polyethylene glycols (PEGs). These compounds are straight-chain molecules. The carbohydrates, such as mannose, ribose, sucrose, fructose, trehalose, maltose, inositol, and lactose, on the other hand, are cyclic molecules that may contain a keto or aldehyde group. These two classes of compounds have been demonstrated to be effective in stabilizing protein against denaturation caused by elevated temperature and by freeze-thaw or freeze-drying processes. Suitable carbohydrates include: galactose, arabinose, lactose or any other carbohydrate which does not have an adverse affect on a diabetic patient, i.e., the carbohydrate is not metabolized to form unacceptably large concentrations of glucose in the blood. Such carbohydrates are well known in the art as suitable for diabetics. Sucrose and fructose are suitable for use with the compound in non-diabetic applications (e.g. treating obesity).

In certain embodiments, if a stabilizer is included, the compound is stabilized with a polyhydric alcohol such as sorbitol, mannitol, inositol, glycerol, xylitol, and polypropylene/ethylene glycol copolymer, as well as various polyethylene glycols (PEG) of molecular weight 200, 400, 1450, 3350, 4000, 6000, 8000 and even higher). Mannitol is the preferred polyhydric alcohol in some embodiments. Another useful feature of the lyophilized formulations of the present invention is the maintenance of the tonicity of the lyophilized formulations described herein with the same formulation component that serves to maintain their stability. In some embodiments, mannitol is the preferred polyhydric alcohol used for this purpose.

The United States Pharmacopeia (USP) states that antimicrobial agents in bacteriostatic or fungistatic concentrations must be added to preparations contained in multiple dose containers. They must be present in adequate concentration at the time of use to prevent the multiplication of microorganisms inadvertently introduced into the preparation while withdrawing a portion of the contents with a hypodermic needle and syringe, or using other invasive means for delivery, such as pen injectors. Antimicrobial agents should be evaluated to ensure compatibility with all other components of the formula, and their activity should be evaluated in the total formula to ensure that a particular agent that is effective in one formulation is not ineffective in another. It is not uncommon to find that a particular antimicrobial agent will be effective in one formulation but not effective in another formulation.

A preservative is, in the common pharmaceutical sense, a substance that prevents or inhibits microbial growth and may be added to pharmaceutical formulations for this purpose to avoid consequent spoilage of the formulation by microorganisms. While the amount of the preservative is not great, it may nevertheless affect the overall stability of the peptide.

While the preservative for use in the pharmaceutical compositions can range from 0.005 to 1.0% (w/v), in some embodiments range for each preservative, alone or in combination with others, is: benzyl alcohol (0.1-1.0%), or m-cresol (0.1-0.6%), or phenol (0.1-0.8%) or combination of methyl (0.05-0.25%) and ethyl or propyl or butyl (0.005%-0.03%) parabens. The parabens are lower alkyl esters of para-hydroxybenzoic acid. A detailed description of each preservative is set forth in *Remington's Pharmaceutical Sciences* (Id.)

Engineered polypeptides may not have a tendency to adsorb onto the glass in a glass container when in a liquid form, therefore, a surfactant may not be required to further stabilize the pharmaceutical formulation. However, with regard to compounds which do have such a tendency when in liquid form, a surfactant should be used in their formulation. These formulations may then be lyophilized. Surfactants frequently cause denaturation of protein, both of hydrophobic disruption and by salt bridge separation. Relatively low concentrations of surfactant may exert a potent denaturing activity, because of the strong interactions between surfactant moieties and the reactive sites on proteins. However, judicious use of this interaction can stabilize proteins against interfacial or surface denaturation. Surfactants which could further stabilize the engineered polypeptide may optionally be present in the range of about 0.001 to 0.3% (w/v) of the total formulation and include polysorbate 80 (i.e., polyoxyethylene(20) sorbitan monooleate), CHAPS® (i.e., 3-[(3-cholamidopropyl) dimethylammonio]1-propanesulfonate), Brij® (e.g., Brij® 35, which is (polyoxyethylene (23) lauryl ether), poloxamer, or another non-ionic surfactant.

It may also be desirable to add sodium chloride or other salt to adjust the tonicity of the pharmaceutical formulation, depending on the tonicifier selected. However, this is optional and depends on the particular formulation selected. Parenteral formulations preferably may be isotonic or substantially isotonic.

A preferred vehicle for parenteral products is water. Water of suitable quality for parenteral administration can be prepared either by distillation or by reverse osmosis. Water for injection is the preferred aqueous vehicle for use in the pharmaceutical formulations.

It is possible that other ingredients may be present in the pharmaceutical formulations. Such additional ingredients may include, e.g., wetting agents, emulsifiers, oils, antioxidants, bulking agents, tonicity modifiers, chelating agents, metal ions, oleaginous vehicles, proteins (e.g., human serum albumin, gelatin or proteins) and a zwitterion (e.g., an amino acid such as betaine, taurine, arginine, glycine, lysine and histidine). Additionally, polymer solutions, or mixtures with polymers provide the opportunity for controlled release of the peptide. Such additional ingredients, of course, should not adversely affect the overall stability of the pharmaceutical formulation of the present invention.

Containers are also an integral part of the formulation of an injection and may be considered a component, for there is no container that is totally inert, or does not in some way affect the liquid it contains, particularly if the liquid is aqueous. Therefore, the selection of a container for a particular injection must be based on a consideration of the composition of the container, as well as of the solution, and the treatment to which it will be subjected. Adsorption of the peptide to the glass surface of the vial can also be minimized, if necessary, by use of borosilicate glass, for example, Wheaton Type I borosilicate glass #33 (Wheaton Type I-33) or its equivalent (Wheaton Glass Co.). Other vendors of similar borosilicate glass vials and cartridges acceptable for manufacture include Kimbel Glass Co., West Co., Bunder Glas GMBH and Form a Vitrum. The biological and chemical properties of the compound may be stabilized by formulation and lyophilization in a Wheaton Type I-33 borosilicate serum vial to a final concentration of 0.1 mg/ml and 10 mg/ml of the compound in the presence of 5% mannitol, and 0.02% Tween 80.

For formulations to be delivered by injection, in order to permit introduction of a needle from a hypodermic syringe into a multiple-dose vial and provide for resealing as soon as the needle is withdrawn, the open end of each vial is preferably sealed with a rubber stopper closure held in place by an aluminum band.

Stoppers for glass vials, such as, West 4416/50, 4416/50 (Teflon faced) and 4406/40, Abbott 5139 or any equivalent stopper can be used as the closure for pharmaceutical for injection. For formulations including peptidic anti-obesity agents, these stoppers are compatible with the peptide as well as the other components of the formulation. The inventors have also discovered that these stoppers pass the stopper integrity test when tested using patient use patterns, e.g., the stopper can withstand at least about 100 injections. Alternatively, the peptide can be lyophilized in to vials, syringes or cartridges for subsequent reconstitution. Liquid formulations of the present invention can be filled into one or two chambered cartridges, or one or two chamber syringes.

Each of the components of the pharmaceutical formulation described above is known in the art and is described in *Pharmaceutical Dosage Forms: Parenteral Medications*, Vol. 1, 2nd ed., Avis et al. Ed., Mercel Dekker, New York, N.Y. 1992, which is incorporated by reference in its entirety herein.

The manufacturing process for the above liquid formulations generally involves compounding, sterile filtration and filling steps. The compounding procedure involves dissolution of ingredients in a specific order (preservative followed by stabilizer/tonicity agents, buffers and peptide) or dissolving at the same time.

Alternative formulations, e.g., non-parenteral, may not require sterilization. However, if sterilization is desired or necessary, any suitable sterilization process can be used in developing the peptide pharmaceutical formulation of the present invention. Typical sterilization processes include filtration, steam (moist heat), dry heat, gases (e.g., ethylene oxide, formaldehyde, chlorine dioxide, propylene oxide, beta-propiolactone, ozone, chloropicrin, peracetic acid methyl bromide and the like), exposure to a radiation source, and aseptic handling. Filtration is the preferred method of sterilization for liquid formulations of the present invention. The sterile filtration involves filtration through 0.45 um and 0.22 um (1 or 2) which may be connected in series. After filtration, the solution is filled into appropriate vials or containers.

In certain embodiments, the engineered polypeptides described herein are administered peripherally to the subjects. In some embodiments, the liquid pharmaceutical formulations of the present invention are intended for parenteral administration. Suitable routes of administration include intramuscular, intravenous, subcutaneous, intradermal, intraarticular, intrathecal and the like. In some embodiments, the subcutaneous route of administration is preferred. In certain embodiments, mucosal delivery is also preferred. These routes include, but are not limited to, oral, nasal, sublingual, pulmonary and buccal routes which may include administration of the peptide in liquid, semi-solid or solid form. For formulations including engineered polypeptides, administration via these routes can require substantially more compound to obtain the desired biological effects due to decreased bioavailability compared to parenteral delivery.

In addition, parenteral controlled release delivery can be achieved by forming polymeric microcapsules, matrices, solutions, implants and devices and administering them parenterally or by surgical means. Examples of controlled release formulations are described in U.S. Pat. Nos. 6,368, 630, 6,379,704, and 5,766,627, which are incorporated herein by reference. These dosage forms may have a lower bioavailability due to entrapment of some of the peptide in the polymer matrix or device. See e.g., U.S. Pat. Nos. 6,379,704, 6,379,703, and 6,296,842, each of which is incorporated herein by reference in its entirety and for all purposes.

The compounds may be provided in dosage unit form containing an amount of the engineered polypeptide that will be effective in one or multiple doses.

As will be recognized by those in the field, an effective amount of the engineered polypeptide will vary with many factors including the age and weight of the subject, the subject's physical condition, the condition to be treated, and other factors known in the art. An effective amount of the engineered polypeptides will also vary with the particular combination administered. As described herein, administration of the engineered polypeptides in combination may allow for a reduced amount of any of the administered engineered polypeptides to be an effective amount.

Administration can be by oral route, including transcellular, paracellular or receptor-mediated routes. Without wishing to be bound by any theory, the engineered polypeptides containing an exendin as described herein are orally available, in part because of their relatively small size and relative stability to gut enzymes. It has been reported that tight junctions between intestinal cells opened by absorption/permeation enhancers are less than 20 nm wide. See e.g., Chao et al., 1998, J. Drug Targeting, 6:37-43. Accordingly, a sufficiently small (for example, less than 10 kD or 15 kD) engineered polypeptide as described herein can transit the gut wall and bind albumin in the portal system, thereby gaining access to the circulation. Oral delivery of the engineered polypeptides of the present invention may be twice daily, once daily, once other day, once every three days, once weekly, once in two weeks, one in three weeks, or even once a month. Oral delivery systems suitable for other peptides can be used. In one embodiment the oral delivery system may have a relatively rapid uptake profile, e.g. from 1 to 4 hours, in which case the inherently long-duration of action of the engineered polypeptide provides the extended duration of action desired, such as for once daily or once weekly administration. The duration of action can be selected, for example, by choice of ABD and its affinity for albumin. While not wishing to be bound by theory, it is believed that higher affinity to albumin will yield longer circulation times providing longer duration of action. Oral delivery can be tested using known in vitro and in vivo methods. For example, a mouse can be orally gavaged with a solution containing an engineered polypeptide formulated with or without a permeation/absorption enhancer and/or protease inhibitor in order to test orally availability and effect of any added excipient. Either or both pharmacodynamic (therapeutic effects) and pharmacokinetic (drug properties) can be measured over time, such as drug plasma levels, acute or chronic glucose and/or HbA1c lowering, insulin plasma levels, food intake inhibition, weight loss, and/or lipid levels.

B. Effective Dosages

Pharmaceutical compositions provided herein include compositions wherein the active ingredient is contained in a therapeutically effective amount, i.e., in an amount effective to achieve its intended purpose. The actual amount effective for a particular application will depend, inter alia, on the condition being treated. For example, when administered in methods to treat diabetes, such compositions will contain an amount of active ingredient effective to achieve the desired result (e.g. decreasing fasting blood glucose in a subject). When administered in methods to treat obesity, such compositions will contain an amount of active ingredient effective to achieve the desired result (e.g. decrease the body mass).

The dosage and frequency (single or multiple doses) of compound administered can vary depending upon a variety of factors, including route of administration; size, age, sex, health, body weight, body mass index, and diet of the recipient; nature and extent of symptoms of the disease being treated (e.g., the disease responsive to compounds described herein; fasting blood glucose); presence of other diseases or other health-related problems; kind of concurrent treatment; and complications from any disease or treatment regimen. Other therapeutic regimens or agents can be used in conjunction with the methods and compounds of the invention.

Therapeutically effective amounts for use in humans may be determined from animal models. For example, a dose for humans can be formulated to achieve a concentration that has been found to be effective in animals. The dosage in humans can be adjusted by monitoring one or more physiological parameters, including but not limited to blood sugar and body mass, and adjusting the dosage upwards or downwards, as described above and known in the art.

Dosages may be varied depending upon the requirements of the patient and the compound being employed. The dose administered to a patient, in the context of the present invention, should be sufficient to affect a beneficial therapeutic response in the patient over time. The size of the dose also will be determined by the existence, nature, and extent of any adverse side effects. Generally, treatment is initiated with smaller dosages, which are less than the optimum dose of the compound. Thereafter, the dosage is increased by small increments until the optimum effect under circumstances is reached. In one embodiment of the invention, the dosage range is 0.001% to 10% w/v. In another embodiment, the dosage range is 0.1% to 5% w/v.

However, typical doses may contain from a lower limit of about 1 ug, 5 ug, 10 ug, 50 ug, 100 ug to 150 ug per day to an upper limit of about to 50 ug, to 100 ug, to 150 ug, to 200 ug or even to 300 ug of the pharmaceutical compound per week in view of the extended half-life of the engineered polypeptides herein. The doses may be delivered in discrete unit doses at the desired interval, e.g. daily or weekly.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is entirely effective to treat the clinical symptoms demonstrated by the particular patient. This planning should involve the careful choice of active compound by considering factors such as compound potency, relative bioavailability, patient body weight, presence and severity of adverse side effects, preferred mode of administration, and the toxicity profile of the selected agent.

The surprising dose-sparing property of the engineered polypeptides of the present invention, along with their surprisingly long plasma half-life and duration of pharmacological action, provides for a superior pharmaceutical agent. Also surprising in the case of the exendin-containing engineered polypeptides are their oral availability. The superior properties including dose-sparing, allow for lower dosing, thus less or less severe side-effects and improved cost of goods, and/or more cost-effective and simpler formulations for once daily or once weekly administration not currently achieved by the parent compounds alone.

C. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch.1, p. 1, 1975. The exact formulation, route of administration, and dosage can be chosen by the individual physician in view of the patient's condition and the particular method in which the compound is used.

Without wishing to be bound by any theory, it is believed that fusion of an ABD albumin binding domain with a hormone domain as described herein, can provide decreased immunogenicity as judged by a reduction in immune response relative to the hormone domain without ABD fusion. See e.g., WO 2009/016043, incorporated herein by reference in its entirety and for all purposes.

Exemplary HD1, Linker and ABD sequences include:

```
                                           (SEQ ID NO: 1)
HSDGTFTSDLSKQMEEEAVRLFIEWLKNGGPSSGAPPPS-NH2;

(SEQ ID NO: 2)
HGEGTFTSDLSKQMEEEAVRLFIEWLKNGGPSSGAPPPS-NH2;

(SEQ ID NO: 3)
HGEGTFTSDLSKQLEEEAVRLFIEWLKNGGPSSGAPPPS-NH2;

(SEQ ID NO: 4)
HGEGTFTSDLSKQLEEEAVRLFIEWLKQGGPSKEIIS;

(SEQ ID NO: 5)
HAEGTFTSDVSSYLEGQAAKEFIAWLVKGRG;

(SEQ ID NO: 6)
KCNTATCATQRLANFLVRSSNNLGPVLPPTNVGSNTY;

(SEQ ID NO: 7)
KCNTATCATQRLANFLVHSSNNFGAILSSTNVGSNTY;

(SEQ ID NO: 8)
KCNTATCATQRLANFLVHSSNNFGPILPPTNVGSNTY;

(SEQ ID NO: 9)
CGNLSTCMLGTYTQDFNKFHTFPQTAIGVGAP;

(SEQ ID NO: 10)
CSNLSTCVLGKLSQELHKLQTYPRTNTGSGTP;

(SEQ ID NO: 11)
KCNTATCVLGRLSQELHRLQTYPRTNTGSNTY;

(SEQ ID NO: 12)
HGEGTFTSDLSKQMEEEAVRLFIEWLKN;

(SEQ ID NO: 49)
HHHHHH;

(SEQ ID NO: 111)
HGEGTFTSDLSKQMEEEAVRLFIEWLKQGGPSKEIIS;

(SEQ ID NO: 112)
HGEGTFTSDLSKQLEEEAVRLFIEWLKNGGPSSGAPPS;

(SEQ ID NO: 113)
HGEGTFTSDLSKQMEEEAVRLFIEWLKNGGPSSGAPPS;

(SEQ ID NO: 114)
HGEGTFTSDLSKQLEEEAVRLFIEWLKQGGPSKEIISKKKKKK;

(SEQ ID NO: 115)
HGEGTFTSDLSKQMEEEAVRLFIEWLKNGGPSSGAPPPSKKKKKK;

(SEQ ID NO: 116)
HGEGTFTSDLSKQMEEEAVRLFIEWLKQGGPSKEIISKKKKKK;

(SEQ ID NO: 117)
HGEGTFTSDLSKQLEEEAVRLFIEWLKNGGPSSGAPPSKKKKKK;

(SEQ ID NO: 118)
HGEGTFTSDLSKQMEEEAVRLFIEWLKNGGPSSGAPPSKKKKKK;

(SEQ ID NO: 125)
GGGG;

(SEQ ID NO: 126)
GGGGG;

(SEQ ID NO: 127)
[G]nE, wherein n is 1-6;

(SEQ ID NO: 128)
[G]nK, wherein n is 1-6;
```

-continued

[G]ₙD, wherein n is 1-6; (SEQ ID NO: 129)

[G]ₙR, wherein n is 1-6; (SEQ ID NO: 130)

GGGKGGGG; (SEQ ID NO: 131)

GGGNGSGG; (SEQ ID NO: 132)

GGGCGGGG; (SEQ ID NO: 133)

GPNGG; (SEQ ID NO: 134)

[GS]ₙ, wherein n is 1-6; (SEQ ID NO: 135)

[GGS]ₙ, where n is 1-6; (SEQ ID NO: 136)

[GGGS]ₙ, where n is 1-6; (SEQ ID NO: 137)

[GGGGS]ₙ, where n is 1-6; (SEQ ID NO: 138)

[GE]ₙ, where n is 1-10; (SEQ ID NO: 139)

[GGE]ₙ, where n is 1-10; (SEQ ID NO: 140)

[GGGE]ₙ, where n is 1-10; (SEQ ID NO: 141)

[GGGGE]ₙ, where n is 1-10; (SEQ ID NO: 142)

[GD]ₙ, where n is 1-10; (SEQ ID NO: 143)

[GGD]ₙ, where n is 1-10; (SEQ ID NO: 144)

[GGGD]ₙ, where n is 1-10; (SEQ ID NO: 145)

[GGGGD]ₙ, where n is 1-10; (SEQ ID NO: 146)

[GK]ₙ, where n is 1-10; (SEQ ID NO: 147)

[GGK]ₙ, where n is 1-10; (SEQ ID NO: 148)

[GGGK]ₙ, where n is 1-10; (SEQ ID NO: 149)

[GGGGK]ₙ, where n is 1-10; (SEQ ID NO: 150)

[GR]ₙ, where n is 1-10; (SEQ ID NO: 151)

[GGR]ₙ, where n is 1-10; (SEQ ID NO: 152)

[GGGR]ₙ, where n is 1-10; (SEQ ID NO: 153)

[GGGGR]ₙ, where n is 1-10; (SEQ ID NO: 154)

[EAAAK]ₙ, where n is 1-10; (SEQ ID NO: 155)

-continued (SEQ ID NO: 300)
LA X3 AK X6 X7 AN X10 ELD X14 YGVSDF YKRLI X26

KAKTVEGVEALK X39 X40 IL X43 X44 LP, wherein independently of each other X3 is selected from E, S, Q and C; X6 is selected from E, S and C; X7 is selected from A and S; X14 is selected from A, S, C and K; X10 is selected from A, S and R; X26 is selected from D and E; X39 is selected from D and E; X40 is selected from A and E; X43 is selected from A and K; X44 is selected from A, S and E; the leucine at position 45 is present or absent; and the proline at position 46 is present or absent;

(SEQ ID NO: 678)
LA X3 AK X6 X7 AN X10 ELD X14

YGVSDFYKRLIDKAKTVEGVEALKDAILAALP where independently of each other X3 is selected from E, S, Q and C; X6 is selected from E, S and C; X7 is selected from A and S; X10 is selected from A, S and R; and X14 is selected from A, S, C and K; leucine at position 45 is present or absent; and proline at position 46 is present or absent; and see Table 1, Table 2, Table 3 and FIG. 1.

Exemplary embodiments of the engineered polypeptides comprising an exendin, an exendin analog or an active fragment thereof, method of use thereof, and pharmaceuticals compositions described herein and include:

Embodiment 1. An engineered polypeptide comprising: an albumin binding domain polypeptide (ABD) sequence, and a first peptide hormone domain (HD1) sequence selected from an exendin sequence, an exendin analog sequence or an active fragment sequence thereof. Embodiment 2. The engineered polypeptide according to embodiment 1, further comprising a first linker (L1) covalently linking said HD1 sequence and said ABD sequence. 3. The engineered polypeptide according to embodiment 1 or 2, wherein said engineered polypeptide comprises said ABD sequence as a C-terminal moiety and said HD1 sequence as an N-terminal moiety. 4. The engineered polypeptide according to embodiment 3, comprising the structure: HD1-ABD. 5. The engineered polypeptide according to embodiment 3, comprising the structure: HD1-L1-ABD. 6. The engineered polypeptide according to any one of embodiments 1 to 5, wherein said HD1 sequence is said exendin or exendin analog sequence. 7. The engineered polypeptide according to embodiment 6, wherein said exendin sequence is exendin-4 sequence and the exendin analog sequence is Leu14 exendin-4 sequence. 8. The engineered polypeptide according to embodiment 6, wherein said exendin fragment sequence is the sequence of exendin-4(1-28), exendin-4(1-29), exendin-4(1-30), exendin-4(1-31) or exendin-4(1-32). 9. The engineered polypeptide according to embodiment 6, wherein said exendin or exendin analog sequence is selected from the group of sequences consisting of:

(SEQ ID NO: 3)
HGEGTFTSDLSKQLEEEAVRLFIEWLKNGGPSSGAPPPS, (SEQ ID NO: 4)
HGEGTFTSDLSKQLEEEAVRLFIEWLKQGGPSKEIIS, (SEQ ID NO: 2)
HGEGTFTSDLSKQMEEEAVRLFIEWLKNGGPSSGAPPPS,

-continued

HGEGTFTSDLSKQMEEEAVRLFIEWLKQGGPSKEIIS, (SEQ ID NO: 111)

HGEGTFTSDLSKQLEEEAVRLFIEWLKNGGPSSGAPPS, (SEQ ID NO: 112)

HGEGTFTSDLSKQMEEEAVRLFIEWLKNGGPSSGAPPS, (SEQ ID NO: 113)

HGEGTFTSDLSKQLEEEAVRLFIEWLKQGGPSKEIISKKKKKK, (SEQ ID NO: 114)

HGEGTFTSDLSKQMEEEAVRLFIEWLKNGGPSSGAPPPSKKKKKK, (SEQ ID NO: 115)

HGEGTFTSDLSKQMEEEAVRLFIEWLKQGGPSKEIISKKKKKK, (SEQ ID NO: 116)

HGEGTFTSDLSKQLEEEAVRLFIEWLKNGGPSSGAPPSKKKKKK and (SEQ ID NO: 117)

HGEGTFTSDLSKQMEEEAVRLFIEWLKNGGPSSGAPPSKKKKKK. (SEQ ID NO: 118)

10. The engineered polypeptide according to any one of the previous embodiments, wherein said exendin or exendin analog comprises a modification at position corresponding to His1 selected from the group consisting of L-histidine, D-histidine, desamino-histidine, 2-amino-histidine, beta-hydroxy-histidine, homohistidine. N-alpha-acetyl-histidine, alpha-fluoromethyl-histidine, alpha-methyl-histidine, 3-pyridylalanine, 2-pyridylalanine, 4-pyridylalanine, 4-imidazoacetyl, des-amino-histidyl (imidazopropionyl), beta-hydroxy-imidazopropionyl, N-dimethyl-histidyl and beta-carboxy-imidazopropionyl. 11. The engineered polypeptide according to any one of the previous embodiments, wherein said analog comprises exendin-4 comprising a modification at position corresponding to His1 and is selected from the group consisting (4-imidazoacetyl) exendin-4, (des-amino-histidyl) exendin-4 (or (imidazopropionyl) exendin-4), (beta-hydroxy-imidazopropionyl) exendin-4, (N-dimethyl-histidyl) exendin-4 and (beta-carboxy-imidazopropionyl) exendin-4. 12. The engineered polypeptide according to any one of the previous embodiments, wherein said exendin analog sequence has at least 70% amino acid sequence identity with exendin-4, to an exendin analog of embodiment 9 or to the exendin fragment of embodiment 8. 13. The engineered polypeptide according to any one of embodiments 1 to 12, wherein said exendin analog has at least 80% identity with exendin-4, to an exendin analog of embodiment 9 or to the exendin fragment of embodiment 8. 14. The engineered polypeptide according to the previous embodiment, wherein said exendin analog has at least 90% identity with exendin-4, to an exendin analog of embodiment 9 or to the exendin fragment of embodiment 8. 15. The engineered polypeptide according to the previous embodiment, wherein said exendin analog has at least 95% identity with exendin-4, to an exendin analog of embodiment 9 or to the exendin fragment of embodiment 8. 16. The engineered polypeptide according to any one of the previous embodiments, wherein said exendin analog sequence has from 1 to 5 amino acid modifications selected independently from any one or combination of an insertion, deletion, addition and substitution. Embodiment 17. The engineered polypeptide according to any one of the preceding embodiments, wherein said ABD sequence comprises an amino acid sequence selected from the amino acid sequence comprising: formula (i) LA X3 AK X6 X7 AN X10 ELD X14 YGVSDF YKRLI X26 KAKTVEGVEALK X39 X40 IL X43 X44 LP (SEQ ID NO: 300) wherein independently of each other X3 is selected from E, S, Q and C; X6 is selected from E, S and C; X7 is selected from A and S; X14 is selected from A, S, C and K; X10 is selected from A, S and R; X26 is selected from D and E; X39 is selected from D and E; X40 is selected from A and E; X43 is selected from A and K; X44 is selected from A, S and E; the leucine at position 45 is present or absent; and the proline at position 46 is present or absent; and formula (ii) an amino acid sequence which has at least 95% identity to the sequence defined in (i), with the proviso that $X_7$ is not L, E or D; or alternatively, with the proviso that the amino acid sequence is not defined by the following sequence, as defined in PCT Published Application No. WO 2009/016043: LAEAK $X_a$ $X_b$ A X $X_d$ EL $X_e$ KY GVSD $X_5$ YK $X_8$ $X_9$ I $X_{11}$ $X_{12}$ A $X_{14}$ TVEGV $X_{20}$ AL $X_{23}$ $X_{24}$ $X_{25}$ ILAALP (SEQ ID NO: 679) wherein independently of each other, $X_a$ is selected from V and E; $X_b$ is selected from L, E and D; $X_c$ is selected from N, L and I; $X_d$ is selected from R and K; $X_e$ is selected from D and K; and $X_5$ is selected from Y and F; $X_8$ is selected from N, R and S; $X_9$ is selected from V, I, L, M, F and Y; $X_{11}$ is selected from N, S, E and D; $X_{12}$ is selected from R, K and N; $X_{14}$ is selected from K and R; $X_{20}$ is selected from D, N, Q, E, H, S, R and K; $X_{23}$ is selected from K, I and T; $X_{24}$ is selected from A, S, T, G, H, L and D; and $X_{25}$ is selected from H, E and D. 18. The engineered polypeptide according to embodiment 17, wherein said ABD sequence comprises an amino acid sequence comprising: formula (i) LA X3 AK X6 X7 AN X10 ELD X14 YGVSDF YKRLI X26 KAKTVEGVEALK X39 X40 IL X43 X44 LP (SEQ ID NO: 300) wherein independently of each other X3 is selected from E, S, Q and C; X6 is selected from E, S and C; X7 is selected from A and S; X14 is selected from A, S, C and K; X10 is selected from A, S and R; X26 is selected from D and E; X39 is selected from D and E; X40 is selected from A and E; X43 is selected from A and K; X44 is selected from A, S and E; the leucine at position 45 is present or absent; and the proline at position 46 is present or absent. 19. The engineered polypeptide according to embodiment 17, wherein said ABD sequence comprises an amino acid sequence comprising formula (ii) an amino acid sequence which has at least 95% identity to the sequence defined in (i), with the proviso that $X_7$ is not L, E or D; or alternatively, with the proviso that the amino acid sequence is not defined by the following sequence, as defined in PCT Published Application No. WO 2009/016043: LAEAK $X_a$ $X_b$ A $X_c$ $X_d$ EL $X_e$ KY GVSD $X_5$ YK $X_8$ $X_9$ I $X_{11}$ $X_{12}$ A $X_{14}$ TVEGV $X_{20}$ AL $X_{23}$ $X_{24}$ $X_{25}$ ILAALP (SEQ ID NO: 679) wherein independently of each other, $X_a$ is selected from V and E; $X_b$ is selected from L, E and D; $X_c$ is selected from N, L and I; $X_d$ is selected from R and K; $X_e$ is selected from D and K; and $X_5$ is selected from Y and F; $X_8$ is selected from N, R and S; $X_9$ is selected from V, I, L, M, F and Y; $X_{11}$ is selected from N, S, E and D; $X_{12}$ is selected from R, K and N; $X_{14}$ is selected from K and R; $X_{20}$ is selected from D, N, Q, E, H, S, R and K; $X_{23}$ is selected from K, I and T; $X_{24}$ is selected from A, S, T, G, H, L and D; and $X_{25}$ is selected from H, E and D. 20. The engineered polypeptide according to any one of the preceding embodiments, wherein said ABD sequence comprises an amino acid sequence selected from the amino acid sequence comprising: formula (iii) LA X3 AK X6×7 AN X10 ELD X14 YGVSDF YKRLIDKAKT VEGVEALKDA ILAALP (SEQ ID NO: 678) wherein independently of each other X3 is selected from E, S, Q and C; X6 is selected from E, S and C; X7 is selected from A and S; X10 is selected from A, S and R; X14 is selected from A, S, C and K; the leucine at position 45 is present or absent; and the proline at position 46 is present or absent; and formula (iv) an amino acid sequence which has at least 95% identity to the sequence defined in (iii) with the proviso that $X_7$ is not L, E or D; or alternatively, with the proviso that the amino acid sequence is not defined by the following sequence, as defined in PCT Published Application No. WO 2009/016043: LAEAK $X_a$ $X_b$ A X, $X_d$ EL $X_e$ KY GVSD $X_5$ YK $X_8$ $X_9$ I $X_{11}$ $X_{12}$ A $X_{14}$ TVEGV $X_{20}$ AL $X_{23}$ $X_{24}$ $X_{25}$ ILAALP (SEQ ID NO: 679) wherein independently of each other, $X_a$ is selected from V and E; $X_b$ is selected from L, E and D; $X_c$ is selected from N, L and I; $X_d$ is selected from R and K; $X_e$ is selected from D and K; and $X_5$ is selected from Y and F; $X_8$ is selected from N, R and S; $X_9$ is selected from V, I, L, M, F and Y; $X_{11}$ is selected from N, S, E and D; $X_{12}$ is selected from R, K and N; $X_{14}$ is selected from K and R; $X_{20}$ is selected from D, N, Q, E, H, S, R and K; $X_{23}$ is selected from K, I and T; $X_{24}$ is selected from A, S, T, G, H, L and D; and $X_{25}$ is selected from H, E and D. 21. The engineered polypeptide according to embodiment 20, wherein said ABD sequence comprises an amino acid sequence comprising: formula (iii) LA X3 AK X6×7 AN X10 ELD X14 YGVSDF YKRLIDKAKT VEGVEALKDA ILAALP (SEQ ID NO: 678) wherein independently of each other X3 is selected from E, S, Q and C; X6 is selected from E, S and C; X7 is selected from A and S; X10 is selected from A, S and R; X14 is selected from A, S, C and K; the leucine at position 45 is present or absent; and the proline at position 46 is present or absent. 22. The engineered polypeptide according to embodiment 20, wherein said ABD sequence comprises an amino acid sequence comprising formula (iv) an amino acid sequence which has at least 95% identity to the sequence defined in (iii), with the proviso that $X_7$ is not L, E or D; or alternatively, with the proviso that the amino acid sequence is not defined by the following sequence, as defined in PCT Published Application No. WO 2009/016043: LAEAK $X_a X_b$ A $X_c X_d$ EL $X_e$ KY GVSD $X_5$ YK $X_8 X_9$ I $X_{11} X_{12}$ A $X_{14}$ TVEGV $X_{20}$ AL $X_{23} X_{24} X_{25}$ ILAALP (SEQ ID NO: 679) wherein independently of each other, $X_a$ is selected from V and E; $X_b$ is selected from L, E and D; $X_c$ is selected from N, L and I; $X_d$ is selected from R and K; $X_e$ is selected from D and K; and $X_5$ is selected from Y and F; $X_8$ is selected from N, R and S; $X_9$ is selected from V, I, L, M, F and Y; $X_{11}$ is selected from N, S, E and D; $X_{12}$ is selected from R, K and N; $X_{14}$ is selected from K and R; $X_{20}$ is selected from D, N, Q, E, H, S, R and K; $X_{23}$ is selected from K, I and T; $X_{24}$ is selected from A, S, T, G, H, L and D; and $X_{25}$ is selected from H, E and D. 23. The engineered polypeptide according to any one of the preceding embodiments, wherein X6 is S in the ABD. 24. The engineered polypeptide according to any one of the preceding embodiments, wherein X6 is E in the ABD. 25. The engineered polypeptide according to any one of the preceding embodiments, wherein X3 is S in the ABD. 26. The engineered polypeptide according to any one of the preceding embodiments, wherein X3 is E in the ABD. 27. The engineered polypeptide according to any one of the preceding embodiments, wherein X3 is Q in the ABD. 28. The engineered polypeptide according to any one of the preceding embodiments, wherein X7 is A in the ABD. 29. The engineered polypeptide according to any one of the preceding embodiments, wherein X7 is S in the ABD. 30. The engineered polypeptide according to any one of the preceding embodiments, wherein X10 is A in the ABD. 31. The engineered polypeptide according to any one of the preceding embodiments, wherein X10 is S in the ABD. 32. The engineered polypeptide according to any one of the preceding embodiments, wherein X10 is R in the ABD. 33. The engineered polypeptide according to any one of the preceding embodiments, wherein X14 is S in the ABD. 34. The engineered polypeptide according to any one of the preceding embodiments, wherein X14 is C in the ABD. 35. The engineered polypeptide according to any one of the preceding embodiments, wherein X14 is K in the ABD. 36. The engineered polypeptide according to any one of the preceding embodiments, wherein X14 is A in the ABD. 37. The engineered polypeptide according to any one of the preceding embodiments, wherein X26 is D in the ABD. 38. The engineered polypeptide according to any one of the preceding embodiments, wherein X26 is E in the ABD. 39. The engineered polypeptide according to any one of the preceding embodiments, wherein X39 is D in the ABD. 40. The engineered polypeptide according to any one of the preceding embodiments, wherein X39 is E in the ABD. 41. The engineered polypeptide according to any one of the preceding embodiments, wherein X40 is A in the ABD. 42. The engineered polypeptide according to any one of the preceding embodiments, wherein X40 is E in the ABD. 43. The engineered polypeptide according to any one of the preceding embodiments, wherein X43 is A in the ABD. 44. The engineered polypeptide according to any one of the preceding embodiments, wherein X43 is K in the ABD. 45. The engineered polypeptide according to any one of the preceding embodiments, wherein X44 is A in the ABD. 46. The engineered polypeptide according to any one of the preceding embodiments, wherein X44 is S in the ABD. 47. The engineered polypeptide according to any one of the preceding embodiments, wherein X44 is E in the ABD. 48. The engineered polypeptide according to any one of the preceding embodiments, wherein the leucine at position 45 in the ABD is present. 49. The engineered polypeptide according to any one of the preceding embodiments, wherein the leucine at position 45 in the ABD is absent. 50. The engineered polypeptide according to any one of the preceding embodiments, wherein the proline at position 46 in the ABD is present. 51. The engineered polypeptide according to any one of the preceding embodiments, wherein the proline at position 46 in the ABD is absent. 52. The engineered polypeptide according to any one of the preceding embodiments, wherein the ABD binds to albumin such that the $k_{off}$ value of the interaction is at most 5×10-5 s-1. 53. The engineered polypeptide according to any one of the preceding embodiments, wherein the ABD binds to albumin such the $k_{off}$ value of the interaction is at most 5×10-6 s-1. 54. The engineered polypeptide according to any one of the preceding embodiments, wherein the ABD sequence is selected from any one of the ABD sequences disclosed herein, or from Table 1, or from FIG. 1 or SEQ ID NO: 301-444. 55. The engineered polypeptide according to any one of the preceding embodiments, wherein the ABD sequence is selected from an amino acid sequence selected from any one of SEQ ID NO:304-305, SEQ ID NO:307-308, SEQ ID NO:310-311, SEQ ID NO:313-314, SEQ ID NO:316-317, SEQ ID NO:319-320, SEQ ID NO:322-323, SEQ ID NO:325-326, SEQ ID NO:328-329, SEQ ID NO:331-332, SEQ ID NO:334-335, SEQ ID NO:337-338, SEQ ID NO:341-342 and SEQ ID NO:349-350. 56. The engineered polypeptide according to any one of the preceding embodiments, wherein the ABD sequence comprises a sequence selected from an amino acid sequence from any one of the sequences of Table 1 or FIG. 1. 57. The engineered polypeptide according to any one of the preceding embodiments, wherein the ABD sequence further comprises one or more additional amino acid residues positioned at the N- and/or the C-terminal of the sequence defined in formula (i) or (iii). 58. The engineered polypeptide according to the preceding embodiment, wherein the one or more additional amino acid residues comprise a serine residue at the N-terminal of the ABD sequence. 59. The engineered polypeptide according to any one of the preceding embodiments, wherein the one or more additional amino acid residues comprise a glycine residue at the N-terminal of the ABD sequence. 60. The engineered polypeptide according to any one of the preceding embodiments, wherein the one or more additional amino acid residues comprise a glutamic acid residue or cysteine residue at the N-terminal of the ABD sequence. 61. The engineered polypeptide according to any one of the preceding embodiments, wherein the one or more additional amino acid residues comprise an alanine residue at the N-terminal of the ABD sequence. 62. The engineered polypeptide according to any one of the preceding embodiments, wherein the one or more additional amino acid residues comprise a glycine residue at the C-terminal of the ABD sequence. 63. The engineered polypeptide according to any one of the preceding embodiments, wherein the one or more additional amino acid residues comprise a cysteine residue at the C-terminal of the ABD sequence. 64. The engineered polypeptide according to any one of the preceding embodiments, wherein the ABD comprises an amino acid sequence selected from any one of SEQ ID NO:445-450 and SEQ ID NO:462-463. 65. The engineered polypeptide according to any one of the preceding embodiments, wherein the ABD comprises no more than two cysteine residues. 66. The engineered polypeptide according to the preceding embodiment, wherein the ABD sequence comprises no more than one cysteine residue. 67. The engineered polypeptide according any one of the preceding embodiments, wherein the exendin sequence or exendin analog sequence or fragment thereof is conjugated to the ABD via a thiol group of a cysteine residue at position $X_{14}$ of the polypeptide. 68. The engineered polypeptide according to embodiment 18, wherein said ABD is GSLAEAKEAANAELDSYGVSDFYKRLIDKAKTVEG-VEALKDAILAALP (SEQ ID NO: 463) or GSLAEAKEAANAELDSYGVSDFYKRLIDKAKTVEGVEALKDAILAAL (SEQ ID NO: 700). 69. The engineered polypeptide according to embodiment 18, wherein said ABD sequence comprises any one of the peptide sequences selected from the group consisting of: the sequences from Table 1, FIG. 1 or any of the tables herein. 70. The engineered polypeptide according to any one of embodiments 1 to 69, wherein said ABD sequence comprises an ABD analog having at least 95% identity with the ABD of formula i) or iii) or with any one of the ABDs of the Table 1, FIG. 1 or any of the tables herein. 71. The engineered polypeptide according to any one of embodiments 1 to 70, wherein said linker L1 is a peptide of from 1 to 30 amino acids or less than 30 amino acids. 72. The engineered polypeptide according to any one of embodiments 1 to 71, wherein said linker L1 is selected from the 20 naturally occurring amino acids. 73. The engineered polypeptide according to any one of embodiments 1 to 72, wherein said linker L1 comprises a non-natural amino acid incorporated by chemical synthesis, post-translational chemical modification or by in vivo incorporation by recombinant expression in a host cell. 74. The engineered polypeptide according to any one of embodiments 1 to 73, wherein said linker L1 amino acids are selected from glycine, alanine, proline, asparagine, glutamine, and lysine. 75. The engineered polypeptide according to any one of embodiments 1 to 74, wherein said linker L1 amino acid is glycine. 76. The engineered polypeptide according to any one of embodiments 1 to 74, wherein said linker L1 comprises a majority of amino acids that are sterically unhindered. 77. The engineered polypeptide according to any one of embodiments 1 to 76, wherein said linker L1 comprises polyglycine, polyalanine, poly(Gly-Ala) or poly(Gly-Ser). 78. The engineered polypeptide according to any one of embodiments 1 to 77, wherein said linker L1 comprises the sequence $(Gly)_3$, $(Gly)_4$ (SEQ ID NO: 125), or $(Gly)_5$ (SEQ ID NO: 126), $(Gly)_3Lys(Gly)_4$ (SEQ ID NO: 131); $(Gly)_3AsnGlySer(Gly)_2$ (SEQ ID NO: 132); $(Gly)_3Cys(Gly)_4$ (SEQ ID NO: 133); GlyProAsnGlyGly (SEQ ID NO: 134), GG, GGG, GGS, or GGGS (SEQ ID NO: 192). 79. The engineered polypeptide according to any one of embodiments 1 to 74, wherein said linker L1 comprises a combination of Gly and Ala. 80. The engineered polypeptide according to any one of embodiments 1 to 74, wherein said linker L1 comprises a combination of Gly and Ser. 81. The engineered polypeptide according to any one of embodiments 1 to 80, wherein said linker L1 is selected from the group consisting of a glycine rich peptide. 82. The engineered polypeptide according to any one of the embodiments 1 to 81, wherein said linker L1 comprises an N-terminal TG dipeptide. 83. The engineered polypeptide according to any one of embodiments 1 to 82, wherein said linker L1 comprises a C-terminal AS dipeptide. 84. The engineered polypeptide according to any one of embodiments 1 to 83, wherein said linker L1 comprises an N-terminal TG dipeptide and a C-terminal AS dipeptide. 85. The engineered polypeptide according to any one of embodiments 1 to 84, wherein said linker L1 is selected from the group consisting of TG-(GGGS)1 (SEQ ID NO: 848), TG-(GGGS)2 (SEQ ID NO: 849), TG-(GGGS)$_3$ (SEQ ID NO: 850), TG-(GGGS)$_4$ (SEQ ID NO: 851), TG-(GGGS)$_5$ (SEQ ID NO: 852), (GGGS)1-AS (SEQ ID NO: 853), (GGGS)2-AS (SEQ ID NO: 854), (GGGS)3-AS (SEQ ID NO: 855), (GGGS)4-AS (SEQ ID NO: 856), (GGGS)5-AS (SEQ ID NO: 857), TG-(GGGS)1-AS (SEQ ID NO: 195), TG-(GGGS)2-AS (SEQ ID NO: 858), TG-(GGGS)3-AS (SEQ ID NO: 859), TG-(GGGS)4-AS (SEQ ID NO: 860), and TG-(GGGS)5-AS (SEQ ID NO: 861). 86. The engineered polypeptide according to any one of embodiments 1 to 85, wherein said linker L1 TG and/or AS are absent or are replaced by a pair of amino acids selected from T, A, S, and G. 87. The engineered polypeptide according to any one of embodiments 1 to 86, having affinity for serum albumin with a dissociation constant less than about $10^{-6}$ mol/L. 88. The engineered polypeptide according to embodiment 87, having affinity for serum albumin with a dissociation constant less than about $10^{-9}$ mol/L. 89. The engineered polypeptide according to embodiment 88, having affinity for serum albumin with a dissociation constant less than about $10^{-12}$ mol/L. 90. The engineered polypeptide according to any one of embodiments 1 to 89, wherein the polypeptide has a duration of action of at least 1 day. 91. The engineered polypeptide according to embodiment 90, wherein the polypeptide has a duration of action of at least 3 days. 92. The engineered polypeptide according to embodiment 91, wherein the polypeptide has a duration of action of at least 6 days. 93. The engineered polypeptide according to embodiment 92, wherein the polypeptide has a duration of action of at least 6 days in a human subject. 94. The engineered polypeptide according to embodiment 91, wherein the polypeptide has a duration of action of at least 7 days. 95. The engineered polypeptide according to embodiment 92, wherein the polypeptide has a duration of action of at least 7 days in a human subject. 96. The engineered polypeptide according to any one of the preceding embodiments, wherein the engineered polypeptide is selected from the group consisting of any one of the sequences of Table 2 or Table 3 herein. 97. The engineered polypeptide according to any one of the preceding embodiments, wherein the engineered polypeptide is selected from the group consisting of:

```
                                                  (SEQ ID NO: 727)
HGEGTFTSDLSKQLEEEAVRLFIEWLKQGGPSKEIISTGGGGSASGSLAE

AKEAANAELDSYGVSDFYKRLIDKAKTVEGVEALKDAILAALP;

(SEQ ID NO: 728)
HGEGTFTSDLSKQLEEEAVRLFIEWLKNGGPSSGAPPKSTGGGGSASGSL

AEAKEAANAELDSYGVSDFYKRLIDKAKTVEGVEALKDAILAALP;

(SEQ ID NO: 729)
HGEGTFTSDLSKQLEEEAVRLFIEWLKNGGPSSGAPPPSTGGGGSASGSL

AEAKEAANAELDSYGVSDFYKRLIDKAKTVEGVEALKDAILAAL;

(SEQ ID NO: 730)
HGEGTFTSDLSKQMEEEAVRLFIEWLKNGGPSSGAPPPSTGGGGSASGSL

AEAKEAANAELDSYGVSDFYKRLIDKAKTVEGVEALKDAILAALP;
```

(SEQ ID NO: 731)
HGEGTFTSDLSKQMEEEAVRLFIEWLKNGGPSSGAPPPSGGSLAEAKEAA
NAELDSYGVSDFYKRLIDKAKTVEGVEALKDAILAALP;

(SEQ ID NO: 732)
HGEGTFTSDLSKQLEEEAVRLFIEWLKNGGPSSGAPPPSTGGGGSASGSL
AEAKEAANAELDSYGVSDFYKRLIDKAKTVEGVEALKDAILAALP;

(SEQ ID NO: 733)
HGEGTFTSDLSKQLEEEAVRLFIEWLKNGGPSSGAPPPSGGSLAEAKEAA
NAELDSYGVSDFYKRLIDKAKTVEGVEALKDAILAALP;

(SEQ ID NO: 734)
HGEGTFTSDLSKQLEEEAVRLFIEWLKQGGPSKEIISTGGGGSASGSLAE
AKEAANAELDSYGVSDFYKRLIDKAKTVEGVEALKDAILAAL;

(SEQ ID NO: 735)
HGEGTFTSDLSKQLEEEAVRLFIEWLKNGGPSSGAPPKSTGGGGSASGSL
AEAKEAANAELDSYGVSDFYKRLIDKAKTVEGVEALKDAILAAL;

(SEQ ID NO: 736)
HGEGTFTSDLSKQLEEEAVRLFIEWLKNGGPSSGAPPPSTGGGGSASGSL
AEAKEAANAELDSYGVSDFYKRLIDKAKTVEGVEALKDAILAA;

(SEQ ID NO: 737)
HGEGTFTSDLSKQMEEEAVRLFIEWLKNGGPSSGAPPPSTGGGGSASGSL
AEAKEAANAELDSYGVSDFYKRLIDKAKTVEGVEALKDAILAAL;

(SEQ ID NO: 738)
HGEGTFTSDLSKQMEEEAVRLFIEWLKNGGPSSGAPPPSGGSLAEAKEAA
NAELDSYGVSDFYKRLIDKAKTVEGVEALKDAILAAL;

(SEQ ID NO: 739)
HGEGTFTSDLSKQLEEEAVRLFIEWLKNGGPSSGAPPPSGGSLAEAKEAA
NAELDSYGVSDFYKRLIDKAKTVEGVEALKDAILAAL;

(SEQ ID NO: 740)
HGEGTFTSDLSKQLEEEAVRLFIEWLKQGGPSKEIISTGGGGSASGSLAE
AKEAANAELDSYGVSDFYKRLIDKAKTVEGVEALKDAILAA;

(SEQ ID NO: 741)
HGEGTFTSDLSKQLEEEAVRLFIEWLKNGGPSSGAPPKSTGGGGSASGSL
AEAKEAANAELDSYGVSDFYKRLIDKAKTVEGVEALKDAILAA;

(SEQ ID NO: 742)
HGEGTFTSDLSKQMEEEAVRLFIEWLKNGGPSSGAPPPSTGGGGSASGSL
AEAKEAANAELDSYGVSDFYKRLIDKAKTVEGVEALKDAILAA;

(SEQ ID NO: 743)
HGEGTFTSDLSKQMEEEAVRLFIEWLKNGGPSSGAPPPSGGSLAEAKEAA
NAELDSYGVSDFYKRLIDKAKTVEGVEALKDAILAA;

(SEQ ID NO: 744)
HGEGTFTSDLSKQLEEEAVRLFIEWLKNGGPSSGAPPPSTGGGGSASGSL
AEAKEAANAELDSYGVSDFYKRLIDKAKTVEGVEALKDAILAA;
and (SEQ ID NO: 745)
HGEGTFTSDLSKQLEEEAVRLFIEWLKNGGPSSGAPPPSGGSLAEAKEAA
NAELDSYGVSDFYKRLIDKAKTVEGVEALKDAILAA.

98. The engineered polypeptide according to any one of the preceding embodiments, wherein the engineered polypeptide is selected from the group consisting of:

(SEQ ID NO: 727)
HGEGTFTSDLSKQLEEEAVRLFIEWLKQGGPSKEIISTGGGGSASGSLAE
AKEAANAELDSYGVSDFYKRLIDKAKTVEGVEALKDAILAALP;

(SEQ ID NO: 728)
HGEGTFTSDLSKQLEEEAVRLFIEWLKNGGPSSGAPPKSTGGGGSASGSL
AEAKEAANAELDSYGVSDFYKRLIDKAKTVEGVEALKDAILAALP;

(SEQ ID NO: 729)
HGEGTFTSDLSKQLEEEAVRLFIEWLKNGGPSSGAPPPSTGGGGSASGSL
AEAKEAANAELDSYGVSDFYKRLIDKAKTVEGVEALKDAILAAL;

(SEQ ID NO: 730)
HGEGTFTSDLSKQMEEEAVRLFIEWLKNGGPSSGAPPPSTGGGGSASGSL
AEAKEAANAELDSYGVSDFYKRLIDKAKTVEGVEALKDAILAALP;

(SEQ ID NO: 731)
HGEGTFTSDLSKQMEEEAVRLFIEWLKNGGPSSGAPPPSGGSLAEAKEAA
NAELDSYGVSDFYKRLIDKAKTVEGVEALKDAILAALP;

(SEQ ID NO: 732)
HGEGTFTSDLSKQLEEEAVRLFIEWLKNGGPSSGAPPPSTGGGGSASGSL
AEAKEAANAELDSYGVSDFYKRLIDKAKTVEGVEALKDAILAALP;

(SEQ ID NO: 733)
HGEGTFTSDLSKQLEEEAVRLFIEWLKNGGPSSGAPPPSGGSLAEAKEAA
NAELDSYGVSDFYKRLIDKAKTVEGVEALKDAILAALP;

(SEQ ID NO: 734)
HGEGTFTSDLSKQLEEEAVRLFIEWLKQGGPSKEIISTGGGGSASGSLAE
AKEAANAELDSYGVSDFYKRLIDKAKTVEGVEALKDAILAAL;

(SEQ ID NO: 735)
HGEGTFTSDLSKQLEEEAVRLFIEWLKNGGPSSGAPPKSTGGGGSASGSL
AEAKEAANAELDSYGVSDFYKRLIDKAKTVEGVEALKDAILAAL;

(SEQ ID NO: 737)
HGEGTFTSDLSKQMEEEAVRLFIEWLKNGGPSSGAPPPSTGGGGSASGSL
AEAKEAANAELDSYGVSDFYKRLIDKAKTVEGVEALKDAILAAL;

(SEQ ID NO: 738)
HGEGTFTSDLSKQMEEEAVRLFIEWLKNGGPSSGAPPPSGGSLAEAKEAA
NAELDSYGVSDFYKRLIDKAKTVEGVEALKDAILAAL;
and (SEQ ID NO: 739)
HGEGTFTSDLSKQLEEEAVRLFIEWLKNGGPSSGAPPPSGGSLAEAKEAA
NAELDSYGVSDFYKRLIDKAKTVEGVEALKDAILAAL.

99. The engineered polypeptide according to any one of the previous embodiments wherein the engineered polypeptide comprises Cmpd 5, Cmpd 9 or Cmpd 11. 100. The engineered polypeptide according to any one of the previous embodiments wherein the engineered polypeptide has at least 95% sequence identity with said engineered polypeptide. 101. The engineered polypeptide according to any one of the previous embodiments wherein the engineered polypeptide has at least 98% sequence identity with said engineered polypeptide. 102. The engineered polypeptide according to any one of the previous embodiments, which elicits no or a reduced immune response upon administration to the mammal, as compared to the immune response elicited upon administration to the mammal of the exendin that is not attached to the ABD or that is attached to an ABD described in PCT Published Appl. No. WO 2009/016043 that has not been modified for reduced immunogenicity as described herein. 103. The engineered polypeptide according to any one of the previous embodiments, for use as a medicament. 104. The engineered polypeptide according to any one of the previous embodiments, wherein said engineered polypeptide has a plasma half-life suitable for a twice daily administration. 105. The engineered polypeptide according to any one of the previous embodiments, wherein said engineered polypeptide has a plasma half-life suitable for once daily administration. 106. The engineered polypeptide according to any one of the previous embodiments, wherein said engineered polypeptide has a plasma half-life suitable for a twice weekly administration. 107. The engineered polypeptide according to any one of the previous embodiments, wherein said engineered polypeptide has a plasma half-life suitable suitable for a once weekly administration. 108. The engineered polypeptide according to any one of the previous embodiments, wherein said engineered polypeptide has a plasma half-life of at least 40 hours. 109. The engineered polypeptide according to any one of the previous embodiments, wherein said engineered polypeptide has a plasma half-life of at least 60 hours. 110. The engineered polypeptide according to any one of the previous embodiments, wherein said engineered polypeptide has a plasma half-life of at least 72 hours. 111. A composition comprising an engineered polypeptide according to any one of the previous embodiments and a pharmaceutically acceptable excipient. 112. The composition according to embodiment 111, that is aqueous. 113. The composition according to embodiment 111, that is solid. 114. The composition according to any one of the preceding embodiments, for use as a medicament. 115. The composition according to any one of the preceding embodiments wherein the engineered polypeptide is a lyophilized solid. 116. The composition according to any one of the preceding embodiments, further comprising human serum albumin. 117. A pharmaceutical composition comprising an engineered polypeptide according to any one of the previous embodiments. 118. The pharmaceutical composition of embodiment 117, comprising the engineered polypeptide and a pharmaceutically acceptable excipient. 119. The pharmaceutical composition according to any one of the preceding embodiments, that is aqueous. 120. The pharmaceutical composition according to any one of the preceding embodiments, that is solid. 121. The pharmaceutical composition according to any one of the preceding embodiments, for use as a medicament. 122. The pharmaceutical composition according to any one of the preceding embodiments wherein the engineered polypeptide is a lyophilized solid. 123. The pharmaceutical composition according to any one of the preceding embodiments, further comprising human serum albumin. 124. The pharmaceutical composition according to any one of the previous embodiments, wherein said pharmaceutical composition is a pharmaceutical composition for intramuscular, intravenous, subcutaneous, intradermal, intraarticular, intrathecal, mucosal, oral, nasal, sublingual, pulmonary or buccal delivery. 125. The pharmaceutical composition according to any one of the previous embodiments, wherein said pharmaceutical composition is a pharmaceutical composition for subcutaneous delivery. 126. The pharmaceutical composition according to any one of the previous embodiments, wherein said pharmaceutical composition is a pharmaceutical composition for delivery by injection. 127. The pharmaceutical composition according to any one of the previous embodiments, wherein said pharmaceutical composition is a pharmaceutical composition for oral delivery. 128. The pharmaceutical composition according to embodiment 127, wherein said pharmaceutical composition is a pharmaceutical composition for oral delivery and comprises a solid form. 129. The pharmaceutical composition according to embodiment 128, wherein said pharmaceutical composition is a pharmaceutical composition for oral delivery and comprises a tablet, granules, microparticles or a capsule. 130. The pharmaceutical composition according to any one of the previous embodiments, wherein said pharmaceutical composition is a sustained release or long lasting pharmaceutical composition. 131. The pharmaceutical composition according to any one of the previous embodiments, wherein said pharmaceutical composition is a twice daily administered pharmaceutical composition. 132. The pharmaceutical composition according to any one of the previous embodiments, wherein said pharmaceutical composition is a once daily administered pharmaceutical composition. 133. The pharmaceutical composition according to any one of the previous embodiments, wherein said pharmaceutical composition is a twice weekly administered pharmaceutical composition. 134. The pharmaceutical composition according to any one of the previous embodiments, wherein said pharmaceutical composition is a once weekly pharmaceutical composition. 135. A pharmaceutical composition according to any one of the previous embodiments, for treating a disease or disorder in a subject in need of such treatment. 136. The pharmaceutical composition of embodiment 135 wherein the disease or disorder is diabetes, overweight, obesity, Alzheimer's disease, Parkinson's disease, fatty liver disease, dyslipidemia, coronary artery disease, stroke, short bowel syndrome (SBS), hyperlipidemia, nonalcoholic steatohepatitis (NASH), nonalcoholic fatty liver disease (NAFLD), hypoglycemia unawareness (HU), restrictive lung disease including sarcoidosis, or metabolic syndrome X. 137. The pharmaceutical composition of embodiment 136 wherein said disease or disorder is diabetes, overweight, obesity, SBS or Parkinson's disease. 138. The pharmaceutical composition of embodiment 137 wherein said diabetes is type I diabetes, type II diabetes, prediabetes, gestational diabetes, HIV-treatment-induced diabetes, steroid-induced diabetes, or latent autoimmune diabetes in adults (LADA). 139. The engineered polypeptide or pharmaceutical composition of any one of embodiments 1 to 138 wherein the engineered polypeptide provides for once weekly administration. 140. A method for treating a disease or disorder in a subject, comprising administering an engineered polypeptide according to any one of the previous embodiments to a subject in need thereof in an amount effective to treat said disease or disorder. 141. The method according to embodiment 140, wherein said disease or disorder is diabetes, overweight, obesity, Alzheimer's disease, Parkinson's disease, fatty liver disease, dyslipidemia, coronary artery disease, stroke, short bowel syndrome (SBS), hyperlipidemia, nonalcoholic steatohepatitis (NASH), nonalcoholic fatty liver disease (NAFLD), hypoglycemia unawareness (HU), restrictive lung disease including sarcoidosis, or metabolic syndrome X. 142. The method according to embodiment 140, wherein said disease or disorder is diabetes, overweight, obesity, Alzheimer's disease, fatty liver disease, dyslipidemia, coronary artery disease, stroke, SBS, hyperlipidemia or Parkinson's disease. 143. The method according to embodiment 142, wherein said disease or disorder is diabetes, overweight, obesity, SBS or Parkinson's disease. 144. The method according to embodiment 143, wherein said disease or disorder is type I diabetes, type II diabetes or prediabetes. 145. The method according to embodiment 142, wherein said disease or disorder is type II diabetes. 146. The method according to embodiment 142, wherein said disease or disorder is dyslipidemia or hyperlipidemia. 147. A polynucleotide encoding an engineered polypeptide according to any one of the preceding embodiments. 148. An expression vector comprising a polynucleotide according to embodiment 147. 149.

A host cell comprising an expression vector according to claim 148. 150. A method of producing the engineered polypeptide of any one of the preceding embodiments, comprising expressing a polynucleotide encoding the engineered polypeptide. 151. A method of producing the engineered polypeptide according to any one the preceding embodiments by non-biological peptide synthesis using amino acids and/or amino acid derivatives having reactive side-chains protected, the non-biological peptide synthesis comprising: step-wise coupling of the amino acids and/or the amino acid derivatives to form a polypeptide according to any one of the preceding embodiments having reactive side-chains protected, removing the protecting groups from the reactive side-chains of the polypeptide, and folding of the resulting polypeptide in aqueous solution. 152. A method of producing the engineered polypeptide according to any one of the preceding embodiments, comprising: producing an exendin, producing an ABD, and conjugating the produced ABD with the produced exendin.

VII. Examples

Examples 1-5 are provided to illustrate, amongst other things, the superior properties of the ABDs described herein, e.g. reduced immunogenicity properties, compared to previous ABDs.

Example 1

Cloning, Expression, Purification and Characterization of Albumin Binding Polypeptides In this example, eight different albumin binding polypeptides, PEP07913 (SEQ ID NO:453), PEP07912 (SEQ ID NO:457), PEP07914 (SEQ ID NO:458), PEP07968 (i.e. DOTA conjugated to PEP07911, SEQ ID NO:459), PEP06923 (SEQ ID NO:454), PEP07271 (SEQ ID NO:455), PEP07554 (SEQ ID NO:456) and PEP07844 (SEQ ID NO:461), the amino acid sequences of which are set out in FIG. 1, were cloned, purified and characterized.
Material and Methods.
Cloning of Albumin Binding Polypeptide Variants.

Mutations in G148-GA3 were generated using site directed mutagenesis with the appropriate oligonucleotides to obtain the desired albumin binding polypeptide variants. The gene fragments were amplified by PCR with primers adding specific endonuclease sites as well as an N-terminal MGSS sequence (SEQ ID NO: 844) preceding the albumin binding polypeptide variants. The fragments were cleaved with NdeI and NotI, purified and ligated to a cloning vector, the plasmid pAY02556 (containing an origin of replication from pBR322, a kanamycin resistance gene and a T7 promoter for expression of the gene of interest), restricted with the same enzymes. Ligations were transformed to electrocompetent *E. coli* TOP10 cells. The transformed cells were spread on TBAB plates (30 g/l tryptose blood agar base) supplemented with 50 μg/ml of kanamycin, followed by incubation at 37° C. overnight. The colonies were screened using PCR and sequencing of amplified fragments was performed using the biotinylated oligonucleotide and a BigDye® Terminator v3.1 Cycle Sequencing Kit (Applied Biosystems), used in accordance with the manufacturer's protocol. The sequencing reactions were purified by binding to magnetic streptavidin coated beads using a Magnatrix 8000 (NorDiag AB), and analyzed on ABI PRISM® 3100 Genetic Analyzer (PE Applied Biosystems). All albumin binding polypeptide variants were subcloned as monomers and the constructs encoded by the expression vectors were MGSS-[PP###] ("MGSS" disclosed as SEQ ID NO: 844), where PP### corresponds to the 46 amino acid residues constituting the sequence of the albumin binding polypeptide.

In addition, the gene fragments of G148-GA3, PP007 (SEQ ID NO:307), PP013 (SEQ ID NO:313) and PP037 (SEQ ID NO:337) were amplified by PCR with primers adding specific endonuclease sites as well as a hexahistidin sequence (SEQ ID NO: 49), a TEV protease site and a glycine residue before the 46 amino acid residues constituting the sequence of the albumin binding polypeptide. The polypeptides PEP07913 (SEQ ID NO:453), PEP07912 (SEQ ID NO:457), PEP07914 (SEQ ID NO:458) and PEP07968 (SEQ ID NO:459) correspond to the albumin binding polypeptides G148-GA3, PP007 (SEQ ID NO:307), PP013 (SEQ ID NO:313) and PP037 (SEQ ID NO:337) with glycine residues added. The fragments were cleaved with XbaI and NotI, purified and ligated to a cloning vector, the plasmid pAY02512 (containing an origin of replication from pBR322, a kanamycin resistance gene and a T7 promoter for expression of the gene of interest. The cloning site is preceded by a sequence encoding a peptide containing a hexahistidine tag (SEQ ID NO: 49) followed by a cleavage site for the TEV protease), restricted with the same enzymes. Ligation, transformation and sequence verification were performed as described above. The four albumin binding polypeptide variants G148-GA3, PP007, PP013 and PP037 were subcloned as monomers and the constructs encoded by the expression vectors were MGSSHHHHHHLQSSGVDLGTENLYFQG-[PP###], where MGSSHHHHHHLQSSGVDLGTENLYFQG is SEQ ID NO:600, and "PP###" represents a ABD sequence described herein.
Protein Expression.

The albumin binding polypeptide variants were expressed in *E. coli* BL21 (DE3) either with an N-terminal MGSS-extension ("MGSS" disclosed as SEQ ID NO: 844) or with an N-terminal His6-tag (SEQ ID NO: 49) followed by a TEV-protease recognition site and a glycine residue. A colony of each albumin binding polypeptide variant was used to inoculate 4 ml TSB+YE medium supplemented with kanamycin to a concentration of 50 μg/ml. The cultures were grown at 37° C. for approximately 5 hours. 3 ml from each of the cultures was used to inoculate 800 ml TSB+YE supplemented with kanamycin to a concentration of 50 μg/ml in parallel bio reactors (Greta system, Belach Bioteknik AB). The cultivations were performed at 37° C., with aeration at 800 ml/minute and an agitation profile to keep dissolved oxygen levels above 30%, to an OD600 of 2, which was followed by addition of IPTG to a final concentration of 0.5 mM. Cultivation was continued for five hours after which the cultivation was cooled to 10° C., aeration was stopped and agitation lowered to 300 rpm. Cell pellets were harvested by centrifugation (15600×g, 4° C., 20 minutes) and stored at −20° C. until purification.
Purification of Albumin Binding Polypeptide Variants with a His6-Tag (SEQ ID NO: 49) and a TEV-protease Site.

Frozen cell pellets harboring soluble hexahistidine-tagged polypeptides ("hexahistidine" disclosed as SEQ ID NO: 49) PEP07913 (SEQ ID NO:453), PEP07912 (SEQ ID NO:457), PEP07914 (SEQ ID NO:458) and PEP07968 (SEQ ID NO:459) were suspended in 35 ml binding buffer (20 mM sodium phosphate, 0.5 M NaCl, 20 mM imidazole, pH 7.4) with an addition of 1000 U Benzonase® (1.01654.001, Merck) and disrupted by ultrasonication. For each of the polypeptides, the ultrasonicated suspension was clarified by centrifugation (1 h, 37000×g, 4° C.) and the supernatant was loaded onto a His GraviTrap™ column (11-0033-99, GE Healthcare). The column was washed with 10 ml washing buffer (20 mM sodium phosphate, 0.5 M NaCl, 60 mM imidazole, pH 7.4), before eluting the polypeptide with 3 ml elution buffer (20 mM sodium phosphate, 0.5 M NaCl, 0.5 M imidazole, pH 7.4). The buffer was exchanged to a cleavage buffer (50 mM Tris-HCl, 150 mM NaCl, pH 8) using PD-10 desalting column (17-0851-01, GE Healthcare). The amount of polypeptide product was determined by measuring the absorbance at 280 nm before adding DTT to a final concentration of 5 mM. His6-tagged TEV protease ("His6" disclosed as SEQ ID NO: 49) was added to the cleavage buffer at a 1:10 mass ratio relative to the polypeptide product. The cleavage was performed over night under slow mixing at 4° C. Imidazole was added to the cleavage mix, to a concentration of 20 mM, before loading the mix onto a His GraviTrap™ column (11-0033-99, GE Healthcare) for removing cleaved His6-tags (SEQ ID NO: 49), His6-tagged TEV protease ("His6" disclosed as SEQ ID NO: 49) and His6-tagged uncleaved product ("His6" disclosed as SEQ ID NO: 49).

For each variant, the flow-through, containing the albumin binding polypeptide variant, was further purified by reversed phase chromatography (RPC), as follows. The flow-through fraction was loaded on 1 ml Resource 15 RPC column (GE Healthcare), previously equilibrated with RPC A Buffer (0.1% TFA in water). After column wash with 10 column volumes (CV) RPC A Buffer, bound polypeptides were eluted with a linear gradient of 0-50% RPC B Buffer (0.1% TFA in acetonitrile) during 10 CV. The flow rate was 2 ml/min and the absorbance at 280 nm was monitored. Fractions containing albumin binding polypeptide variant were identified by SDS-PAGE analysis and pooled.

The RPC-purified albumin binding polypeptide variants were further purified by gel filtration on 120 ml Superdex 75 (GE Healthcare) packed in an XK16 column (GE Healthcare). The running buffer was 1×PBS, and the flow rate 2 ml/min. Fractions containing pure albumin binding polypeptide variant were pooled and concentrated to approximately 1.3 mg/ml. Finally, the concentrate was purified from trace amounts of remaining endotoxins by using 1 ml columns of AffinityPak Detoxi-Gel Endotoxin removing gel (Pierce, prod#20344), according to the manufacture's recommendations.

The albumin binding polypeptide variant PEP07911 was conjugated with Mal-DOTA before the RPC-purification step, as follows. The buffer of the flow-through fraction from the IMAC-FT purification step was exchanged to 0.2 M NaAc, pH 5.5, using a disposable PD-10 desalting column (GE Healthcare). Maleimido-mono-amide-DOTA (Macrocyclics, cat. no. B-272) was added at 5-fold molar excess and incubated for 60 minutes at 30° C. under continuous shaking. The resulting polypeptide was denoted PEP07968.

Purification of Albumin Binding Polypeptide-Variants without His6-Tag (SEQ ID NO: 49).

Frozen cell pellets harboring soluble albumin binding polypeptide variants PEP06923 (SEQ ID NO:454), PEP07271 (SEQ ID NO:455), PEP07554 (SEQ ID NO:456) and PEP07844 (SEQ ID NO:461) were suspended in 20 mM Tris-HCl, pH 8 and disrupted by ultrasonication. For each of the polypeptide variants, the ultrasonicated suspension was clarified by centrifugation (30 min, 32000×g, 4° C.) and the supernatant was loaded onto a HSA-Sepharose column (GE Healthcare). After washing with TST-buffer (25 mM Tris-HCl, 1 mM EDTA, 200 mM NaCl, 0.05% Tween 20, pH 8.0), followed by 5 mM NH4Ac, pH 5.5, bound albumin binding polypeptide variant was eluted with 0.5 M HAc, pH 3.2.

The albumin binding polypeptide variants were further purified by reversed phase chromatography (RPC), as follows. For each of the variants, the eluate from the HSA-affinity purification step was loaded on 1 ml Resource 15 RPC column (GE Healthcare), previously equilibrated with RPC A Buffer (0.1% TFA in water). After column wash with 10 CV RPC A Buffer, bound polypeptides were eluted with a linear gradient of 0-50% RPC B Buffer (0.1% TFA in acetonitrile) during 10 CV. The flow rate was 2 ml/min and the absorbance at 280 nm was monitored. Fractions containing pure albumin binding polypeptide variants were identified by SDS-PAGE analysis and pooled. Finally, the buffer was exchanged to 1×PBS (2.68 mM KCl, 137 mM NaCl, 1.47 mM KH2PO4, 8.1 mM Na2HPO4, pH 7.4) using a disposable PD-10 desalting column (GE Healthcare).

Characterization of Purified Albumin Binding Polypeptide-Variants.

The concentration was assessed by measuring the absorbance at 280 nm using a NanoDrop® ND-1000 Spectrophotometer. The proteins were further analyzed with SDS-PAGE and LC-MS.

For the SDS-PAGE analysis, approximately 10 μg of each albumin binding polypeptide variant was mixed with NuPAGE LDS Sample Buffer (Invitrogen), incubated at 70° C. for 15 min and loaded onto NuPAGE 4-12% Bis-Tris Gels (Invitrogen). The gels were run with NuPAGE MES SDS Running Buffer (Invitrogen) in an XCell II SureLock Electrophoresis Cell (Novex) employing the Sharp Prestained Standard (Invitrogen) as molecular weight marker and using PhastGel BlueR (GE Healthcare) for staining.

To verify the identity of the albumin binding polypeptide variants, LC/MS analyses were performed using an Agilent 1100 LC/MSD system, equipped with API-ESI and a single quadruple mass analyzer. Approximately 10 μg of each of the purified albumin binding polypeptide variants was loaded on a Zorbax 300SB-C8 Narrow-Bore column (2.1×150 mm, 3.5 μm, Agilent Technologies) at a flow-rate of 0.5 ml/min. Polypeptides were eluted using a linear gradient of 10-70% solution B for 15 min at 0.5 ml/min. The separation was performed at 30° C. The ion signal and the absorbance at 280 and 220 nm were monitored. The molecular weights of the purified albumin binding polypeptide variants were confirmed by MS.

Results.

The expression levels of the albumin binding polypeptide variants were 10-30 mg product/g cell pellet, as estimated from SDS-PAGE analysis.

For all variants, the purity, as determined by SDS-PAGE analysis, exceeded 95% and the LC/MS analysis verified the correct molecular weights. After purification, between 1 and 8 mg of pure polypeptide was obtained for each of the eight albumin binding polypeptide variants.

Example 2

Affinity Determination for Albumin Binding Polypeptides

In this example, PEP06923 (SEQ ID NO:454), PEP07271 (SEQ ID NO:455), PEP07844 (SEQ ID NO:461), PEP07912 (SEQ ID NO:457), PEP07913 (SEQ ID NO:453), PEP07914 (SEQ ID NO:458) and PEP07968, (i.e. DOTA-conjugated to PEP07911, SEQ ID NO:459), synthesized or expressed and purified in Example 1 were characterized for affinity to human serum albumin (HSA) using a Biacore instrument. PEP07913 corresponds to the amino acid sequence of G148-GA3 with addition of a N-terminal glycine residue, whereas PEP07271, PEP07844, PEP07912, PEP07914 and PEP07968 correspond to the albumin binding polypeptides of PP001 (SEQ ID NO:301), PP043 (SEQ ID NO:343), PP007 (SEQ ID NO:307), PP013 (SEQ ID NO:313) and PP037 (SEQ ID NO:337) with different N-terminal amino acid additions.

Material and Methods.

Biosensor analysis on a Biacore2000 instrument (GE Healthcare) was performed with HSA (Albucult®, Novozyme), immobilized by amine coupling onto the carboxylated dextran layer of the surfaces of CM-5 chips (research grade; Biacore) according to the manufacturer's recommendations. Surface 1 of the chip was activated and deactivated and used as a reference cell (blank surface) during injections, whereas surface 2 comprised HSA immobilized to 731 resonance units (RU) and surface 4 comprised HSA immobilized to 955 RU. The purified albumin binding polypeptide variants were diluted in running buffer HBS-EP (GE Healthcare) to 2.5 nM, 10 nM and 40 nM, and injected at a constant flow-rate of 50 μl/min for 5 minutes, followed by injection of HBS-EP for 60 minutes. The surfaces were regenerated with one injection of 25 μl HCl, 10 mM. The affinity measurements were performed in two sets; in the first set HBS-EP, PEP06923, PEP07271, PEP07912, PEP07913, PEP07914 and PEP07968 were injected (chip surface 2), and in the second set HBS-EP, PEP06923, PEP07844, PEP07912 and PEP07914 were injected (chip surface 4). PEP06923 was injected twice in each run as a control. The results were analyzed with a BiaEvaluation software (GE Healthcare). Curves of the blank surface were subtracted from the curves of the ligand surfaces.

Results.

Figure 2:
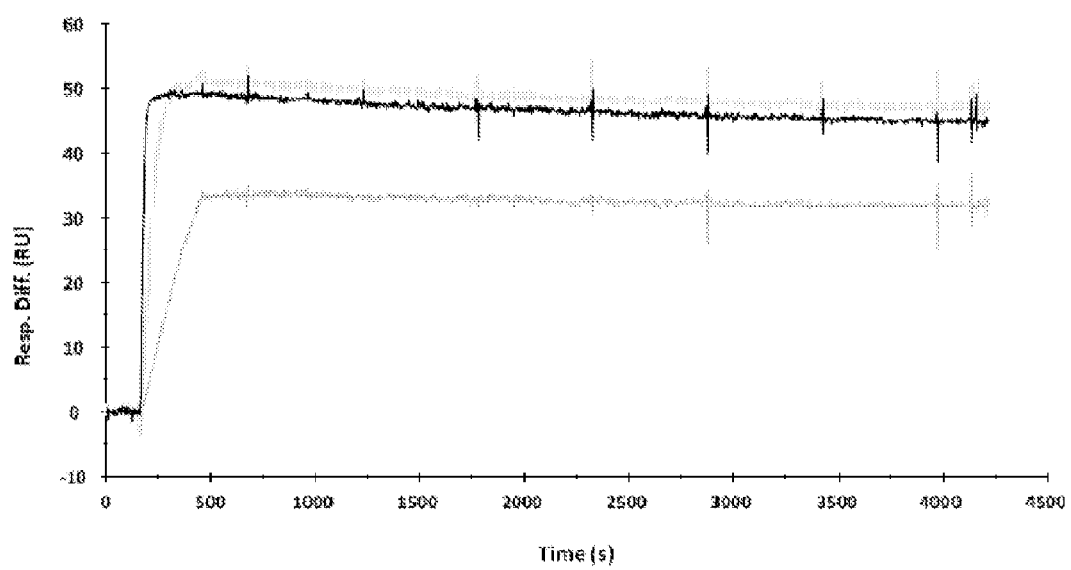
FIG. 2 shows the result of binding analysis performed in a Biacore instrument for investigating the binding of the albumin binding polypeptide PEP07912 (SEQ ID NO: 457) to human serum albumin. Three different concentrations of purified protein (40 nM, fat gray line; 10 nM, black line; and 2.5 nM, gray line) were injected over a surface with 955 RU of immobilized human serum albumin.

The Biacore 2000 instrument has a technical limitation, hindering measurements of very high affinity. Hence, the purpose of the Biacore study was not to determine the exact kinetic parameters of the albumin binding polypeptide variants' affinity for HSA. However, the results provide a quantitative estimation of the relative affinities of these polypeptides for albumin. After subtraction of reference surface and buffer injection, curves were fitted to a 1:1 (Langmuir) binding model using BIAevaluation software with correction for mass transfer and with RUmax set as a local parameter. Curves are shown in FIG. 2. The relative $K_D$, $k_a$ ($k_{on}$) and $k_d$ ($k_{off}$) values were estimated and are presented in the Tables below.

TABLE 5

Kinetic parameters ($k_a$, $k_d$ and $K_D$) of albumin binding polypeptides to HSA, 1st set

| | $k_a$ (Ms$^{-1}$) | $k_d$ (s$^{-1}$) | $K_D$ (M) |
|---|---|---|---|
| PEP07913 | $5.7 \times 10^5$ | $9.3 \times 10^{-4}$ | $1.6 \times 10^{-9}$ |
| PEP06923 (1) | $2.9 \times 10^7$ | $2.9 \times 10^{-5}$ | $9.9 \times 10^{-13}$ |
| PEP06923 (2) | $2.6 \times 10^7$ | $2.8 \times 10^{-5}$ | $1.1 \times 10^{-12}$ |
| PEP07271 | $3.9 \times 10^6$ | $2.9 \times 10^{-5}$ | $7.5 \times 10^{-12}$ |
| PEP07912 | $4.6 \times 10^6$ | $2.8 \times 10^{-5}$ | $6.2 \times 10^{-12}$ |
| PEP07914 | $3.5 \times 10^6$ | $2.5 \times 10^{-5}$ | $7.2 \times 10^{-12}$ |
| PEP07968 | $3.0 \times 10^6$ | $2.7 \times 10^{-5}$ | $9.0 \times 10^{-12}$ |

TABLE 6

Kinetic parameters ($k_a$, $k_d$ and $K_D$) of albumin binding polypeptides to HSA, 2nd set

| | $k_a$ (Ms$^{-1}$) | $k_d$ (s$^{-1}$) | $K_D$ (M) |
|---|---|---|---|
| PEP06923 (1) | $2.0 \times 10^7$ | $2.6 \times 10^{-5}$ | $1.3 \times 10^{-12}$ |
| PEP06923 (2) | $2.1 \times 10^7$ | $2.5 \times 10^{-5}$ | $1.2 \times 10^{-12}$ |
| PEP07912 | $5.4 \times 10^6$ | $2.8 \times 10^{-5}$ | $5.2 \times 10^{-12}$ |
| PEP07914 | $3.8 \times 10^6$ | $2.6 \times 10^{-5}$ | $6.9 \times 10^{-12}$ |
| PEP07844 | $5.4 \times 10^6$ | $2.3 \times 10^{-5}$ | $4.4 \times 10^{-12}$ |

As shown in Table 5 and 6, PEP07271 (SEQ ID NO:455), PEP07844 (SEQ ID NO:461), PEP07912 (SEQ ID NO:457), PEP07914 (SEQ ID NO:458) and PEP07968 (PEP07911 conjugated with DOTA, SEQ ID NO:459) all seem to have approximately the same affinity for HSA, widely exceeding the affinity of the parent G148-GA3 (PEP07913; SEQ ID NO:453). The HSA affinity of these polypeptides is slightly lower compared to PEP06923 (SEQ ID NO:454), despite similar off-rate.

Example 3

Determination of Melting Temperature (Tm) for Albumin Binding Polypeptides

In this example, the albumin binding polypeptide variants PEP07913 (SEQ ID NO:453), PEP06923 (SEQ ID NO:454), PEP07271 (SEQ ID NO:455), PEP07554 (SEQ ID NO:456), PEP07912 (SEQ ID NO:457), PEP07914 (SEQ ID NO:458), PEP07968 (PEP07911 conjugated with DOTA, SEQ ID NO:459) and PEP07844 (SEQ ID NO:461), expressed and purified as described in Example 1, and the albumin polypeptide variant PEP07975 (i.e. DOTA-conjugated PEP07834, SEQ ID NO:460, via Cys14 with maleimido-mono-amide-DOTA (Macrocyclics, Cat. No. B-272), were analyzed by CD analysis. PEP07913 corresponds to the sequence of G148-GA3 having an N-terminal glycine residue, PEP06923 is an engineered high affinity derivative previously described by Jonsson et al, supra, whereas PEP07271, PEP07554, PEP07912, PEP07914, PEP07968, PEP07844 and PEP07975 are examples of the 46 amino acid residues albumin binding polypeptides of PP001 (SEQ ID NO:301), PP007 (SEQ ID NO:307), PP013 (SEQ ID NO:313), PP037 (SEQ ID NO:337) and PP043 (SEQ ID NO:343) having different N-terminal amino acid additions according to the present disclosure.

Material and Methods.

Purified albumin binding polypeptide variants were diluted in 1×PBS, to final concentrations between 0.4 and 0.5 mg/ml. Circular dichroism (CD) analysis was performed on a Jasco J-810 spectropolarimeter in a cell with an optical path-length of 1 mm. In the variable temperature measurements, the absorbance was measured at 221 nm from 20° to 90° C., with a temperature slope of 5° C./min.

Results.

The melting temperatures (Tm) of the different albumin binding polypeptide variants were calculated by determining the midpoint of the transition in the CD vs. temperature plot. The results are summarized in Table 7 below.

TABLE 7

Determined Tm values of tested albumin binding polypeptide variants

| Variant | SEQ ID NO: # | N-terminal sequence[3] | Tm (° C.) |
|---|---|---|---|
| PEP07913 | SEQ ID NO: 453 | G<u>L</u> | 61 |
| PEP06923 | SEQ ID NO: 454 | GSS<u>L</u> | 57 |
| PEP07271 | SEQ ID NO: 455 | GSS<u>L</u> | 65 |
| PEP07554 | SEQ ID NO: 456 | GSS<u>L</u> | 58 |

TABLE 7-continued

Determined Tm values of tested albumin binding polypeptide variants

| Variant | SEQ ID NO: # | N-terminal sequence[3] | Tm (° C.) |
|---|---|---|---|
| PEP07912 | SEQ ID NO: 457 | GL | 53 |
| PEP07914 | SEQ ID NO: 458 | GL | 59 |
| PEP07968 | SEQ ID NO: 159[1] | GL | 53 |
| PEP07975 | SEQ ID NO: 160[1,2] | AL | 50 |
| PEP07844 | SEQ ID NO: 461 | GSSL | 65 |

[1]The peptide is conjugated with maleimide-DOTA at the cysteine
[2]The peptide is amidated at the C-terminus
[3]Leucine (underlined) is the residue in position 1 of the 46 amino acid sequence of the albumin binding polypeptide as defined in the first aspect of the present disclosure "GSSL" in Table 7 disclosed as SEQ ID NO: 845.

The polypeptide PEP07968 is identical to PEP07912, except for the former having a cysteine residue in position 14, which is conjugated with maleimide DOTA, and the latter a serine residue. Thus, the DOTA modification should not affect the melting temperature. Also PEP07975 is maleiamide-conjugated with DOTA using Cys14, and is identical to PEP07968 except for the C-terminal amide (resulting from the peptide synthesis) and for having an N-terminal alanine instead of a glycine. Furthermore, comparing PEP07912 and PEP07554 reveals that an N-terminal serine gives a higher melting temperature than a glycine in the same position (5° C. difference in Tm). Thus, all albumin binding polypeptide variants according to the present disclosure show Tm above 55° C., except PEP07912 and DOTA-conjugated variants. Taking into consideration the importance of the N-terminal portion, all the tested albumin binding polypeptides are superior to the derivative of Jonsson et al, e.g. PEP06923.

Example 4

Serum Response Analysis

The percentage of human serum containing IgG, capable of binding to a set of albumin binding polypeptides as disclosed herein was analyzed by ELISA. In total, 149 serum samples corresponding to 127 individuals were screened.

Material and Methods.

ELISA plates (96-well, half area plates (Costar, cat. No. 3690)) were coated with 50 μl/well of Albucult® (Novozyme) diluted to 8 μg/ml in coating buffer (Sigma, cat. No. 3041). The plates were coated over night for three days at 4° C. On the day of analysis, the plates were washed twice with tap water and blocked for 2 hours with 100 μl of phosphate buffered saline (PBS) containing 0.05% casein (PBSC). The plates were emptied and 50 μl/well of the albumin binding polypeptides PEP07913 (SEQ ID NO:453), PEP06923 (SEQ ID NO:454), PEP07271 (SEQ ID NO:455), PEP07912 (SEQ ID NO:457), PEP07554 (SEQ ID NO:456), PEP07914 (SEQ ID NO:458), PEP07968 (DOTA conjugated PEP07911, SEQ ID NO:459) and PEP07844 (SEQ ID NO:461), diluted to 2 μg/ml in PBSC were added according to a pre-made plate layout. After incubation for two hours at room temperature (RT), the plates were washed in PBSC four times using an automated ELISA washer. The 149 serum samples from 129 individuals were diluted 50 times in PBSC by adding 24 μl serum to 1174 μl PBSC. 50 μl of the diluted sera was added per well according to the pre-made plate layout. Each serum sample was tested as a singlet. Positive and negative controls were included on each plate and for each albumin binding polypeptide. Albumin binding antibodies (50 μl 0.5 μl/ml immunoglobulin solution prepared in house from sera from primates immunized with PEP06923) was added as a positive control and 50 μl PBSC was used as a negative control. The plates were incubated for one hour at RT and subsequently washed four times in PBSC using an automated ELISA washer. The bound IgG was detected with 50 μl/well of anti-human IgG (Southern Biotech, cat no 2040-05) diluted 10 000 times in PBSC. After washing four times in PBSC using an automated ELISA washer, 50 μl/well of substrate was added (Pierce cat. No. 34021). The reaction was stopped after 10-15 minutes by the addition of 50 μl H2SO4 to each well, prior to measuring the absorbance using a multi-well plate reader (Victor3, Perkin Elmer).

Results.

Figures 3A, 3B, 3C:
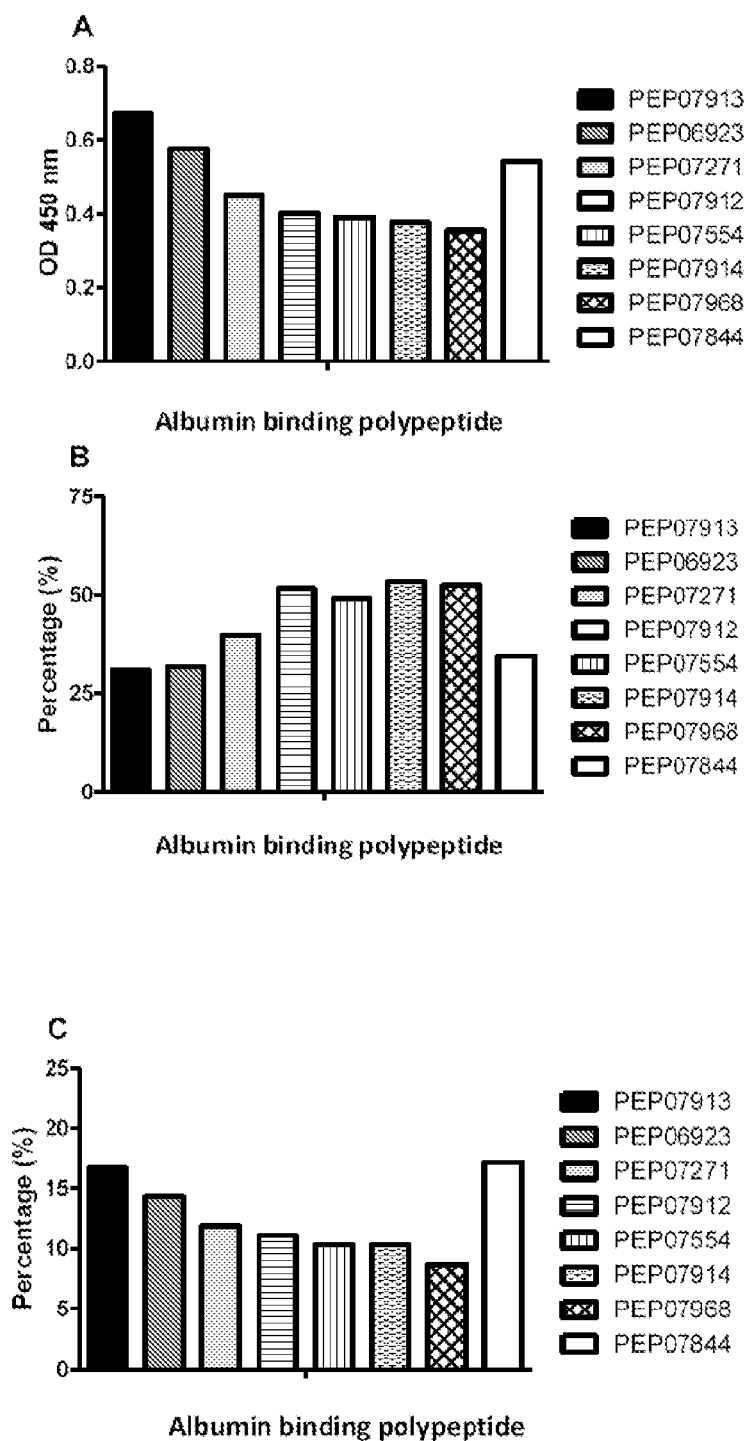
FIGS. 3A-C show the result of binding analysis performed by ELISA for investigating the binding of the albumin binding polypeptides PEP07913 (SEQ ID NO:453), PEP06923 (SEQ ID NO:454), PEP07271 (SEQ ID NO:455), PEP07912

Of the 149 sera screened for IgG binding to the albumin binding polypeptides, 23 were negative for all eight polypeptides (OD-value<0.1), i.e. showed no IgG bound to the polypeptides. The analysis was performed with the 126 sera that were positive for one or more albumin binding polypeptides. The average absorbance was calculated (FIG. 3A) and the percentage of sera with OD-values values either <0.15 (FIG. 3B) or >1.0 (FIG. 3C). The highest average OD-value and the highest percentage of serum with IgG binding were obtained with PEP07913 (SEQ ID NO:453), PEP06923 (SEQ ID NO:454) and PEP07844 (SEQ ID NO:461), whereas least reactivity was found against PEP07968 (DOTA conjugated PEP07911, SEQ ID NO:459), PEP07914 (SEQ ID NO:458) and PEP07954 (SEQ ID NO:456).

Thus, the most reactive albumin binding polypeptides were the parental G148-GA3 (PEP07913, SEQ ID NO:453) and the previously affinity improved derivative (PEP06923, SEQ ID NO:454), having helix 1 retained from G148-GA3. The third of the more reactive polypeptides (PEP07844, SEQ ID NO:461) contains the original lysine in position 14 in helix 1. This residue is intended for conjugation, and will therefore not be exposed when used as such. The identical albumin binding polypeptide variant, except for having an alanine in position 14 (PEP07554, SEQ ID NO:456), is one of the least reactive.

Example 5

Immunogenicity Testing of Albumin Binding Polypeptides

PEP07913 (SEQ ID NO:453), PEP07912 (SEQ ID NO:457), PEP07914 (SEQ ID NO:458), and PEP07968 (i.e. DOTA conjugated PEP07911, SEQ ID NO:159) were screened for their ability to induce T cell proliferation in peripheral blood mononuclear cells (PBMC) from 52 human Caucasian individuals (obtained from CRI-Labo Medische Analyse, Gent, Belgium). PEP07913 corresponds to the sequence of G148-GA3 having an N-terminal glycine residue, whereas PEP07912, PEP07914 and PEP07968, are examples of the 46 amino acid residues albumin binding polypeptides of PP007 (SEQ ID NO:7), PP013 (SEQ ID NO:13) and PP037 (SEQ ID NO:37) having different N-terminal amino acid additions according to the present disclosure.

Materials and Methods.

PBMCs, prepared according to standard cell biological methods, were added to a tissue culture (TC) treated 96-well round bottom plate (Falcon) in an amount of 300 000 PBMCs/well. The cells were stimulated by addition of 100 μl/well of albumin binding polypeptides PEP07913, PEP07912, PEP07914 and PEP07968 in AIMV medium (Invitrogen) additionally containing 900 μg/ml (3-fold molar excess) of recombinant human albumin (Albucult®, Novozyme). This corresponded to a final concentration of albumin binding polypeptide of 30 μg/ml. The stimulation was done in eight-replicates, i.e. the same albumin binding polypeptide was added to eight wells in identical amounts and under the same conditions. In positive control wells, the cells were stimulated with either 30 μg/ml Keyhole Limpet Hemocyanin (KLH, Calbiochem) or 30 μg/ml tetanus toxoid (TT, Statens Serum Institut). In negative control wells, only AIMV medium with or without 900 μg/ml of albumin were added.

Cell proliferation was assessed after seven days of culturing using Alexa Fluor 488 Click-iT EdU flow cytometry assay kit (Invitrogen). 1 μM/well of EdU incorporation marker was added on day six. On day seven, cells were washed, dissociated from the plate, washed again and stained for 30 minutes with anti-CD3-PerCP reagent (Becton Dickinson) and anti-CD4-Alexa647 reagent (Becton Dickinson). Following staining, the cells were washed, fixed (BD cellfix, BD biosciences), permeabilized (using saponin) and stained for EdU by addition of Click-iT reagent according to the manufacturer's protocol (Invitrogen). After completed staining, cells were washed again and analyzed using flow cytometry (FACSCantoII, BD Biosciences). To assess the number of proliferating cells, a fixed number of fluospheres (Invitrogen) was added to each well before analysis. All staining procedures and washes were performed directly in the 96-well plate.

The raw FACSCantoII data were gated hierarchically on CD3+ CD4+ T cells and the number of gated cells as well as their fluorescence intensity of EdU-Alexa Flour 488 incorporation marker were recorded. The mean values of the number of proliferating cells/eight-plicate of protein treated wells were compared to the positive and negative controls and the resulting ratios, described as stimulation indices (SI), were calculated. Based on the SI and the variation between replicates, threshold SI-values were set to 2.0 and 0.5 for stimulation and inhibition, respectively.
Results.

The albumin binding polypeptides PEP07913, PEP07912, PEP07914 and PEP07968 were assessed for their immunogenic potential in the presence of 3-fold excess of recombinant human albumin in a target human population using an in vitro PBMC proliferation assay. Compared to the albumin control, PEP07913 induced CD3+ CD4+ T cells proliferation in 6 of 52 donors, PEP07912 in 5 of 52 donors and PEP07914 and PEP07968 in 1 of 52 donors (FIG. 4A).

The mean stimulation index (SI) for all 52 donors was not significantly different for PEP07914 and PEP07968 compared to the negative control containing recombinant human albumin (p=0.79 and 0.48 respectively, FIG. 4B). The SI for PEP07913 was significantly higher (p=0.002) whereas the SI for PEP07912 was higher but not significant (p=0.03, FIG. 4B).

As compared to buffer only, the number of responding individuals was 10 for PEP07912, 7 for PEP07912, 2 for PEP07914, 1 for PEP07968, 2 for recombinant human albumin, and 49 and 51 for the two positive controls TT and KLH, respectively (FIG. 4C). The albumin binding polypeptides were ranked according to their immunogenicity in the following order: PEP07913>PEP07912>PEP07914>PEP07968. Both PEP07914 and PEP07968 were defined as non-immunogenic. The above results thus demonstrate that the immunogenic potential of the albumin binding polypeptides of the present disclosure is low, as compared to the positive controls.

Example 6

A Purification of an Exendin Analog-ABD Type Engineered Polypeptide

Method. Engineered polypeptides have been produced having an N-terminal extension which incorporates a His$_6$ (SEQ ID NO:49) "tag" as known in the art, for example as in sequence: MAHHHHHHVGTGSNENLYFQHGEGTFTS-DLSKQLEEEAVRLFIEWLKQG GPSKEI-ISTGGGGSASLAEAKVLANRELDKYGVS-DFYKRLINKAKTVEGVEALKLHIL AALP (SEQ ID NO: 846) which contains ABD00239 rather than an ABD of the present invention and yields Cmpd 684, provides an example of recombinant synthesis applicable to the engineered polypeptides of the present invention starting from, for example, a similar expression peptide, e.g. MAHHHHHH-VGTGSNENLYFQHGEGTFTSDL-SKQLEEEAVRLFIEWLKQGGPSKEIIS TGGGGSASGSLAEAKEAANAELDSYGVS-DFYKRLIDKAKTVEGVEALKDAILAALP (SEQ ID NO: 838), which yields mature engineered polypeptide HGEGT-FTSDLSKQLEEEAVRLFIEWLKQG-GPSKEIISTGGGGSASGSLAEAKEAANAE LDSYGVS-DFYKRLIDKAKTVEGVEALKDAILAALP (SEQ ID NO: 727) (Cmpd 5).

Preparation of Cell Extract.

In order to prepare the cell extract, cell pellets from 50 mL of cell cultures were completely resuspended in 60 mL of lysis buffer (50 mM TrisHCl, 150 mM NaCl, pH 8.0). Resuspended cells were run through a microfluidizer (Microfluidics, MA) at 100 PSI three times. Cell extracts were centrifuged for 30 min at 16,000×g to remove debris. EGTA (150 mM stock) was added to cell extract to a final concentration of 3 mM.

Ni-NTA Chromatography.

Ten mL of 50% suspension of Ni-NTA superflow was packed to a 15 mL empty column. The column was washed with 10 mL of water, 50 mL of lysis buffer, and 20 mL of lysis buffer with 3 mM EGTA (50 mM TrisHCl, 150 mM NaCl, pH8.0, 3 mM EGTA). Cell extract was carefully added on the top of Ni-NTA column, and the flow-through was collected. The column was washed with 30 mL of lysis buffer with EGTA (50 mM TrisHCl, 150 mM NaCl, pH8.0, 3 mM EGTA). Ten mL of elution buffer (25 mM TrisHCl, 50 mM NaCl, 250 mM imidazole, pH8.0) was added to the top of column, and the elution fractions (2 mL/fraction) were collected. SDS-PAGE was run to check the flow through and each fraction. Fractions containing the His-tagged compound were pooled.

TEV Protease Digestion.

His$_6$-tagged compound ("His$_6$" disclosed as SEQ ID NO: 49) was diluted three fold with 25 mM TrisHCl, 50 mM NaCl, pH8.0. β-mercaptoethanol (0.1%) and 2% of Turbo TEV protease (2 mg/mL, 10,000 units/mg, Accelagen), were added, and the result was mixed and incubated at RT for 2 hours and at 4° C. over night.

Removal of Cleaved His-Tag and Turbo TEV with Ni-NTA.

Six mL of 50% suspension of Ni-NTA superflow was packed to a 15 mL empty column. The column was washed with 20 mL of water and 20 mL of 50 mM TrisHCl, 100 mM NaCl, 45 mM imidazole, pH8.0. The TEV digest reaction was diluted 2-fold with 50 mM TrisHCl, 150 mM NaCl, pH8.0. Diluted digest reaction was carefully added to the top of Ni-NTA column, and the flow-through was collected. Ten mL of 50 mM TrisHCl, 100 mM NaCl, 45 mM imidazole, pH8.0, was added to the column to elute any unbound protein. The flow-throughs were collected and combined.

First Size Exclusion Chromatography (SEC).

The Ni-NTA flow-through was filtered with 0.2 um filter. Superdex 75 HiLoad 26/60 column was pre-equilibrated with 390 mL of PBS. Filtered flow-through was injected to the HiLoad 26/60 column with a sample pump. Protein was eluted with 1.5 CV of PBS, and the monomer peak was pooled.

Second Size Exclusion Chromatograph.

The first SEC pool was filtered with 0.2 um filter. A Superdex 75 HiLoad 26/60 column was pre-equilibrated with 390 mL of PBS. Filtered flow-through was injected to the column HiLoad 26/60 with a sample pump. Protein was eluted with 1.5 CV of PBS, and the monomer peak was pooled.

Third Size Exclusion Chromatography.

The second SEC pool was filtered with 0.2 um filter. A Superdex 75 HiLoad 26/60 column was pre-equilibrated with 390 mL of PBS. Filtered flow-through was injected to the column HiLoad 26/60 with a sample pump. Protein was eluted with 1.5 CV of PBS, and the monomer peak was pooled.

Removal of Residual Endotoxin with EndoTrap Red.

The third SEC pool still contained ~20 EU/mg of endotoxin, which was removed by the use of EndoTrap Red. Briefly, 0.5 mL of gel slurry was activated by adding 1 mL of Regeneration Buffer to the slurry and mix by gently shaking the tube for approximately 5 seconds. The supernatant was centrifuged and aspirated. This step was repeated two additional times. One mL of Equilibration Buffer was added, and mixing was conducted by gently shaking the tube for approximately 5 seconds. The supernatant was centrifuged and aspirated. This step was repeated two additional times. Protein sample (5.5 mL) was added to the resin and incubated for 90 minutes at RT, with gentle rocking or rotating of the tube while incubating. The result was centrifuged at 1200×g for 5 minutes, and the supernatant was transferred to a clean tube.

Results.

The final purified protein migrated on SDS-PAGE gel as approximately a 6 kD protein under the conditions employed. The LC-MS showed a correct molecular weight of 9827 dalton. The protein yield was 3.3 mg from 50 mL of cell culture.

Example 7

Activities of Exendin-ABD Engineered Polypeptides

Exendin-ABD engineered polypeptides of the invention retained sufficient exendin activity in an in vitro cell activation assay. Additionally, the engineered polypeptides provided dramatically improved duration of action for blood glucose lowering and body weight loss, as when compared to exendin-4, when administered as a single dose to a mammal Surprisingly, duration of action can be extended to at least 1 day, even at least 4 days, and even at least 7 days, or longer, in a rodent model, which can translate to at least one week duration of action in a human subject, thus suitable for twice daily, once daily, three times weekly, twice weekly or even once weekly administration.

Example 8

Albumin Binding

Characterization of the binding of engineered polypeptide compounds to albumin can be performed by any number of methods, including Biacore described herein. In this example binding measurements were conducted with a BioRad ProteOn XPR36 system (Bio-Rad Laboratories, Hercules Calif., USA; ProteOn XPR36 Protein Interaction Array System catalog number #176-0100), using a GLC sensor chip at 25 degrees C. For amine coupling the GLC chip was activated for 5 minutes using a 1:1 mixture of sulfo-NHS/EDC diluted 30-fold from the initial stock in water as shown below. Each albumin sample was diluted to 25 ug/ml in 10 mM Na acetate pH 5.0 and injected for 5 minutes over separate sensor surfaces. Each surface was then blocked with 1 M ethanolamine pH 8.5. Each albumin was coupled at a density of 2000-5000 in resonance units. The binding of an engineered polypeptide was tested using 5 nM as the highest concentration in a three-fold dilution series. The running buffer contained 10 mM HEPES pH 7.4, 150 mM NaCl, 3 mM EDTA and 0.005% tween-20. All samples were tested using a 3-fold dilution series. Each concentration series was tested in duplicate. The dissociation phase for the highest concentration was monitored for 3 hours.

The relative $K_D$ measured for the engineered polypeptides are presented in Table 8 below. The results show that the albumin binding polypeptides associate with albumins with high affinity. The number in parentheses represents the standard deviation in the last significant digit. As seen from the following table the exendin polypeptides fused to albumin binding domains of ABD00239 (to create polypeptides Cmpd 684 or Cmpd 088) or an ABD of the present invention (to create engineered polypeptides of the invention, e.g. Cmpd 5) retain extremely high affinity for serum albumin from various species, especially human serum albumin, even compared to the unconjugated ABD PEP07986 itself. The engineered polypeptides retain high affinity even compared to the identical exendin analog-linker construct fused to prior ABD00239 in place of the new PEP7986 (compare Cmpd 684 to Cmpd 5).

TABLE 8

| Cmpd | Human SA | Dog SA | Monkey SA | Mouse SA | Rat SA |
| --- | --- | --- | --- | --- | --- |
| ABD00239 | 16.1 (4) pM | 201 (2) pM | 123 (1) pM | 1.24 (1) nM | 18.3 (5) pM |
| PEP07986 | 9.5 (2) pM | 126 (2) pM | 84.0 (8) pM | 160 (2) pM | 5.7 (2) pM |
| Cmpd 088 | 84.7 (9) pM | 397 (2) pM | 77.5 (6) pM | 1.332 (6) nM | 16 (1) pM |
| Cmpd 684 | 68 (1) pM | 513 (3) pM | 90.9 (9) pM | 1.253 (8) nM | 200 (200) pM |
| Cmpd 5 | 160 (1) pM | 606 (4) pM | 140 (1) pM | 300.2 (5) pM | 12.5 (2) pM |
| Cmpd 11 | 251 pM | 2450 pM | 431 pM | 1029 pM | 51 pM |

Example 9

Activity of Compounds in a GLP-1 Receptor Functional Assay

Functional activity of the compounds can be determined using a cell line expressing GLP-1 receptor. See for example United States Patent Application Publication US20110097751A1, incorporated by reference for the assay method. In this example, functional activity was determined using cells that endogenously express GLP-1R, and cAMP induction is detected as a measure of exendin activity. An HTRF assay kit was used (Cisbio International (Bedford, Mass.). The bioassay used the rat thyroid carcinoma 6-23 (clone 6) cells in the cell-based assay using the HTRF® cAMP dynamic 2 1,000 assay kit, available from Cisbio as Catalog No. 62AM4PEB. The HTRF® standards and calibrations are prepared following the instructions in the kit. Accumulation of cAMP is measured following 30 minutes of compound treatment using the HTRF (CisBio) cell-based cAMP assay kit in 384-well format. Efficacy of peptides is determined relative to cell treatment with 10 uM forskolin (a constitutive activator of adenylate cyclase), and potency (EC50) of peptides is determined by the analysis of a concentration-response curve using non-linear regression analysis fitted to a 4-parameter model. The results of the GLP-1 receptor functional activity (cAMP induction) for potency (EC50) are provided in the following Table 9.

TABLE 9

GLP-1R Functional Activity

| Description | GLP-1R Functional activity (EC$_{50}$) in nM |
|---|---|
| Exendin-4 | 0.004 |
| [Leu$^{14}$, Gln$^{28}$] Exendin-4(1-32)-fGLP-1)33-37) (SEQ ID NO: 4) | 0.016 |
| Exendin-4 (1-28) amide | 0.011 |
| Cmpd 088 | 0.131 |
| Cmpd 5 | 0.486 |
| Cmpd 6 | 0.560 |
| Cmpd 7 | 0.904 |
| Cmpd 8 | 0.612 |
| Cmpd 9 | 3.21 |
| Cmpd 10 | 0.575 |
| Cmpd 11 | 1.28 |

Characterization of the in vitro activity of the engineered polypeptide compounds in the presence of serum albumin was demonstrated. Assays can be run in the presence and absence of an albumin, particularly human serum albumin. The data above was determined in the presence of about 0.1% bovine serum albumin (BSA). The following Table 10 presents functional activity of receptor activation (cAMP induction) assay described above, but in the presence of serum albumin from various species and at increased amounts. As can be seen, surprisingly, even when Cmpd 11 is bound to serum albumin, such as to human serum albumin, despite the presence of the ABD and the large serum albumin with its potential for steric hindrance and change in the apparent Stoke's radius of the compounds resulting from albumin binding, the engineered polypeptide retains GLP-1 receptor agonist activity. Given the picomolar affinity of ABD and the engineered polypeptides to some species of serum albumin, e.g. human serum albumin, the engineered polypeptide is believed to be effectively fully bound to albumin present in the assay (and thus also fully bound in vivo in circulating blood). Because of the extremely high affinity of compound binding to albumin (as above) and the presence of a high concentration of serum albumin in the blood, it is expected that the compounds will exist essentially in the bound state in vivo yet surprisingly provide sufficient exendin functions (as demonstrated herein).

TABLE 10

GLP-1R Functional Activity in Varying Amounts of Serum Albumin

| | GLP-1R Activation: cAMP Induction EC50 (nM) | | | |
|---|---|---|---|---|
| Cmpd | 0.1% Bovine Albumin | 1% Bovine Albumin | 1% Human Albumin | 1% Rat Albumin |
| GLP-1 (7-36) amide | 0.0306 | 0.0058 | 0.0112 | 0.0179 |
| Cmpd 684 | 0.7854 | 0.2204 | 0.185 | 0.2473 |

TABLE 10-continued

GLP-1R Functional Activity in Varying Amounts of Serum Albumin

| | GLP-1R Activation: cAMP Induction EC50 (nM) | | | |
|---|---|---|---|---|
| Cmpd | 0.1% Bovine Albumin | 1% Bovine Albumin | 1% Human Albumin | 1% Rat Albumin |
| Cmpd 088 | 1.1013 | 0.2234 | 0.2022 | 0.2164 |
| Cmpd 11 | 0.8719 | 0.1774 | 0.2079 | 0.1854 |

Example 10

OGTT DOA (Oral Glucose Tolerance Test Duration of Action) in Vivo Activity

The effect of lowering blood glucose prior to oral gavage (1.5 k/kg dextrose) and at 30 min after gavage were investigated 1 day post dose with indicated compounds, dosed at 25 nmol/Kg, with results shown in the following table. Drug was administered to 4-hr fasted NIH/Swiss mice. At 24 hours post drug administration, an OGTT was performed to assess duration of compound activity. Blood glucose was measured with a OneTouch® Ultra® (LifeScan, Inc., a Johnson & Johnson Company, Milpitas, Calif.). * p<0.05 vs. vehicle control; ANOVA, Dunnett's test. Glucose lowering as percent lowering compared to vehicle is given (negative value indicates lowering of glucose) at 30 minutes post gavage. This OGTT DOA indicates drug activity is present at least 24 hours (for the period of time prior to the OGTT) after drug was administered. Results are presented in Table 11. Exendin-4 (unconjugated to ABD), Leu14 exendin-4 (unconjugated to ABD) and unconjugated ABD EP07986 are inactive in this assay when dosed at t-24 hours, even when provided at even higher doses. When the unconjugated exendin compounds are given at 30 nmol/kg immediately before an OGTT, both exendin-4 and Leu14 exendin-4 provide a −41% change in glucose from basal. Cmpd 12, having a C-terminally truncated exendin-4 (1-28) fused to an ABD via a relatively short linker (HGEGTFTSDLSKQLEEEAVRLFIEWLKNTGGGG-SASGSLAEAKEAANAELDSYGVS DFYKRLIDKAKTVEGVEALKDAILAALP; SEQ ID NO:847) was active in vitro against the GLP-1 receptor, but did not display 24 duration in this duration assay. In this case, increasing the linker length is expected to result in a desirable 24 or longer duration in this assay. This duration of action assay as well as the other in vivo assays presented herein demonstrate that the improved engineered polypeptides are extremely stable to human plasma and human cell membrane proteases.

TABLE 11

OGTT DOA

| Description | Percent glucose lowering compared to vehicle |
|---|---|
| Cmpd 5 | −19, −22 |
| Cmpd 6 | −22 |
| Cmpd 7 | −16 |
| Cmpd 8 | −18, −17 |
| Cmpd 9 | −12 |
| Cmpd 10 | −12 |
| Cmpd 11 | −23 |

Example 11

Effect of an Exendin-Albumin Binding Domain Polypeptide in Diabetic Ob/Ob Mice

To demonstrate the effect of chronic exposure of an exendin fused to a first generation albumin binding domain polypeptide (as disclosed in PCT Published Application No. WO 2009/016043) on glucose lowering (e.g. HbA1c) and body weight loss, ob/ob/mice (diabetic) were treated with an exendin fused at its C-terminus to an albumin binding domain type polypeptide designated ABD00239 (an ABD previously disclosed in PCT Published Application No. WO 2009/016043 and not an ABD of the present invention), but which provides an example of activities of the present improved engineered polypeptides using the new improved ABDs disclosed herein, e.g. PEP7986. The time course of the effect of the test compound on body weight, glucose lowering and $HbA_{1c}$ lowering in ob/ob mice was investigated post dose, with values at 4 weeks presented in FIGS. 5A to 5C. As depicted in FIG. 5C significant body weight loss attends treatment with 25 and 250 nmol/kg of the compound IP twice each week for 28 days. FIGS. 5A and 5B depict changes in glucose (% pre-treatment) (FIG. 5B) and in HbA1c (% pre-treatment) (FIG. 5A). Points represent mean±s.d. (standard deviation). The test compound was injected sc on day=0 immediately following baseline sample collection in non-fasted male ob/ob mice. Unless indicated otherwise, blood glucose measures described herein employed a OneTouch® Ultra® device (LifeScan, Inc. Miliptas. The effect observed for the 25 nmol/kg biw (twice weekly) dose was approximately that observed for exendin-4 given at ~7.2 nmol/kg/d by continuous infusion (CSI). Thus at a comparable dose, the exendin-4-GGS-ABD00239 compound (Cmpd 088) matched the glycemic and body weight loss effects of the maximally efficacious dose of exendin-4. At 250 nmol/kg, Cmpd 088 was twice as effective as the maximally efficacious dose of exendin-4. Further, surprisingly, at equimolar dosing the Cmpd 088 was more effective than liraglutide [N-epsilon-(gamma-Glu(N-alpha-hexadecanoyl))-Lys26,Arg34]-GLP-1-(7-37)-acid, an albumin binding GLP-1 derivative, for blood glucose lowering, HbA1c lowering and body weight loss (data not shown).

Surprisingly, despite the reduced in vitro potency compared to unconjugated exendin-4 as observed above, the acute (within 6 hours) in vivo activity of an exendin fused to an albumin binding polypeptide disclosed herein is similar to that of unconjugated exendin with regard to maximum efficacy and only slightly less (several fold) with regard to potency (ED50; e.g.), such as when measured by reduction of food intake in mice (data not shown). Even more surprisingly the effect of chronic exposure of an exendin fused to the albumin binding polypeptides disclosed herein was nearly as potent as exendin-4 (continuously infused) but was able to provide a greater maximal effect. Furthermore, in light of the very high affinity for mouse or rat albumin and low off rates, all of the engineered compounds are effectively bound to albumin in the in vivo assays (as well as in the in vitro assays). Thus the improved engineered polypeptides retain GLP-1R functional activity even when bound to albumin. This is surprising in part because albumin compounds, e.g. liraglutide, have been reported as significantly active only when dissociated from albumin. And others have reported a need to remove proteolytically a GLP-1 or exendin from an albumin binding peptide to which it was conjugated in order to obtain GLP-1 receptor function. Accordingly, the in vivo activities of the improved engineered polypeptides described throughout this application are even more impressive.

Example 12

Long Duration and Action of the Engineered Polypeptides in Vivo

To further demonstrate the long half-life and long duration of activity of the engineered polypeptides described herein, the pharmacokinetic (PK) and pharmacodynamic (PD) properties were determined using rats. Pharmacokinetic profile and biological activity of an exemplary engineered polypeptide subcutaneously dosed in normal Harlan Sprague-Dawley (HSD) rats is presented. The recombinant engineered compounds Cmpd 11 (having Leu14 exendin-4 fused at its C-terminus via a glycine linker to PEP07986) and Cmpd 9 were injected subcutaneously at t=0 at 25 nmol/kg into normal HSD rats. Blood was collected via tail bleed at t=1 hour, 3 hours, 6 hours, 24 hours, 48 hours, 72 hours, 96 hours and 168 hours from fed HSD male rats. Food and body weights were measured daily. FIGS. 6A (Cmpd 11) and 7A (Cmpd 9) depict effect of compound to reduce food intake. FIGS. 6B (Cmpd 11) and 7B (Cmpd 9) depict effect of compound to reduce body weight. FIG. 6C (Cmpd 11) and 7C (Cmpd 9) depict a PK profile of the compound after a single dose. Points represent mean±sd. In the figures, vehicle is solid square, Cmpd 11 is open inverted triangle and Cmpd 9 is closed triangle. The plasma maximal concentration in FIG. 6C is equivalent to about 25,000 picomolar.

Exposure of up to seven (7) days was observed for these exemplary engineered polypeptides Cmpd 11, with a half-life of forty-two (42) hours, and Cmpd 9 with a half-life of forty-six (46) hours, in rats by this route of administration. By allometric scaling and in view of the strong affinity of the engineered polypeptides for human albumin, physical and biological activity duration at least as long and even longer is expected in human subjects. Accordingly, the compounds have use for at least daily, twice weekly, and even weekly administration, especially in human subjects.

Example 13

Long Duration and Action and Absolute Plasma Half-life of the Engineered Polypeptides in Vivo Pharmacokinetic profile and biological activity of an exemplary engineered polypeptide intravenously dosed in normal Harlan Sprague-Dawley (HSD) rats is presented, from which an absolute plasma half-life can be calculated. The recombinant engineered compound Cmpd 11 was injected intravenously at t=0 at 2 nmol/kg into normal HSD rats. Unconjugated exendin-4 and exendin-4 analog Leu14 exendin-4 were injected at 2 nmol/kg intravenously. Blood was collected via tail bleed at t=1 hour, 3 hours, 6 hours, 24 hours, 48 hours, 72 hours, 96 hours and 168 hours from fed HSD male rats. Food and body weights were measured daily. FIG. 8A depicts effect of Cmpd 11 to reduce food intake. FIG. 8B depicts effect of Cmpd 11 to reduce body weight. FIG. 8C depicts a PK profile of Cmpd 11 after a single IV dose. As expected the half-life of the unconjugated exendins is less than 15 minutes. An absolute half-life for the exemplary engineered polypeptide Cmpd 11 is estimated at about at least 12.3 hours. Points represent mean±sd.

Exposure of up to four days was observed for this exemplary engineered polypeptide, even at these relatively low doses, by this route of administration. By allometric scaling and in view of the strong affinity of the engineered polypeptides for human albumin, physical and biological activity duration at least as long and even longer is expected in human subjects. Accordingly, the compounds have use for at least twice daily (e.g. morning and night), at least daily, twice weekly, and even once weekly administration, especially in human subjects.

Example 14

Sub-Chronic Dosing Provides Superimpositioning and Exendin-like Pharmacology

To demonstrate the effect of sub-chronic exposure of an exemplary engineered polypeptide in vivo, Cmpd 11 was administered subcutaneously twice weekly or daily for 14 days. Food intake inhibition, body weight decrease and plasma levels of Cmpd 11 were determined daily. Normal lean HSD rats were treated subcutaneously with 25 nmol/kg Cmpd 11 over 14 days as indicated in FIGS. 9A-9F, either twice weekly (BIW; open inverted trangles) as indicated by the down arrows or daily (QD; open square). Both BIW and QD administration inhibited daily food intake compared to vehicle (closed circle), as shown by cumulative food intake FIG. 9A, percent change in daily food intake FIG. 9B and percent change in cumulative food intake FIG. 9C. Both BIW and QD administration resulted in body weight loss as indicated by the reduction in total body weight FIG. 9D and greater percent negative change in body weight FIG. 9E compared to vehicle. FIG. 9F depicts a PK profile of Cmpd 11 given BIW or QD. Points represent mean±s.d. (standard deviation) with 4 to 6 animals per point. The test compound was injected subcutaneously on day=0 immediately following baseline sample collection.

As can be seen both modes of administration provide a superimpositioning effect leading to higher plasma levels of compound upon each subsequent dose, until a steady state is obtained. With as little as 11 days of treatment, the efficacy observed for the BIW (twice weekly) dose began to approximate that observed for Leu14 exendin-4 given at ~7.2 nmol/kg/d by continuous infusion (CSI)—about 7% lower vehicle-corrected body weight at steady state level. The QD dosing provides a smoother profile, however, when translated to larger animals and those having longer inherent albumin plasma-half-lifes, smoother plasma levels approximating the QD pattern observed in the rats, are expected for BIW, thrice weekly and even weekly administration of this and any engineered polypeptide described herein. The QD dose with this engineered polypeptide achieved or surpassed efficacy of the unconjugated infused exendin or exendin analog during the short treatment period, which is therefore expected to be the case for each of the engineered polypeptides described herein.

Example 15

Lack of Vacuolization

With some drugs, such as some pegylated proteins, undesirable vacuoles can form in cytoplasm of epithelial cells lining the proximal convoluted tubules, which is an undesirable toxicity measure. The engineered albumin binding compounds of the present application do not form kidney vacuoles. C57BL6 female mice (n=2 cages, 3 mice/cage) were weighed daily 3 hours prior to lights out. Immediately after weighing, on days 0-6 mice were injected subcutaneously with test compound. Mice were sacrificed on day 7 and kidneys submitted for histopathology. Severity score for cytoplasmic vacuolation of renal cortical tubular epithelial cells was as follows: score 1=minimal (8-15%); 2=mild (16-35%); 3=moderate (36-60%); 4=marked (>60%). A positive control compound known to cause vacuole formation was scored as 3. The ABD polypeptide PEP07986 itself scored 0. The engineered polpeptide Cmpd 5 scored 0.

Example 16

Oral Delivery Achieves Systemic Distribution

Oral delivery with intestinal uptake was investigated using Cmpd 088. Diabetic db/db mice were dosed orally (peroral via gavage) with 240 nmol/kg of the following compounds, an exendin analog [Leu14, Gln28]Exendin-4-(1-32)-fGLP-1-(33-37) acid and Cmpd 088. The data demonstrate that the engineered peptides are orally bioavailable, even in a formulation PBS/propylene glycol (50:50) absent other specific excipients that might enhance delivery and uptake. Compared to the exendin analog, Cmpd 088 (both at 1 mg/kg dose) at more than twice the molecular weight of the exendin analog is also orally bioavailable in the same formulation. The results indicate that both compounds were active when dosed orally, and equally efficacious under the conditions tested to 120 minutes. The results are presented in FIG. 10. Points represent mean+/-sd. Peptides were dosed peroral by gavage at t=0 immediately following the taking of a baseline sample. Mice were 2-hour fasted db/db mice. Accordingly, the improved engineered polypeptide compounds presented herein have use for at least twice daily (e.g. morning and night), at least daily, thrice weekly, twice weekly, and even once weekly oral administration, especially in human subjects.

What is claimed is:

1. An engineered polypeptide comprising:
   an albumin binding domain polypeptide (ABD), and
   a first peptide hormone domain (HD1) comprising an exendin sequence, an exendin analog sequence or an active fragment sequence thereof,
   wherein said ABD comprises at least 95% identity to SEQ ID NO:300, with the proviso that $X_7$ is not L, E or D; or alternatively, with the proviso that the amino acid sequence is not SEQ ID NO:679.

2. The engineered polypeptide according to claim 1, further comprising a first linker (L1) covalently linking said HD1 and said ABD.

3. The engineered polypeptide according to claim 1, wherein said HD1 is exendin-4(1-28) (SEQ ID NO: 980), exendin-4(1-29) (SEQ ID NO: 981), exendin-4(1-30) (SEQ ID NO: 680), exendin-4(1-31) (SEQ ID NO: 982) or exendin-4(1-32) (SEQ ID NO: 983).

4. The engineered polypeptide according to claim 1, wherein said HD1 is selected from the group of sequences consisting of:

HGEGTFTSDLSKQMEEEAVRLFIEWLKNGGPSSGAPPPS, (SEQ ID NO: 2)

HGEGTFTSDLSKQLEEEAVRLFIEWLKNGGPSSGAPPPS, (SEQ ID NO: 3)

HGEGTFTSDLSKQLEEEAVRLFIEWLKQGGPSKEIIS, (SEQ ID NO: 4)

HGEGTFTSDLSKQMEEEAVRLFIEWLKNGGPSSGAPPPS, (SEQ ID NO: 2)

HGEGTFTSDLSKQMEEEAVRLFIEWLKQGGPSKEIIS, (SEQ ID NO: 111)

HGEGTFTSDLSKQLEEEAVRLFIEWLKNGGPSSGAPPS, (SEQ ID NO: 112)

HGEGTFTSDLSKQMEEEAVRLFIEWLKNGGPSSGAPPS, (SEQ ID NO: 113)

HGEGTFTSDLSKQLEEEAVRLFIEWLKQGGPSKEIISKKKKKK, (SEQ ID NO: 114)

HGEGTFTSDLSKQMEEEAVRLFIEWLKNGGPSSGAPPPSKKKKKK, (SEQ ID NO: 115)

HGEGTFTSDLSKQMEEEAVRLFIEWLKQGGPSKEIISKKKKKK, (SEQ ID NO: 116)

HGEGTFTSDLSKQLEEEAVRLFIEWLKNGGPSSGAPPSKKKKKK (SEQ ID NO: 117)

and

HGEGTFTSDLSKQMEEEAVRLFIEWLKNGGPSSGAPPSKKKKKK. (SEQ ID NO: 118)

5. The engineered polypeptide according to claim 1, wherein the ABD is selected from the group consisting of: SEQ ID NOs: 301-463, 500-502, and 862-950.

6. The engineered polypeptide according to claim 1, having affinity for serum albumin with a dissociation constant less than about $10^{-6}$ mol/L.

7. The engineered polypeptide according to claim 1, wherein the engineered polypeptide is selected from the group consisting of:

```
                                                          (SEQ ID NO: 727)
HGEGTFTSDLSKQLEEEAVRLFIEWLKQGGPSKEIISTGGGGSASGSLAEAKEAANAELD
SYGVSDFYKRLIDKAKTVEGVEALKDAILAALP;

(SEQ ID NO: 728)
HGEGTFTSDLSKQLEEEAVRLFIEWLKNGGPSSGAPPKSTGGGGSASGSLAEAKEAANA
ELDSYGVSDFYKRLIDKAKTVEGVEALKDAILAALP;

(SEQ ID NO: 729)
HGEGTFTSDLSKQLEEEAVRLFIEWLKNGGPSSGAPPPSTGGGGSASGSLAEAKEAANA
ELDSYGVSDFYKRLIDKAKTVEGVEALKDAILAAL;

(SEQ ID NO: 730)
HGEGTFTSDLSKQMEEEAVRLFIEWLKNGGPSSGAPPPSTGGGGSASGSLAEAKEAANA
ELDSYGVSDFYKRLIDKAKTVEGVEALKDAILAALP;

(SEQ ID NO: 731)
HGEGTFTSDLSKQMEEEAVRLFIEWLKNGGPSSGAPPPSGGSLAEAKEAANAELDSYGV
SDFYKRLIDKAKTVEGVEALKDAILAALP;

(SEQ ID NO: 732)
HGEGTFTSDLSKQLEEEAVRLFIEWLKNGGPSSGAPPPSTGGGGSASGSLAEAKEAANA
ELDSYGVSDFYKRLIDKAKTVEGVEALKDAILAALP;

(SEQ ID NO: 733)
HGEGTFTSDLSKQLEEEAVRLFIEWLKNGGPSSGAPPPSGGSLAEAKEAANAELDSYGV
SDFYKRLIDKAKTVEGVEALKDAILAALP;

(SEQ ID NO: 734)
HGEGTFTSDLSKQLEEEAVRLFIEWLKQGGPSKEIISTGGGGSASGSLAEAKEAANAELD
SYGVSDFYKRLIDKAKTVEGVEALKDAILAAL;

(SEQ ID NO: 735)
HGEGTFTSDLSKQLEEEAVRLFIEWLKNGGPSSGAPPKSTGGGGSASGSLAEAKEAANA
ELDSYGVSDFYKRLIDKAKTVEGVEALKDAILAAL;

(SEQ ID NO: 736)
HGEGTFTSDLSKQLEEEAVRLFIEWLKNGGPSSGAPPPSTGGGGSASGSLAEAKEAANA
ELDSYGVSDFYKRLIDKAKTVEGVEALKDAILAA;

(SEQ ID NO: 737)
HGEGTFTSDLSKQMEEEAVRLFIEWLKNGGPSSGAPPPSTGGGGSASGSLAEAKEAANA
ELDSYGVSDFYKRLIDKAKTVEGVEALKDAILAAL;

(SEQ ID NO: 738)
HGEGTFTSDLSKQMEEEAVRLFIEWLKNGGPSSGAPPPSGGSLAEAKEAANAELDSYGV
SDFYKRLIDKAKTVEGVEALKDAILAAL;

(SEQ ID NO: 739)
HGEGTFTSDLSKQLEEEAVRLFIEWLKNGGPSSGAPPPSGGSLAEAKEAANAELDSYGV
SDFYKRLIDKAKTVEGVEALKDAILAAL;

(SEQ ID NO: 740)
HGEGTFTSDLSKQLEEEAVRLFIEWLKQGGPSKEIISTGGGGSASGSLAEAKEAANAELD
SYGVSDFYKRLIDKAKTVEGVEALKDAILAA;

(SEQ ID NO: 741)
HGEGTFTSDLSKQLEEEAVRLFIEWLKNGGPSSGAPPKSTGGGGSASGSLAEAKEAANA
ELDSYGVSDFYKRLIDKAKTVEGVEALKDAILAA;

(SEQ ID NO: 742)
HGEGTFTSDLSKQMEEEAVRLFIEWLKNGGPSSGAPPPSTGGGGSASGSLAEAKEAANA
ELDSYGVSDFYKRLIDKAKTVEGVEALKDAILAA;
```

-continued (SEQ ID NO: 743)
HGEGTFTSDLSKQMEEEAVRLFIEWLKNGGPSSGAPPPSGGSLAEAKEAANAELDSYGV

SDFYKRLIDKAKTVEGVEALKDAILAA;

(SEQ ID NO: 744)
HGEGTFTSDLSKQLEEEAVRLFIEWLKNGGPSSGAPPPSTGGGGSASGSLAEAKEAANA

ELDSYGVSDFYKRLIDKAKTVEGVEALKDAILAA;
and (SEQ ID NO: 745)
HGEGTFTSDLSKQLEEEAVRLFIEWLKNGGPSSGAPPPSGGSLAEAKEAANAELDSYGV

SDFYKRLIDKAKTVEGVEALKDAILAA.

8. A polynucleotide encoding an engineered polypeptide according to claim 1.

9. An expression vector comprising a polynucleotide according to claim 8.

10. A host cell comprising an expression vector according to claim 9.

11. A method of producing the engineered polypeptide of claim 1, the method comprising expressing a polynucleotide encoding the engineered polypeptide or synthesizing the polypeptide by non-biological peptide synthesis.

* * * * *